(12) United States Patent
Chatterjee et al.

(10) Patent No.: US 7,083,943 B1
(45) Date of Patent: Aug. 1, 2006

(54) POLYNUCLEOTIDES RELATED TO MURINE ANTI-IDIOTYPE ANTIBODY 11D10 AND METHODS OF USE THEREOF

(76) Inventors: Malaya Chatterjee, 3512 Reeves Dr., Fort Wright, KY (US) 41017; Kenneth A. Foon, 183 Bayview Dr., San Carlos, CA (US) 94070; Sunil K. Chatterjee, 3512 Reeves Dr., Fort Wright, KY (US) 41017

( * ) Notice: Subject to any disclaimer, the term of this patent is extended or adjusted under 35 U.S.C. 154(b) by 0 days.

(21) Appl. No.: 08/836,455

(22) PCT Filed: Dec. 19, 1996

(86) PCT No.: PCT/US96/20757

§ 371 (c)(1),
(2), (4) Date: May 9, 1997

(87) PCT Pub. No.: WO97/22699

PCT Pub. Date: Jun. 26, 1997

Related U.S. Application Data

(63) Continuation-in-part of application No. 08/766,350, filed on Dec. 13, 1996, now Pat. No. 6,949,244.
(60) Provisional application No. 60/035,345, filed on Jan. 29, 1995.

(51) Int. Cl.
*C12P 12/06* (2006.01)

(52) U.S. Cl. .................. 435/69.1; 435/320.1; 435/325; 435/327; 536/23.1; 536/23.5; 530/387.2; 530/387.3

(58) Field of Classification Search ............... 435/69.1, 435/327, 91.1, 320.1, 325, 70.1; 536/23.1, 536/23.53, 23.4, 23.5, 24.3; 429/131.1; 530/387.2, 530/388.1, 388.8, 387.3; 424/131.1, 135.1, 424/138.1, 185.1
See application file for complete search history.

(56) References Cited

U.S. PATENT DOCUMENTS

| | | | |
|---|---|---|---|
| 3,996,345 A | 12/1976 | Ullman et al. | |
| 4,436,728 A | 3/1984 | Ribi et al. | |
| 4,675,287 A | 6/1987 | Reisfeld et al. | |
| 4,683,195 A | 7/1987 | Mullis et al. | |
| 4,683,202 A | 7/1987 | Mullis | |
| 4,693,966 A | 9/1987 | Houghton et al. | |
| 4,722,840 A | 2/1988 | Valenzuela et al. | |
| 4,726,947 A | 2/1988 | Shimada et al. | |
| 4,754,065 A | 6/1988 | Levenson et al. | |
| 4,800,159 A | 1/1989 | Mullis et al. | |
| 4,904,596 A | 2/1990 | Hakomori | |
| 4,918,164 A | 4/1990 | Hellstrom et al. | |
| 5,009,995 A | 4/1991 | Albino et al. | |
| 5,053,224 A | 10/1991 | Koprowski et al. | |
| 5,057,540 A | 10/1991 | Kensil et al. | |
| 5,077,284 A | 12/1991 | Loria et al. | |
| 5,091,177 A | 2/1992 | Hellstrom et al. | |
| 5,134,075 A | 7/1992 | Hellstrom et al. | |
| 5,171,568 A | 12/1992 | Burke et al. | |
| 5,208,146 A | 5/1993 | Irie | |
| 5,240,833 A | 8/1993 | Nudelman et al. | |
| 5,242,824 A | 9/1993 | Hellstrom et al. | |
| 5,270,202 A | 12/1993 | Raychaudhuri | |
| 5,407,684 A | 4/1995 | Loria et al. | |
| 5,808,033 A | * 9/1998 | Gourlie et al. | |
| 5,840,299 A | * 11/1998 | Bendig et al. | |
| 6,274,143 B1 | * 8/2001 | Chatterjee et al. | 424/131.1 |

FOREIGN PATENT DOCUMENTS

| | | |
|---|---|---|
| EP | 0280209 | 8/1988 |
| EP | 0329400 | 9/1993 |
| EP | 0 438 803 B1 | 3/1997 |
| WO | WO 86/00909 | 2/1986 |
| WO | WO 89/07268 | 8/1989 |
| WO | WO 89/11537 | 11/1989 |
| WO | WO 91/11465 | 8/1991 |
| WO | WO 91/16924 | 11/1991 |
| WO | WO 92/08495 | 5/1992 |
| WO | WO 92/16231 | 10/1992 |
| WO | WO 93/06233 | 4/1993 |
| WO | WO 94/05329 | 3/1994 |
| WO | WO 94/11508 | 5/1994 |

OTHER PUBLICATIONS

Houdebine. Journal of Biotechnology 1994, 34: 269–287.*

Verma et al. Nature 1997, 389: 239–242.*

Amalfitano et al. Current Gene Therapy 2002, 2: 111–133.*

Pandha et al. Current Opinion in Investigational Drugs 2000; 1 (1): 122–134.*

Memorandum: Amy P. Patterson, MD, Department of Health and Human Services, Jan. 14, 2003, pp. 1–3.*

Chakrabarti S, et al. Gene. Apr. 15, 1989; 77 (1): 87–93.*

Herlyn, D, et al, 1995, Cloned antigens and antiidiotypes, Hybridoma, vol. 14, No. 2, pp. 159–166.*

(Continued)

*Primary Examiner*—Larry R. Helms
*Assistant Examiner*—Stephen L. Rawlings
(74) *Attorney, Agent, or Firm*—Morrison & Foerster LLP

(57) ABSTRACT

The present invention provides a monoclonal and-idiotype antibody 11D10 that elicits an immune response against a specific epitope of a high molecular weight mucin of human milk fat globule (HMFG) and a hybridoma that produces 11D10. The hybridoma that produces 11D10 was selected by specific procedures. 11D10 inducts an Immunological response to HMFG in mice, rabbits, monkeys and patients with advanced HMFG-associated tumors. This invention provides compositions derived from polynucleotide sequences encoding the variable light and/or variable heavy regions of monoclonal anti-idiotype antibody 11D10, as well as polypeptides encoded thereby. The invention also provides compositions which can be used in the detection or treatment of HMFG-associated tumors.

34 Claims, 28 Drawing Sheets

OTHER PUBLICATIONS

Zeytin, HE, et al, 2000, Construction and characterization of DNA vaccines encoding the single–chain variable fragment of the anti–idiotype antibody 1A7 mimicking the tumor–associated antigen GD2, Cancer Gene Therapy, vol. 7, No. 11, pp. 1426–1536.*

Gavilondo, JV, et al, 2000, Antibody engineering at the millennium, Biotechniques, vol. 29, No. 1, pp. 128–145.*

Editor, 1995, Instructions for authors, Cancer Research, vol. 55, No. 1, pp. 202–208.*

Benvenuti, F, et al, 2001, Anti–idiotypic antibodies induced by genetic immunisation are directed exclusively against combined VL/VH determinants, Gene Therapy, vol. 8, No. 20, pp. 1555–1561.*

Benvenuti, F, et al, 2000, Anti–idiotypic DNA vaccines for lymphoma immunotherapy require the presence of both variable region genes for tumor protection, Gene Therapy, vol. 7, No. 7, pp. 605–611.*

Stevenson, FK, et al, 1995, Idiotypic DNA vaccines against B–cell lymphoma, Immunological Reviews, vol. 145, pp. 211–228.*

Spooner, RA, et al, 1995, DNA vaccination for cancer treatment, Gene Therapy, vol. 2, No. 3, pp. 173–180.*

Kennedy, RC, et al, 1985, Vaccines utilizing internal image anti–idiotypic antibodies that mimic antigens of infectious organisms, Biotechniques, vol. 3, No. 5, pp. 404–410.*

Bodey, B, et al, 2000, Failure of cancer vaccines: the significant limitations of this approach to immunotherapy, Anticancer Research, vol. 20, pp. 2665–2676.*

Browning et al Cell vol. 72 847–856, Mar. 1993.*

Mo et al Eur J Immuno vol. 23 2503–2510, 1993.*

Liu et a; J Immunology vol. 139(10) 3521–3526, Nov. 1987.*

Chatterjee et al Cancer Immuno Immunother vol. 38 75–82, 1994.*

Rudikoff et al Proc Natl Acad Sci USA vol. 79 1979, 1982.*

Panka et al Proc Natl Acad Sci USA vol. 85 3080–3084, May 1988.*

Amit et al Science vol. 233 747–753, 1986.*

De Waele et al Eur J Biochem vol. 176 287–295, 1988.*

Shlomchik et al J Exp Med vol. 171 265–297, Jan. 1990.

Kavaler et al J Immunology vol. 145 2312–2321 No. 7, Oct. 1990.

Seidman et al Nature vol. 280 370, Aug. 1979.

Darsley et al EMBO J vol. 4(2) 393–398, 1985.

Charkabroty et al Proc Amer Assoc Cancer Res vol. 35 p. 497 Abstract No. 2963, Mar. 1994.*

Chatterjee et al Antigen and Antibody Molecular Engineering in Breast Cancer Diagnosis and Treatment 139–148, 1994.*

Chakraborty et al J Immunotherapy vol. 18(2) 95–103, 1995.*

Cancer Research, Jan. 1, 1995, vol. 55(1):pp. 202–208.*

Altschul et al., "Basic local alignment search tool" (1990) *J. Mol Biol.* 215:403–410.

Barry et al., "Protection against mycoplasma infection using expression–library immunization" (1995) *Nature* 377:632–635.

Bhattacharya–Chatterjee et al., "Anti–idiotype antibodies as potential therapeutic agents for human breast cancer" *Antigen and Antibody Molecular Engineering in Breast Cancer Diagnosis and Treatment*, Eds. R.L. Ceriani (1994), pp. 139–148.

Bhattercharya–Chatterjee et al., "Idiotypic antibody immunotherapy of cancer" (1994) *Cancer Immunol. Immunother.* 38:75–82.

Bhattacharya–Chatterjee et al., "Idiotype vaccines against human T cell acute lymphoblastic leukemia" (1987) *J. Immunol.* 139:1354–1360.

Bhattacharya–Chatterjee et al., "Idiotype vaccines against human T cell leukemia". II. Generation and characterization of a monoclonal idiotype cascade (Ab1, Ab2, and Ab3) (1988) *J. Immunol.* 141:1398–1403.

Bhattacharya–Chatterjee et al., "Murine monoclonal anti–idiotype antibody as a potential network antigen for human carcinoembryonic antigen" (1990) *J. Immunol.* 145:2758–2765.

Bird et al., "Single–chain antigen–binding proteins" (1988) *Science* 242:423–426.

Ceriani et al., "Characterization of cell surface antigens of human mammary epithelial cells with monoclonal antibodies prepared against human milk fat globule" (1983) *Somatic Cell Genet.* 9:415–427.

Ceriani et al., "Immunotherapeutic preclinical evaluation of anti–human mild fat globule MoAbs Mc5 and BrE–1" (1991) *Antibody Immunoconjugates and Radiopharmaceuticals* 3:181–198.

Ceriani et al., "Surface differentiation antigens of human mammary epithelial cells carried on the human mild fat globule" (1977) *Proc. Natl. Acad. Sci. USA* 74:582–586.

Chakraborty et al., "Immune responses in advanced breast cancer patients treated with an anti–idiotype antibody vaccine", (1997) *Amer. Acad. Canc. Res.*, Abstract (1 page total).

Chakraborty et al., "Induction of human breast cancer specific antibody responses in cynomolgus monkeys by a murine monoclonal anti–idiotype antibody", (1995) *Cancer Res.* 55:1525–1530.

Chakraborty et al., "Induction of human breast cancer specific antibody responses in cynomolgus monkeys by a murine monoclonal anti–idiotype antibody", (1994) Abstracts from proceedings of American Assoc. for Cancer Research vol. 35, Abstract No. 2963.

Chakraborty et al., "Preclinical evaluation in non–human primates of an anti–idiotypic antibody that mimicks that carcinoembryonic antigen" *J. Immunother.* (1995) 18:95–103.

Chatterjee et al., "Antiidiotype (Ab2) vaccine therapy for cutaneous T–cell lymphoma" (1993) *Ann. N.Y. Acad. Sci.* 690:376–377.

Cheresh et al., "Biosynthesis and expression of the disialoganglioside $G_{D2}$, a relevant target antigen on small cell lung carcinoma for monoclonal antibody–mediated cytolysis" (1986) *Cancer Res.* 46:5112–5118.

Cheresh et al., "Disialoganglioside GD3 on human melanoma serves as a relevant target antigen for monoclonal antibody–mediated tumor cytolysis"(1985) *Proc. Natl. Acad. Sci USA* 82:5155–5159.

Cochran et al., "In vitro mutagenesis of the promoter region for a vaccinia virus gene: Evidence for tandem early and late regulatory signals" (1985) *J. Virol.* 54:30–37.

Cockett et al., "High level expression of tissue inhibitor of metalloproteinases in Chinese hamster ovary cells using glutamine synthetase gene amplification" (1990) *Bio/Technology* 8:662–667., Corcoran et al., "GM–CSF produced by recombinant vaccinia virus or in GM–CSF transgenic mice has no effect in vivo on murine cutaneous leishmaniasis" (1988) *J. Parasit.* 74:763–767.

DeFreitas et al., "Human antibody induction to the idiotypic and anti–idiotypic determinants of a monoclonal antibody against a gastrointestinal carcinoma antigen" (1985) *Curr. Top Microbiol. Immunol.* 119:75–89.

Dohlsten et al., "Monoclonal antibody–superantigen fusion proteins: Tumor–specific agents for T–cell–based tumor therapy" (1994) *Proc. Natl. Acad. Sci. USA* 91:8945–8949.

Ey et al., "Isolation of pure $IgG_1$, $IgG_{2a}$ and $IgG_{2b}$ immunoglobulins from mouse serum using protein A–sepharose" (1978) *Immunochemistry* 15:429–436.

Fiedler et al., "High–level production and long–term storage of engineered antibodies in transgenic tobacco seeds" (1995) *Biotechnology* 13:1090–1093.

Flexner et al., "Attenuation of live recombinant vaccinia virus vectors by expression of human interleukin–2" (1988) *Vaccines 88*, Cold Spring Harbor Laboratory, pp. 179–184.

Herlyn et al., "Anti–idiotype immunization of cancer patients: Modulation of the immune response" (1987) *Proc. Natl. Acad. Sci. USA* 84:8055–8059.

Herlyn et al., "Monoclonal anticolon carcinoma antibodies in complement–dependent cytotoxicity" (1981) *Int. J. Cancer* 27:769–774.

Holmes et al., "Correlation of cell–surface phenotype with the establishment of interleukin 3–dependent cell lines from wild–mouse murine leukemia virus–induced neoplasms" (1985) *Proc. Natl. Acad. Sci. USA* 82:6687–6691.

Honjo et al., "Cloning and complete nucleotide sequence of mouse immunoglobulin γ1 chain gene" (1979) *Cell* 18:559–568.

Horn et al., "Cancer gene therapy using plasmid DNA: Purification of DNA for human clinical trials" (1995) *Human Gene Therapy* 6:565–573.

Hruby et al., "Fine structure analysis and nucleotide sequence of the vaccinia virus thymidine kinase gene" (1983) *Proc. Natl. Acad. Sci. USA* 80:3411–3415.

Hunter "Standardization of the chloramine–T method of protein iodination" (1970) *Proc. Soc. Exp. Biol. Med.* 133:989–992.

Jaffee et al., "High efficiency gene transfer into primary human tumor explants without cell selection" (1993) *Cancer Res.* 53:2221–2226.

Jerne, "Towards a network theory of the immune system" *Ann. Immunol.* (1974) 125:373–389.

Kantor et al., "Antitumor activity and immune responses induced by a recombinant carcinoembryonic antigen–vaccinia virus vaccine" (1992) *J. Natl. Cancer Inst.* 84:1084–1091.

Larocca et al., "High level expression in *E. coli* of an alternate reading frame of pS2 mRNA that encodes a mimotope of human breast epithelial mucin tandem repeat" (1992) *Hybridoma* 11:191–201.

Lindenmann, "Speculations on idiotypes and homobodies" (1973) *Ann. Immunol.* 124:171–184.

Mackett et al., "The construction and characterisation of vaccinia virus recombinants expressing foreign genes" (1985) *DNA Cloning, vol. II*, D. M. Glover, ed., IRL Press, pp. 191–211.

Mackett et al., "Vaccinia virus: A selectable eukaryotic cloning and expression vector" (1982) *Proc. Natl. Acad. Sci. USA* 79:7415–7419.

Maloney et al., "Monoclonal anti–idiotype antibodies against the murine B cell lymphoma 38C13: Characterization and use as probes for the biology of the tumor in vivo and in vitro" (1985) *Hybridoma* 4:191–209.

McBride et al., "Induction of tolerance to a murine fibrosarcoma in two zones of dosage—the involvement of suppressor cells" (1986) *Br. J. Cancer* 53:707–711.

Merrifield "Solid phase peptide synthesis. I. The synthesis of a tetrapeptide" (1963) *J. Am. Chem. Soc.* 85:2149–2154.

Mittleman et al., "Human high molecular weight melanoma–associated antigen (HMW–MAA) mimicry by mouse anti–idiotypic monoclonal antibody MK2–23: Induction of humoral anti–HMW–MAA immunity and prolongation of survival in patients with stage IV melanoma" (1992) *Proc. Natl. Acad. Sci. USA* 89:466–470.

Moss "Vaccinia virus: A tool for research and vaccine development" (1991) *Science* 252:1662–1667.

Mukerjee et al., "Generation of anti–anti–idiotype (ab3) that recognize human breast cancer", *Fed. Amer. Soc. Exp. Bio.* (Abstracts, Apr. 5–9, 1992) Abstract No. 6505.

Mukerhee et al., "Syngeneic monoclonal anti–idiotype antibodies against a monoclonal antibody to human breast cancer–associated antigen", *Fed. Amer. Soc. Exp. Bio.* (Abstracts, Apr. 21–25, 1991) Abstract No. 7792.

Oi et al., "Chimeric antibodies" (1986) *BioTechniques* 4:214–221.

Oi et al., "Immunoglobulin–producing hybrid cell lines" (1980) *Selected Methods of Cellular Immunology*, Mishell & Shiigi eds., W. H. Freeman and Company. pp. 351–372.

Parham, "On the fragmentation of monoclonal IgG1, IgG2a, and IgG2b from BALB/c mice" (1983) *J. Immunol.* 131:2895–2902.

Peterson et al., "Biochemical and histological characterization of antigens preferentially expressed on the surface and cytoplasm of breast carcinoma cells identified by monoclonal antibodies against the human milk fat globule" (1990) *Hybridoma* 9:221–235.

Posnett et al., "A novel method for producing anti–peptide antibodies" (1988) *J. Biol. Chem.* 263:1719–1725.

Seon et al., "Monoclonal antibody SN2 defining a human T cell leukemia–associated cell surface glycoprotein" (1984) *J. Immunol.* 132:2089–2095.

Shin et al., "Production and properties of chimeric antibody molecules" (1989) *Meth. Enzym.* 178:459–476.

Solin et al., "Immunoglobulin constant kappa gene alleles in twelve strains of mice" (1993) *Immunogenetics* 37:401–407.

Spooner et al., "DNA vaccination for cancer treatment" (1995) *Gene Therapy* 2:173–180.

Takahashi et al., "Induction of $CD8^+$ cytotoxic T cells by immunization with purified HIV–1 envelope protein in ISCOMs" (1990) *Nature* 344:873–875.

Tam "High–density multiple antigen–peptide system for preparation of antipeptide antibodies" (1989) *Meth. Enz.* 168:7–15.

Tang et al., "Genetic immunization is a simple method for eliciting an immune response" (1992) *Nature* 356:152–154.

Taylor–Papadimitriou et al., "Monoclonal antibodies to epithelium–specific components of the human mild fat globule membrane: Production and reaction with cells in culture" (1981) *Int. J. Cancer* 28:17–21.

Towbin et al., "Electrophoretic transfer of proteins from polyacrylamide gels to nitrocellulose sheets: Procedure and some applications" (1979) *Proc. Natl. Acad. Sci. USA* 76:4350–4354.

Tripathi et al., "Anti–idiotype–cytokine fusion protein for breast cancer therapy", (1997) *Amer. Acad. Canc. Res.*, Abstract (1 page total).

Wang et al., "Immunization by direct DNA inoculation induces rejection of tumor cell challenge" (1995) *Human Gene Therapy* 6:407–418.

Sequence Analysis of 11D10 Heavy Chain Nucleotide, pp. 1–33.

Sequence Analysis of 11D10 Heavy Chain Peptide, pp. 1–21.

Sequence Analysis of 11D10 Light Chain Nucleotide, pp. 1–30.

Sequence Analysis of 11D10 Heavy Chain Peptide, pp. 1–16.

* cited by examiner

Figure 1

```
      M    G    A    P    A    Q    I    L    G    F
     ATG  GGG  GCC  CCT  GCT  CAG  ATT  CTT  GGG  TTC

L    L    L    L    F    P    G    T    R    C
     TTG  TTG  CTC  TTG  TTT  CCA  GGT  ACC  AGA  TGT
     (leader, -20-1)

D    I    Q    M    T    Q    S    P    S    S
     GAC  ATC  CAG  ATG  ACC  CAG  TCT  CCA  TCC  TCC
      L    S    A    S    L    G    Q    R    V    S
     TTA  TCT  GCC  TCT  CTG  GGA  CAA  AGA  GTC  AGT
      L    T    C
     CTC  ACT  TGT   (fr.1, 1-23)

R    A    S    Q    D    I    G    I    N    L
     CGG  GCA  AGT  CAG  GAC  ATT  GGT  ATT  AAC  TTA
      H
     CAT   (cdr1, 24-34)

T    L    Q    Q    E    P    D    G    T    I
     TGG  CTT  CAG  CAG  GAA  CCA  GAT  GGA  ACT  ATT
      K    R    L    I    Y
     AAA  CGC  CTG  ATC  TAC   (fr2., 35-49)

A    T    S    S    L    G    S
     GCC  ACA  TCC  AGT  TTA  GGT  TCT   (cdr2, 50-56)

G    V    P    K    R    F    S    G    S    R
     GGT  GTC  CCC  AAA  AGG  TTC  AGT  GGC  AGT  AGG
      S    G    S    D    Y    S    L    T    I    S
     TCT  GGG  TCA  GAT  TAT  TCT  CTC  ACC  ATC  AGC
      S    L    E    S    E    D    F    V    A    Y
     AGC  CTT  GAG  TCT  GAA  GAT  TTT  GTA  GCC  TAT
      Y    C
     TAC  TGT   (fr3, 57-88)

L    Q    Y    A    S    S    P    Y    T
     CTA  CAA  TAT  GCT  AGT  TCT  CCG  TAC  ACG
     (cdr3, 89-97)

F    G    G    G    T    K    L    E    I    K
     TTC  GGA  GGG  GGG  ACC  AAG  CTG  GAA  ATA  AAA
     (fr4, 98-107)

R    A    D    A    A    P    T    V    S    I
     CGG  GCT  GAT  GCT  GCA  CCA  ACT  GTA  TCC  ATC
      F    P    P    S    S    K    L    G
     TTC  CCA  CCA  TCC  AGT  AAG  CTT  GGG
```

```
  M   E   C   S   W   V   F   L   F   L   L   S   I   T   T   G   V
ATG GAA TGC AGC TGG GTC TTT CTC TTC CTC CTG TCA ATA ACT ACA GGT GTC
Met Glu Cys Ser Trp Val Phe Leu Phe Leu Leu Ser Ile Thr Thr Gly Val

H   S
CAC TCC
His Ser    (leader)

Q   A   Y   L   Q   Q   S   G   A   E   L   V   R   S
CAG GCT TAT CTA CAG CAG TCT GGG GCT GAG CTG GTG AGG TCT
Gln Ala Tyr Leu Gln Gln Ser Gly Ala Glu Leu Val Arg Ser

G   A   S   V   K   M   S   C   K   A   S   G   Y   T   L   T
GGG GCC TCA GTG AAG ATG TCC TGC AAG GCT TCT GGC TAC ACA TTG ACC
Gly Ala Ser Val Lys Met Ser Cys Lys Ala Ser Gly Tyr Thr Leu Thr
(1-30. Fr. #1)

S   Y   N   M   H
AGT TAC AAT ATG CAC
Ser Tyr Asn Met His    (31-35. CDR 1)

W   V   K   Q   T   P   G   Q   G   L   E   W   I   G
TGG GTA AAG CAG ACA CCT GGA CAG GGC CTG GAA TGG ATT GGA
Trp Val Lys Gln Thr Pro Gly Gln Gly Leu Glu Trp Ile Gly
(36-49. Fr. #2)

N   I   F   P   G   N   G   D   T   Y   Y   N   Q   K   F   K   G
AAT ATT TTT CCT GGA AAT GGT GAT ACT TAC TAC AAT CAG AAG TTT AAG GGC
Asn Ile Phe Pro Gly Asn Gly Asp Thr Tyr Tyr Asn Gln Lys Phe Lys Gly
(50-66. CDR 2)

K   A   S   L   T   A   D   T   S   S   S   T   A   Y   M   Q
AAG GCC TCA TTG ACT GCA GAC ACA TCC TCC AGC ACA GCC TAC ATG CAG
Lys Ala Ser Leu Thr Ala Asp Thr Ser Ser Ser Thr Ala Tyr Met Gln

I   S   S   L   T   S   E   D   S   A   V   Y   F   C   A   R
ATC AGC AGC CTG ACA TCT GAA GAC TCT GCG GTC TAT TTC TGT GCA AGA
Ile Ser Ser Leu Thr Ser Glu Asp Ser Ala Val Tyr Phe Cys Ala Arg
(67-98. Fr. #3)

G   N   W   E   G   A   L   D   Y
GGG AAC TGG GAG GGT GCT CTG GAC TAC
Gly Asn Trp Glu Gly Ala Leu Asp Tyr
(99-107. CDR 3)

W   G   Q   G   T   S   V   T   V   S   S
TGG GGT CAA GGA ACC TCA GTC ACC GTC TCC TCA
Trp Gly Gln Gly Thr Ser Val Thr Val Ser Ser
(108-118. Fr. #4)

A   K   T   T   P   P   P   V   Y   P   L   V   P   G   S   L
GCC AAA ACG ACA CCC CCA CCC GTC TAT CCA CTG GTC CCT GGA AGC TTG GG
Ala Lys Thr Thr Pro Pro Pro Val Tyr Pro Leu Val Pro Gly Ser Leu
(constant region)
```

DIQMTQSPSSLSASLGQRVSLTC — Framework #1, 1–23

RASQDIGINLH — CDR-1, 24–34

TLQQEPDGTIKRLIY — Framework #2, 35–49

ATSSLGS — CDR-2, 50–56

GVPKRFSGSRSGSDYSLTISSLES EDFVAYYC — Framework #3, 57–88

LQYASSPYT — CDR-3, 89–97

FGGGTKLEIK — Framework #4, 98–107

QAYLQQSGAELVRSGASVKMSCKASGYTLT — Framework #1, 1–30

SYNMH — CDR-1, 31–35

WVKQTPGQGLEWIG — Framework #2, 36–49

NIFPGNGDTYYNQKFKG — CDR-2, 50–66

KASLTADTSSSTAYMQISSLTSEDSAVYFCAR — Framework #3, 67–98

GNWEGALDY — CDR-3, 99–107

WGQGTSVTVSS — Framework #4, 108–118

FIG. 3B

>gb|L41880|MUSIKCC Mus musculus immunoglobulin kappa chain mRNA, 5' end of cds.
```
 67 GACATCCAGATGACCCAGTCTCCATCCTCCTTATCTGCCTCTCTGGGAGAAAGAGTCAGT 126
127 CTCACTTGTCGGGCAAGTCAGGACATTGGTAGTAGCTTAAACTGGCTTCAGCAGGAACCA 186
187 GATGGAACTATTAAACGCCTGATCTACGCCACATCCAGTTTAGATTCTGGTGTGCCCAAA 246
247 AGGTTCAGTGGCAGTAGGTCTGGGTCAGATTATTCTCTCACCATCAGCAGCCTTGAGTCT 306
307 GAAGATTTTGTAGACTATTACTGTCTACAATATGCTAGTTCTCCGTACACGTTCGGAGGG 366
367 GGGACCAAGCTGGAAATAAAA 387
```

>gb|L48667|MUSX Mus musculus (cell line C3H/F2-15) chromosome 6 anti-DNA antibody light chain mRNA.
```
  1 GANATCCAGATGACCCAGTCTCCATCCTCCTTATCTGCCTCTCTGGGAGAAAGAGTCAGT 60
 61 CTCACTTGTCGGGCAAGTCAGGACATTGGTAGTAGCTTAAACTGGCTTCAGCAGGAACCA 120
121 GATGGAACTTTTAAACGCCTGATCTACGCCACATCCAGTTTAGATTCTGGTGTCCCCAAA 180
181 AGGTTCAGTGGCAGTAGGTCTGGGTCAGATTATTCTCTCACCATCAGCAGCCTTGAGTCT 240
241 GAAGATTTTGTAGACTATTACTGTCTACAATATGCTAGTTGTCCGTACACGTTCGGAGGG 300
301 GGGACCAAGCTGGAAATAAAA 321
```

>gb|J00565|MUSIGKAC1 Mouse ig kappa active gene: vk41 v-j region.
```
313 GACATCCAGATGACCCAGTCTCCATCCTCCTTATCTGCCTCTCTGGGAGAAAGAGTCAGT 372
373 CTCACTTGTCGGGCAAGTCAGGACATTGGTAGTAGCTTAAACTGGCTTCAGCAGGAACCA 432
433 GATGGAACTATTAAACGCCTGATCTACGCCACATCCAGTTTAGATTCTGGTGTCCCCAAA 492
493 AGGTTCAGTGGCAGTAGGTCTGGGTCAGATTATTCTCTCACCATCAGCAGCCTTGAGTCT 552
553 GAAGATTTTGTAGACTATTACTGTCTACAATATGCTAGTTCTCCGTGGACGTTCGGTGGA 612
613 GGCACCAAGCTGGAAATCAAA 633
```

>emb|V00808|MMIGK7 Part of the murine gene for kappa-immunoglobulin leader peptide and variable part (cell line MOPC41).
```
314 GACATCCAGATGACCCAGTCTCCATCCTCCTTATCTGCCTCTCTGGGAGAAAGAGTCAGT 373
374 CTCACTTGTCGGCCAAGTCAGGACATTGGTAGTAGCTTAAACTGGCTTCAGCAGGAACCA 433
434 GATGGAACTATTAAACGCCTGATCTACGCCACATCCAGTTTAGATTCTGGTGTCCCCAAA 493
494 AGGTTCAGTGGCAGTAGGTCTGGGTCAGATTATTCTCTCACCATCAGCAGCCTTGAGTCT 553
554 GAAGATTTTGTAGACTATTACTGTCTACAATATGCTAGTTCTCCGTGGACGTTCGGTGGA 613
614 GGCACCAAGCTGGAAATCAAA 634
```

>gb|I03643|I03643 Sequence 4 from patent US 4642334.
```
  1 GACATCCAGATGACCCAGTCTCCATCCTCCTTATCTGCCTCTCTGGGAGAAAGAGTCAGT 60
 61 CTCACTTGTCGGCCAAGTCAGGACATTGGTAGTAGCTTAAACTGGCTTCAGCAGGAACCA 120
121 GATGGAACTATTAAACGCCTGATCTACGCCACATCCAGTTTAGATTCTGGTGTCCCCAAA 180
181 AGGTTCAGTGGCAGTAGGTCTGGGTCAGATTATTCTCTCACCATCAGCAGCCTTGAGTCT 240
241 GAAGATTTTGTAGACTATTACTGTCTACAATATGCTAGTTCTCCGTGGACGTTCGGTGGA 300
301 GGCACCAAGCTGGAAATCAAA 321
```

>gb|M59920|MUSIGKAA3 Mouse IG germline chain mRNA V-J region, partial cds.
```
  1 ATCCAGATGACCCAGTCTCCATCCTCCTTATCTGCCTCTCTGGGAGAAAGAGTCAGTCTC 60
 61 ACTTGTCGGGCAAGTCAGGACATTGGTAGTAGCTTAAACTGGCTTCAGCAGGAACCAGAC 120
121 GGAACTATTAAACGCCTGATCTACGCCACATCCAGTTTAGATTCTGGTGTCCCCAAAAGG 180
181 TTCAGTGGCAGTAGGTCTGGGTCAGATTATTCTCTCACCATCAGCAGCCTTGAGTCTGAA 240
241 GATTTTGTAGACTATTACTGTCTACAATATGCTAGTTCTCCGTGGACGTTCGGTGGAGGC 300
301 ACCAAGCTGGAAATCAAA 318
```

FIG. 4A

>gb|M36246|MUSIGLAFA Mouse Ig kappa-chain mRNA V region, partial cds, from
             hybridoma H220-23.
    1 TCTCCATCCTCCTTATCTGCCTCTCTGGGAGAAAGAGTCAGTCTCACTTGTCGGGCAAGT 60
   61 CAGGACATTGGTAGTAGCTTAAACTGGCTTCAGCAGGAACCAGATGGAACTATTAAACGC 120
  121 CTGATCTACGCCACATCCAGTTTAGATTCTGGTGTCCCCAAAAGGTTCAGTGGCAGTAGG 180
  181 TCTGGGTCAGATTATTCTCTCACCATCAGCAGCCTTGAGTCTGAAGATTTTTGTAGACTAT 240
  241 TACTGTCTACAATATGCTAGTTCTCCGTACACGTTCGGAGGGGGGACCAAGCTGNAAATA 300
  301 AAA 303

>emb|Z22118|MDIGKVBS M.domesticus IgK variable region.
    1 GACATCCAGATGACCCAGTCTCCATCCTCCTTATCTGCCTCTCTGGGAGAAAGAGTCAG 60
   61 CTCACTTGTCGGGCAAGTCAGGAAATTAGTGGTTACTTAAGCTGGCTTCAGCAGAAACCA 120
  121 GATGGAACTATTAAACGCCTGATCTACAGCACATCCACTTTAAATTCTGGTGTCCCAAAA 180
  181 AGGTTCAGTGGCAGTAGGTCTGGGTCAGATTATTCTCTCACCATCAGCAGCCTTGAGTCT 240
  241 GAAGATTTTGCAGACTATTACTGTCTACAATATGCTAGTTCTCCGTACACGTTCGGAGGG 300
  301 GGGACCAAACTGGAAATAAAA 321

>gb|M64168|MUSIGKAFT Mouse Ig active kappa-chain mRNA V-region.
    4 TCTCCATCCTCCTTATCTGCCTCTCTGGGAGAAAGAGTCAGTCTCACTTGTCGGGCAAGT 63
   64 CAGGACATTGGTAATAGCTTAAACTGGCTTCAGCAGGAACCAGATGGAACTATTAAACGC 123
  124 CTGATCTACGCCACATCCAGTTTAGATTCTGGTGTCCCCAAAAGGTTCAGTGGCAGTAGG 183
  184 TCTGGGTCAGATTATTCTCTCACCATCAGCAGCCTTGAATCTGAAGATTTTGTAGTCTAT 243
  244 TACTGTCTACAATATGCTAGTTATACGTACACGTTCGGAGGGGGGACCAAGTTGGAACTA 303
  304 AAA 306

>emb|X02177|MMIGGVJ1 M.musculus mRNA for IgG kappa light chain(partial)
             Cloop 1
   42 GACATCCAGATGACCCAGTCTCCATCCTCCTTATCTGCCTCTCTGGGAGAAAGAGTCAGT 101
  102 CTCACTTGTCGGGCAAGTCAGGAAATTAGTGGTTACTTAAGCTGGCTTCAGCAGAAACCA 161
  162 GATGGAACTATTAAACGCCTGATCTACGCCGCATCCACTTTAGATTCTGGTGTCCCAAAA 221
  222 AGGTTCAGTGGCAGTAGGTCTGGGTCAGATTATTCTCTCACCATCAGCAGCCTTGAGTCT 281
  282 GAAGATTTTGCAGACTATTACTGTCTACAATATCTTAGTTATCCGCTCACGTTCGGTGCT 341
  342 GGGACCAAGCTGGAGCTGAAA 362

FIG. 4B

>gb|L48668|MUSY Mus musculus (cell line C3H/F2-20) chromosome 12 anti-DNA antibody heavy chain mRNA.

```
  1 CAGGCTTATNTACAGCAGTCTGGGGCTGAGCTGGTGAGGCCTGGGGCCTCAGTGAAGATG  60
 61 TCCTGCAAGGCTTCTGGCTACACATTTACCAGTTACAATATGCACTGGGTAAAGCAGACA 120
121 CCTAGACAGGGCCTGGAATGGATTGGAGCTATTTATCCAGGAAATGGTGATACTTCCTAC 180
181 AATCAGAAGTTCAAGGGCAAGGCCACACTGACTGTAGACAAATCCTCCAGCACAGCCTAC 240
241 ATGCAGCTCAGCAGCCTGACATCTGAAGACTCTGCGGTCTATTTCTGTGCAAGA       294
295 ---------------                                             311
312 TGCTATGGACTACTGGGGTCAAGGAACCTCAGTCACCGTCTCCTCA              357
```

>gb|L48680|MUSAL Mus musculus (cell line C3H/F2-3) chromosome 12 anti-DNA antibody heavy chain mRNA.

```
  1 CAGGCTTATGTACAGCAGTCTGGGGCTGAGCTGGTGAGGCCTGGGGCCTCAGTGAAGATG  60
 61 TCCTGCAAGGCTTCTGGCTACAGATTTACCAGTTACAATATGCACTGGGTAAAGCAGACA 120
121 CGTAGACAGGGCCTGGAATGGATTGGAGCAATTTATCCAGGAAATGGTGATACTTCCTAT 180
181 AATCAGAAGTTCAAGGGCAAGGCCACACTGATTGTAGACAAATCCTCCAGCACAGCCTAC 240
241 ATGCAGCTCAGCAGCCTGACATCTGAAGACTCTGCGGTCTATTTCTGTGCAAGAGAGA   298
299 GGGGTAACTACGTAGGACATATGGACTACTGGGGTCAAGGAACCTCAGTCACCGTCTCC  357
358 TCA                                                         360
```

>emb|X64805|MMAIDHCH M.musculus mRNA for anti-Id mAB 114 heavy chain, variable region.

```
  1 CAGGCTTATCTACAGCAGTCTGGGGCTGAGCTGGTAAGGCCTGGGTCCTCAGTGAAGATG  60
 61 TCCTGCAAGGCTTCTGGCTACACATTTACCAGTTACAATATGCACTGGGTAAAGCAGACA 120
121 CCTAGACAGGGCCTGGAATGGATTGGAGCTATTTATCCAGGAAATGGTGATACTTCCTAC 180
181 AATCAGAAGTTCAAGGGCAAGGCCACACTGACTGTAGACAAATCCTCCAGCACAGCCTAC 240
241 ATGCAGCTCAGCAGCCTGACATCTGAAGACTCTGCGGTCTATTTCTGTGCAAGAGGGGAT 300
301 TACTCCGGTAGTATAGACTACTGGGGCCAAGGCACCACTCTCACAGTCTCCTCA       354
```

>gb|M17953|MUSIGHXW Mouse Ig rearranged H-chain V-region mRNA VJ1.

```
 96 CAGGCTTATCTACAGCAGTCTGGGGCTGAGCTGGTGAGGCCTGGGGCCTCAGTGAAGATG 155
156 TCCTGCAAGGCTTCTGGCTACACATTTACCAGTTACAATATGCACTGGGTAAAGCAGACA 215
216 CCTAGACAGGGCCTGGAATGGATTGGAGCTATTTATCCAGGAAATGGTGATACTTCCTAC 275
276 AATCAGAAGTTCAAGGGCAAGGCCACACTGACTGTAGACAAATCCTCCAGCACAGCCTAC 335
336 ATGCAGCTCAGCAGCCTGACATCTGAAGACTCTGCGGTCTATTTCTGTGCAAGAGTG    392
393 -------------------------------                              427
428 CTGGGGCACAGGGACCACGGTCACCGTCTCC                              458
```

>gb|I05921|I05921 Sequence 37 from patent EP 0274394.

```
 96 CAGGCTTATCTACAGCAGTCTGGGGCTGAGCTGGTGAGGCCTGGGGCCTCAGTGAAGATG 155
156 TCCTGCAAGGCTTCTGGCTACACATTTACCAGTTACAATATGCACTGGGTAAAGCAGACA 215
216 CCTAGACAGGGCCTGGAATGGATTGGAGCTATTTATCCAGGAAATGGTGATACTTCCTAC 275
276 AATCAGAAGTTCAAGGGCAAGGCCACACTGACTGTAGACAAATCCTCCAGCACAGCCTAC 335
336 ATGCAGCTCAGCAGCCTGACATCTGAAGACTCTGCGGTCTATTTCTGTGCAAGAGTG    392
393 -------------------------------                              427
428 CTGGGGCACAGGGACCACGGTCACCGTCTC                               457
```

FIG. 5A

>emb|Z22117|MDIGGVBC M.domesticus IgG variable region.
```
  2 AGGTCCAGCTGCAGCAGTCTGGACCTGAGCTGGTAAAGCCTGGGGCTTCAGTGAAGATAT  61
 62 CCTGCAAGGCTTCTGGATACACATTCACTGACTACTACATGCACTGGGTGAAGCAGAAGC 121
122 CTGGGCAGGGCCTTGAGTGGATTGGAGAGATTTATCCTGGAAGTGGTAATACTTACTACA 181
182 ATGAGAAGTTCAAGGGYAAGGCCTCACTGACTGCAGACAAATCCTCCAGCACAGCCTACA 241
242 TGCAGCTCAGCAGCCTGACATCTGAGGACTCTGCAGTCTATTTCTGTGCAAGACGTTACT 301
302 ------------- 314
315 TGCTATGGACTACTGGGGTCAAGGAACCTCAGTCACCGTCTCCTCA 360
```

>gb|M15224|MUSIGLAF Mouse IgM H-chain lambda rearranged anti-Dns hybridoma VDJ4 region of J558 family mRNA.
```
  1 CAGGTTCAGCTCCAGCAGTCTGGGGCTGAGCTGGCAAGACCTGGGGCTTCAGTGAAGTTG  60
 61 TCCTGCAAGGCTTCTGGCTACACCTTTACTAGCTACTGGATGCAGTGGGTAAAACAGAGG 120
121 CCTGGACAGGGTCTGGAATGGATTGGGGCTATTTATCCTGGAGATGGTGATACTAGGTAC 180
181 ACTCAGAAGTTCAAGGGCAAGGCCACATTGACTGCAGATAAATCCTCCAGCACAGCCTAC 240
241 ATGCAACTCAGCAGCTTGGCATCTGAGGACTCTGCGGTCTATTACTGTGCAAGAG 295
296 ------------------ 314
315 TGCTATGGACTACTGGGGTCAAGGAACCTCAGTCACCGTCTCCTCA 360
```

>gb|M15226|MUSIGLAH H-chain lambda rearranged anti-Dns hybridoma VDJ4 region of J558 family mRNA.
```
  1 CAGGTTCAGCTCCAGCAGTCTGGGGCTGAGCTGGCAAGACCTGGGGCTTCAGTGAAGTTG  60
 61 TCCTGCAAGGCTTCTGGCTACACCTTTACTAGCTACTGGATGCAGTGGGTAAAACAGAGG 120
121 CCTGGACAGGGTCTGGAATGGATTGGGGCTATTTATCCTGGAGATGGTGATACTAGGTAC 180
181 ACTCAGAAGTTCAAGGGCAAGGCCACATTGACTGCAGATAAATCCTCCAGCACAGCCTAC 240
241 ATGCAACTCAGCAGCTTGGCATCTGAGGACTCTGCGGTCTATTACTGTGCAAGA 294
295 --------------------- 317
318 TGCTATGGACTACTGGGGTCAAGGAACCTCAGTCACCGTCTCCTCA 363
```

>gb|M15225|MUSIGLAG H-chain lambda rearranged anti-Dns hybridoma VDJ4 region of J558 family mRNA.
```
  1 CAGGTTCAGCTCCAGCAGTCTGGGGCTGAGCTGGCAAGACCTGGGGCTTCAGTGAAGTTG  60
 61 TCCTGCAAGGCTTCTGGCTACACCTTTACTAGCTACTGGATGCAGTGGGTAAAACAGAGG 120
121 CCTGGACAGGGTCTGGAATGGATTGGGGCTATTTATCCTGGAGATGGTGATACTAGGTAC 180
181 ACTCAGAAGTTCAAGGGCAAGGCCACATTGACTGCAGATAAATCCTCCAGCACAGCCTAC 240
241 ATGCAACTCAGCAGCTTGGCATCTGAGGACTCTGCGGTCTATTACTGTGCAAGA 294
295 ---------------- 311
312 TGCTATGGACTACTGGGGTCAAGGAACCTCAGTCACCGTCTCCTCA 357
```

>gb|M20835|MUSIGKCLP Mouse IgMk rearranged heavy-chain mRNA variable region (V-D-J) anti-DNA autoantibody.
```
106 CAGGTCCAACTGCAGCAGCCTGGTGCTGAGCTTGTGAAGCCTGGGGCCTCAGTGAAGCTG 165
166 TCCTGCAAGGCTTCTGGCTACACTTTCACCAGCTACTGGATAAACTGGGTGAAGCAGAGG 225
226 CCTGGACAAGGCCTTGAGTGGATTGGAAATATTTATCCTGGTAGTAGTAGTACTAACTAC 285
286 AATGAGAAGTTCAAGAGCAAGGCCACACTGACTGTAGACACATCCTCCAGCACAGCCTAC 345
346 ATGCAGCTCAGCAGCCTGACATCTGACGACTCTGCGGTCTATTATTGTGCAAGACG 401
402 --------------- 416
417 TGCTATGGACTACTGGGGTCAAGGAACCTCAGTCACCGTCTCCTCA 462
```

FIG. 5B

```
                                R                ES        P
Q G L E W I G N I F P G N G D T Y Y N Q          V_H (NEAR CDR 2)
        :       : :       : | |
                R         E S     P
G S T A P P A H G V T S A P D T R P A P          HMFG REPEAT (DIRECT)
  : |             | |         |       |
D G T I K R L I Y A T S S L G S G V P L          V_L (NEAR CDR 2)

P     S E           R                 P
P A P R T D P A S T V G H A P P A T S G P A P    HMFG REPEAT (REV.)
    :     | | :   | : : :       | | | :   : :
H T L Q Q E P D G T I K R L I Y A T S S L G S    V_L (NEAR CDR 2)
            : | | :           : : : |
A Y Y C L Q Y A S S P Y T F G G G T K L E I K    V_L (NEAR CDR 2)
```

FIG. 23

```
11D10:  1   DIQMTQSPSSLSASLGQRVSLTCRASQDIGINLHTLQQEPDGTIKRLIYATSSLGSGVPK 60

1   23   ................E............SS.NW....................D..... 82
   2   23   ................E............SS.NW....................D..... 82
   3   23   ................E............SS.NW....................D..... 82
   4   23   ................E......P....SS.NW....................D..... 82
   5    1   ................E............SS.NW....................D..... 60
   6    1   ................E............SS.NW....................D..... 59
   7    1   ................E............RS.NW....................D..... 60
   8    1   ................E........E.SGY.SW...K.........S..T.N..... 60
   9    1   ................E............SS.NW....................D..... 54
  10    1   ................E........E.SGY.SW...K............A.T.D..... 60
  11    1   ....X...........E..............NS.NW....................D..... 55
  12    1   ................E....A....E..GY.SW...K............A.T.D..... 60
  13   14   ................E........E.SGY.SW...K............A.T.D..... 73
  14    1   EL..............E........E.SGY.SW...K............A.T.D..... 60
  15    2   ELVL............E........E.NGY.GW...K............A.T.H..... 61

11D10:  61  RFSGSRSGSDYSLTISSLESEDFVAYYCLQYASSPYTFGGGTKLEIK   107

```
11D10:  1 QAYLQQSGAELVRSGASVKMSCKASGYTLTSYNMHWVKQTPGQGLEWIGNIFPGNGDTYY 60

1     1 ..............P.S.............F............R.......A.Y......S. 60
  2    20 ..............P...............F............R.......A.Y......S. 79
  3     1 EVQ.....P...KP....I.......F.D.Y.....K........E.Y..S.N... 60
  4     1 .IQ.....P...P.....I.......F.D.YI....R..E......W.Y..S.N.K. 60
  5     1 .VQ.....P...KP....L.......F.D.TI.....S........W.Y..S.N.K. 60
  6     1 .VQ..E......KP....L.......F...W......R.........K.N.S..R.N. 60
  7    20 .VQ........AKP............F.A.W......R.........Y.N.NT.Y.E. 79
  8     1 EVQ.........KP....L.......F...W......R.........E.D.SDSY... 60
  9     1 .VQ....E...A.P............F.R.W......R...A....A.Y...S..N. 60
 10     1 .VQ..........P.T...I......F.N.WLG....R..H......D.Y..G.Y.N. 60
 11    20 .VQ........AKP............F...R......R.........Y.N.ST.Y.E. 79
 12     1 .VQ........AKP............F...W......R.........Y.N.ST.Y.E. 60
 13     1 .IQ.....P...P.....I.......F.D.YI....R..E......W.Y..S.N.K. 60
 14     1 .VQ..........P.T........A...F.N.WIG....R..H......D.Y..G.Y.N. 60
 15     1 EVQ.....TV.A.P............F...W......R.........A.Y...S..R. 60

11D10: 61 NQKFKGKASLTADTSSSTAYMQISSLTSEDSAVYFCARG===NWEG===ALDYWGQGTSVTVSS 118

1    61 ........T..V.K........L...............===DYS.===SI........TL.... 118
  2    80 ........T..V.K........L...............xxxxxxxx=xx.V..T..T.... 140
  3    61 .E..........K.........L...............xxxxxxx===.M............. 120
  4    61 .E......T..V..........L...............===xxx===.M............. 117
  5    61 .D......TM...K........L...............===VAR.S===.M............. 119
  6    61 .E...S.T..V.K........L...........Y....xxxxxxxxx........T..... 123
  7    80 ..N..D..T....K........L..........Y.T.xxx.Y..===.M............. 139
  8    61 ........T..V.K........F..........Y...xxxxxxx===xM............. 120
  9    61 ........K...V..A.....EL...A......Y...S===RYR.===SM............. 119
 10    61 .E......T.............L..............P===HYY.===SG........TL.... 118
 11    80 .....D..T....K........L....F.....Y....===x.===VF........TL.... 135
 12    61 .....D..T....K........L..........L.Y...W===VYYY===.M............. 118
 13    61 .E......T..V..........L...............===xxx===.M............. 117
 14    61 .E......T.............L..........I.Y...P===FYFY===.M........C.... 118
 15    61 ........K...V..A.....EL...N......Y.T..===GLFT===.M............. 115
```

FIG. 26B

*Light Chain*

```
                                         **********         ******
VL consensus: 1 DIQMTQSPSSLSASLGERVSLTCRASQDIGSSLNWLQQEPDGTIKRLIYATSSLDSGVPK 60
11D10:        1 ................Q............IN.HT..................G..... 60

HMFG fragments:                                              GSTAPPAHRVISAPESRPPP
                                                           ppprsepastvrhappatsg

*********
VL consensus: 61 RFSGSRSGSDYSLTISSLESGDFVDYYCLQYASSPYTFGGGTKLEIK 107
11D10        61 .......................A....................... 107

HMFG fragments:                    ppprsepastvrhappatsg
```

*Heavy Chain*

```
                                          *****          **********
VH consensus: 1 QVQLQQSGAELVRPGASVKMSCKASGYTFTSYWMHWVKQRPGQGLEWIGAIYPGNGDTNY 60
11D10:        1 .AY.........S................L...N......T.........N.F......Y. 60

HMFG fragments:                                                    APDIRPPP

******                         *********
VH consensus: 61 NQKFKGKATLTADTSSSTAYMQLSSLTSEDSAVYFCARGxxxGAMDYWGQGTSVTVSS 118
11D10:        61 ........S..............I..............NWE..L.............. 118
```

FIG. 26C

# POLYNUCLEOTIDES RELATED TO MURINE ANTI-IDIOTYPE ANTIBODY 11D10 AND METHODS OF USE THEREOF

CROSS-REFERENCE TO RELATED APPLICATIONS

This application is a §371 of application Ser. No. PCT/US96/20757, filed Dec. 19, 1996, which is a continuation-in-part and claims priority to U.S. Ser. No. 08/766,350, filed Dec. 13, 1996, which claims the benefit of provisional application Ser. Nos. 60/035,345, converted from U.S. Ser. No. 08/591,965, filed Jan. 29, 1996, and 60,031,306, converted from U.S. Ser. No 08/575,762, filed Dec. 20, 1995, each of which provisional applications are incorporated by reference in their entirety.

STATEMENT OF RIGHTS TO INVENTIONS MADE UNDER FEDERALLY SPONSORED RESEARCH

This invention was made in part during work supported by a grant from the National Institutes of Health RO1 CA 47860, CA 56701, PO1 CA 59306, CA57165, RO1 CA 6000, UO1 65748 and CRF Grant PO1 CA 42767. The government has certain rights in the invention.

TECHNICAL FIELD

This invention relates to monoclonal anti-idiotype antibodies. More specifically, it relates to anti-idiotype antibody 11D10 and polynucleotide and polypeptide sequences for 11D10, which elicits an immune response against a specific epitope of human milk fat globule (HMFG).

BACKGROUND OF THE INVENTION

In spite of extensive medical research and numerous advances, cancer remains the second leading cause of death in the United States. Breast cancer is the most common cause of cancer deaths in women. While the traditional modes of therapy, such as surgery, radiotherapy and chemotherapy, are widely used and are in many instances successful, there is still a significant failure rate, especially for solid tumors. The still existing high death rate from cancers such as breast compels the need for alternative modes of therapy.

The immunotherapy of human cancer using tumor cells or tumor-derived vaccines has been disappointing for several reasons. It has been consistently difficult to obtain large quantities or purified tumor-associated antigens which are often chemically ill-defined and difficult to purify. In addition, there remains the problem of immunobiological response potential against tumor antigens, or in other words, the question of whether a cancer patient can effectively mount an immune response against his or her tumor. Tumor-associated antigens (TAA) are often a part of "self" and usually evoke a very poor immune response in a tumor-bearing host due to tolerance to the antigens, such as T cell-mediated suppression, Moreover, cancer patients tend to be immunosuppressed, and only respond to certain T-dependent antigens.

Immunobiologists have learned that a poor antigen (in terms of eliciting an immune response) can be turned into a strong antigen by changing the molecular environment. Changes of hapten carrier allow T cell helper cells to become active, making the overall immune response stronger. Thus, changing the carrier can also turn a tolerogenic antigen into an effective antigen. McBridge et al. (1986) *Br.* *J. Cancer* 53:707. Often the immunological status of a cancer patient is suppressed such that the patient is only able to respond to certain T-dependent antigens and not to other antigen forms. From these considerations, it would make sense to introduce molecular changes into the tumor associated antigens before using them as vaccines. Unfortunately, this is impossible to accomplish for most tumor antigens, because they are not well defined and are very hard to purify.

The network hypothesis of Lindemann ((1973) *Ann. Immunol.* 124:171–184) and Jerne ((1974) *Ann. Immunol.* 125:373–389) offers an elegant approach to transform epitope structures into idiotypic determinants expressed on the surface of antibodies. According to the network concept, immunization with a given tumor associated antigen will generate production of antibodies against this tumor-associated antigen, termed Ab1; this Ab1 is then used to generate a series of anti-idiotype antibodies against the Ab1, termed Ab2. Some of these Ab2 molecules can effectively mimic the three-dimensional structure of the tumor-associated antigen identified by the Ab1 These particular anti-idiotypes called Ab2β fit into the paratopes of Ab1, and express the internal image of the tumor-associated antigen. The Ab2β can induce specific immune responses similar to those induced by the original tumor-associated antigen and can, therefore, be used as surrogate tumor-associated antigens. Immunization with Ab2β can lead to the generation of anti-anti-idiotype antibodies (Ab3) that recognize the corresponding original tumor-associated antigen identified by Ab1. Because of this Ab1-like reactivity, the Ab3 is also called Ab1' to indicate that it might differ in its other idiotopes from Ab1.

A potentially promising approach to cancer treatment is immunotherapy employing anti-idiotype antibodies. In this form of therapy, an antibody mimicking an epitope of a tumor-associated protein is administered in an effort to stimulate the patient's immune system against the tumor, via the tumor associated protein. WO 91/11465 describes methods of stimulating an immune response in a human against malignant cells or an infectious agent using primate anti-idiotype antibodies. However, not all anti-idiotype antibodies can be used in therapeutic regimens against tumors. First, only a fraction of antibodies raised against an Ab1 are limited in their reactivity to the paratope of Ab1 (i.e., are non-reactive against features shared with other potential antibodies in the host). Second, anti-idiotype antibodies are not necessary immunogenic. Third, even if an anti-idiotype elicits an immune response, only a fraction of these immunogenic anti-idiotopes elicit an immune response against the tumor antigen and not against other antigens with less specificity. Moreover, since different cancers have widely varying molecular and clinical characteristics, it has been suggested that anti-idiotype therapy should be evaluated on a case by case basis, in terms of tumor origin and antigens express.

Anti-Id monoclonal antibodies structurally resembling tumor-associated antigens have been used as antigen substitutes in cancer patients. Herlyn et al. (1987) *PNAS* 84:8055–8059; Mittleman et al. (1992) *PNAS* 89:466–470, Chatterjee et al. (1993) *Ann. N.Y. Acad. Sci.* 690:376–377. It has been proposed that the anti-Id provides a partial analog of the tumor-associated antigen in an immunogenic context Human milk fat globules (HMFG) are milk fat globules secreted into breast milk by the breast epithelial cell, and are composed of fat droplets enveloped by plasma membrane. As such, HMFG is a rich source of epithelial membrane-associated antigens. One antigen component of HMFG is a high molecular weight, membrane-associated mucin that is associated with breast and other cancers such as ovarian, lung, and pancreas. The mucin contains a protein with known amino acid sequences derived from the cDNA. Semipurified HMFG is available in small quantities from several sources and can be used in serological assays. Peterson et al. (1990) *Hybridoma* 9:221–235. However, HMFG is extremely difficult to isolate and purify, and purified HMFG is not available for patient immunization or animal studies. Further, inasmuch as some of the epitopes on HMFG are shared by normal tissues, specifically by non-penetrating glycoproteins, immunization with intact HMFG molecule might trigger potentially harmful autoimmune reactions. An immune reaction against a tumor-associated epitope, on the other hand, would be much more desirable.

A series of murine monoclonal antibodies (mAbs) that recognize components of HMFG have been described that are primarily associated with human breast carcinomas and not with most normal tissues. Chatterjee et al. (1993) *Ann. N.Y. Acad. Sci.* 690:376–377; Ceriani et al. (1983) *Somatic Cell Genet*, 9:415–427. Among these mAbs, MC-10 (BrE-1) is the most restricted and specific, reacting with a large molecular weight (MW, 400,000) mucin-like protein present at high density end on >80% breast cancer cells and minimally expressed on a few normal tissues, such as the epithelial lining of lung and kidney tubules. Ceriani et al. (1983); Ceriani et al, (1990) *Antibody Immunoconjugates and Radiopharmaceuticals* 3:181–198.

Recurrent breast cancer is not curable by standard therapies. Thus, new therapeutic approaches for this disease are needed. The present invention overcomes the deficiencies in the prior art by providing a monoclonal anti-idiotype antibody (11D10) as an antigen (Ag) that elicits an immune response against HMFG in non-human primates, which may be useful for treating anti-tumor immunity in patients with advanced HMFG-associated cancer (such as breast cancer).

All publications cited herein are hereby incorporated by reference in their entirety.

SUMMARY OF THE INVENTION

The present invention provides a murine monoclonal anti-idiotype antibody, 11D10, which is able to elicit an immune response against a high molecular weight mucin of human milk fat globule (HMFG). This invention also encompasses polypeptides comprising at least a portion of a variable region of an anti-idiotype antibody 11D10 and polynucleotides encoding these polypeptides. The invention also includes pharmaceutical compositions and vaccines comprising 11D10, 11D10 polypeptides and/or 11D10 polynucleotides. Also included in the present invention are diagnostic kits and methods of using 11D10, 11 D10 polypeptides and/or 11D10 polynucleotides, including methods of treating HMFG-associated tumors.

Further, an object of the invention is to provide a composition and method of use of anti-idiotype (anti-Id) monoclonal 11D10 polynucleotides and polypeptides to induce anti-tumor immunity in patients with HMFG-associated disease, such as breast cancer.

Accordingly, in one aspect, the invention includes a monoclonal anti-idiotype antibody 11D10 produced by a hybridoma cell line ATCC No. 12020 or progeny thereof.

In another aspect, the invention includes a hybridoma cell line designated ATCC No. 12020 and progeny thereof.

In another aspect, the invention also includes isolated polynucleotides comprising a sequence encoding a polypeptide: having immunological activity of monoclonal anti-idiotype antibody 11D10, wherein the polypeptide comprises at least 5 contiguous amino acids of a variable region of 11D10.

In another aspect, the invention provides isolated polynucleotides that are comprised of a region of at least 15 contiguous nucleotides, said region capable of forming a stable duplex with a polynucleotide consisting of light chain variable encoding sequence of SEQ ID NO:1 under conditions where the region does not form a stable hybrid with SEQ ID NO:5 through SEQ ID NO:14. The invention also provides isolated polynucleotides that are comprised of a region of at least 15 contiguous nucleotides, said region capable of forming a stable duplex with a polynucleotide consisting of heavy chain variable encoding sequence of SEQ ID NO:3 under conditions where the region does not form a stable hybrid with SEQ ID NO:15 through SEQ ID NO:32.

Another aspect of the invention is cloning and expression vectors comprising the polynucleotides of the invention. Also included are host cells comprising the polynucleotides of the invention.

Another aspect of the invention are polypeptides having immunological activity of monoclonal anti-idiotype antibody 11D10, wherein the polypeptides comprise a sequence of at least 5 contiguous amino acids from a variable region of 11D10.

In another aspect, 11D10 polypeptides are provided that contain a region of homology to HMFG.

In another aspect, the invention provides fusion polypeptides comprising a 11D10 polypeptide(s). Also included in the invention are polymeric 11D70 polypeptides as well as humanized antibodies comprising an 11D10 polypeptide(s).

In another aspect, the invention includes pharmaceutical compositions and vaccines comprising an effective amount of 11D10, 11D10 polypeptide(s) and/or 11D10 polynucleotide(s).

In another aspect, the invention provides methods of eliciting an anti-HMFG immune response in an individual with advanced HMFG-associated disease, comprising the step of administering an effective amount of 11D10, 11D10 polynucleotides) and/or polypeptide(s) to the individual.

Another aspect of the invention is methods for removing labeled anti-human milk fat globule (HMFG) antibody from an individual who has received labeled anti-HMFG antibody, the methods comprising administering 11D10.

In another aspect, the invention provides methods of detecting the presence of an anti-HMFG antibody bound to a tumor cell comprising the steps of contacting the tumor cell with 11D10 for a sufficient time to allow binding to the anti-HMFG antibody, and detecting the presence of any 11D10 which is bound to the anti-HMFG antibody.

In another aspect, methods are provided for detecting ant-HMFG immunological response in an individual. These methods comprise contacting a biological sample from the individual with 11D10 under conditions that permit formation of a stable complex between 11D10 and an antibody that binds to 11D10, and detecting any stable complexes formed.

In another aspect, methods are provided for detecting an ant body that binds to 11D10 in a biological sample. These methods entail the steps of contacting antibody from the sample obtained from an individual with a 11D10 or an 11D10 polypeptide under conditions that permit formation of a stable antigen-antibody complex and detecting stable complex formed, if any.

Another aspect of the invention is methods of palliating human milk fat globulin-associated disease in an individual having advanced human milk fat globulin associated disease. These methods entail administration of an effective amount of 11D10 to the individual.

In another aspect, the invention also provides kits for detection or quantitation comprising 11D10, 11D10 polypeptide(s) or 11D10 polynucleotides) in suitable packaging.

The above and other objects of the invention will become readily apparent to those of skill in the relevant art from the following detailed description and figures, wherein only the preferred embodiments of the invention are shown and described, simply by way of illustration of the best rode of carrying out the invention. As is readily recognized, the invention is capable of modifications within the skill of the relevant art without departing from the spirit and scope of the invention.

BRIEF DESCRIPTION THE DRAWINGS

FIG. 1 depicts the cDNA sequence (SEQ ID NO:1 and the amino acid sequence (SEQ ID NO:2) of the light chain variable region of 11D10 and adjoining residues. The CDRs and framework regions are indicated. There were clerical errors in FIG. 1 as originally submitted. In the corrected figures, the correct translation show A, or alanine, for amino acid-18, and E, or glutamic acid for amino acid 81 (SEQ ID NO:2).

FIG. 2 depicts the cDNA sequence (SEQ ID NO:3) and the amino acid sequence (SEQ ID NO:4) of the heavy chain variable region of 11D10 and adjoining residues.

FIG. 3 depicts the amino acid sequence of the light chain variable region (Amino acids 1–107 of SEQ ID NO:2; FIG. 3A) and the heavy chain variable region (Amino acids 1–118 of SEQ ID NO:4; FIG. 3B) of 11D10. Each variable region consists of 4 framework regions and 3 CDRs. There were clerical errors in FIG. 3A as originally submitted. For FIG. 3A, the correct translation shows E, or glutamic acid, for amino acid-81.

FIG. 4 depicts 10 polynucleotide sequences that most closely matched the 11D10 light chain variable region encoding sequence in a database search. These sequences have the designations SEQ ID NO:5 through SEQ ID NO:14.

FIG. 5 depicts 10 nucleotide sequences that most closely match the 11D10 heavy chain variable region encoding sequence in a database search. These sequences have the designations SEQ ID NO:15 through SEQ ID NO:32. Dashes correspond to omitted regions that are not homologous to SEQ ID NO:3.

FIG. 6 is a bar graph depicting anti-Id specificities of 11D10 (IgG1, κ). Binding of 125I-labeled 11D10 (~25,000 cpm) to various mouse monoclonal proteins and anti-HMFG (breast TAA) antibodies was determined using a direct RA The isotypes of the monoclonal proteins are: MC-10 (BrE-1, IgG2b,κ), first bar, 1E3 (IgG|,κ), second bar, 4DC6 (IgG1,I), third bar, BrE-3 (IgG1,k) fourth bar, Hy-Clone IgG2b, fifth bar; Hy-Clone IgG3,k, sixth bar; IgG3, Hy-Clone IgA, seventh bar, and MOPC 104E (IgM,I), eighth bar, RWP1–1 (IgUb,k), ninth bar.

Figure 12:
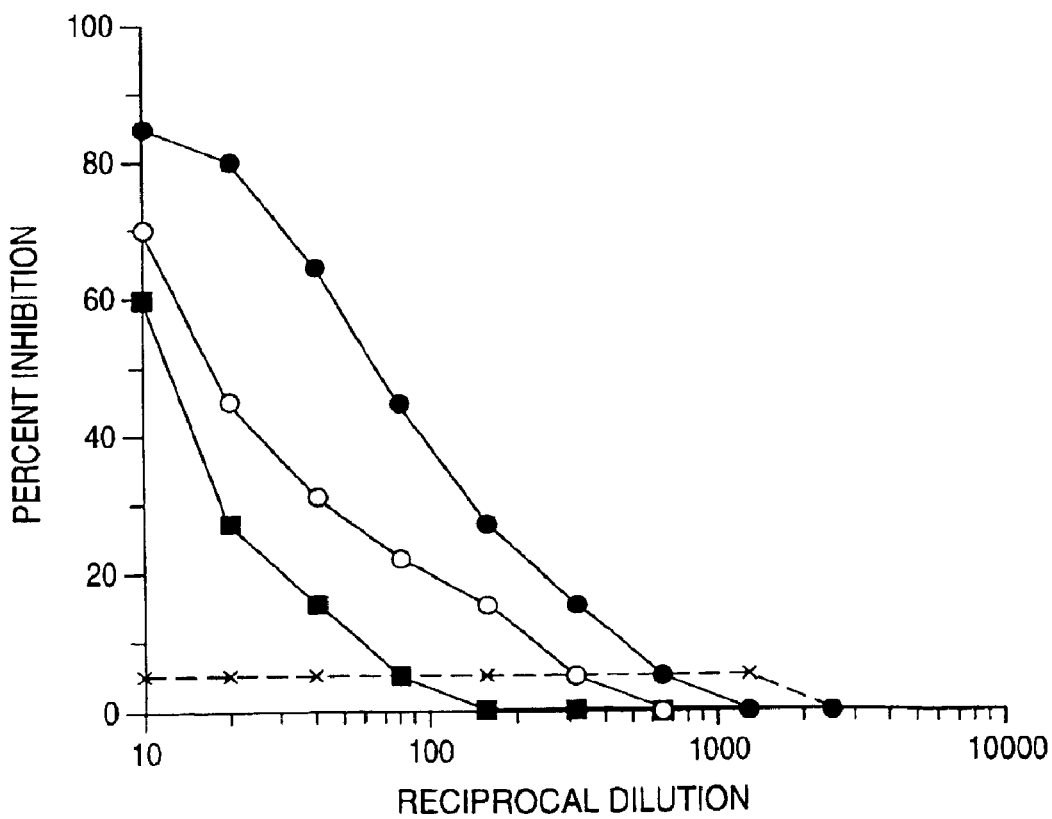

FIG. 12 is a graph depicting inhibition of Ab1 (mAb MC-10) binding to 11D10 (Ab2) by monkey (PRO 723) Ab3 Sera by RIA. Solid circles denote serum after 3 immunizations; open circles denote serum after 2 immunizations; solid squares denote serum after 1 immunization; crosses denote preimmune serum.

Figure 13:
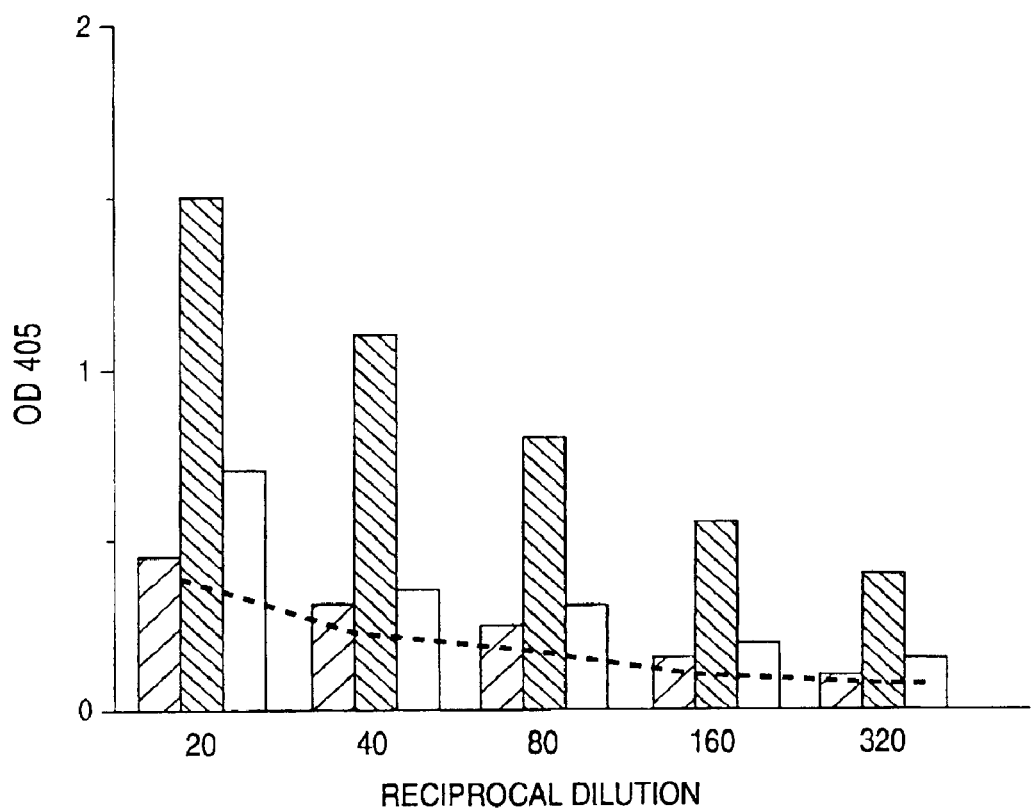

FIG. 13 is a bar graph depicting binding of monkey Ab3 sera to the breast cancer cell line MCF-7 by ELISA. Open hatched bar denotes preimmune sera; hatched bar denotes immune sera; stippled bar denotes control sera. Dotted line denotes binding of monkey Ab3 sera to melanoma cell line M21P6.

Figure 14:
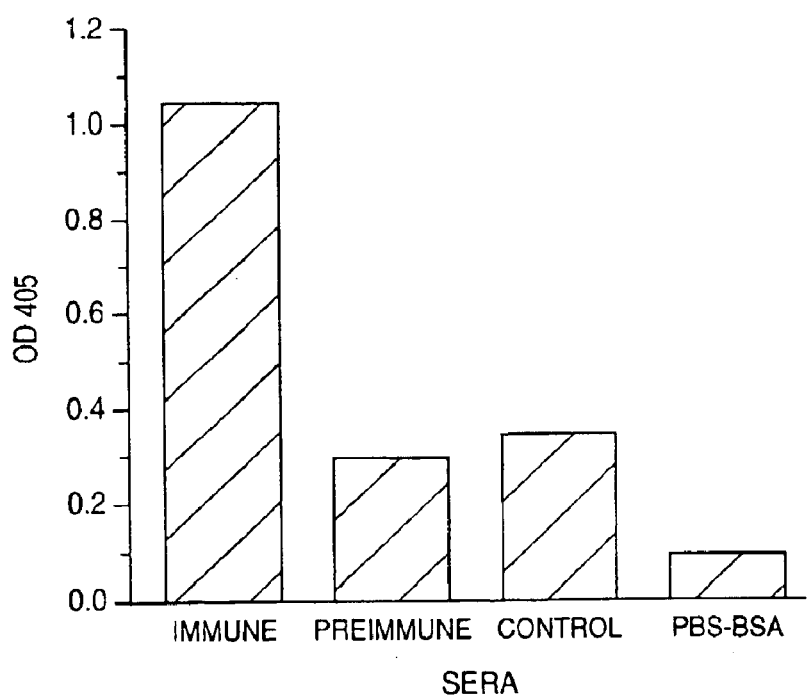

FIG. 14 is a bar graph depicting binding of monkey Ab3 sera to semi-purified HMFG by ELISA. First bar, immune sera; second bar, preimmune sera; third bar, control sera; fourth bar, bovine serum albumin (BSA).

Figure 15A:
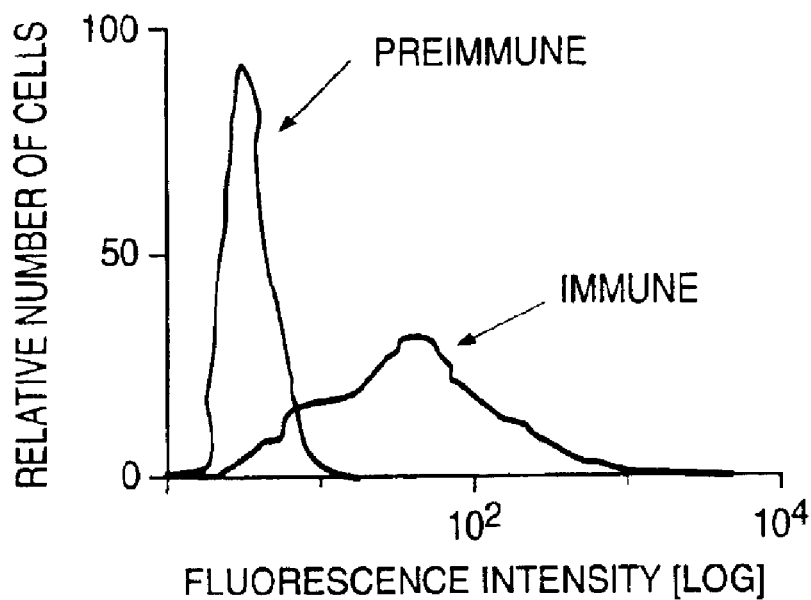
Figure 15B:
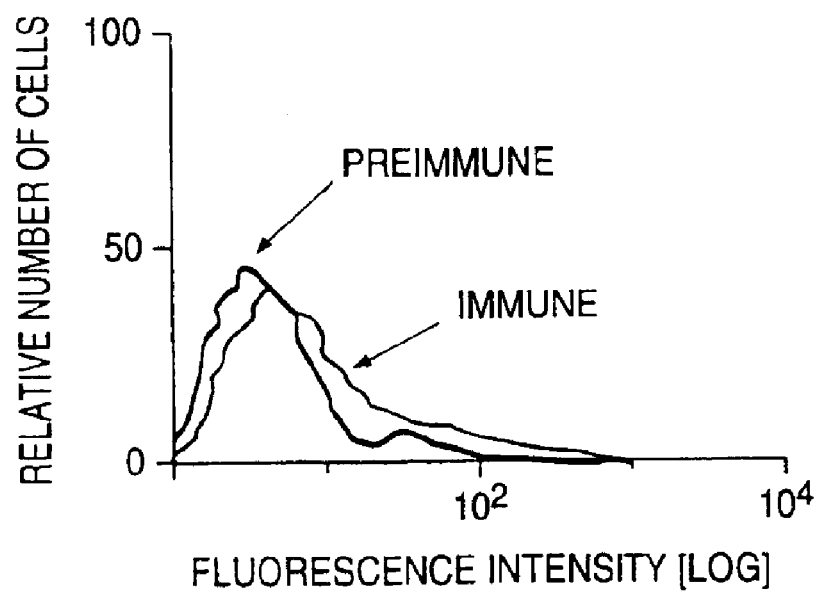

FIGS. 15A and 15B depict immune flow cytometry analysis of MCF-7 cells with monkey Ab3 sera. In FIG. 15A tumor cells were reacted with preimmune sera and Ab3 sera (1:100 dilution) from monkeys immunized with 11D10. In FIG. 15B, MOLT-4 cells that do not express HMFG were reacted with preimmune and immune monkey Ab3 sera raised against 11D10.

Figure 16:
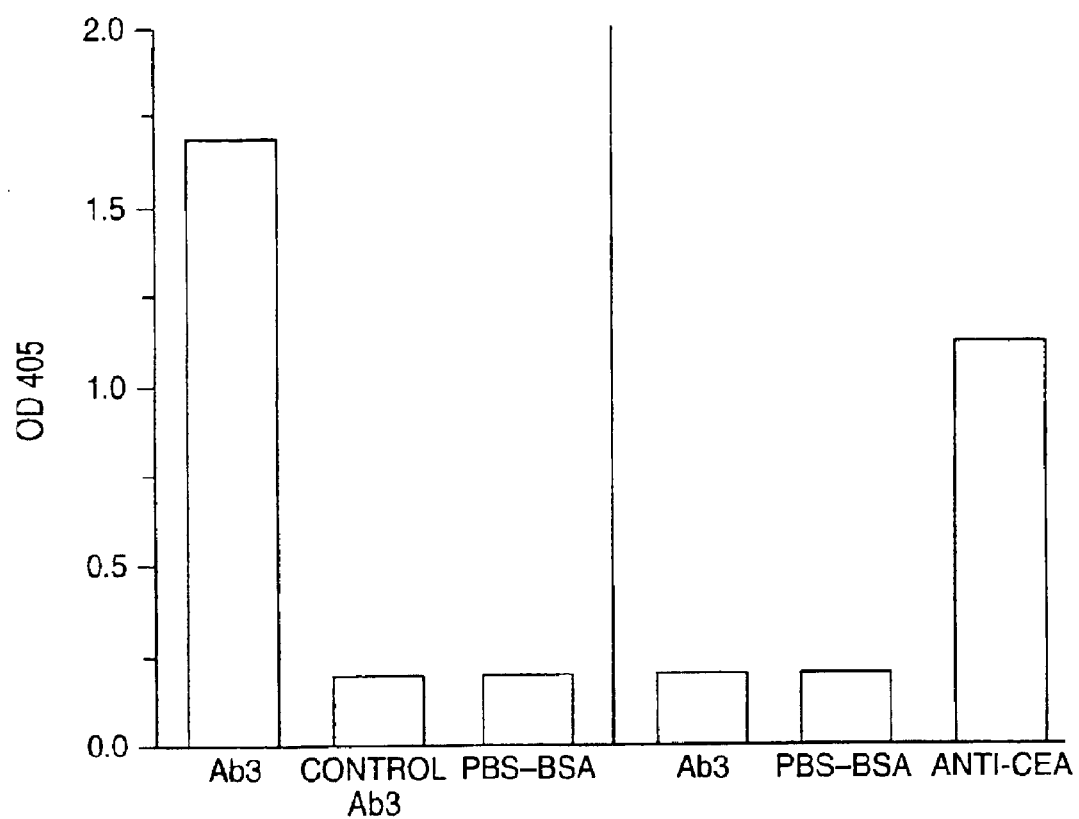

FIG. 16 is a bar graph depicting binding of purified monkey Ab3 to HMFG or to purified CEA by ELISA. The left portion of the figure represents plates coated with HMFG; the right portion of the figure represents plates coated with CEA For the left figure portion, the first bar denotes Ab3; the second bar denotes control Ab3; the third bar denotes PBS-BSA For the right figure portion, the first bar denotes Ab3; the second bar denotes PBS-BSA, the third bar denotes anti-CEA.

Figure 17:

FIG. 17 is a half-tone reproduction of a slot blot analysis with HMFG or purified CEA. Polyvinylidene difluoride membrane was absorbed with different concentrations of HMFG (Lanes 1 and 2) and CEA (Lanes 3 end 4). The membranes were incubated with Ab1 (Lane 1), purified Ab3 (Lanes 2 and 3), and anti-CEA mAb (a control Ab1) (Lane 4).

Figure 18:
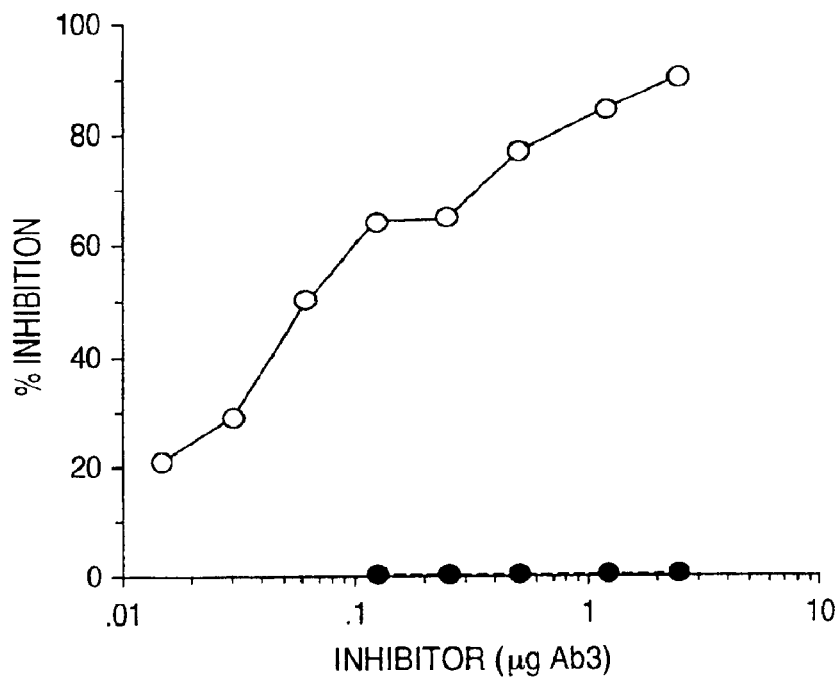

FIG. 18 is a graph depicting inhibition of Ab1 binding to MCF-7 cells by purified Ab3. Open circles denote Ab3 purified from monkey immunized with 11D10; closed circles denote control Ab3 purified from monkey immunized with control 3H1.

Figure 19:
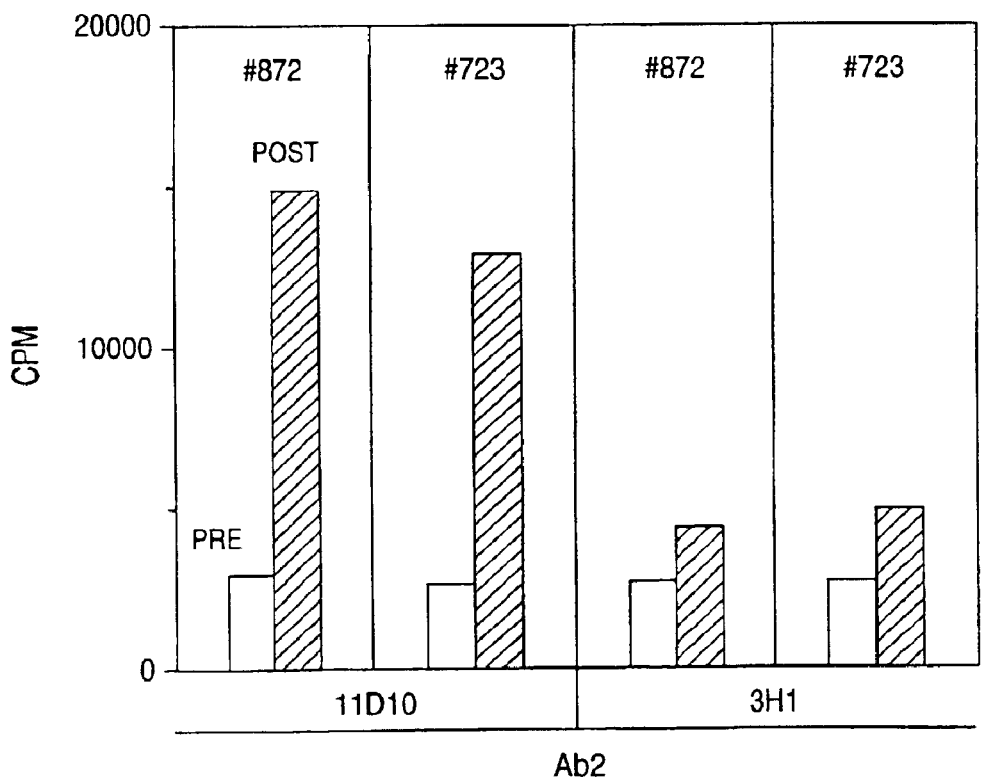

FIG. 19 is a bar graph depicting a T-cell proliferation assay with monkey peripheral blood mononuclear cells (PSM). The lefthand portion of the graph denotes PBMs stimulated with 11D10; the righthand portion of the graph denotes PBMs stimulated with 3H1. For each portion (half), the left box denotes PBMs from monkey #872; the righthand portion denotes PBMs from money #723. Open bars denote pre-immune sera; solid bars denote post-immune sera.

Figure 20:
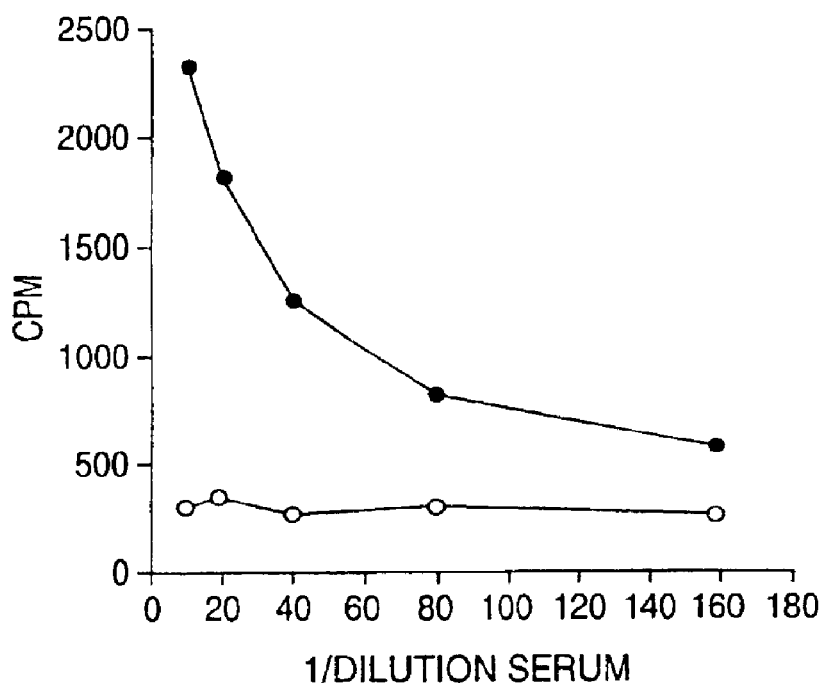

FIG. 20 is a graph depicting Ab3 reactivity in a patient's serum (patient #1) after administration of 11D10 as measured by radioimmunoassay. Open circles denote pre-immune sera; solid circles denote post-immune sera.

Figure 21:
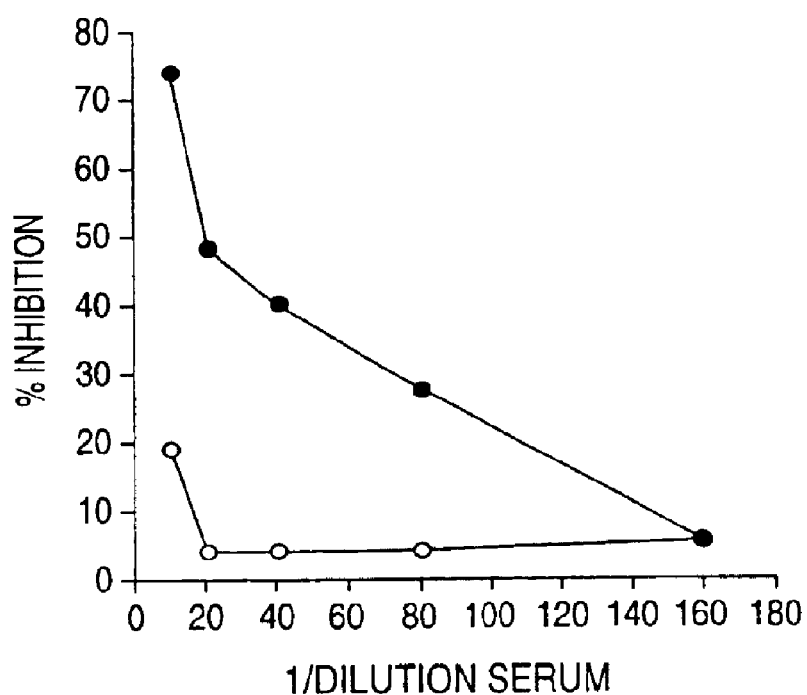

FIG. 21 is a graph depicting inhibition of Ab1 binding to 11D10 by a patient's serum (patient #1). Open circles denote pre-immune sera; solid circles denote past-immune sera.

Figure 22:
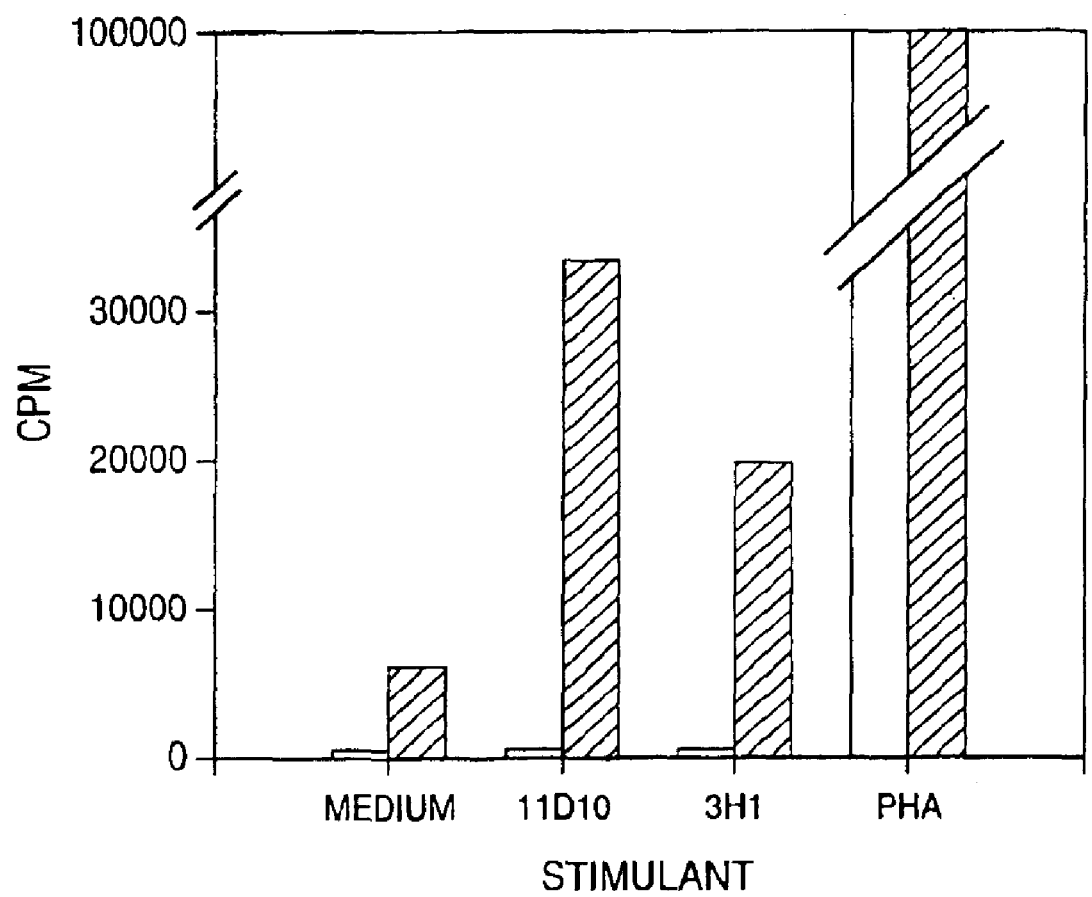

FIG. 22 is a bar graph depicting T cell proliferation by a patient's peripheral blood lymphocytes. For each pair of bars, the open bar denotes pre-immune cells; the solid bar denotes post-immune cells. Stimulants tested are: the medium, first pair of bars; 11D10, second lair of bars; 3H1, third pair of bars; PHA, fourth pair of bars.

FIG. 23 depicts selected amino acid sequence comparisons between light (Amino acids 41–60, 34–56 and 85–107 of SEQ ID NO:2) and heavy (Amino acids 43–62 of SEQ ID NO:4) chain variable regions of 11D10 and tandem repeats of HMFG (SEQ ID NO:33 and SEQ ID NO:34). Matching amino acids are denoted by a solid line.

Figure 24:
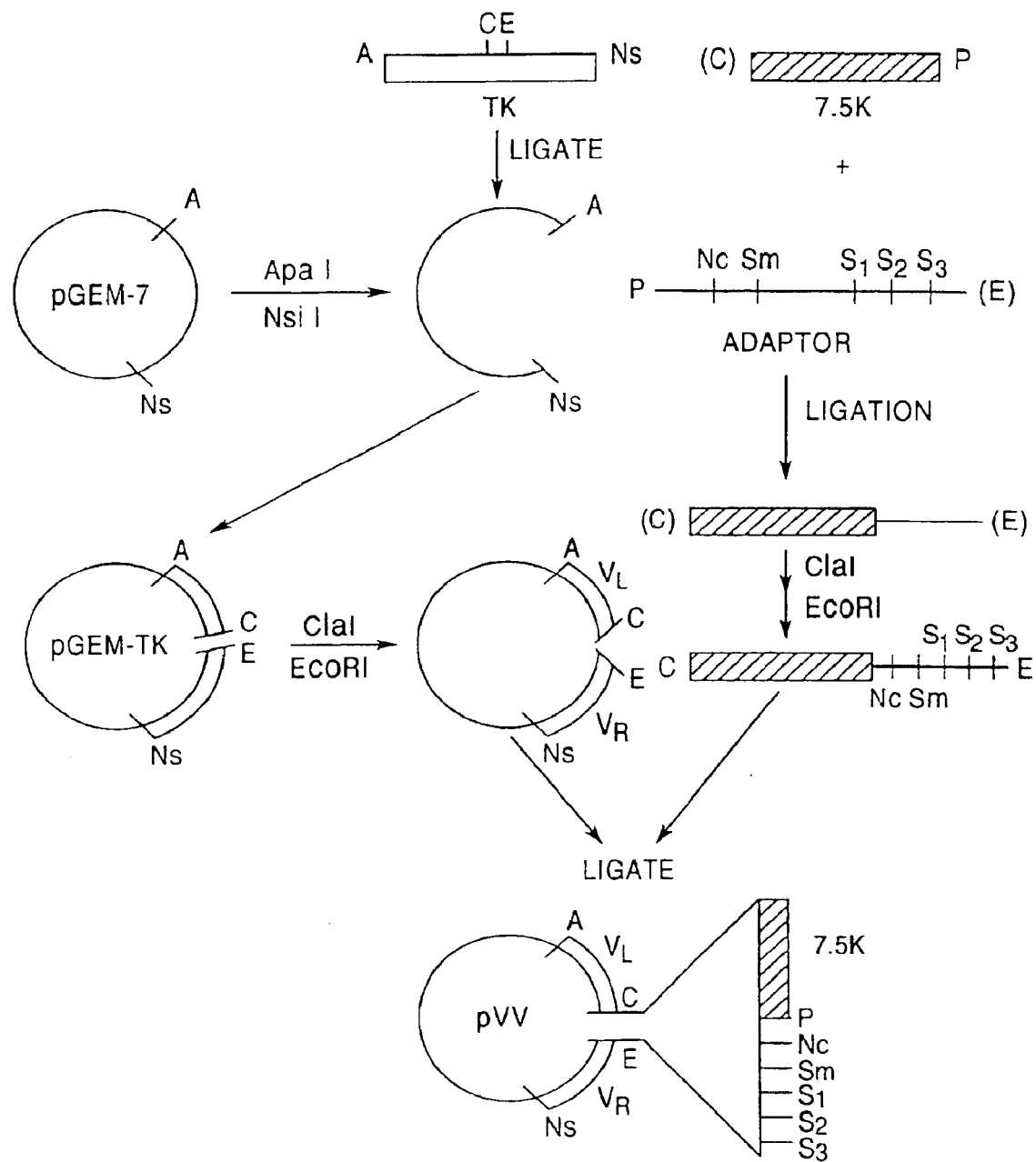

FIG. 24 depicts the scheme for construction of pW, a generic vaccinia vector (plasmid) for expression of 11D10 polynucleotides. The darkened box denotes vaccinia TK gene; the hatched box denotes the 7.5 K vaccinia promoter. Restriction sites are: A, Apa I; Ns, Nsi I; C, Cla I; E, Eco RI; P, Psi I; Nc, Nco I; Sm, Sma I. (E) and (C) denote potential EcoRI and ClaI sites, respectively. Three stop codons are indicated by S1, S2 and S3. VL and VR represent left and right vaccinia flanking sequences. TK and 7.5 K were obtained by IPCR using DNA from wild type WR strain of vaccinia.

Figure 25A:
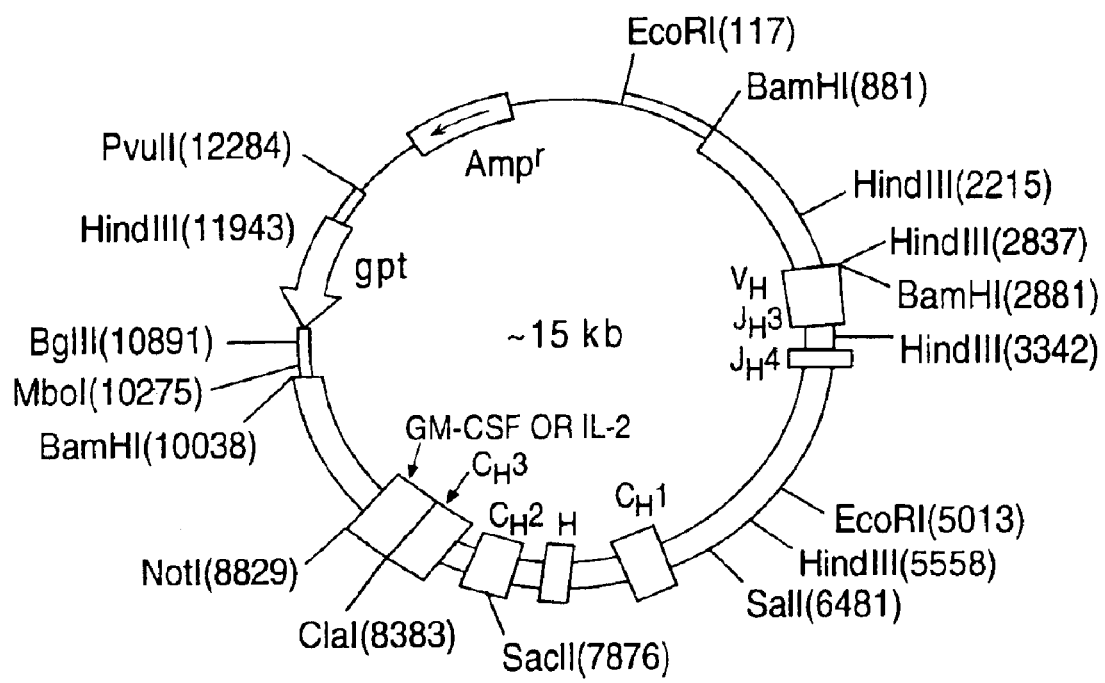
Figure 25B:
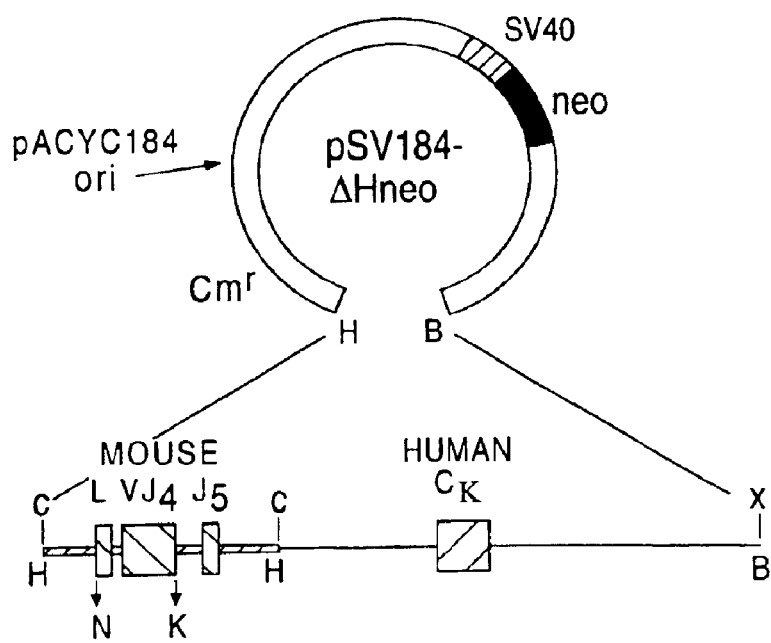

FIG. 25 depicts plasmids suitable for production of a 11D10 fusion protein (FIG. 25A) and a chimera (FIG. 25B).

FIG. 26 (A–C) (SEQ ID NO:47 through 57)is a listing in which the amino acid sequences of the 11D10 variable region are compared with 15 light and heavy chain immunoglobulin sequences obtained from a GenBank database search. Panel A shows the closest sequences to the mature 11D10 light chain variable region (contained in SEQ ID NO:2); Panel B shows the closest sequences to the mature 11D10 heavy chain variable region (contained In SEQ ID NO:4). Residues that are identical with 11D10 are indicated by a dot (.); gaps introduced to improve alignment about the heavy chain VDJ junction are indicated by double: lines (=). Panel C shows variable region consensus sequences for the light and heavy chains (SEQ ID NO:47 and SEQ ID NO:48), and compares them with the sequences of 11D10. The variable region of 11D10 shows unique splicing differences about the VDJ junction of the heavy chain, and an additional 18 point differences from the prototype sequences located in both the light and heavy chain.

Figure 27A:
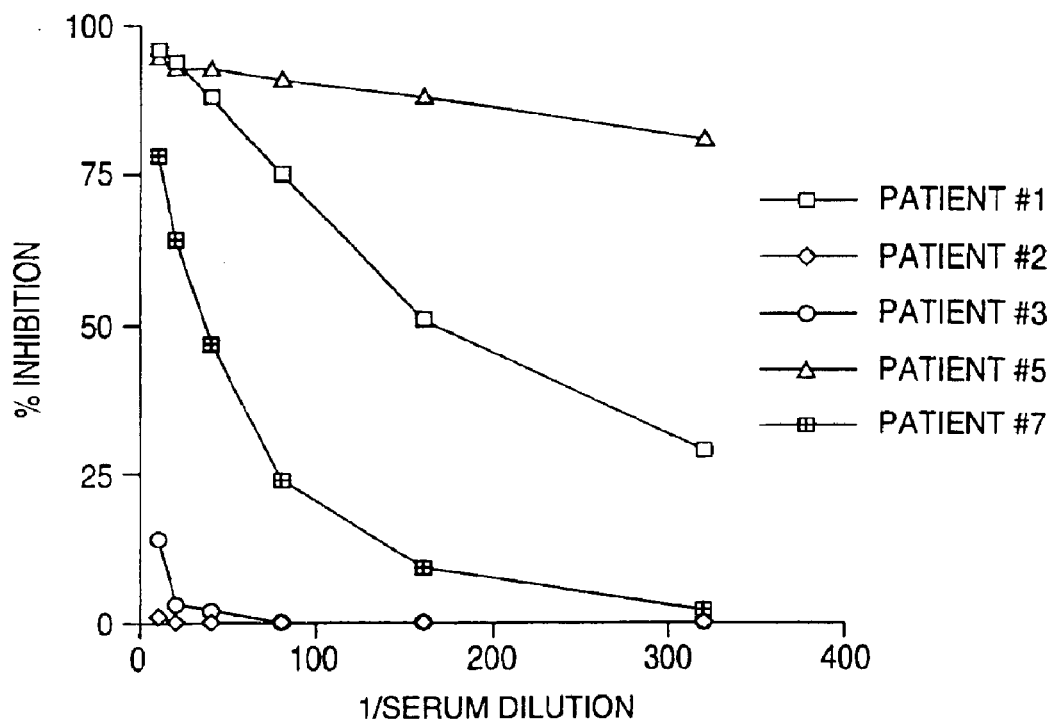
Figure 27B:
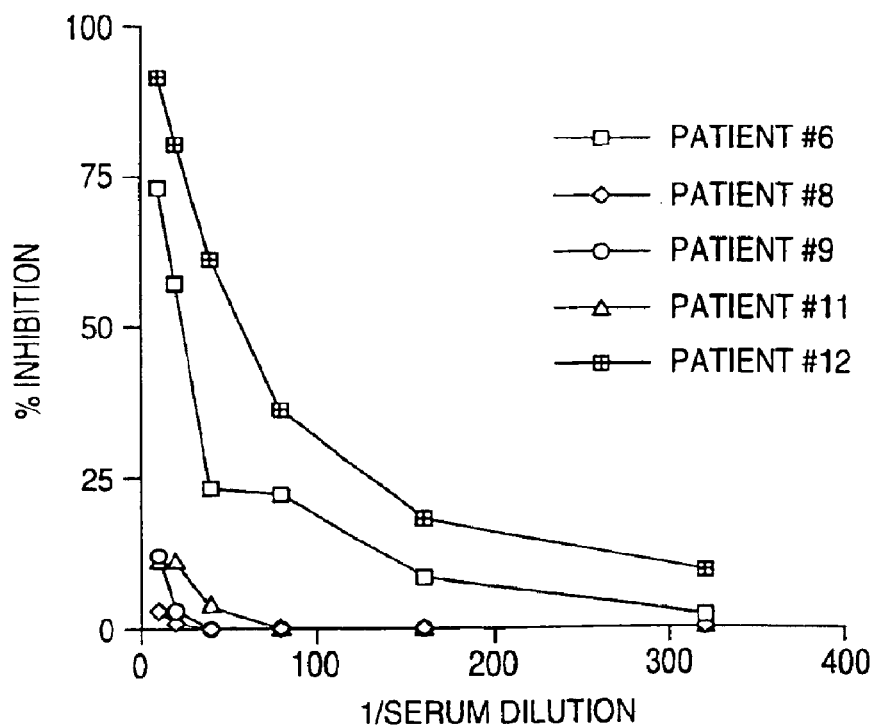

FIGS. 27A and 27B are graphs depicting inhibition of Ab1 binding to 11D10 by patients' sera. FIG. 27A shows data for patients #1 (open square), #2 (open diamond), #3 (open circle), #5 (open triangle), and #7 (square with hatch). Figure shows data for patients #6 (open square), #8 (open diamond), #9 (open circle), #11 (open triangle), and #12 (square with hatch). Open circles denote pre-immune sera; solid circles denote post-immune sera.

Figure 28:
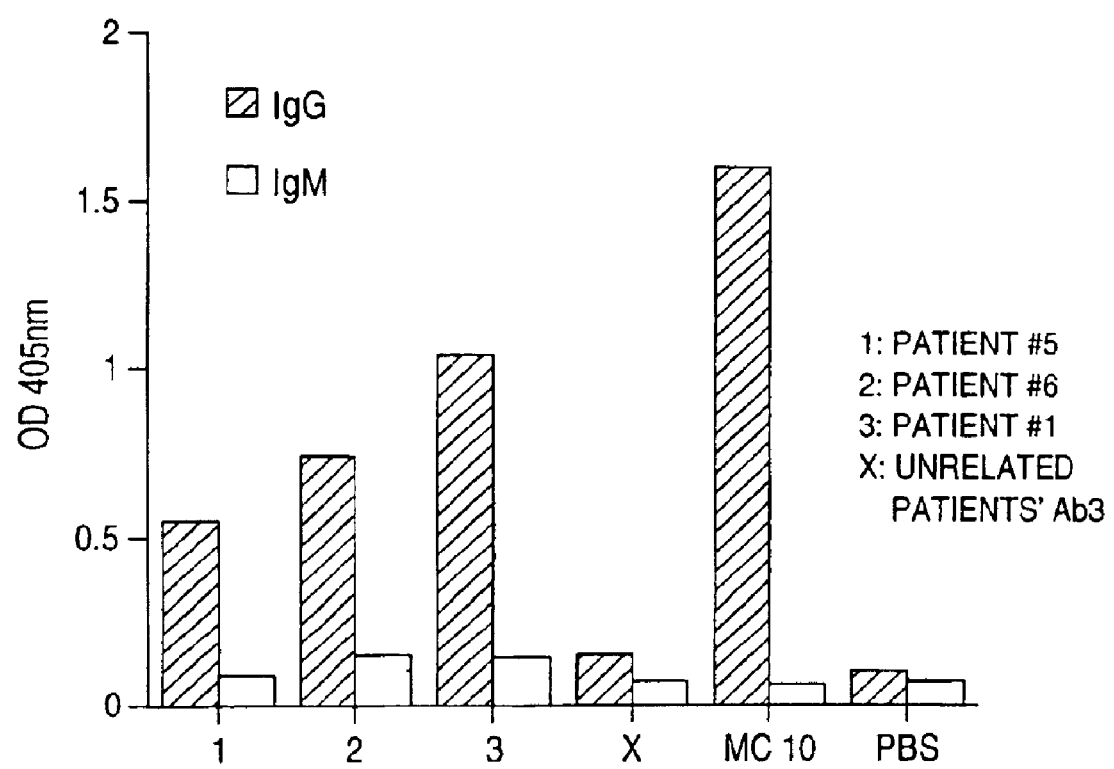

FIG. 28 is a bar graph depicting reactivity of affinity-purified Ab3 from patients' sera after administration of 11D10 as measured by radioimmunoassay (RIA; patients #5 (first pair of bars), #6 (second pair of bars), and #1 (third pair of bars)). The fourth pair of bars ("X") denotes an unrelated patient's Ab3. The fifth pair of bars denotes MC10; the sixth pair of bars denotes phosphate buffered saline (PBS). For each pair of bars, the solid bar indicates IgG and the open bar imitates IgM. Open circles denote pre-immune sera; solid circles denote post-immune sera.

Figure 29A:
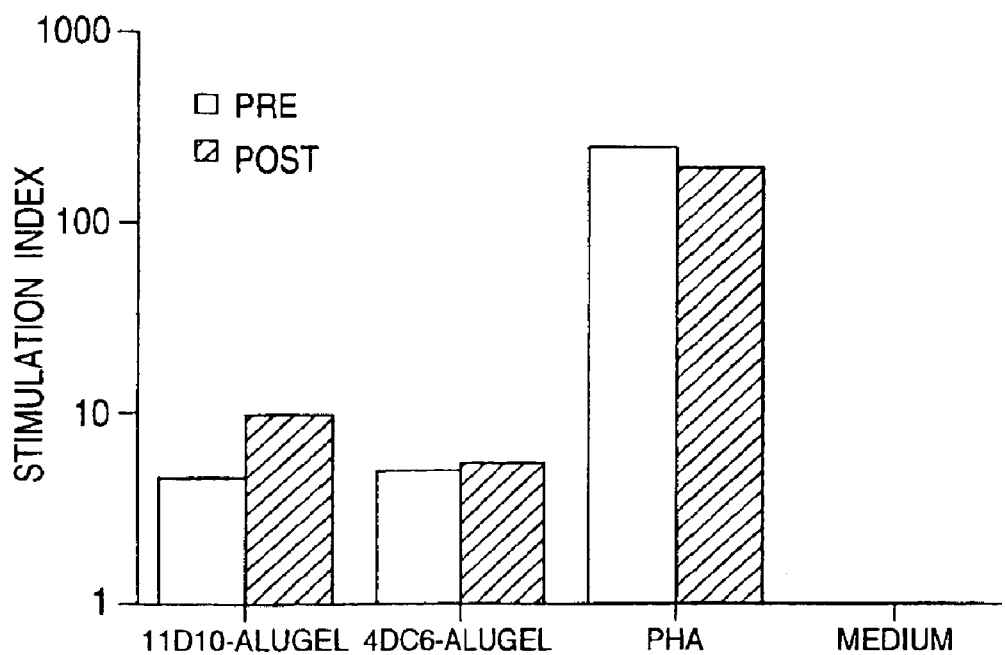
Figure 29B:
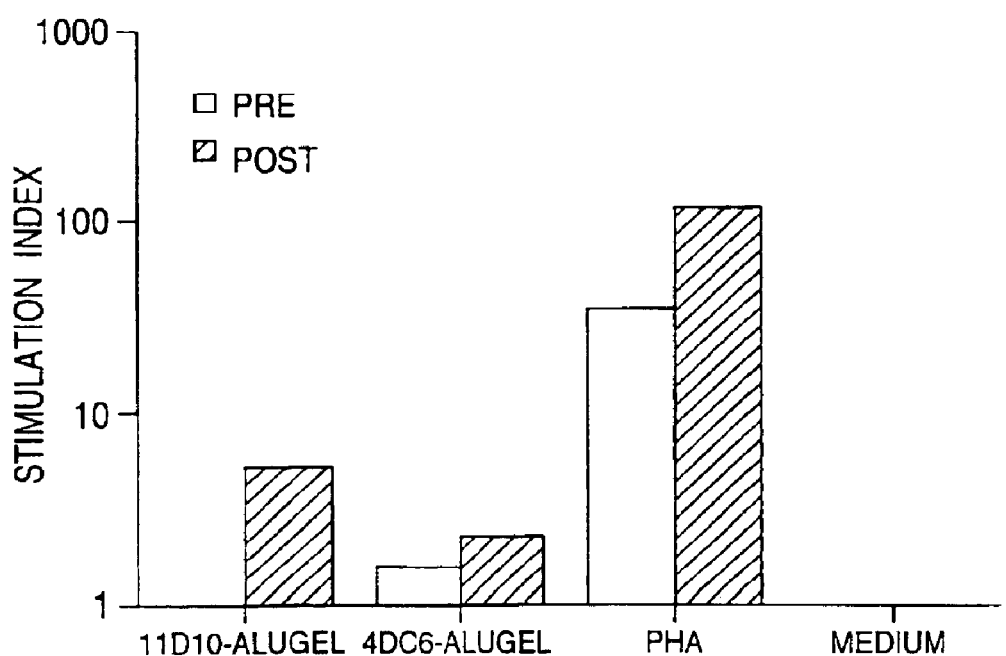

FIGS. 29A and 29B are bar graphs depicting T-cell proliferation by patients" peripheral blood lymphocytes. For each pair of bars, the open bar denotes pre-immune cells; the solid (or shaded) bar denotes post-immune cells. FIG. 29A shows data for patient #1. FIG. 29B shows data for patient #5. Stimulants tested are: 11D10l , first pair of bars; 4DC6, second pair of bars; PHA, third set of bars; medium, fourth pair of bars.

MODES FOR CARRYING OUT THE INVENTION

We have discovered a monoclonal anti-idiotype antibody, 11D10, which escapes immune tolerance and induces a specific immune response against a distinct and specific epitope of human milk fat globule (HMFG), a breast cancer-associated antigen. The immune response elicited by 11D10 typically comprises both humoral and cellular responses. Thus, 11D10 is expected to be useful in treating HMFG-associated disease. A hybridoma that produces 11D10 has been deposited with the American Type Culture Collection (ATCC) 10801 University Boulevard, Manassas, Va., 20110-2209 on Jan, 17, 1996 under the provisions of the Budapest Treaty for the International Recognition of the Deposit of Microorganisms for the Purposes of Patent Procedure. It was accorded Accession Number 12020. A complete description of 11D10, including its generation and characterization, is found in commonly-ownerd patent application Ser. No. 081575,762 (U.S. Provisional Application No. 60/31,306).

Cancer patients are often immunosuppressed and tolerant to various tumor associated antigens (TAA), including HMFG. Triggering an active immune response to such TAA represents an important challenge in cancer therapy. The present inventors use a network theory approach to vaccine therapy using internal image antigens. Immunization with a given antigen generates the production of antibodies against the antigen. As used herein, "Ab1" represents anti-tumor monoclonal antibody; "Ab2" represents anti-idiotypic monoclonal antibody; and "Ab3" represents anti-anti-idiotypic monoclonal antibody.

We have found that 11D10 Is effective in eliciting an immune response (humoral and/or cellular) against HMFG in all mammals tested in which HMFG is not an auto (self) antigen. Importantly, we have also discovered that 11D10 elicits an immune response in patients with advanced HMFG-associated disease, particularly breast cancer. This is especially significant, as many of these patients, either due to the nature of their previous treatment or their disease or both, are moderately to severely compromised, and often received 11D10 as a final option. While not wishing to be bound by a particular theory, one way that the elicitation of an immune response may occur is that the 11D10 combining site may present a region that partly resembles an epitope in HMFG, in the context of other epitopes which renders it more immunogenic. The epitope of HMFG which resembles that of 11D10 is identified by the anti-HMFG mAb MC-10 (Ab1), which recognizes a distinct and specific epitope on HMFG, and was used to immunize syngeneic BALB/c mice for the production of anti-Id mAb 11D10. These studies indicate that the antibody of this invention is useful for the generation of an immune response and treatment of HMFG-associated disease, such as breast cancer in an individual with advanced disease. We also believe that 11D10 will be effective in treatment of HMFG-associated disease in individuals with high tumor burden. It is also useful for detection of Ab1 and/or Ab3.

We have also discovered polynucleotide sequences encoding the variable regions of 11D10 and the polypeptide fragments of 11D10 encoded thereby. Thus, the present invention encompasses polynucleotide sequences encoding the anti-idiotype antibody 11D10 and functionally equivalent fragments thereof, polypeptide fragments of 11D10, recombinant methods for producing these 11D10 polynucleotides and polypeptides, pharmaceutical and vaccine compositions comprising 11D10 polynucleotides and polypeptides, diagnostic kits comprising 11D10 polynucleotides and polypeptides and methods using 11D10 polypeptides and/or 11D10 polynucleotides. These polypeptides and polynucleotides are useful for assessment and treatment of HMFG-associated disease, such as breast cancer These and other uses of 11D10 polynucleotides and 11D10 polypeptides of this invention will be discussed in more detail below.

The full sequences of the 11D10 light and heavy chain constant regions have not been determined, but are expected to be identical or nearly identical to those of other mouse immunoglobulin molecules.

For the mouse kappa light chain constant region, four genetic allotypes encoding two protein allotypes have been published by Solin et al. (1993) Immunogenetics 37:401–407, which is hereby incorporated herein by reference. FIG. 1 of Solin et al. depicts mouse and rat immunoglobulin kappa chain gene sequences, comparing the sequences within the kappa chain constant region for different strains and highlighting allotypic differences. Included are kappa chain constant region sequences for BALB/c, PL, SJL, and M. spretus. Other naturally occurring allotypes are possible.

The mouse γ1 heavy chain constant region DNA sequence from newborn mice has been published by Honjo et al. (1979) Cell 18:559–568, which is hereby incorporated herein by reference. FIG. 5 of Honjo et al. shows the germ-line DNA sequence, along with the encoded protein sequence. Shown in the line above is another protein sequence obtained from the mouse myeloma MOPC 21. Other naturally occurring allotypes are possible.

Among the 10 database DNA sequences matched most closely to that of the 11D10 light chain variable region, none was identical. There were about 6–27 differences with the 11D10 DNA sequence, corresponding to about 6–17 amino acid differences. The sixth matched sequence (designation >gb/M59920/MUSI QKAA3) was a mouse kappa VJ germ-like sequence, and probably represents the prototype gene from which the 11D10 light chain was derived. The 11D10 DNA sequences differ from the germline sequence at 14 positions, corresponding to about 7 amino acid point differences.

Among the 10 database DNA sequences matched most closely to that of the 11D10 heavy chain variable region, none was identical. Nine of the 10 sequences were 3–12 base pairs longer, due to splicing differences within the VDJ junction. In addition, there were about 15–43 point differences compared with the 11D10 DNA, sequence outside the junction, corresponding to about 11–23 amino acid differences.

Thus, there were at least about 18 amino acid differences between the amino acid sequences encoded by the 11D10 DNAs and those encoded by the most closely matched database DNAs. The point differences likely have arisen by somatic mutation of germline sequences during development of the antibody-producing cell in the animal used to generate it.

The amino acid sequences of the 11D10 variable region were compared with those of other known immunoglobulin molecules (Example 2). Both the light and heavy chain polypeptide variable region sequences for 11D10 are unique.

Among the 50 database amino acid sequences matched most closely to that of the 11D10 light chain variable region, none was identical. 11D10 differed from the fifteen closest sequences by a minimum of 7 and an average of about 12 substitution differences, which comprised non-conservative substitutions throughout the variable region.

Among the 50 database amino acid sequences matched most closely to that of the 11D10 heavy chain variable region, none was identical. The following summarizes the main points deduced from the comparison.

The most closely matched sequence had 11 substitutions between residues 1 and 98 (before the VDJ junction), 7 substitution differences after residue 98.

11 D10 differed in length from most of the heavy chain sequences by 1–5 residues.

There were an average of about 30 insertions, deletions and substitution differences between 11D10 and the 50 matched sequences.

FIG. 26 Panel C provides a comparison of the 11D10 amino acid light and heavy chain sequences with consensus sequences derived from the database sequences. Other than splicing differences about the heavy chain VDJ junction, there are at least 18 differences between 11D10 and the consensus sequences that have likely arisen from somatic mutation during antibody maturation. Point differences occur throughout the light and heavy chain variable region.

Particularly of interest in developing 11D10 derivatives with 11D10 immunologic activity are regions of the 11D10 polynucleotide or polypeptide sequence comprising a portion of the heavy chain VDJ junction. Also of interest are regions spanning at least one, preferably 2, more preferably 3 or more of the point differences between the 11D10 amino acid sequences or the amino acid sequences encoded by SEQ ID NO:5 through SEQ ID NO:32.

The useful materials and processes of the present invention are made possible by the provision of 11D10 and the polynucleotide sequences encoding 11D10. These sequences allow for design of polypeptides which can be useful, for example, as vaccines for treatment of HMFG-associated disease or as reagents for detecting the presence of Ab1 and/or Ab3. In addition, these sequences allow the design of polynucleotides which are useful as probes and primers for the detection and amplification of target regions of 11D10, as well as 11D10 polynucleotides that are useful as vaccines.

Definitions

As used herein, the terms "11D10", "11D10 antibody" and "11D10 monoclonal antibody" are used interchangeably to refer to immunoglobulin-produced by the 11D11) hybridoma cell line deposited with the ATCC. The generation and characterization of 11D10 is described in Example 1. 11D10 is an anti-idiotype antibody (Ab2) which contains an epitope that at least partially resembles a distinct and specific epitope of human milk fat globule (HMFG) primarily expressed in high density by breast carcinoma cells. Different biological functions are associated with 11D10, including, but not limited to, binding to Ab1 and/or Ab3 and an ability to induce an immune response (humoral and/or cellular) against HMFG. Unless otherwise specified, the term "intact 11D10" refers to the amino acid sequence of the entire molecule of 11D10. A "fragment" of 11D10 is a portion of 11D10. Also included in the definition of "11D10" are fragments produced by enzymatic cleavage and/or chemical treatment of intact antibody that comprise both the entire heavy and light chain variable regions of 11D10 and are capable of binding MC-10 in a standard immunoassay, such as Fat, F(ab')2, and F(ab').

As used herein, "immunological activity" of 11D10 refers to any of the following activities: (a) ability to bind Ab1 (MC-10); (b) ability to inhibit the binding of 11D10 to MC-10 (Ab1) or MC-10 to HMFG in a specific manner, or (c) ability to elicit a specific immune response, particularly an antibody (humoral) response, and/or a T cell response, and the effector functions that result therefrom. Included in an antibody response are antibody-mediated functions such as antibody-dependent cell cytotoxicity (ADCC) and complement-dependent cytotoxicity (CDC). T cell response includes T helper cell function, cytotoxic T cell function, inflammation inducer T cells, and T cell suppression. Immunological activity is measurable by using standard methods known in the art, such as radioimmunoassay (RIA), enzyme-linked immunoabsorbent assay (ELSA), complement fixation, opsonization, detection of T cell proliferation, and various 51Cr release assays. These methods are known in the art and are described, inter alia, herein. A compound able to elicit a specific immune response according to any of these criteria is referred to as "immunogenic." "Immunogenicity" refers to a capability to elicit a specific humoral and/or cellular immune response.

11D10 "activity", "function(s)", or "characteristic(s)" are used interchangeably and refer to various features of 11D10, Examples of 11D10 function(s) include, but are not limited to, binding to Ab1 and/or Ab3, inducing Ab3 and/or inducing a cellular immune response, preferably an anti-HMFG response, and amelioration or palliation of HMFG-associated disease.

An antibody that has "identifying characteristics" that are identical to another antibody means that an antibody possesses structural (i.e., physical) and/or functional (i.e., chemical) properties that are the same as another antibody, Similarly, a hybridoma having "identifying characteristics" of a cell of a hybridoma cell line is a hybridoma that has structural and/or functional properties that the the same as the hybridoma cell line to which it is being compared. For purposes of this invention, identifying characteristics of an antibody include, but are not limited to those associated with 11D14, as discussed above; identifying characteristics of a hybridoma are those associated with a hybridoma which produces 1 I D10.

A "variable region" of 11D10 refers to the variable region of the 11D10 light chain or the variable region of the 11D10 heavy chain, either alone or in combination.

GM-GSF, IL-2, and other biologically active molecules referred to herein are meant to include fragments and derivatives based on the respective parent molecule that have the same biologic or physiologic function.

As used herein, "progeny" of a hybridoma are descendants of a hybridoma, which may or may not be completely identical to the original (parent) cell due to mutation or other adaptation, but that produce a monoclonal antibody that maintains the ability to escape immune tolerance, i.e., to cause an immune reaction against HMFG.

"HMFG" is an abbreviation for human milk fat globule. HMFG has several proteinaceous (and thus antigenic) components. As used herein, it refers to a semi-purified extract of an HMFG-expressing breast cancer cell line, as prepared by the method of Ceriani et al. ((1977) Proc. Natl. Acad. Sci. USA 74:582–586), along with antigenically related substances, including HMFG expressed on breast cancer cells and more highly purified purifications. Contained in HMFG is a high molecular weight mucin of known amino acid sequence, an epitope of which is recognized by the monoclonal antibody MC-10 used as Ab1 in raising 11D10. Accordingly, anti-HMFG immunological reactivity induced by immunizing an animal with 11D10 preferably binds a polypeptide epitope related to that recognized by MC-10.

For purposes of this invention, "HMFG-associated disease" or "HMFG-associated tumors" are disease conditions or tumors that are associated with an HMFG antigen, especially expressed on the cell surface, that binds to MC-10 (Ab1).

As used herein, a "polynucleotide" is a polymeric form of nucleotides of any length, which contain deoxyribonucleotides, ribonucleotides, and/or their analogs. The terms "polynucleotide" and "nucleotide" as used herein are used interchangeably. Polynucleotides may have any three-dimensional structure, and may perform any function, known or unknown. The term "polynucleotide" includes double-, single-stranded, and triple-helical molecules. Unless otherwise specified or required, any embodiment of the invention described herein that is a polynucleotide encompasses both the double-stranded form and each of two complementary single-stranded firms known or predicted to make up the double stranded form.

The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. Analogs of purines and pyrimidines are known in the art, and include, but are not limited to, aziridinylcytosine, 4-acetylcytosine, 5-fluorouracil, 5-bromouracil, 5-carboxymethylaminomethyl-2-thiouracil, 5-carboxymethyl-aminomethyluracil, inosine, N6-isopentenyladenine, 1-methyadenine, 1-methylpseudouracil, 1-methylguanine, 1-methylinosine, 2,2-dimethylguanine, 2-methyladenine, 2-metlhylguanine, 3-methylcytosine, 5-methylcytosine, pseudoruacil, 5-pentynyluracil and 2,6-diaminopurine. The use of uracil as a substitute for thymine in a deoxyribonucleic acid is also considered an analogous form of pyrimidine.

If present, modification to the nucleotide structure may be imparted before or after assembly of the polymer. The sequence of nucleotides may be interrupted by non-nucleotide components. A polynucleotide may be further modified after polymerization, such as by conjugation with a labeling component. Other types of modifications included in this definition are, for example, "caps", substitution of one or more of the naturally occurring nucleotides with an analog, internucleotide modifications such as, for example, those with uncharged linkages (e.g., methyl phosphonates, phosphotriesters, phosphoamidates, cabamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s).

Further, any of the hydroxyl groups ordinarily present in the sugars may be replaced by phosphonate groups, phosphate groups, protected by standard protecting groups, or activated to prepare additional linkages to additional nucleotides, or may be conjugated to solid supports. The 5' and 3' terminal OH groups can be phosphorylated or substituted with amines or organic capping groups moieties of from 1 to 20 carbon atoms. Other hydroxyls may also be denvatized to standard protecting groups.

Polynucleotides can also contain analogous forms of ribose or deoxyribose sugars that are generally known in the art, including, but not limited to, 2'-O-methyl-, 2'-O-allyl, 2'-fluoro- or 2'-azido-ribose, carbocyclic sugar analogs, α-anomeric sugars, epimeric sugars such as arabinose, xyloses or tyxoses, pyranose sugars, furanose sugars, sedoheptuloses, acyclic analogs and abasic nucleoside analogs such as methyl riboside.

As noted above, one or more phosphodiester linkages may be replaced by alternative linking groups. These alternative linking groups include, but are not limited to, embodiments wherein phosphate is replaced by P(O)S ("thioate"), P(S)S ("dithioate"), "(O)NR2 ("amidate"), P(O)R, P(O)OR', CO or CH2 ("formacetal"), in which each R or R' is Independently H or substituted or unsubstituted alkyl (1–20 C) optionally containing and ether (—O—) linkage, aryl, alkenyl, cycloalky, cycloalkenyl or araldyl. Not all linkages in a polynucleotide need be identical.

Although conventional sugars and bases will be used in applying the method of the invention, substitution of analogous forms of sugars, purines and pyrimidines can be advantageous in designing a final product, as can alternative backbone structures like a polyamide back bone.

A "fragment" (also called a "region") of a 11D10 polynucleotide (i.e., a polynucleotide encoding 11D10) is a polynucleotide comprised of at least 9 contiguous nudeotides of a variable region of 11D10 (i.e., encoding at least a portion of an 11D10 variable region). Preferred fragments are comprised of a region encoding at least 5 contiguous amino acids of a variable region of 11D10, more preferably, at least 10 contiguous amino acids of a variable region, and even more preferably at least 15 contiguous amino acids of a variable region, The term "recombinant" polynucleotide as used herein intends a polynucleotide of genomic, cDNA, semisynthetic, or synthetic origin which, by virtue of its origin or manipulation: (1) is not associated with all or a portion of a polynucleotide with which it is associated in nature, (2) is linked to a polynucleotide other than that to which it is linked in nature, or (3) does not occur in nature.

The terms "polypeptide", "oligopeptide", "peptide" and "protein" are used interchangeably herein to refer to polymers of amino acids of any length. The polymer may be linear or branched, it may comprise modified amino acids, and it may be interrupted by non-amino acids The terms also encompass an amino acid polymer that has been modified naturally or by intervention; for example, disulfide bond formation, glycoasylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of this invention are based upon an antibody, the polypeptides can occur as single chains or associated chains.

A polypeptide "fragment" (also called a "region") of 11D10 is a polypeptide comprising an amino acid sequence of 11D10 that has at least 5 contiguous amino acids of a sequence of 11D10, more preferably at least 8 contiguous amino acids, and even more preferably at least about 10 contiguous amino acids, wherein at least 3 of the amino acids are from a variable region of 11D10. For purposes of this invention, a fragment of 11D10 can be identified and characterized by any of the following functions: (a) homology to HMFG; (b) ability to bind Ab1 or Ab3; (c) ability to elicit an immune response (i.e., humoral and/or cellular response), preferably an immune response that is anti-HMFG; (d) ability to effect amelioration, delay, or slowing of HMFG-associated tumors and/or amelioration or palliation of the HMFG-associated disease state. Items (b), (c), or (d) fall within the term "immunologically reactive". A 11D10 fragment can have any, more than one, or all of the above identified functions. Methods for determining these functions (a) through (d) will be described below.

A 11D10 polypeptide which is "homologous" to HMFG or "shares homology" with HMFG means that, when the amino acid sequences of HMFG and a 11D10 polypeptide are aligned in any manner, including in the same or reverse orientation with respect to each other, at least 2, preferably 3, more preferably 4, contiguous amino acids within the polypeptide match with HMFG. Because functional peptide fragments can be very small for purposes of this invention, only a few amino acids may match (for example, the requisite number of contiguous amino acids required for a binding site and/or antigen presentation can be as few as 2 to 5 amino acids). A 11D10 polypeptide that "contains a region of homology" to HMFG shares homology to HMFG within its amino acid sequence, as defined above.

A "fusion polypeptide" is a polypeptide comprising regions in a different position in the sequence than occurs in nature. The regions may normally exist in separate proteins and are brought together in the fusion polypeptide; or they may normally exist in the same protein but are placed in a new arrangement in the fusion polypeptide.

As used herein, an "immune response" refers to a humoral response, a cellular response or both.

A "functionally equivalent fragment" of a 11D10 polypeptide or polynucleotide preserves at least one property and/or function of the 11D10 polypeptide or polynucleotide. For example, the sequences may be varied by adding additional nudeotides or peptides as known in the art, such that the functionality of the sequence to induce immunity is not altered. Other examples are deletion and/or substitution of sequences. Alternatively, the sequences can be varied by substituting nucleotides or amino acids, or a combination of addition, deletion, or substitution. As is evident to one of skilled in the art, functionality of a polypeptide sequence to induce immunity includes other characteristics and/or activities of the sequence, such as binding to Ab1 and/or Ab3. Further, it is evident to one skilled in the art that "inducing immunity" includes any aspect of the immune response, such as a humoral response or cellular response. It is also clear that functionality of a polynucleotide sequence depends in part upon its intended use, and any functionality that is preserved in a fragment of a polynucleotide satisfies this definition. For instance, a "functionally equivalent fragment" of a 11D10 polynucleotide can be one in which an ability to hybridize is preserved, as the desired polynucleotide can be used as a probe. Alternatively, a "functionally equivalent fragment" of a 11D10 polynucleotide can mean that the polynucleotide encodes a fragment of 11D10 (which includes a portion of the variable region that has a function associated with intact 11D10, and preferably a function associated with inducing anti-HMFG immunity. A functionally equivalent fragment of a 11D10 polypeptide or polynucleotide can have the same, enhanced, or decreased function when compared to the 11D10 polypeptide or polynucleotide. Other functions of 11D10 have been listed above. A functionally equivalent fragment has at least 9 nucleotides or at least 5 amino acids, preferably has at least 15 nucleotides or at least 10 amino acids, even more preferably has at least 25 nucleotides or at least 20 amino acids.

A "cell line" or "cell culture" denotes higher eukaryotic cells gown or maintained in vitro. It is understood that the descendants of a cell may not be completely identical (either morphologically, genotypically, or phenotypically) to the parent cell.

A "vector" is a self-replicating nucleic acid molecule that transfers an inserted nucleic acid molecule into and/or between host cells. The term includes vectors that function primarily for insertion of a nucleic acid molecule into a cell, replication of vectors that function primarily for the replication of nucleic acid, and expression vectors that function for transcription and/or translation of the DNA or RNA Also included are vectors that provide more than one of the above functions.

A "host cell" includes an individual cell or cell culture which can be or has been a recipient for vectors) or for incorporation of nucleic acid molecules and/or proteins. Host cells include progeny of a single host cell, and the progeny may not necessarily be completely identical (in morphology or in genomic of total DNA complement) to the original parent cell due to natural, accidental, or deliberate mutation. A host cell includes cells transfected in vivo with a polynucleotides) of this invention.

"Expression vectors" are defined as polynucleotides which, when introduced into an appropriate host cell, can be transcribed and translated into a polypeptide(s). An "expression system" usually connotes a suitable host cell comprised of an expression vector that can function to yield a desired expression product.

A "signal sequence" is a short amino acid sequence that directs newly synthesized secretory or membrane proteins to and through cellular membranes such as the endoplasmic reticulum. Signal sequences are typically in the N-terminal portion of a polypeptide and are cleaved after the polypeptide has crossed the membrane.

"Heterologous" means derived from (i.e., obtained from) a genotypically distinct entity from the rest of the entity to which it is being compared. For example, a polynucleotide may be placed by genetic engineering techniques into a plasmid or vector derived from a different source, thus becoming a heterologous polynucleotide, A promoter which is linked to a coding sequence with which it is not linked is a heterologous promoter.

An "isolated" or "purified" antibody, polynucleotide or polypeptide is one that is substantially free of the materials with which it is associated in nature. By substantially free is meant at least 50%, preferably at least 70%, more preferably at least 80%, and even more preferably at least 90% free of the materials with which it is associated in nature.

A "vaccine" is a pharmaceutical composition for human or animal use, which is administered with the intention of conferring the recipient with a degree of specific immunological reactivity against a particular target, or group of targets. The immunological reactivity may be antibodies or cells (particularly B cells, plasma cells, T helper cells, and cytotoxic T lymphocytes, and their precursors) that are immunologically reactive against the target or any combination thereof. For purposes of this invention, the target is tumor associated antigen HMFG or any tumor related antigen bound by 11D10. The immunological reactivity may be desired for experimental purposes, for treatment of a particular condition, or for the elimination of a particular substance.

A "stable duplex" of polynucleotides, or a "stable complex" formed between any two or more components in a biochemical reaction, refers to a duplex or complex that is sufficiently long-lasting to persist between formation of the duplex or complex and subsequent detect on, including any optional washing steps or other manipulation that may take place in the interim.

A biological "sample" encompasses a variety of sample types obtained from an individual and is typically used in a diagnostic procedure or assay. The definition encompasses blood and other liquid samples of biological origin, solid tissue samples such as ;a biopsy specimen or tissue cultures or cells derived therefrom and the progeny thereof. The definition also includes samples that have been manipulated in any way after their procurement, such as by treatment with reagents, solubilization, or enrichment for certain components, such as proteins or polynucleotides. The term "biological sample' encompasses a clinical sample, and also includes cells in culture, cell supernatants, cell lysates, serum, plasma, biological fluid, and tissue samples.

As used herein, "treatment" is an approach for obtaining beneficial or desired clinical results. For purposes of this invention, beneficial or desired clinical results include, but are not limited to, alleviation of symptoms, diminishment of extent of disease, stabilized (i.e., not worsening) state of disease, preventing spread (i.e., metastasis) of disease, delay or slowing of disease progression, amelioration or palliation of the disease state, and remission (whether partial or total), whether detectable or undetectable. "Treatment" can also mean prolonging survival as compared to expected survival if not receiving treatment.

"Palliating" a disease means that the extent and/or undesirable clinical manifestations of a disease state are lessened and/or time course of the progression is slowed or lengthened, as compared to not administering 11D10, 11D10 polynucleotide(s), and/or 11D10 polypeptide(s).

An "effective amount" is an amount sufficient to effect beneficial or desired clinical results. An effective amount can be administered in one or more administrations. For purposes of this invention, an effective amount of 11D10, 11D10 polynucleotide, and/or 11D10 polypeptide is an amount that is sufficient to induce an immune response, particularly an anti-HMFG response. In terms of treatment, an "effective amount" of 11D10, 11D10 polynucleotide, and/or 11D10 polypeptide is amount that is sufficient to palliate, ameliorate, stabilize, reverse, slow or delay the progression of the HMFG-associated disease stale. Detection and measurement of these indicators of efficacy are discussed below.

An "individual" is a vertebrate, preferably a mammal, more preferably a human. Mammals include, but are not limited to, farm animals, sport animals, and pets.

General Techniques

The practice of the present invention will employ, unless other wise indicated, conventional techniques of molecular biology (including recombinant techniques), microbiology, cell biology, biochemistry and immunology, which are within the skill of the art. Such techniques are explained fully in the literature, such as, "Molecular Cloning: A Laboratory Manual", second edition (Sambrook et al., 1989); "Oligonucleotide Synthesis" (M. J. Gait ed., 1984); "Animal Cell Culture" (R. I. Freshney, ed., 1987); "Methods in Enzymology" (Academic Press, Inc.); "Handbook of Experimental Immunology" (D. M. Wei & C. C. Blackwell, eds.); "Gene Transfer Vectors for Mammalian Cells" (J. M. Miller & M. P. Calos, eds., 1987); "Current Protocols in Molecular Biology" (F. M. Ausubel et al., eds., 1987); "PCR: The Polymerase Chain Reaction", (Mullis et al., eds., 1994); "Current Protocols in Immunology" (J. E. Coligan et al., eds., (1991).

These techniques are applicable to the production of the polynucleotides and polypeptides of the invention, and, as such, are to be considered when contemplating these inventive aspects. Particularly useful systems for individual aspects will be discussed below.

11D10

In one embodiment, the invention includes a monoclonal anti-idiotype antibody (referred to herein as an "anti-Id") produced by hybridoma cell line ATCC No, 12020 or progeny thereof. Also included in this invention is a hybridoma cell line designated ATCC No. 12020 and progeny thereof. Generation and characterization is described in Example 1 and below.

In another embodiment, the invention includes a purified antibody having identifying characteristics identical to antibody produced by the hybridoma cell line designated ATCC No. 12020. The invention also includes a hybridoma having all the identifying characteristics of a cell of the hybridoma cell line designated ATCC No. 12020.

The invention also encompasses 11D10 conjugated to a label capable of producing a detectable signal. These conjugated antibodies are useful, for example, in detection systems such as quantitation of Ab1 (and/or Ab3) or imaging. Such labels are known in the art and include, but are not limited to, radioisotopes, enzymes, fluorescent compounds, chemiluminescent compounds, bioluminescent compounds, and other antibodies. The labels may be covalently linked to 11D10, or conjugated to the 11D10 through a secondary reagent, such as a second antibody, protein A, or a biotin-avidin complex. Methods of labeling antibodies are known in the art and need not be described in detail herein.

Generation and Selection of 11D10

Selection of an Ab1 to raise the anti-Id (Ab2). A series of cell-type specific murine monoclonal antibodies ("mAbs") have been generated that recognize components of human milk fat globule (HMFG) membranes associated with breast carcinomas, but not with most normal tissues. Ceriani et al. (1983); Taylor-Papadimitriou et al. (1981) *Int. J. Cancer* 28:17–21. Among these mAbs, MC-10 (also called BrE1) is quite restricted and specific in the sense that it reacts with a large molecular weight (MW 400,000) mucin present in only minute amounts in human mammary epithelial cells and increased by at least 10-fold on breast carcinoma cells. WO 8907268; EP 401247. The antibody is cytotoxic for breast cancer cells in in vitro studies. Ceriani et al. (1983); Peterson et al. (1990).

mAb MC-10 has a very restricted histopathological distribution in normal tissues. MC-10 only binds some areas of the epithelial lining of the lung and scattered distal convoluted tubules of the kidney, with no apparent histopathological binding to normal breast and many other normal epithelia (colon, pancreas, stomach, thyroid, bladder, liver) and other normal tissues (adrenal, brain, lymph node, myocardium, ovary, spleen, testis). On the other hand, a high percentage of different human tumors, including breast, endometrium, lung, ovary, and pancreas bind mAb MC-10 intensely. The formalin fixed tumors studied for MG-10 binding (number positive/total number) include: breast carcinoma (CA) (144/182), colon CA (3/27) duodenum CA (0/1), endometrium CA (7/14), kidney CA (0/11), lung CA (41/47), ovary CA (20/26), pancreas CA (9/15), prostate CA (0/2), salivary gland CA (0/3), stomach CA (2/7), thyroid CA (0/7), hepatocholangio CA (8/33), islet cell CA (0/2), lymphoma (0/20), melanoma (0/23), meningioma (0/5), Merkel cell CA (4/9), mesothelioma (1/11), neuroblastoma (0/2), oncocytoma (1/1), paraganglioma (0/10), pileoadenoma (0/7). Among the sarcomas: unclassified (0/1), alveolar (0/1), angiosarcoma (0/1), clear cell (0/2), cystosarcoma (0/1), epithelioid (5/12), Ewing's (0/1), fibrosarcoma (0/1), leiomyoma (0/2), liposarcoma (0/1), malignant fibrohistiocytoma (0/2), synovial mesothelioma (0/7), spindle cell CA (5/16), undifferentiated (1/9); schwannoma (0/3), seminoma (0/4), teratoma (0/3), thymoma (0/8), transitional CA (5/10), undifferentiated CA (7/29), Warthin's tumor (0/1). Ceriani et al. (1990). We have also studied hematopoietic cells for the presence of MC-10 Ag by FAGS analysis in our laboratory and found those cells, inducting granulocytes and platelets, negative for antigen. The positive control MCF-7 cells s gained heavily with mAb MC-10 Thus, 11D10 has the potential to be used in a wide variety of cancers in which HMFG is detected.

mAb MC-10 was thus chosen for production of anti-Id because it defines a unique and specific epitope of a high molecular weight mucin of human milk fat globule (HMFG), primarily expressed at high density by human breast cancer and some other tumor cells but is nit found on normal adult tissues by immunoperoxidase staining, or hematopoietic cells including granulocytes by flow cytometry analysis.

The breast cancer-associated epitope defined by monoclonal antibody MC-10 is a suitable target for active immunotherapy against these tumors. This Ag is expressed by >80% of cases of breast cancer and is present at high density on tumor tissues as compared to a few normal tissues which contain this Ag in trace amounts. Ceriani et al. (1983); Taylor-Papadimitriou et al. (1991). The Ag is shed into the circulation only In trace amounts. Peterson et al, (1990) *Hybridoma* 9221–235. The low level of circulating Ag apparently does not interfere with the binding of radiolabeled anti-HMFG mAbs to tumor targets in in vivo studies in advanced breast cancer patients. The restricted specificity of MC-10 together with its high binding capacity to representative breast cancer cell lines MCF-7 and SKBR3 makes it an excellent target for generating Ab2 hybridomas. We obtained purified MC-10 (IgG2bκ) (Lot. No. 5319001) to generate an anti-idiotype.

Generation of monoclonal anti-idiotype hybridomas and selection of 11D10. 11D10 was obtained by immunizing naive mice with MC-10 anti-HMFG antibody to obtain an anti-idiotype response. Syngeneic BALB/c mice were immunized four times with MC-10 (Ab1) and their spleen cells were fused with the non-secretory mouse myeloma P3-653 cells. To obtain an anti-idiotype with all the features are desired, an extensive screening process was employed which included the following four important steps: (1) Positive selection for antibody binding to MC-10; (2) Negative selection against antibody recognizing isotypic or allotypic determinants; (3) Positive selection for an ability to inhibit the binding of MC-10 to HMFG; (4) Positive selection for an ability to induce a humoral immune response against the original tumor-associated antigen (HMFG) in both mice and rabbits.

Several Ab2 hybridomas were obtained that were specific for the immunizing Id of MC-10 and did not react with any isotypic or allotypic determinants. To determine whether these Ab2 were directed against the paratope of MC-10, the binding of radiolabeled MC-10 to the breast tumor cell line MCF-7 and SKBr3 was studied in the presence of varying amounts of Ab2 hybridoma culture supernatants. Ab2s able to inhibit MC-10 binding to these cells were grown and purified from ascites fluid for further studies. Different purified Ab2 were prepared as vaccines and injected into naive mice and rabbits on a biweekly schedule. After 4 injections, serum samples were titered for the presence of Ab3 that bound not only to the immunizing Ab2, but also to HMFG. The Ab2 reproducibly inducing the highest titer of Ab3 with the desired specificity was designated 11D10, Further details of the method used to obtain 11D10 are provided in Example 1.

Figure 7:
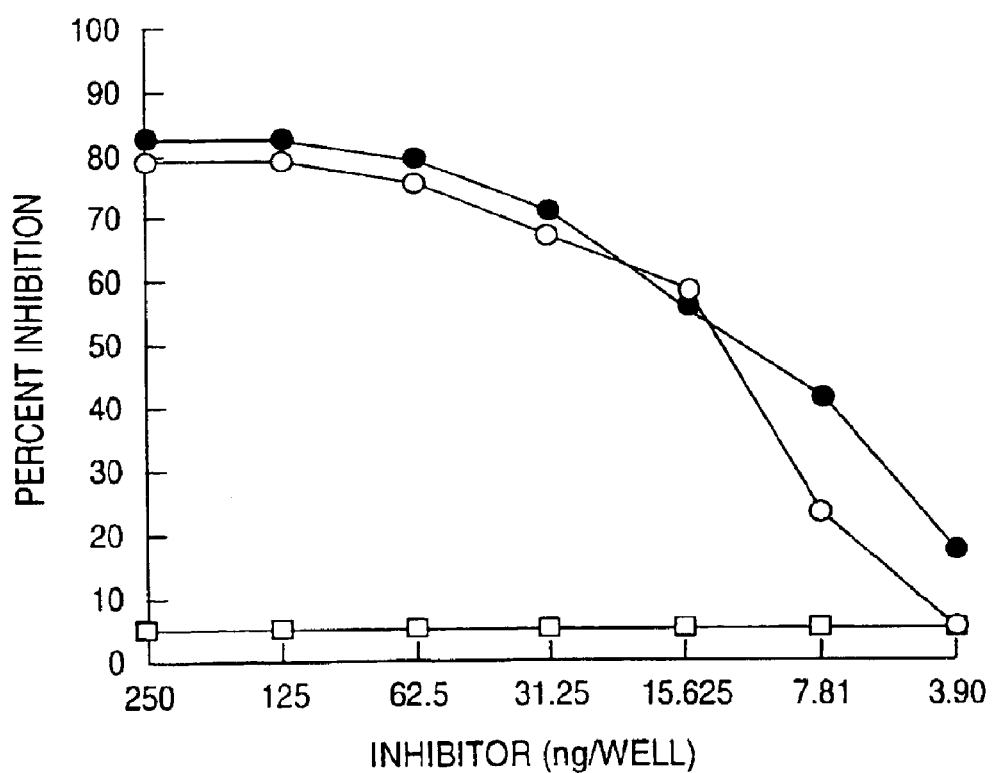
FIG. 7 is a graph depicting inhibition of MC-10 (BrE-1) binding to MCF-7 and SKBR3 cells by purified Ab2. Solid circles denote 11D10 competing for binding to MCF-7 cells; open circles denote 11D10 binding to SKBR3 cells; open squares denote 3H1 binding to MCF-7 or SKBR3 cells.

The immune response in animals immunized with 11D10 has been further characterized. Immune sera from both mice and rabbits immunized with 11D10 competed with MC-10 for binding to the breast carcinoma cell line MCF-7 or SKBr3 and inhibited the binding of radioiodinated MC-10 to 11D10 (FIG. 7). This indicated that the Ab3 in mice and rabbits may share idiotopes with Ab1 (MC-10) and probably binds to the same epitope as Ab1.

Monoclonal Ab3 that bind to MC-10 positive antigen have also been obtained from mice immunized with 11D10. The Ab3 (both polyclonal as well as monoclonal) reacted with semi-purified HMFG Ag by dot blot analysis and stained MCF-7 cells by immunoperoxidase method. In addition, rabbit Ab3 sera opsonized the tumor cell lines MCF-7 or SK Br3 in a complement-mediated cytoxicity (CMC) assay.

We have also discovered that administration of 11D10 to non-human primates (cynomolgus monkeys) generates an immune response, both humoral and cellular (Example 3; *Cancer Res.* (1995) 55:1525–1530). Ab3 produced in response to 11D10 was specific for HMFG (FIGS. 12–17). The antibody (Ab3) concentration was quite high, as 1.32 mg of purified Ab3 was recovered from 30 ml serum (44 μg/ml serum). As little as 100 ng of this purified Ab3 was able to inhibit the binding of >60% of radiolabeled Ab1 to the HMFG-positive breast cancer cell line MCF-7.

In addition to humoral immunity, the cellular immune response in monkeys was studied by T-cell proliferation assay. Substantial proliferation was noted when immune peripheral blood lymphocytes (PBL) from the monkey which received 11D10 were challenged in vitro with 11D10 but not with unrelated control Ab2, 3H1 (FIG. 19), suggesting Id-specific cellular proliferation.

With regard to clinical application of anti-idiotypic antibodies for immunotherapy, the demonstration of induction of specific anti-TAA antibodies in different species of animals is an essential requirement.

Importantly, although humans with HMFG-associated tumors are tolerized to the HMFG antigen, we have also found that 11D10 escapes immune tolerance and elicits an immune response in individuals with advanced human milk fat globule associated disease, particularly breast cancer. Three patients with HMFG-positive advanced breast cancer, and who had failed standard therapies, were administered 11D10 (Example 5). Initial data indicated all three of these patients developed antibodies that were anti-HMFG (FIGS. 20–21); patient #2 was non-specific binding, but had some Ab3 reactivity). In addition, one of the patients exhibited a cellular immune response as evidenced by a T cell proliferation assay (FIG. 22). Upon further analysis (using affinity purified Ab3), it was found that only one of these three patients developed antibodies that were anti-HMGF (FIGS. 27 and 28; Example 10). Upon assessing additional patients (total of 12) as they accrued to this study (Example 10), we found that five out of 10 patients tested developed anti-HMFG antibodies as assessed by inhibition of binding of radiolabeled MC-10 (Ab1) to 11D10. A total of four patients (#1, 5, 6 and 12) exhibited a cellular immune response (FIG. 29). A more detailed description of this study is found in Examples 5 and 10.

Preparation of 11D10

The antibody of this invention can be obtained several ways. 11D10 can be produced from the hybridoma ATCC 12020 described herein. Methods of antibody isolation are well known in the art. See, for example, Harlow and Lane (1988) *Antibodies: A Laboratory-Manual*, Cold Spring Harbor Laboratory, New York, and Sambrook et al. (1989) *Molecular Cloning: A Laboratory Manual*, Cold Spring Harbor Laboratory. The antibody can be obtained from the hybridoma via tissue culture or from mouse ascites and purified using conventional techniques for antibody purification. These techniques are known in the art. For example, the cells can be cultured in a suitable medium, and spent medium can be used as an antibody source. Optionally, matrix-coated channels or beads and cell co-cultures may be included to enhance growth of antibody-producing cells. For the production of large amounts of antibody, it is generally more convenient to obtain an ascites fluid. Such methods are known in the art, and generally comprise injecting hybridoma cells into an immunologically naive histocompatible or immunotolerant mammal, especially a mouse. The mammal is optionally primed for ascites production by prior administration of a suitable composition; for example, Pristane. Preferably, 11D10 is purified from BALB/c ascites using recombinant Protein G-agarose chromatography followed by Protein A-CL-sepharaose 4B chromatography.

Alternatively, 11D10 can be chemically synthesized using the sequences and information provided herein and techniques known in the art, for example, a commercially available automated peptide synthesizer such as those manufactured by Applied Biosystems, Inc. (Foster City, Calif.).

The 11D10 antibody is of the IgG1 mouse subclass, and may be isolated by any technique suitable for immunoglobulins of this isotype. Purification methods may include salt precipitation (for example, with ammonium sulfate), ion exchange chromatography (for example, on a cationic or anionic exchange column run at neutral pH and eluted with step gradients of increasing ionic strength), gel filtration chromatography (including gel filtration HPLC), and chromatography on affinity resins such as protein A, protein G, hydroxyapatite, and anti-immunoglobulin. 11D10 may also be purified on affinity columns comprising the MC-10 paratope; for example, in the form of a purified Ab1 or Ab3.

11D10 may also be obtained by employing routine recombinant methods such as described in Sambrook et al. (1989). For instance, using the sequences and information provided herein, a polynucleotide encoding either the 11D10 heavy or light chain can be cloned into a suitable expression vector (which contains control sequences for transcription, such as a promoter). The expression vector is in turn introduced into a host cell. The host cell is grown under suitable conditions such that the polynucleotide is transcribed and translated into a protein. Heavy and light chains of 1' 010 may be produced separately, and then combined by disulfide bond rearrangement Alternatively, vectors with separate polynucleotides encoding each chain of 11D10, or a vector with a single polynucleotide encoding both chains as separate transcripts, may be transfected into a single host cell which may then produce and assemble the entire molecule. Preferably, the host cell is a higher eukaryotic cell that can provide the normal carbohydrate complement of the molecule. The 11D10 thus produced in the host cell can be purified using standard techniques in the art. A polynucleotide encoding 11D10 for use in the production of 11D10 by any of these methods can in turn be obtained from the hybridoma producing 11D10, or the produced synthetically or recombinantly from the DNA sequence provided herein.

If 11D10 is to be administered to an individual, 11D10 is preferably at least 80% pure, more preferably at least 90% pure, even more preferably at least 95% pure, still more preferably about 97% pure, even more preferably about 99% pure, even more preferably at least about 99.5% pure, as well as free of pyrogens and other contaminants. In this context, the percent purity is calculated as a weight percent of the total protein content of the preparation.

Uses for 11D10 and Methods Using 11D10

11D10 has several uses. It may be used to elicit an immune response in an individual having advanced HMFG-associated tumors and thus treat those individuals for HMFG-associated tumors. Preferably, the immune response is anti-HMFG. Further, 11D10 may be used to detect antibodies that bind to HMFG or 11D10. 11D10 may also be used to remove unwanted excess labeled Ab1 from the circulation of patients previously treated with labeled monoclonal anti-HMFG antibodies. The label may be any label attached to the antibody suitable for its intended use, including, for example, radioisotopes, toxic moieties such as toxins, and drugs. 11D10 is also useful for enhancing tumor detection in imaging.

Use of 11D10 to elicit an immune response or in treatment, the present invention includes methods of eliciting an immune response in an individual having advanced HMFG associated disease, such as HMFG-associated tumors, that entail administering an effective amount of 11D10 to the individual. In this context, an "effective amount" is an amount sufficient to elicit an immune response, whether humoral and/or cellular. Preferably, the immune response includes the production of anti-HMFG.

Suitable subjects for administration of 11D10 antibody may be identified by a number of different criteria. Experimental animals may be administered 11D10, for example, to study the effect of 11D10 on the immune response, or to obtain useful reagents, such as anti-HMFG specific antibodies and cell lines.

In a preferred embodiment, 11D10 may be used to elicit an in immune response and/or for treatment of and/or for palliating advanced HMFG-associated disease, such as HMFG-associated tumors. An "HMFG-associated tumor" is one that contains an HMFG antigen (i.e., an antigen associated with HMFG), especially expressed on the surface of tumor cells, such as breast, endometrium carcinoma, ovarian, transitional and undifferentiated carcinoma (other examples have been described above). As used herein, "advanced" NMFG-associated tumors means that there is detectable metastasis, that is, detectable tumor masses at sites other than the primary site of the tumor. Masses are preferably detected by imaging techniques known in the art such as X-ray or CT scan. For eliciting an immune response, palliation, or treatment, an effective amount of 11D10 is administered to an individual with advanced HMFG-associated tumor(s). Administration of an effective amount of 11D10 to individuals with advanced HMFG-associated may delay or slow the rate of progression of the disease or ameliorate disease, in comparison with other individuals who are not so treated.

It is understood that for some situations involving advanced HMFG-associated tumors, particularly advanced breast cancer, the individual receiving 11D10 may be moderately to severely immunocompromised, either due to the nature of previous treatment, the disease itself, or both. Thus, the time required to mount an immune response and/or the number of injections of 11D10 and/or the amount of 11D10 per administration may vary. For example, an individual may require a longer time to elicit an immune response once 11 1310 has been administered. In this case, it is recommended that the individual continue to be monitored for an immune response, even if no initial (i.e., within the first month) no immune response has been detected. As another example, an individual may require more than the average number of injections to elicit an immune response.

One possible indication of effectiveness of administration of 11D10, whether for eliciting a immune response and/or treatment, or whether administration of 11D10 is indicated, is the density of HMFG on the tumor cells. This density can vary widely from individual to individual, and may vary over the course of administration of 11D10 and/or over the course of the disease. As used herein, "density' of HMFG can refer to either or both of the following: (a) the number of cells per total cells in a given biological sample that have HMFG on their surface; (b) the amount of HMFG on the surface of each cell. Density (a) is calculated by noting the number of cells in a sample that are stained or otherwise indicate that HMFG is present divided by the total number of cells. This density would be preferably greater than about 20%, more preferably greater than about 30%, more preferably greater than about 50%, even more preferably greater than about 70%, even more preferably greater than about 80%, most preferably greater than about 90%. Thus, the invention includes administration of 11D10 to an individual having density of HMFG greater than about 20%, preferably greater than 30%, more preferably greater than 70%, even more preferably greater than about 80%, most preferably greater than about 90%.

Density (b) is indicated by the relative intensity of staining (or intensity of any measurement indicating the presence of HMFG) of cells in a sample from one individual relative to, for example, a sample from another individual. For this density, one skilled in the art can make an empirical determination of density. Density (b) is relative to normal tissues (i.e., cells lacking HMFG, or unaffected cells), so preferred ranges may be about 1.5 fold, preferably about 3 fold, more preferably about 10 fold higher expression over unaffected cells, as detected by immunohistochemical staining density. Unaffected cells could also be from the same individual.

This is not to say that individuals with lower densities, for example, less than about 50% are not indicated for administration of 11D10. While not wishing to be bound d by a single theory, it is possible that administration of 11D10 could elicit a series of immuno-reactions that result in a more general response that is effective against a HMFG-associated tumor, such as a cytotoxic T cell response. A lower density, however, may indicate that additional therapies are desirable.

It is understood that density can also be used as an indicator of extent of disease and response to administration of 11D10. For example, a sample taken from in individual at the onset of 11D10 administration may exhibit about 80% density (i.e., about 80% of the cells exhibit HMFG). After receiving 11D10, a sample taken from the same location may exhibit only about 50% density, indicating that HMFG-expressing cells are being destroyed. Similarly, if the intensity of staining of a sample from an individual receiving 11D10 diminishes Upon receiving 11D10, this indicates that HMFG-bearing tumor cells are being destroyed.

For purposes of raising an immune response or providing treatment to individuals with advanced HMFG-associated tumors, 11D10 is administered parenterally, preferably intracutaneously. Other routes of administration include, but are not limited to, intramuscular, subcutaneous and intradermal. 11D10 can also be administered indirectly, by treatment of cultured cells followed by introduction of these cultured cells into an individual.

The amount of 11D10 administered depends upon several factors, such as the condition of the individual and the route of administration. Preferably, the dose per administration will range from about 0.1 mg to about 20 mg. More preferably, the dose will range from at out 0.5 mg; more preferably, from about 1 mg to about 8 mg. Preferably, the dose is about 2 to 8 mg. 11D10 is typically administered bi-weekly for four injections, followed by monthly injections as required. Timing of subsequent injections (i.e., a maintenance dose) will depend, inter alia, upon the condition and response of the individual being treated. Ab3 levels can be monitored, for example, preferably by the diagnostic methods described herein, to determine when maintenance (booster) administrations should be given, which would typically be about every three months.

Preferably, 11D10 is administered with a pharmaceutically acceptable excipient. A pharmaceutically acceptable excipient is a relatively inert substance that facilitates administration of a pharmacologically effective substance. For example, an excipient can give form or consistency to the vaccine composition, or act as a diluent. Suitable excipients include but are not limited to stabilizing agents, wetting and emulsifying agents, salts for varying osmolarity, encapsulating agents, buffers, and skin penetration enhancers. Examples of pharmaceutically acceptable excipients are described in Remington's Pharmaceutical Sciences (Alfonso R. Gennaro, ed., 18th edition, 1990).

Preferably, 11D10 is used with an adjuvant which enhances presentation of 11D10 or otherwise enhances the immune response against 11D10. Suitable adjuvants include aluminum hydroxide, alum, QS-21 (U.S. Pat. No. 5,057,540), DHEA (U.S. Pat. Nos. 5,407,684 and 5,077,284) including its precursors and modified forms, (e.g., DHEAS, the sulfonated form of DHEA), beta-2 microglobulin (WO 91/16924), muramyl dipeptides, muramyl tripeptides (U.S. Pat. No. 5,171,568) and monophosphoryl lipid A (U.S. Pat No. 4,436,728; WO 92116231) and its derivatives, e.g., Detox™, and BCG (U.S. Pat. No. 4,726,947). Other suitable adjuvants include, but are not limited to, aluminum salts squalene mixtures (SAF-1), muramyl peptide, saponin derivatives, mycobacterium wall preparations, mycolic acid derivatives, nonionic block copolymer surfactants, Quil A, cholera toxin B subunit, polyphosphazene and derivatives, and immunostimulating complexes (ISCOMs) such as those described by Takahashi et al. (1990) Nature 344:873–875. For veterinary use and for production of antibodies in animals, mitogenic components of Freund's adjuvant can be used.

The choice of an adjuvant will depend in part on the stability of the vaccine in the presence of the adjuvant, the route of administration, and the regulatory acceptability of the adjuvant, particularly when intended for human use. For instance, alum is approved by the United States Food and Drug Administration (FDA) for use as an adjuvant in humans and will be used in our clinical trials. The 11D10 can be administered in a precipitated form; for example, alum-precipitated 11D10 can be used. Preparation of aluminum hydroxide precipitated 11D10 is described in Examples 3 and 4. If OS-21 is used, preferably 100 µg is used for each dose which preferably is administered subcutaneously within about 30 minutes of mixing with 11D10 (with care taken to mix gently). If Detox™ is used, preferably 0.12 ml is used for each dose, which is preferably administered subcutaneously within about 30 minutes of mixing with 11D10. Manufacturers generally can provide recommendations regarding amounts, volume, preparation, and route(s) of administration.

Alternatively, 11D10 can be encapsulated, for example, in liposomes. Liposomes suitable for packaging polypeptides for delivery to cells are known in the art.

11D10 can be heat treated before administration, and the heat treatment can be in the presence of adjuvant, for example, alum. For instance, 11D10 can be heated at about 40 to 60° C., preferably 45° C. to 55° C., for a period of about 5 minutes to 2 hours, preferably 15 minutes to 1 hour. Heat treatment is more preferably at 45° C. for 30 minutes in a sterile vial, in a water bath. The heat treatment can occur anytime before administration. Preferably, heat treatment is within 7 days of administration. Other heat treatment procedures can be used, as long as the desired activity of 11D10 is not significantly compromised.

For the purpose of raising an immune response, 11D10 may be administered in an unmodified form. It may sometimes be preferable to modify 11D10 to improve its immunogenicity. Methods of improving immunogenicity include, inter alia, crosslinking with agents such as gluteraldehyde or bifunctional couplers, or attachment to a polyvalent platform molecule. Immunogenicity may also be improved by coupling to a protein carrier, particularly one that comprises T cell epitopes.

11D10 can be used alone or in conjunction with other agents which promote the desired activity/objective. In this context, an "agent" can be any of a variety of substances. Further, "in conjunction with" means that the agent can be used concomitantly, before, or after 11D10. A desired activity is any activity which facilitates, enhances, promotes, or modulates the desired objective in using 11D10. Agents which may be used include, but are not limited to, cytokines, lymphokines, adjuvants, and drugs. Agents also include substances which facilitate delivery of 11D10, such as liposomes, or substances which promote delivery of 11D10 to a particular target, for example, a cellular receptor. For example, 11D10 can be administered with a cytokine such as GM-CSF.

In order to determine the effect of administration with 11D10, an individual may be monitored for either an antibody (humoral) or cellular immune response against HMFG, or a combination thereof.

To determine the level of HMFG antibody (Ab3) in a biological sample, for example, serum or plasma is obtained from the individual. The sample may optionally be enriched for immunoglobulin before the assay is conducted, although this is not usually required. If a mouse immunoglobulin (such as 11D10) is to be used as an assay reagent, the sample is preferably pretreated to remove anti-mouse immunoglobulin activity. This may be performed, for example, by depletion on a mouse immunoglobulin column, or by mixing non-specific mouse immunoglobulin into the sample and removing any immunoprecipitate formed.

To conduct the assay, anti-HMFG that may be in the sample is contacted with a non-limiting amount of an antigenic equivalent of HMFG. This maybe isolated HMFG, nitrocellulose with HMFG affixed by direct blotting or by transfer from a polyacrylamide gel, cells expressing HMFG (such as MCF-7 or SKBR3 cells), membrane preparations from such cells, or fixed tissue sections containing HMFG. Alternatively, an anti-idiotype, particularly 11D10 may be used.

Once the immune complex has formed, it is generally separated from uncomplexed HMFG analog, and the amount of complex present is determined. The complex may be separated, for example, by centrifugation to collect cells or an immunoprecipitate, or capture by a solid phase. The amount of complex present may be measured by providing the HMFG analog with a label either directly, or by incubating with a secondary reagent. Alternatively, a competition assay may, be performed, in which the sample is first incubated with the HMFG analog, and then a non-limiting amount of a labeled anti-HMFG reagent is added which competes with the anti-HMFG which may be present in the sample. Suitable labels include radiolabels, enzyme labels, fluorescent labels, and chemiluminescent labels. A standard curve is constructed using solutions known to contain no anti-HMFG, and solutions with various relative concentrations of anti-HMFG, in place of the sample. The sample containing the unknown amount of anti-HMFG is generally assayed in parallel, and the relative amount of anti -HMFG contained therein is determined by comparison with the standard curve. Preferred assays for determining anti-HMFG levels using 11D10 antibody are described in more detail in a following section.

The isotype of the anti-HMFG antibody may be determined by including in the immunoassay an isotype-specific reagent, either at the separation or the labeling stage. For example, anti-human IgG may be used to separate or detect antibody of the IgG class present in a clinical sample of human origin. Presence of specific ant-HMFG of the IgG class generally indicates a memory response. Presence of anti-HMFG of the IgM class generally indicates ongoing immunostimulation, such as may be due to the presence of an HMFG expressing tumor, or ongoing treatment with 11D10.

If desired, anti-HMFG antibody detected in a biological sample may be further characterized; for example, by competition with anti-MC10 (Ab1) to determine whether, they are specific for related epitopes on HMFG. Competition assays between Ab1 and Ab3 are described in detail in the Example section.

Anti-HMFG antibody may also be tested to determine whether it is cytotoxic. Complement mediated cytotoxicity (CMC) is determined, for example, by using HMFG-expressing target cells (such as MCF-7 or SKBR3) labeled with 51Cr. Labeling may be accomplished try incubating about 106 cells with ~200 µCi Na251CrO4 for 60 minutes at 37° C., followed by washing. The assay is conducted by incubating the antibody (or clinical sample containing the antibody) with the target cells. The opsonized cells are then washed and incubated with a source of complement; for example, guinea pig serum pre-adsorbed to remove intrinsic antibody activity. After a suitable incubation period at 37°, release of 51Cr into the medium is determined and compared with that from unopsonized control cells. Release of 51Cr into the medium is determined and compared with that from unopsonized control cells. Release of 51Cr correlates with CMC activity.

Another way of characterizing the anti-HMFG antibody is by testing is ability to participate in an ADCC response (Cheresh et al. (1986), Cancer Res. 46:5112), Radiolabeled HMFG-expressing target cells are incubated with the anti-HMFG (in the form of heat-inactivated serum), and effector cells. Normal human peripheral blood mononuclear cells (PBMC) are suitable effector cells, and preferably are used at an effector:target ratio of about 100. After approximately 4 hours at 37° C., the proportion of released 51Cr is determined as a measure of ADCC activity.

The cellular immune response in a subject being administered 11D10 may be quantified by conducting standard functional assays for specific T cell activity.

One type of assay measures T cell proliferation. In this test, peripheral blood mononuclear cells (PBMC) are obtained from a whole blood sample collected) from the treated subject. For experimental animals, spleen cells may also be used. T cells may be enriched, for example, by centrifugation on a gradient such as Ficoll(TM). The cells are then cultured in the presence of HMFG or (more usually) irradiated HMFG expressing cells at various concentrations. Preferably, the stimulator cells are autologous with the responder cells, particularly in terms of histocompatibility Class II antigens.

Another type of assay measures T cell cytotoxicity. In this test, an enriched T-cell population is used to effect lysis of 51Cr-labeled HMFG expression target cells, prepared as before. Preferably, the effector cells are autologous with the target cells, particularly in terms of histocompatibility Class I antigens. The cell population may optionally be pre-stimulated with HMFG or a relevant cell line. The T cells are then combined at various ratios with about 104 labeled target cells; for example, in wells of a microliter plate. The plate is optionally centrifuged to initiate cell contact, and the cells are cultured together for 4–16 hours at 37° C. The percent specific release of 51Cr into the medium is measured in comparison with labeled targets cultured alone (negative control) and targets lysed with a detergent such as 0.1% Triton (TM) X-100 (positive control).

Other relevant measurements to determine the effect of 11D10 administration include clinical tests as may be appropriate in determining the progression of cancer of the suspected type. Such tests may include inflammatory indicators, mammography, and radioscintigraphy, such as are described elsewhere in this disclosure.

Use of 11D10 to conduct immunoassays. Another way that 11D10 can be used is to assay for the presence of an antibody or other immune component that binds to 11D10, or to HMFG. Such components may be present following therapeutic administration of 11D10, or may spontaneously arise due to the presence of an HMFG-expressing tumor in an immunocompetent host. Assays may be conducted on biological samples, usually clinical samples.

In one embodiment of this invention, 11D10 is used to detect the presence of an anti-HMFG, particularly anti-11D10 idiotype, that may be present in a biological sample. The sample is suitably prepared before conducting the assay, optionally by enriching for antibody, activity. If the biological sample is suspected of containing antibody activity against non-idiotypic regions of 11D10 (particularly anti-mouse immunoglobulin), it is preferable to remove them or conduct the assay so as to avoid their detection. Anti-mouse immunoglobulin antibody can be removed from a sample, for example, by precipitation with normal mouse IgG or adsorption with a mouse Ig adsorbant. Binding of anti-mouse immunoglobulin antibody, particularly that specific for the Fc region, can be minimized by judicious choice of the reagents of the assay. F(ab')2 or Fab fragments of 11D10 and other mouse immunoglobulin reagents are especially appropriate.

After the sample is suitably prepared, it is mixed with a excess functional equivalent of 11D10 under conditions that permit formation of a complex between 11D10 and any anti-HMFG that may be present. The amount of complex is then determined, and compared with complexes formed with standard samples containing known amounts of anti-HMFG in the range expected Complex formation may be observed by immunoprecipitation or nephelometry, but it is generally more sensitive to employ a reagent labeled with such labels as radioisotopes like 125I, enzymes like peroxidase and β-galactosidase, or fluorochromes like fluorescein.

Antibody assays may be conducted in fluid phase. For example, anti-HMFG may be mixed with labeled 11D10. Alternatively, the anti-HMFG in the sample may be used to compete with a labeled anti-HMFG for binding sites on 11D10. Generally, bound and unbound label is separated to quantitate the percent bound. Suitable separation methods include gel filtration chromatography, and precipitation with antibody against immunoglobulin of the species from which the sample is obtained, optionally in the presence of polyethylene glycol. Alternatively, the proportion of bound and unbound label may be determined in situ, for example, using fluorescence/quench labeling pairs or enzyme/inhibitor labeling pairs. See, e.g., U.S. Pat. No. 3,996,345 (Ullman et al.).

It is generally more convenient to conduct a capture assay using a reagent linked to a solid phase, such as a polyethylene test tube, microtiter plate well, or magnetic bead. In a competition-type capture assay, unlabeled anti-HMFG in the sample competes with a labeled anti-HMFG reagent for binding to 11D10. The 11D10 may be attached directly to the solid support, or captured later, for example, using an anti-11D10. In this assay, the amount of label associated with the solid phase is inversely related to the amount of anti-HMFG in the sample.

In the sandwich-type capture assay, anti-HMFG is captured by 11D10 attached directly or through a secondary reagent to a solid phase. After washing, the anti-HMFG is detected using anti-immunoglobulin of the appropriate species, or a second 11D10 antibody, to which a label is directly or indirectly attached Alternatively, the anti-immunoglobulin may be attached to the so id phase and labeled 11D10 is used to complete the sandwich. If the anti-immunoglobulin used is isotype specific, then the class of the antibody may also be determined. In this type of assay, the amount of label associated with the solid phase correlates positively with the amount of anti-HMFG in the sample.

Other methods of measuring specific antibody are known it the art, and may be adapted to measure anti-HMFG by using 11D10 as the target antigen. All such adapted methods are embodied in this invention. Further descriptions of particular embodiments are provided in the Example section.

11D10 may also be used to measure the level of cellular anti-HMFG activity, particularly anti-11D10 idiotype. In a preferred example, 11D10 is used to identify anti-HMFG T cells, defined for this purpose as lymphocytes expressing a T cell receptor that binds the 11D10 idiotype. 11D10 may be labeled and contacted with a population of cells suspected of containing anti-HMFG T cells. Alternatively, unlabeled 11D10 may be mixed with the cells, and followed with a labeled secondary reagent such as labeled anti-mouse immunoglobulin or protein A. Suitable labels for this purpose include radiolabels and fluorescent labels. The use of fluorescent labels would also allow anti-HHMFG cells to the separated from non-specific cells in a fluorescence-activated cell sorter.

Use of 11D10 to remove labeled Ab1. The invention also encompasses methods using 11D10 to remove a label, for example radioactivity, from an individual who has received a labeled anti-HMFG antibody (Ab1), for example, for radioscintiligraphy or radiotherapy. One problem common to use of antibody targeted radionuclides (i.e., radioimmunotherapy) has been the presence of excess Ab1 in the system which limits the dosage of radiolabeled antibody for treatment. Further, effective imaging using radiolabeled antibodies is hampered due to excess circulating radiolabeled antibody, which of ten takes several days to clear circulation and tissues. In these methods of the present invention, 11D10 is administered to the individual at a specified time after administration of the labeled anti-HMFG. The intention is for the 11D10 to complex with anti-HMFG at sites other than the tumor, such as in the circulation and interstitial spaces, and thereby promote its clearance. As a result, the level of labeled moiety (such as radioisotope), in unaffected tissues is reduced, and the image of the tumor (in comparison to neighboring tissues) is enhanced. Similarly, when radionuclides are given to subjects for irradiation of a tumor site, it is desirable to reduce collateral exposure of unaffected tissue. This invention thus includes methods of treatment in which a radiolabeled anti-HMFG antibody is administered in a therapeutic dose, and followed by a molar excess of 11D10.

In either of these applications, an amount of 11D10 is chosen that is in sufficient molar excess over the labeled anti-HMFG to locate and bind any anti-HMFG that is no: located at the tumor site. The timing of administration and amount of 11D10 will depend upon the nature of the radiolabeled antibody, the type of radioisotope used and the condition of the individual. Preferably, the molar ratio of 11D10 to the anti-HMFG antibody is at least about 5:1, more preferably about 25:1 to 200:1. Preferably, 11D10 is administered 5 to 24 hours after the individual has received the anti-HMFG antibody.

Use of 11D10 to detect anti-HMFG antibody bound to a tumor cell. The invention also includes methods of detecting the presence of an anti-HMFG antibody bound to a tumor cell comprising the steps of treating the tumor cell with 11D10 for a sufficient time to allow binding to the anti-HMFG antibody, and detecting the presence of any complex formed. The intention is for the 11D10 to detect anti-HMFG that has pre-attached to the tumor cell; or alternatively, to promote the binding of anti-HMFG to the tumor cell try forming a polyvalent anti-HMFG/11D10 immune complex. In the former Instance, the 11D10 is provided with a detectable label or a means by which a label can be attached. In the latter instance, either the anti-HMFG or the 11D10 is provided with a label.

This strategy may be used, for example, to identify an HMFG antigen-bearing cell in a isolated all suspension. The cells are incubated sequentially or simultaneously with anti-HMFG and 11D10, washed, and then the labeled cells are detected. Preferred labels for this embodiment include fluorescent labels, such as fluorescein, rhodamine, and Texas red. Optionally, labeled cells may be separated from unlabeled cells; for example, by sorting in a fluorescence-activated cell sorter or by affinity separation, using any of the solid phase positive or negative immunoselection techniques known in the art.

The strategy may also be used, for example, to detect or image tumors in an affected subject The anti-HMFG and 11D10 are administered (usually sequentially) into the subject and allowed to accumulate at the tumor site. Suitable labels include radiolabels such as 111In, 131I and 99mTc.

The tumor is then detected or visualized using standard techniques of radioscintigraphy.

11D10 Polynucleotides

The invention encompasses polynucleotides encoding the anti-idiotype antibody 11D10 or fragments of 11D10, based on the polynucleotide sequences shown in FIGS. 1 and 2. These polynucleotides are isolated and/or produced by chemical and/or recombinant methods, or a combination of these methods. Unless specifically stated otherwise, the terms "polynucleotides" or "11D10 polynucleotides" shall include all embodiments of the polynucleotides of this invention. The 11D10 polynucleotides of this invention are useful as probes, primers, in expression systems, and in pharmaceutical preparations, including vaccines. Especially useful applications of the polypeptides will be discussed below.

Accordingly, the present invention provides an isolated polynucleotide that contains a sequence encoding a polypeptide having immunological activity of 11D10 wherein the polypeptide comprises at least 5 contiguous amino acids of a variable region of 11D10. In one embodiment, the encoding polynucleotide sequence encodes variable region from the light chain. In another embodiment, the encoding polynucleotide sequence encodes variable region from the heavy chain.

The invention also provides 11D10 polynucleotides that are depicted in FIGS. 1 and 2. In one embodiment, an isolated polynucleotide encoding a polypeptide having immunological activity of 11D10 is provided, wherein the polypeptide comprises at least 5 contiguous amino acids of a variable light chain of 11D10 depicted within SEQ ID NO:2 (FIG. 1). In another embodiment, an isolated polynucleotide encoding a polypeptide having immunological activity of 11D10 is provided, wherein the polypeptide comprises at least 5 contiguous amino acids of a variable heavy chain of 11D10 depicted within SEQ ID NO:4 (FIG. 2). In another embodiment, the (variable region) encoding polynucleotide sequence is depicted within SEQ ID NO:1 (FIG. 1). In another embodiment, the (variable region) encoding polynucleotide sequence is depicted within SEQ ID NO:3 (FIG. 2). The polynucleotide sequence may be similar to those depicted in SEQ ID NO:1 (FIG. 1) or SEQ ID NO:3 (FIG. 2) with minor changes designed to optimize colon usage or stability or may vary significantly. It is within the skill of one in the art, given the amino acid sequence in SEQ ID NO:2 or SEQ ID NO:4, to design such polynucleotides. FIG. 1 depicts the nucleotide sequence SEQ ID NO:1 and derived amino acid sequence (SEQ ID NO:2) of the variable region of the light chain of 11D10. FIG. 2 depicts the nucleotide sequence SEQ ID NO:3 and derived amino acid sequence (SEQ ID NO:4) of the variable region of the heavy chain of 11D10. The nucleotide sequence of SEQ ID NO:1 is 435 base pairs and was obtained from clones as described in Example 2. The polynucleotide sequence of SEQ ID NO:3 is 467 base pairs and was obtained as described in Example 2.

In another embodiment, the invention encompasses a polynucleotide encoding a portion of the 11D10 light chain variable region, comprising at least about 60 contiguous nucleotides, preferably 70 contiguous nucleotides, preferably at least about 80 contiguous nucleotides, s, more preferably at least about 100 contiguous nucleotides, even more preferably at least about 150 contiguous nucleotides of (SEQ ID NO:1. The invention also encompasses a polynucleotide encoding a portion of the 11D10 light chain variable region, comprising at least about 15 contiguous nucleotides, preferably at least about 25 contiguous nucleotides, more preferably at least about 30 contiguous nucleotides of the CDR1 encoding sequence thereof. The invention also encompasses a polynucleotide encoding a portion of the 11D10 light chain variable region, comprising at least about 10 contiguous nucleotide s, preferably at least about 15 contiguous nucleotides, even more preferably at least about 20 contiguous nucleotides of the CDR2 or CDR3 encoding sequence thereof.

In another embodiment, the invention encompasses a polynucleotide encoding a portion of the 11D10 heavy chain variable region, comprising at least about 60 contiguous nucleotides, preferably at least about 70 contiguous nucleotides, preferably at least about 80 contiguous nucleotides, more preferably at least about 100 contiguous nucleotides, even more preferably at least about 150 contiguous nucleotides of SEQ ID NO:3. The invention also encompasses a polynucleotide encoding a portion of the 11D10 heavy chain variable region, comprising at least 10 contiguous nucleotides, preferably at least about 15 contiguous nucleotides of the CDR1 encoding sequence thereof. The invention also encompasses a polynucleotide encoding a portion of the 11D10 heavy chain variable region, comprising at least about 15 contiguous nucleotides, preferably at least about 20 contiguous nucleotides, preferable at least about 25 contiguous nucleotides, more preferably at least about 35 contiguous nucleotides, even more preferably at least abort 50 contiguous nucleotides of the CDR2 or CDR3 encoding sequence thereof.

In another embodiment, the invention encompasses any of the above-described 11D10 polynucleotides, wherein the polynucleotide(s) encodes at least five amino acids of a complementarity defining region (CDR). CDRs are discussed below.

The invention includes modifications to the 11D10 polynucleotides described above such as deletions, substitutions, additions, or changes in the nature of any nucleic acid moieties. A "modification" is any difference in nucleotide sequence as compared to a polynucleotide shown herein to encode a 11D10 polypeptide fragment, and/or any difference in terms of the nucleic acid moieties of the polynucleotide(s). Such changes can be useful to facilitate cloning and modifying expression of 11D10 polynucleotides. Such changes also can be useful for conferring desirable properties to the polynucleotide(s), such as stability. The definition of polynucleotide provided herein gives examples of these modifications.

The invention encompasses 11D10 polynucleotides including full-length (unprocessed), processed, coding, non-coding or portions thereof, provided that these polynucleotides contain a region encoding at least a portion of a variable region of 11D10. Also embodied ant the mRNA and cDNA sequences and fragments thereof that include a portion of the variable region encoding segment.

The invention also encompasses polynucleotides encoding for functionally equivalent variants and derivatives of 11D10 and functionally equivalent fragments thereof which may enhance, decrease or not significantly affect properties of the polypeptides encoded thereby. These functionally equivalent variants, derivatives, and fragments display the ability to induce an immune response, preferably an anti-HMFC immune response. For instance, changes in a DNA sequence that do not change the encoded amino acid sequence, as well as those that result in conservative substitutions of amino acid residues, one or a few amino acid deletions or additions, and substitution of amino acid residues by amino acid analogs are those which will not significantly affect properties of the encoded polypeptide.

Nucleotide substitutions that do not alter the amino acid residues encoded can be useful for optimizing gene expression in different systems. Suitable substitutions are known to those of skill in the art and are made, for instance, to reflect preferred codon usage in the particular expression systems. In another example, alternatively spliced polynucleotides can give rise to a functionally equivalent fragment or variant of 11D10. Alternatively processed polynucleotide sequence variants are defined as polynucleotide sequences corresponding to mRNAs that differ in sequence for one another but are derived from the same genomic region, for example, mRNAs that result from: 1) the use of alternative promoters; 2) the use of alternative polyadenylation sites; or 3) the use of alternative splice sites.

The 11D10 polynucleotides of the invention also include polynucleotides encoding other 11D10 fragments. The polynucleotides encoding 11D10 fragments are useful, for example, as probes, therapeutic agents, and as a template for encoding various functional and/or binding domains of 11D10. Accordingly, the invention includes a polynucleotide that comprises a region of at least 15 contiguous nucleotides, more, preferably at least about 20 contiguous nucleotides, more preferably at least about 25 contiguous nucleotides, more preferably at least about 35 contiguous nucleotides, more preferably at least about 50 contiguous nucleotides, even more preferably at least about 75 contiguous nucleotides, even more preferably at least about 100 contiguous nucleotides, even more preferably at least about 200 contiguous nucleotides, even more preferably at least about 300 contiguous nucleotides that forms a stable hybrid with a polynucleotide encoding light chain or heavy chain variable region of 11D10, but not with other immunoglobulin encoding regions known at the time of filing of this application. In one embodiment, the region is capable of forming a stable duplex with a polynucleotide consisting of light chain variable encoding sequence of SEQ ID NO:1 under conditions where the region does not forms a stable hybrid with SEQ ID NO:5 through SEQ ID NO:14. In another embodiment, the region is capable of forming a stable duplex with a polynucleotide consisting of heavy chain variable encoding sequence of SEQ ID NO:3 under conditions where the region does not form a stable hybrid with SEQ ID NO:5 through SEQ ID NO:32.

In another embodiment, the 11D10 polynucleotide fragments comprise about 15, preferably 20, even more preferably 30 bases of the sequence depicted in FIG. 1 (SEQ ID NO:1) or FIG. 2 (SEQ ID NO:3). A fragment of this approximate size could encode for a binding site for an Ab1 or Ab3 antibody. Suitable fragments are those which hybridize specifically to 11D10 DNA or RNA such that they are effective as primers or probes. The primers are particularly useful in the polymerase chain reaction (PCR).

Hybridization reactions can be performed under conditions of different "stringency". Conditions that increase stringency of a hybridization reaction of widely known and published in the art. See, for example, Sambrook and Maniatis. Examples of relevant conditions include (in order of increasing stringency): incubation temperatures of 25° C., 37° C., 50° C. and 68° C.; buffer concentrations of 10×SSC, 6×SSC, 1×SSC, 0.1×SSC (where SSC is 0.15 M NaCl and 15 mM citrate buffer) and their equivalent using other buffer systems; formamide concentrations of 0%, 25%, 50%, and 75%; Incubation times from 5 minutes to 24 hours; 1, 2, or more washing steps; wash incubation times of 1, 2, or 15 minutes; and wash solutions of 6×SSC, 1×SSC, 0.1×SSC, or deionized water.

"Tm" is the temperature in degrees Centigrade at which 50% of a polynucleotide duplex made of complementary strands hydrogen bonded in anti-parallel direction by Watson-Crick base pairing dissociates into single strands under conditions of the experiment. Tm may be predicted according to a standard formula, such as:

$$Tm=81.5+16.6 \log[Na^+]+0.41 (\%G/C)-0.61 (\%F)-600/L$$

where [$Na^+$] is the cation concentration (usually sodium ion) in mol/L; (%G/C) is the number of G and C residues as a percentage of total residues in the duplex; (%F) is the percent formamide in solution (wt/vol); and L is the number of nucleotides in each strand of the duplex Useful 11D10 polynucleotides encoding fragments of 11D10 can be obtained by generating polynucleotide fragments (based on SEQ ID NO:1 in FIG. 1 or SEQ ID NO:3 in FIG. 2, for example) and testing the polypeptides encoded thereby for the function of interest. Alternatively, given a desired 11D10 polypeptide, a polynucleotide sequence could be derived from the amino acid sequence of the 11D10 polypeptide. For example, 11D10 polypeptides can be tested for their ability to bind Ab1 and/or Ab3, or to elicit an immune response. Assays for these various functions are discussed below.

The invention also includes polynucleotides encoding 11D10 derivatives or variants which contain one or more 11D10 polypeptides, such as polynucleotides encoding scFv, polymers, fusion proteins, and chimeras. These forms of 11D10 are discussed below.

The invention also provides polynucleotides covalently linked with a detectable label. Such polynucleotides are useful, for example, as probes for detection of related nucleotide sequences.

Preparation of 11D10 Polynucleotides

The polynucleotides of this invention can be obtained using chemical :synthesis, recombinant methods, or PCR.

Methods of chemical polynucleotide synthesis are well known in the art and need not be described in, detail herein. One of skill in the art can use the sequences provided herein and a commercial DNA synthesizer to produce a desired DNA sequence.

For preparing 11D10 polynucleotides using recombinant methods, a polynucleotide comprising a desired sequence can be inserted into a suitable vector, and tire vector in turn can be introduced into a suitable host cell for replication and amplification. Polynucleotides may be inserted into host cells by any means known In the art Cells are transformed by introducing an exogenous polynucleotide by direct uptake, endocytosis, transfection, f-mating or electroporation. Once introduced, the exogenous polynucleotide can be maintained within the cell as a non-integrated vector (such as a plasmid) or integrated into the host cell genome. The polynucleotide so amplified can be isolated from the host call by methods well known within the art. See, e.g., Sambrook et al. (1989).

Alternatively, PCR allows reproduction of DNA sequence;. PCR technology is well known in the art and is described in U.S. Pat. Nos. 4,683,195, 4,800,159, 4,754 065 and 4,683,202, as well as *PCR: The Polymerase Chain Reaction*, Mullis et al. eds., Birkauswer Press, Boston (1994).

RNA can be obtained by using the isolated DNA in an appropriate vector and inserting it into a suitable host cell. When the cell replicates and the DNA is transcribed into RNA, the RNA can then be isolated using methods well known to those of skill in the art, as set forth in Sambrook et al., (1989), for example.

If used as a vaccine, plasmids containing 11D10 polynucleotides are prepared as described by Horn et al. ((1995)

*Human Gene Therapy* 6:565–573) which produces a pharmaceutical grade plasmid DNA suitable for administration.
Cloning and Expression Vectors Comprising a 11D10 Polynucleotide The present invention further includes a variety of vectors having cloned therein 11 D10 polynucleotide(s). These vectors can be used for expression of recombinant polypeptides as well as a source of 11D10 polynucleotides. Cloning vectors can be used to obtain replicate copies of the 11D10 polynucleotides they contain, or as a means of storing the polynucleotides in a depository for future recovery. Expression vectors (and host cells containing these expression vectors) can be used to obtain polypeptides produced from the polynucleotides they contain. They may also be used where it is desirable to express 11D10 polypeptides in an individual and thus have intact cells capable of synthesizing the polypeptide, such as in gene therapy. Suitable cloning and expression vectors include any known in the art, e.g., those for use in bacterial, mammalian, yeast and insect expression systems. Specific vectors and suitable host cells are known in the art and need not be described in detail herein. For example, see Gacesa and Ramji, *Vectors*, John Wiley & Sons (1994).

Cloning and expression vectors typically contain a selectable marker (for example, a gene encoding a protein necessary for the survival or growth of a host cell transformed with the vector), although such a marker gene can be carried on another polynucleotide sequence co-introduced into the host cell. Only those host cells into which a selectable gene has been introduced will survive and/or grow under selective conditions. Typical selection genes encode protein(s) that (a) confer resistance to antibiotics or other toxins substances, e.g., ampicillin, neomycyin, methotrexate, etc.; (b) complement auxotrophic deficiencies; or (c) supply critical nutrients not available from complex media. The chic ice of the proper marker gene will depend on the host cell, and appropriate genes for different hosts are known in the art. Cloning and expression vectors also typically contain a replication system recognized by the host.

Suitable cloning vectors may be constructed according to standard techniques, or may be selected from a large number of cloning vectors available in the art. While the cloning vector selected may vary according to the host cell intended to be used, useful cloning vectors will generally have the ability to self-replicate, may possess a single target for a particular restriction endonuclease, and/or may carry genes for a marker that can be used in selecting clones containing the vector. Suitable examples include plasmids and bacterial viruses, e.g., pUC18, mp18, mp19, pBR322, pMB9, ColE1, pCR1, RP4, phage DNAs, and shuttle vectors such as pSA3 and pAT28. These and many other cloning vectors are available from commercial vendors such as BioRad, Strategene, and Invitrogen.

Expression vectors generally are replicable polynucleotide constructs that contain a polynucleotide encoding a 11D10 polypeptide of interest The polynucleotide encoding the 11D10 polypeptide is operatively linked to suitable transcriptional controlling elements, such as promoters, enhancers and terminators. For expression (i.e., translation), one or more translational controlling elements are also usually, required, such as ribosome binding sites, translation initiation sites, and stop codons. These controlling elements (transcriptional and translational) may be derived from 11D10 nucleotides (i.e., the 11D10 gene), or they may be heterologous (i.e., derived from other genes and/or other organisms). A polynucleotide sequence encoding a signal peptide can also be included to allow a 11D10 polypeptide to cross and/or lodge in cell membranes or be secreted from the cell. A number of expression vectors suitable for expression in eukaryotoic cells including yeast, avian, and mammalian cells are known in the art. One example of an expression vector is pcDNA3 (Invitrogen, San Diego, Calif., in which transcription is driven by the cytomegalovirus (CMV) early promoter/enhancer. This vector alto contains recognition sites for multiple restriction enzymes for insertion of the 11D10 polynucleotide of interest. Another example of an expression vector (system) is the baculovirus/insect system.

The vectors containing the polynucleotides of interest can be introduced into the host cell by any of a number of appropriate means, Including electroporation, transfection employing calcium chloride, rubidium chloride, calcium phosphate, DEAE-dextran, or other substances; microprojectile bombardment lipofection; and infection (where the vector is an infectious agent, such as vaccinia virus, which is discussed below). The choice of means of introducing vectors or 11D10 polynucleotides will often depend on the host cell.

Once introduced into a suitable host cell, for example, *E. coli* or COS-7, expression of a 11D10 polypeptide(s) can be determined using any of the assays described herein. For example, presence of 11D10 polypeptide can be detected by RIA or ELISA of the culture supernatant (if the 11D10 polypeptides) is secreted) or cell lysates.

A particularly useful expression vector for 11D10 polynucleotides is a vaccinia virus comprised of a 11D10 polynucleotide sequence, which can also be used in vaccine preparations. Moss (1991) *Science* 252:1662–1667. To introduce polynucleotide sequences encoding 11D10 polypeptide, including 11D10 polypeptide fragments, into vaccinia, the polynucleotide sequence of interest is first inserted into a plasmid containing a vaccinia virus promoter with flanking sequences homologous to vaccinia DNA inessential for replication. Plasmid-containing cells are then infected with vaccinia, which leads to a low level of homologous recombination between plasmid and virus, with resultant transfer of the vaccinia promoter and 11D10 polypeptide-encoding polynucleotide sequence into the vaccinia virus genome. Typically, the 11D10 polynucleotide is inserted into the viral tk (thymidine kinase) gene. Insertion into the tk site attenuates the virus more than 10,000 fold compared to wild type (Flexner et al. (1980) *Vaccine* 88 (Cold Spring Harbor Laboratory), 179–184). Recombinant virus is identified by the tk' phenotype. Preferably, expression of the 11D10 polynucleotide is under the control of the vaccinia early/late promoter (7.5 K), whereby the resultant 11D10 polypeptides can be expressed in infected cells throughout the life cycle of the virus. However, other promoters known in the art can be used, such as pH6, synthetic promoters, SV40 promoters or promoters from adenovirus. Expression of the 11D10 polypeptide(s) occur, in cells infected with the recombinant vaccinia or individuals which are immunized with the live recombinant vaccinia virus. Construction of a vaccinia vector for expression of 11D10 polypeptides is provided in Example 4. Any one of several strains of vaccinia can be used, including, but not limited to, WR, ALVAC, and NYVAC. The ALVAC and NYVAC strains are used to infect avian cells.

A vaccinia vector of this invention can contain one or more polynucleotides encoding a 11D10 polypeptide(s). It can also contain polynucleotide sequences encoding other polypeptides that enhance, facilitate, or modulate the desired result, such as lymphokines, including, but not limited to, IL-2, IL-4 and GM-CSF. A preferred lymphokine is GM-CSF. If GM-CSF is used, it is also ;preferable to eliminate AU-rich elements from the 3' untranslated regions of RNA transcripts and/or eliminate sequences in the 5' untranslated region that are capable of forming a hairpin loop by recombinant methods. Also encompassed by this invention are vaccinia vectors encoding for recombinant 11D10 variants containing 11D10 polypeptides, such as scFvs, chimeras, and polymers (described be low).

Host Cells Transformed with 11D10 Polynucleotides

Another embodiment of this invention are host cells transformed with (i.e., comprising) 11D10 polynucleotides and/or vectors having 11D10 polynucleotide(s) sequences, as described above. Both prokaryotic and eukaryotic host cells may be used. Prokaryotic hosts include bacterial cells, for example *E. coli* and mycobacteria. Among eukaryotic hosts are yeast, insect, avian, plant and mammalian cells. Host systems are known in the art and need not be described in detail herein. One example of a mammalian host cell is NS0, obtainable from the European Collection of Cell Cultures (England). Transfection of NS0 cells with a plasmid, for example, which is driven by a cytomegalovirus (CMV) promoter, followed by amplification of this plasmid in using glutamine synthetase provides a useful system for protein production. Cockett et al. (1990) *BioTechnology* 8:662–667.

The host cells of this invention can be used, inter alia, as repositories of 11D10 polynucleotides and/or vehicles for production of 11D10 polynucleotide and polypeptides. They may also be used as vehicles for in vivo delivery of 11D10 polypeptides.

Uses for and Methods Using 11D10 Polynucleotides

The polynucleotides of this invention have several uses. 11D10 polynucleotides are useful, for example, in expression systems for the recombinant production of 11D10 or 11D10 fragments. They are also useful as hybridization probes to assay for the presence of 11D 10 polynucleotide (or related) sequences in a sample using methods well known to those in the art. Further, 11D10 polynucleotides are also useful as primers to effect amplification of desired polynucleotides. The polynucleotides of this invention are also useful as vaccines and for gene therapy.

11D10 polynucleotides of this invention can be used as primers for amplification of polynucleotides encoding 11D10 or a fragment thereof, such as in a polymerase chain reaction (PCR). PCR has been described above. The conditions for carrying out PCR reactions depend on the specificity desired, which in turn can be adjusted by the primer used and the reaction conditions Such adjustments are known In the art and need not be discussed in detail herein.

11D10 polynucleotides can also be used as hybridization probes for detection of, for example, the presence of 11D10 polynucleotides in a cell. For instance, a 11D1 C polynucleotide could be used as a probe to determine the presence of 11D10 polynucleotide sequences in cells used in gene therapy. For these methods, a suitable cell sample or a sample derived from cells (either of which are suspected of containing 11D10 polynucleotide sequences) is obtained and tested for the presence of 11D10 polynucleotide by contacting the polynucleotides from the sample with the 11D10 polynucleotide probe. The method is conducted to allow hybridization to occur between the 11D10 probe and 11D10 polynucleotide of interest, and the resultant (if any) hybridized complex is detected. Such methods entail procedures well known in the art, such as cell culture, polynucleotide preparation, hybridization, and detection of hybrid complexes formed, if any. Using similar methods, the probes can also be used to detect vectors which are in turn used to produce 11D10 polypeptides, intact 11D10, or recombinant, variant forms of 11D10

The 11D10 polynucleotides of this invention can be used in expression systems to produce 11D10 polypeptides, intact 11D10, or recombinant forms of 11D10, including intact 11D10, which have enhanced, equivalent, or different, desirable properties. These recombinant forms are made by using routine methods in the art. Examples of recombinant forms of 11D10 and 11D10 polypeptides include, but are not limited to, hybrids, chimeras, single chain variants, and fusion proteins containing other components such as cytokines A more detailed description of these recombinant forms of 11D10 and 11D10 polypeptides and how they are made is provided below.

Another use of 11D10 polynucleotides is in vaccines and gene therapy. The general principle is to administer the polynucleotide so that it either promoters or attenuates the expression of the polypeptide encoded therein. Thus, the present invention includes methods of inducing an Immune response and methods of treatment comprising administration of an effective amount 11D1 D polynucleotides) to an individual. In these methods, a 11D10 polynucleotide encoding a 11D10 polypeptide is administered to an individual, either directly or via cells transfected with the 11D10 polynucleotide(s). Preferably, the 11D10 polynucleotide is replicated inside a cell. Thus, the 11D10 polynucleotide(s) is operatively linked to a suitable promoter, such as a heterologous promoter that is intrinsically active in cells of the target tissue type, Entry of the polynucleotide into the cell is accomplished by techniques known in the art, such as via a viral expression vector, such as a vaccinia or adenovirus vector, or association of the polynucleotide with a cationic liposome. Preferably, the 11D10 polynucleotide(s) are in the form of a circular plasmid, preferably in a supercoiled configuration. Preferably, once in cell nuclei, plasmids persist as circular non-replicating episomal molecules. In vitro mutagenesis can in turn be carried out with the plasmid constructs to encode, for example, more immunogenic molecules or T cell epitopes with a desirable HLA motif.

To determine whether plasmids containing 11D10 polynucleotides are capable of expression in eukaryotic cells, eukaryotic cells such as, for example, COS-7, CHO (avian origin), or HeLa (human origin) cells can be transfected with the plasmids. Expression resulting g in a 11D10 polypeptide(s) is then determined by RIA or ELISA. Western blotting with cell lysate using MC-10 (Ab1) as a probe can be performed to check for cell-associated 11D10 polypeptide. Alternatively, for smaller 11D10 polypeptides, expression can be detected, for example, by constructing the plasmid so that the resultant 11D10 polypeptide is labeled recombinantly, such as with an enzymatic label. Further characterization of the expressed 11D10 polypeptide can be achieved by purification of the 11D10 polypeptide followed by performing the functional assays described herein (e.g., cell binding inhibition assay).

This invention also encompasses ex vivo transfection of 11D10 polynucleotides, in which cells removed from individuals are transfected with vectors encoding 11D10 polypeptides and reintroduced into the individual. Suitable transfected cells include, but are not limited to, peripheral blood mononuclear cells.

Therapeutic administration of 11D10 polynucleotides is discussed in more detail below.

11D10 Polypeptides

The present invention encompasses polypeptide fragments of 11D10 containing at least a portion of a variable region of 11D10 and proteins comprising a 11D10 fragment. The polypeptide fragments of 11D10 which may comprise any region or subregion of SEQ ID NO:2 (FIG. 1) or SEQ ID NO:4 (FIG. 2) (provided that the fragments comprise at least a portion of a variable region) are, identified and characterized by any (one or more) of the following criteria: (a) ability to bind to Ab1 and/or Ab3; (b) ability to induce an immune response against HMFG; (c) homology (i.e., substantial sequence identity) to any part of HMFG; (d) ability to palliate, ameliorate, reduce, or delay an HMFG-associated disease, particularly HMFG-associated tumors.

The polypeptide fragments of 11D10 have a variety of uses, including their use in pharmaceutical compositions and vaccines, as a diagnostic tool for monitoring Ab1 and/or Ab3 levels, their use in making antibody that binds to HMFG and their use in removing labeled Ab1 from an individual who has received labeled anti-HMFG antibody.

Unless specifically stated, the term "11D10 polypeptides" shall include all embodiments of the polypeptides of this invention.

The invention includes polypeptides having immunological activity of 11D10, wherein the polypeptide is comprised of a sequence of at least 5 contiguous amino acids from a variable region of 11D10. In one embodiment, the variable region is from a light chain, more particularly, depicted within SEQ ID NO:2 (FIG. 1). In another embodiment, the variable region is from a heavy chain, more particularly, depicted within SEQ ID NO:4 (FIG. 2). In another embodiment, the 5 contiguous amino acids are from a complementarily determining region (CDR).

The amino acid sequences of SEQ ID NO:2 (FIG. 1) and SEQ ID NO:4 (FIG. 2) are presented in FIG. 3 which depicts framework and CDR sequences of the variable regions of the light and heavy chains of 11D10, respectively. The framework sequences are responsible for the correct β-sheet folding of the VL and VH domains and for the interchain interactions that bring domains together. The complementarity determining regions (CDRs) refer to six hypervariable sequences of the variable region (3 from VL and 3 from VH) which together are thought to form the antigen binding site. Delineation of these regions as well as identification of the leader sequences of 11D10 was based on a search and analysis of Kabat's immunologic database by the BLAST program.

Another embodiment of the invention is polypeptide fragments of 11D10 which comprise the sequences selected from the group consisting of the amino acid sequences (fragments) depicted in FIG. 3. These polypeptides represent functional subregions of the light and heavy chain variable regions (i.e., framework and CDR). Preferably, these 11D10 polypeptides comprise a CDR.

The invention also includes a polypeptide fragment of the 11D10 light chain variable region, comprising at least 25 contiguous amino acids, preferably at least 23, more preferably at least 30 contiguous amino acids, even more preferably at least about 35 contiguous amino acids, even more preferably at least about 50 contiguous amino acids of the variable region depicted within SEQ ID NO:2 (FIG. 2), or at least 5 contiguous amino acids, preferably at least 7 contiguous amino acids, preferably, at least 8 contiguous amino adds, more preferably at least about 10 contiguous amino acids of the CDR1 or CDR2 thereof, or at least 7 contiguous amino acids, preferably at least 8 contiguous amino acids, more preferably at least 9 contiguous amino acids of the CDR3 thereof.

In another embodiment, the invention includes a polypeptide fragment of the 11D10 heavy chain variable region, comprising at least 17 contiguous amino acids, preferably at least 20 contiguous amino acids, preferably at least about 25 contiguous amino acids, more preferably at least about 35 consecutive amino acids, even more preferably at least about 50 contiguous am no acids of the variable region depicted within SEQ ID NO:4 (FIG. 1), or 5 contiguous amino acids of the CDR 1 thereof, or at least 6 contiguous amino acids, preferably at least 7 contiguous amino acids, more preferably; at least about 10 contiguous amino acids of the CDR2 or CDR3 thereof.

The size of the 11D10 polypeptide fragments can vary widely, as the length required to effect activity can be very small, while the maximum length typically is not detrimental to effecting activity. The minimum size must be sufficient to provide a desired function. For instance, a binding site on a polypeptide can be as small as about 5 amino acids in length, while other binding sites are formed by convergence of amino acids which are spatially proximal but not in contiguous sequence. Th us, the invention includes polypeptide fragments of 11D10 comprising a portion of the amino acid sequence depicted in SEQ ID NO:2 (FIG. 1) or SEQ ID NO:4 (FIG. 2) in which the 11D10 polynucleotide is about 5 amino acids in length. The invention also provides polypeptide fragments of 11D10 comprising a portion of the amino acid sequence depicted in SEQ ID NO:2 (FIG. 1) or SEQ ID NO:4 (FIG. 2), in which the 11D10 polynucleotide is about 10, 15, 25, 30, 50, 100, or 150 amino acids in length. The invention also provides polypeptide fragments of 11D10 comprising a portion of the amino acid sequence depicted SEQ ID NO:2 (FIG. 1) or SEQ ID NO:4 (FIG. 2) having at least about 5 amino acids and at most about 100 amino acids. As is evident to one skilled in the art, these 11D10 polypeptides, regardless of their size, can also be associated with, c or conjugated with, other substances or agents to facilitate, enhance, or modulate function and/or specificity of a 11D10 polypeptide. Examples of such modifications will be discussed below.

In another embodiment, 11D10 polypeptide fragments are provided that contain a region that is homologous to HMFG, particularly to the 20 amino acid tandem repeat within HMFG. See, eg., Larocca et al. (1992) Hybridoma 11:191–201. Such homologous fragments may at least, in part, nominally resemble the high molecular weight mucin antigen of HMFG, and thus may participate in antigen presentation by mimicking HMFG, the ultimate target antigen. These 11D10 polypeptides may also participate in antigen presentation in association with Class I major histocompatibility complex (MHC) antigens, thus triggering cytotoxic T cell killing. FIG. 23 shows alignments between similar sequences of 11D10 and HMFG, when the amino acid sequences are aligned in both orientations (i.e., aligned in the same and reverse orientations). Examples of regions of homology to HMFG encompassed by This invention are (amino acid numbering based on Amino acids 1–107 of SEQ ID NO:2; FIG. 3); (a) amino acid 51 to amino acid 52; amino acid 54 to amino acid 56; amino acid 92 to amino acid 93 of the light chain; and (b) amino acid 57 to amino acid 58 of the heavy chain. Accordingly, the invention also includes 11D10 polypeptides that comprise the amino acid sequence from about amino acid 50 to about amino acid 53, about amino acid 50 about amino acid 56, about amino acid 92 to about amino acid 93, or about amino acid 90 to about amino acid 94, of the sequence depicted in FIG. 3-A (Amino acids 1–107 of SEQ ID NO:2), as well as polypeptides that comprise from about amino acid 57 to about amino acid 58, about amino acid 55 to about amino acid 58 or, about amino acid 53 to about amino acid 58, of the sequence depicted in FIG. 3-B (Amino acids 1–118 of SEQ ID NO:4).

The invention includes modifications to 11D10 polypeptides including functionally equivalent fragments of the 11D10 polypeptides which do not significantly affect their properties and variants which have enhanced or decreased activity. Modification of polypeptides is routine practice in the art and need not be described in detail herein. Examples of modified polypeptides include polypeptides with conservative substitutions of amino acid residues, one or more deletions or additions of amino acids which do not significantly deleteriously change the functional activity, or use of chemical analogs. Amino acid residues which can be conservatively substituted for one another include but are not limited to: glycine/alanine; valine/isoleucine/leucine; asparagine/glutamine; aspartic acid/glutamic acid, serine/threonine; lysine/arginine; and phenylalanine/tyrosine. These polypeptides also include glycosylated and nonglycosylated polypeptides, as well as polypeptides with other post-translational modifications, such as, for example, glycosylation with different sugars, acetylation, and phosphorylation. Preferably, the amino acid substitutions would be conservative, i.e., the substituted amino acid would possess similar chemical properties as that of the original amino acid. Such conservative substitutions are known in the art, and examples have been provided above. Amino acid modifications can range from changing or modifying one or more amino acids to complete redesign of a region, such as the variable region. Changes in ire variable region can alter binding affinity and/or specificity. Other methods of modification include using coupling techniques known in the art, including, but not limited to, enzymatic means, oxidative substitution and chelation. Modifications can be used, for example, for attachment of labels for immunoassay, such as the attachment of radioactive moieties for radioimmunoassay. Modified 11D10 polypeptides are made using established procedures in the art and can be screened using standard assays known in the art, some of which are described below and in the Examples.

The invention also encompasses fusion proteins comprising one or more 11D10 polypeptides. In one embodiment, a fusion polypeptide is provided that comprises at least 10 contiguous amino acids of variable light chain region depicted within SEQ ID NO:2 (FIG. 1) and at least 10 amino acids of variable heavy chain region depicted within SEQ ID NO:4 (FIG. 2). In another embodiment, the fusion polypeptide contains; a heterologous immunoglobulin constant region. In another embodiment, the fusion polypeptide contains a light chain variable region and a heavy chain variable region of 11D10. For purposes of this invention" a 11D10 fusion protein contains one or more 11D10 polypeptides and another, amino acid sequence to which it is not attached in the native molecule, for example, a heterologous sequence or a homologous sequence from another region. Useful heterologous sequences include, but are not limited to, sequences that provide for secretion from a host cell, enhance immunological reactivity, or facilitate the coupling of the polypeptide to an immunoassay support or a vaccine carrier. Other examples are so-called bacterial "super antigens", such as staphylococcal enterotoxin A (SEA). Dohlsten et al. (1994) Proc. Natl. Acad. Sci. USA 91:8945–8949. For instance, a 11D10 polypeptide can be fused with a bioresponse modifier. Examples of bioresponse modifiers include, but are not limited to, cytokines or lymphokines such as GM-CSF, interleukin-2 (IL-2), interleukin 4 (IL-4), and γ-interferon. Accordingly, the invention includes 11D10 fusion polypeptides that contain GM-CSF or IL-2. FIG. 25 depicts an example of a plasmid construct for a fusion of a 11D10 polypeptide and preferred lymphokines GM-CSF or IL-2. Co-transfection of this plasmid (which, as shown, encodes the 11D10 heavy chain) with a plasmid encoding the 11D10 light chain also yields a 11D10 fusion polypeptide. Preferably, a plasmid encoding an 11D10 light chain is first transfected into Sp2/0 or NS0 cells by protoplast fusion (Shin et al. (1989) Meth. Enzym. 178: 459–476) followed by transfection of a plasmid containing coding sequences for a 11D10 heavy chain by electroporation into high producing clones from the first transfection. Shin et al (1989). These procedures are described in more detail in Example 7.

An antibody (that is, an antibody containing a heavy and light chain) produced as a result of transfection of the above plasmids (whether by co-transfection or sequential transfection) can be detected by any assay that detects formation of a light chain coupled to a heavy chain. Such assays are routine in the art. For instance, non-reducing SDS gel electrophoresis can be used to detect the presence of an antibody molecule that contains both the light and heavy chains, as indicated by molecular weight. Another example of an assay that detects light chain coupled to heavy chain is an ELISA as follows. Microliter plates are coated with goat anti-human kappa light chain antibody at standard concentrations, blocked with BSA and washed. The coated plates are reacted with culture supernatant (if cells expressing various test constructs. After washing, the plates are then treated with goat antihuman gamma-1 antibody with alkaline phosphatase conjugate and developed in the usual manner. Optical density is measured at 405 nm. If the fusion antibody contains a bioreactive molecule, such as a cytokine, the antibody can also be detected by using an assay that measures the reactivity of, for example, the cytokine. Such as says are known in the art and need not be described in detail herein. For example, a GM-CSF fusion 11D10 antibody and/or 11D10 polypeptide can be detected as follows. Plates are coated with goat antihuman kappa antibody, and the coated plates are reacted with culture supernatant (if the fusion is secreted). The reacted plates are then treated with rat antibody to murine GM-CSF/biotin conjugate, and a resultant complex is detected by measuring optical density at 490 nm. These assays are described in more detail in Example 7.

Alternatively, the plasmid of FIG. 25 can be transfected into a (heavy chain loss mutant For example, heavy chain loss mutants can be obtained by treating 2×107 11D10 cells with fluorescein-labeled rabbit anti-mouse IgG (H chain specific, DAKO Corporation, Carpinteria, Calif.) according to the supplier's instruction. The stained and unstained cell populations are analyzed ina fluorescence-activated cell sorter. The unstained cells are collected in a sterilized tube and placed in 96-well plates with 1 cell/well by limiting dilution. The culture supernatants are then assayed by ELISA usinggoat anti-mouse IgG (heavy chain specific) and goat anti-mouse kappa. The clones with kappa-positive and IgG-negative phenotype are subcloned at least 3 times to obtain stable 11D10(-H) mutants. Putative heavy chain loss mutant (11D10(-H)) clones can be isolated and the sequence of the light chain variable region cDNA is determined to verify that the remaining light chain is that of 11D10. Reverse PCR of the mRNA for 11D10 VH is performed with 2 sets of 5'- and 3'-primers, used for cloning of 11D10(-H) cDNA (Example 2). A heavy chain loss mutant should yield no detectable DNA band. Transfection of these cells with the heavy chain construct can then be accomplished using standard methods in thelectroportion.

A 11D10 fusion polypeptide can be created, for example, by chemical synthesis, or by creating and translating a polynucleotide in which the peptide regions are encoded in the desired relationship. These fusion proteins can be useful for enhancing, modifying, and/or facilitating an activity of a 11D10 polypeptide.

The invention also encompasses altered, recombinant forms of 11D10 comprising 11 D10 polypeptide(s), that is, 11D10 polypeptides that contain at least a portion of a variable region of 11D10 as depicted In FIGS. 1 and 2. As used herein, an "altered" or "recombinant" form of 11D10 contains a 11D10 polypeptide(s) in a sequence and/or configuration that is different than that of intact 11D10. A recombinant form of 11D10 antibody included in this invention is a hybrid antibody, in which one pair of heavy and light chains is homologous to those in a first antibody, which the other pair of heavy and light chains is homologous to those in a different second antibody. For purpose; of this invention, one pair of light and heavy chains is from 11D10. Typically, each of these two pairs will bind different epitopes of HMFG. Such hybrids may also be formed using chimeric chains, as set forth below.

In another embodiment, 11D10 chimeras are provided in which the heavy and/or light chains are fusion proteins. Typically the constant domain of the chains is from one particular species and/or class, and the variable domains are from a different species and/or class. For instance, a humanized' 11D10 antibody is one in which the constant region is of human origin, and the variable region is from 11D10 (i.e., murine). Also embodied within the invention is an antibody with a humanized variable region, in which the CDR regions comprise 11D10 amino acid sequences, while the framework regions are derived from human sequences. See, for example, EP 0329400, Also embodied are functional fragments of chimeras. An example is a humanized Fab fragment, which contains a human hinge region, a human first constant region, a human kappa light or heavy chain constant region, and the variable region from 11D10. The humanized 11D10 Fab fragments can in turn be made to form Fab dimers. Typically, the 11D10 fusion proteins and 11D10 chimeras of this invention are made by preparing an expressing a polynucleotide encoding them using recombinant methods described herein, although they may a so be prepared by other means known in the art, including, for example, chemical synthesis.

Another example of altered, recombinant forms of 11D10 encompassed by this invention is altered antibodies, which refers to antibodies in which the amino acid sequence of 11D10 has been varied. Using standard recombinant techniques, 11D10 antibodies can be designed to obtain desired properties. For instance, a change in amino acid sequence can result in greater immunogenicity of the resultant 11D10 polypeptide. The changes range from changing of one or more amino acids to the complete redesign of a region, for example, the constant region. Changes in the constant region, in general, can attain desired cellular process characteristics, e.g., changes in complement fixation, interaction with membranes, and other effector functions. Changes in the variable region may be made to alter binding characteristics. The altered/recombinant 11D10 antibody can also be designed to aid the specific delivery of a substance (such as a lymphokine) to an effector cell. Other amino acid sequence modifications have been discussed above.

The invention also encompasses single chain variable region fragments ("scFv") of 11D10. Single chain variable region fragments are made by linking light and/or heavy chain variable regions by using a short linking peptide. Bird et al. (1988) Science 242: 423–426. An example of s linking peptide is (GGGGS)3 (SEQ ID NO:35), which bridges approximately 3.5 nm between the carboxy terminus of one variable region and the amino terminus of the other variable region. Linkers of other sequences have been designed and used. Bird et al. (1988). Linkers can in turn be modified for additional functions, such as attachment of drugs or attachment to solid supports.

Accordingly, one embodiment of the present invention is a fusion polypeptide comprising at least 10 contiguous amino acids of light chain variable region depicted within SEQ ID NO:2 (FIG. 1) and at least 10 contiguous amino acids of heavy chain variable region depicted within SEQ ID NO:4 (FIG. 2), wherein the amino acid segments are joined by a linker polypeptide of about 5 to 20 amino acids. In another embodiment the fusion polypeptide (scFv) comprises the light chain variable region of the amino acid sequence depicted in SEQ ID NO:2 (FIG. 1) and heavy chain variable region of the amino acid sequence depicted in SEQ ID NO:4 (FIG. 2).

Any peptide having sufficient flexibility and length can be used as a linker in a scFv. Usually the linker is selected to have little to no immunogenicity. Regarding the 11D10 components of scFv, all or a portion of the heavy and/or light chain can be used. Typically, the entire variable regions are included in the scFv. For instance, the light chain variable region can be linked to the heavy chain variable region. Alternatively, a portion of the light chain variable region can be linked to the entire or a portion of the heavy chain variable region. For asymmetrical linkers, such as (GGGGS)3 (SEQ ID NO:35), the scFvs can be assembled in any order, for example, VH—(linker)—VL or VL—(linker)—VH. However, if expressed in E. coli, there may be a difference in the level of expression of these two configurations. It is also possible to construct a hybrid, or biphasic, scFv in which one component is a 11D10 polypeptide, and another component is a different polypeptide, such as a T cell epitope. Tandem scFvs can also be made, such as (X)—(linker)—(X)—(linker)—(X), in which X are 11D10 polypeptides, or combinations of 11D10 polypeptides with other polypeptides.

The single chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or procaryotic, such as E. Coli. Polynucleotides encoding the scFv of interest can be made by routine manipulation, such as ligation of polynucleotides. The resultant scFv can be isolated using standard protein purification techniques known in the art.

A particularly useful system for the production of 11D10 scFv's is plasmid vector pET-22b(+) (Novagen, Madison, Wis.) in E. coli, pET-22b(+) contains a nickel ion binding domain consisting of 6 sequential histidine residues, which serves as a basis for scFv purification. This example (presented in Example 7) is for illustrative purposes only, however, and is not limiting Another example of a vector that can be used is pcDNA3 (Invitrogen, San Diego, Calif.) which has been described above.

If E. coli is used for scFv production, conditions should be such that the scFv polypeptide can assume optimal tertiary and quaternary structure. Depending on the plasmid used (especially the activity of the promoter) and the host cell, it may be necessary to modulate the production of the scFv. For instance, use of a weaker promoter, or expression at lower temperatures, may be necessary to optimize production of the scFv. Alternatively, expression of scFv in eukaryotic cells, such as yeast, insect, plant or mammalian, can be appropriate.

Various scFv's can be tested for binding activity by, for example, testing direct binding to Ab1, or by employing them in competition experiments described herein. Any of the assays described infra for the testing of fragments for 11D10 activity can be employed for testing scFv's. For example, radiolabeled Ab1 (MC-10) is reacted with HMFG+ cells, such as MCF-7 cells, in the absence or presence (in increasing amounts) of the scFv to be tested. The observed percent inhibition is compared to 11D10 or another Ab2. A 11D10 scFv is characterized as capable of binding if the scFv inhibits binding of Ab1 to the HMFG-positive cells when compared to a negative control, such as an unrelated anti-idiotype) antibody. Alternatively, scFvs can be characterized using other immunological assays described herein, such as ability to elicit an immune response. Further, svFvs can be constructed with or without an immunoglobulin leader sequence (for secretion), depending on whether a secreted or cell-associated from of scFv is desired.

In another embodiment, single chain 11D10 antibody poly peptides without a linker, or with a very short, inflexible linker, are provided. These so-called "bivalent" antibodies are unable to engage in infra-chain interaction due to the absence of a linker (or the presence of a very short linker) and thus interact with other single chains, forming "diabodies". For instance, a bivalent 11D10 antibody polypeptide can be made using recombinant methods in either of the following configurations: VL—V M or VH—VL.

The invention also encompasses polymeric forms of 11D10 polypeptides. As used herein, a polymeric form of a 11D10 polypeptide contains a plurality (i.e., more than one) of 11D10 polypeptides. In one embodiment, linear polymers of 11D10 polypeptides are provided These 11D10 linear polymers may be conjugated to carrier. These linear polymers can comprise multiple copies of a single 11D10 polypeptide, or combinations of different 11D10 polypeptides, and can have tandem 11D10 polypeptides, or 11D10 polypeptides separated by other amino acid sequences. These linear polymers can be made using standard recombinant methods well known in the art In another embodiment, 11D10 multiple antigen peptides (MAPS) are provided. MAPs have a small immunologically inert core having radially branching lysine dendrites, onto which a number of 11D10 polypeptides can be anchored (i.e., covalently attached). Posnett et al. (1988) J. Biol. Chem. 263:1719–1725; Tam (1989) Meth. Enz. 168:7–15. The result is a large macromolecule having a high molar ratio of 11D10 polypeptides to core. MAPs are useful, efficient immunogens as well as useful antigens for assays such as ELISA, 11D10 MAPs can be made synthetically and can be obtained commercially (Quality Controlled Biochemicals, Inc., Hopkinton, Mass.). In a typical MAP system, a core matrix is made up of three levels of lysine and eight amino acids for anchoring 11D10 polypeptides. The MAP may be synthesized by any method known in the art, for example, a solid-phase method, for example, R. B. Merrifield (1963) J. Am. Chem. Soc. 85:2149.

In another embodiment of the invention, the immunogenicity of the 11D10 polypeptides can be enhanced by preparing them in expression systems in which they are fused with or assembled with particle-forming proteins such as, for example, that associated with hepatitis B surface antigen. See, e.g., U.S. Pat. No. 4,722,840. Constructs wherein the 11D10 polypeptide is linked directly to the particle-forming protein coding sequences produce hybrids which are immunogenic with respect to the 11D10 polypeptide. In addition, all of the vectors prepared include epitopes specific to HBV, having various degrees of immunogenicity, such as, for example, the pre-S peptide. Thus, particles constructed from particle forming protein which include 11D10 sequences are immunogenic with respect to 11D10 and HBV. These forms of 11D10 polypeptides can be made in eukaryotic cells, such as yeast or mammalian cells.

In another embodiment, 11D10 polypeptides can be conjugated with carrier. In instances where the 11D10 polypeptide is correctly configured so as to provide a binding site, but is too small to be immunogenic, the polypeptide many be linked to a suitable carrier. A number of techniques for obtaining such linkage are known in the art and need not be described in detail herein. Any carrier can be used which does not itself induce the production of antibodies harmful to the host. Suitable carriers are typically large, slowly metabolized macromolecules such as proteins; polysaccharides, such as latex functionalized sepharose, agarose, cellulose, cellulose beads and the like; polymeric amino acids, such as polyglutamic acid, polylysine, and the like; amino acid copolymers; and inactive virus particles or attenuated bacteria, such as Salmonella. Especially useful protein substrates are serum albumins, keyhole limpet hemocyanin, immunoglobulin molecules, thyroglobulin, ovalbumin, tetanus toxoid, and other proteins well known to those of skill in the art. As is evident to one skilled in the art, the above-described recombinant forms of 11D10 polypeptides and 11D10, such as fusion proteins, can in turn be fused with other amino acid sequences. For instance, a 11D10 scFv can be fused to a cytokine, such as IL-2. FIG. 25 provides an example of a plasmid construct that produces such a fusion protein.

11D10 polypeptides of the invention can be identified in a number of ways. For example, the variable regions of the light and heavy chains can be screened by preparing a series of short polypeptides that together span the entire variable region amino acid sequence. By starting with, for example, 50mer or 20mer polypeptides, it would be routine to test each polypeptide for the presence of a desired property. Screening such polypeptides is well within the skill of the art. It is also known to carry out a computer analysis of a protein sequence to identify potentially interesting polypeptides, for example, homology to HMFG, or a computer algorithm based on molecular recognition theory to identify putative regions associated with idiotype-anti-idiotype contact, and then prepare these polypeptides comprising these regions for testing.

Those skilled in the art will readily appreciate that the various forms and derivatives of 11D10 described in this section may be combined in various ways to produce other 11D10 polypeptides with desirable properties. For instance, 11D10 polypeptides with modified residues maybe comprised in a MAP. In another example, a 11D10 scFv is fused to a cytokine, such as IL-2.

Preparation of Polypeptides

The polypeptides of this invention can be made by procedures known in the art. The polypeptides can be produced by proteolytic or other degradation of 11D10, by recombinant methods (i.e., single or fusion polypeptides) as described above or by chemical synthesis. 11D10 polypeptides, especially shorter polypeptides up to about 50 amino acids, are conveniently made by chemical synthesis. Methods of chemical synthesis are known in the art and are commercially available. For example, a 11D10 polypeptide could be produced by an automated polypeptide synthesizer employing the solid phase method.

Preferably, the polypeptides are at least partially purified from other cellular constituents. Preferably, the polypeptides are at least 50% pure. In this context, purity is calculated as a weight percent of the total protein content of the preparation. More preferably, the proteins are 50–75% pure. More highly purified polypeptides may also be obtained and are encompassed by the present invention, For clinical use, the polypeptides are preferably highly purified, at least about 80% pure, preferably at least about 90% pure, more preferably at least about 95% pure, even more preferably at least at out 99% pure, and free of pyrogens and other contaminants. Methods of protein purification are known in the art and are not described in detail herein. Alternatively, if a 11D10 polypeptides) is expressed in a suitable storage medium, such as a plant seed, the 11D10 polypeptide need not be purified and could even be administered without purification. Fiedler et at. (1995) Biotechnology 13:1090–1093.

11D10 polypeptides can be obtained from intact 11D10, which can in turn be isolated from the hybridoma (ATCC HB12020) producing 11D10, which is described in co-owned U.S. patent application Ser. No. 081575,762 (Provisional No. 60/031,306). Techniques of isolating antibodies from hybridomas are well known in the art. See, e.g., Harlow and Lane (1988). Once intact 11D10 is obtained, 11D10 polypeptides can be obtained by degradation of intact 11D10, by using, for example, proteolytic enzymes (proteinases). Examples of proteolytic enzymes include, but are not limited to, trypsin, plasmin, and thrombin. Intact 11D10 can be incubated with one or more proteinases, or the digestions can be performed sequentially. The nature and extent of the proteolytic cleavage will depend upon the desired polypeptide length as well as the enzymes used. These techniques are well known in the art. Alternatively, or in addition, intact 11D10 can be treated with disulfide reducing agents to disassociate the molecule.

11 D10 polypeptides can be made by chemical synthesis using techniques known in the art.

11D10 polypeptides can also be made by expression systems, using recombinant methods. The availability of 11D10 polynucleotides encoding 11D10 polypeptides permits the construction of expression vectors encoding intact 11D10, functionally equivalent fragments thereof, or recombinant forms of 11D10. A polynucleotide encoding the desired 11D10 polypeptide, whether in fused or mature form, and whether or not containing a signal sequence to permit secretion, may be ligated into expression vectors suitable for any convenient host. Both eukaryotic and prokaryotic host systems can be used. The polypeptide is then isolated from lysed cells or from the culture medium and purified to the extent needed for its intended use. Purification or isolation of the polypeptides expressed in host systems can be accomplished by any method known in the art. For example, cDNA encoding intact 11D10 or a fragment thereof can be operatively linked to a suitable promoter, inserted into an expression vector, and transfected into a suitable host cell. The host cell is then cultured under conditions that allow transcription and translation to occur, and the desired polypeptide is recovered. Other controlling transcription or translation segments, such as signal sequences that direct the polypeptide to a specific cell compartment (i.e., for secretion), can also be used. Examples of prokaryotic host cells are known in the art and include, for example, E. coli. Examples of eukaryotic host cells are known in the art and include yeast, avian, insect, plant, and animal cells such as COS7, HeLa, CHO and other mammalian cells.

The polypeptides of this invention can also be expressed using recombinant vaccinia virus as a vector. This application would be especially useful in vaccine formulations, as a vaccinia virus carrier containing heterologous antigenic determinants has proven to be successful immunogens. Expression of 11D10 polypeptides in vaccinia vectors, and their use, is discussed above and infra.

Characterization of 11D10 Polypeptides

The 11D10 polypeptides of this invention can be characterized in several ways. For instance, a 11D10 polypeptide can be tested for its ability to bind to Ab1 and/or Ab3. Alternatively, 11D10 polypeptides can be tested for their ability to elicit an immune response, preferably an anti-HMFG response. 11D10 polypeptides can also be tested for their ability to palliate or ameliorate HMFG-associated disease, such as HMFG-associated tumors. It is understood that only one of these properties need be present in order for a polypeptide to come within this invention, although more than one of these properties may be present.

The ability of a 11D10 polypeptide to bind Ab1 and/or Ab3 can be assessed several ways. In one test, binding of the 11D10 polypeptide(s) to Ab1 can be tested directly, for example, by radioimmunoassay (RIA), for example, by reacting radiolabeled 11D10 polypeptide with Ab1 or Ab3 coated on microtiter plates, as is described in Example 1.

In another procedure, binding to Ab1 or Ab3 is determined by competitive immunoassay, in one variation of this procedure, binding of labeled 11D10 polypeptide(s) or functional equivalent fragments to Ab1 (MC-10) is measured in the presence of different Ab1, other Ab2s, 11D10 or analogs thereof, other 11D10 polypeptide(s), HMFG or extracts containing HMFG, or other proteins. Percent inhibition is calculated according to the following formula:

$$\% \text{ inhibition} = \left[1 - \left(\frac{R_T - R_C}{R_{MAX} - R_C}\right)\right] \times 100\%$$

In another variation, the test fragment with putative 11D10 activity is tested for its ability to interfere with the binding between Ab1 and Ab2, or Ab1 and HMFG. This test may be more sensitive in some applications, because lower affinity interaction between 11D10 and Ab1 may be too weak to form a stable bond, but be adequate to interfere with the binding of another ligand-receptor pair when present at sufficient concentration. The HMFG may be provided as purified antigen or HMFG-expressing cells. The assay may be conducted by labeling either the Ab1 or the HMFG or Ab2, and optionally immobilizing the other member of the ligand-receptor pair on a solid support for ease of separation. The test fragment is incubated with the labeled reagent, and then the mixture is presented to the immobilized target or test cell to determine if the test fragment is able to inhibit binding. Degree of inhibition correlates with 11D10 activity.

Various examples of competition assays are presented infra in the Example section. One test that indicates 11D10 polypeptide activity is to measure the binding of radiolabeled Ab1 (MC-10) to semipurified or purified HMFG in the presence of varying amounts of 11D10 polypeptide(s). See, for example, Example 1. The Ab1-HMFG mixture is then added to plates coated with 11D10 polypeptide(s) and binding is compared with binding of labeled Ab1 alone. Preferably, this test is performed with nonsaturating amounts of labeled Ab1 to detect changes in binding with small amounts of competitive HMFG. An example of this test as performed with intact 11D10 is provided in Example 1. In another competition assay, HMFG positive target cells (such as MCF-7 or SKBR3) are grown in 96-well tissue culture plates as a confluent monolayer. Binding of radio-labeled Ab1 (MC-10) in the absence and presence of 11D10 polypeptides is determined. The degree of inhibition can be compared with that of intact 11D10 or other 11D10 polypeptides. An example of this competitive assay using intact 11D10 is provided in Example 1. Another example of this assay, comparing the extent of inhibition between a 11D10 scFv and intact 11D10, is shown in Example 8.

A 11D10 polypeptide is considered to bind Ab1 if there is inhibition when compared to a negative control, such as an unrelated anti-idiotype antibody which does not bind to Ab1.

With all of the above-described assays, it is clear to one of skill in the art that the labeled molecule can be labeled in various ways, such as with radioisotopes (i.e., $^{125}$I) and non-radioactive labels, such as biotinylated molecules, and molecules for enzymatic detection, fluorescent labels and chemiluminescent labels.

The above discussed tests can also be used to compare characteristics of various 11D10 polypeptide fragments. For example, competitive assays can be conducted in which a first 11D10 polypeptide competes for binding to Ab1 (MC-10) in the presence of varying amounts of a second 11D10 polypeptide. Such tests can indicate relative degrees of binding affinities or other characteristics.

Another way of characterizing 11D10 polypeptides is testing their ability to generating an immune response. As used herein, "immune response" indicates either a humoral response, a cellular response, or both. As used herein, the "ability to elicit an immune response" pertains to any individual, including human.

The ability of a 11D10 polypeptide to generate a humoral response can be determined by testing for the presence of an antibody that binds to the 11D10 polypeptide(s) after administration of the 11D10 polypeptide(s). It is understood that this antibody (Ab3) was not present, or was present in lower amounts, before administration of the 11D10 polypeptide(s). Immunogenicity is preferably tested in individuals without a previous anti-11D10 response. Examples of suitable individuals include, but are not limited to, mice, rabbits, monkeys and humans. For this test, an individual is administered a 11D10 polypeptide(s). The amount per administration and number of administrations will vary, depending on the individual. Based on our previous studies using intact 11D10, a mouse requires approximately 100 µg of KLH-coupled 11D10 polypeptide in the presence of CFA and IFA per dose and three administrations. Monkeys require approximately 2 mg. For purposes of this invention the range of 11D10 polypeptide(s) that can be administered to humans is from about 10 µg to 10 mg, preferably 100 µg to 10 mg, preferably 500 µg to 8 mg, more preferably 1 mg to 4 mg, even more preferably about 2 mg.

Presence of an Ab3 can be determined by first pre-incubating sera with autologous immunoglobulin to block antibodies against isotypic and allotypic determinants and then testing sera for binding to HMFG and/or the 11D10 polypeptide(s), for example, using ELISA or RIA. For instance, different dilutions of pre-reacted sera are reacted with 11D10 (or 11D10 polypeptide) coated on microtiter plates. An unrelated Ab2 serves as a control. After washing, the Ab3-11D10 complex is labeled using, for example, $^{125}$I-labeled 11D10 in a homogeneous sandwich assay. Results from this assay are compared to those obtained before administration of the 11D10 polypeptide. A more detailed description of such an assay for detection of Ab3 elicited by intact 11D10 in mice is provided in Example 1. Alternatively, binding to HMFG positive cells, such as human colon carbinoma LS174-T cells, can be tested using immune flow cytometry.

Binding of Ab3 to HMFG can also be determined by immunoprecipitation or immunoreactivity with HMFG-positive tissue samples, or dot blot analysis. In one method of dot blot analysis, a semi-purified extract of HMFG is directly blotted to a nitrocellulose filter. The filter is then incubated with sera containing Ab3, and the reaction developed by enzyme-conjugated anti-immunoglobulin (Example 1). If the Ab3 binds to HMFG, a positive blot should appear. For testing with tissue samples, an immunoperoxidase assay can be used (Example 1).

If desired, Ab3 elicited by 11D10 polypeptide(s) can be further characterized. For example, competition assays can be performed to determine whether Ab3 share Ab1 idiotopes. In this test, serum from an individual immunized with a 11D10 polypeptide is tested for inhibition of binding of labeled 11D10 polypeptide (or intact 11D10) to Ab1. Inhibition indicates that Ab3 and Ab1 contain at least similar binding determinants. Similarly, competition of Ab3 with Ab1 for binding to HMFG (whether partially purified, purified, or on the surface of a HMFG-positive cell) can be tested by coincubating a fixed amount of labeled Ab1 (MC-10) with different dilutions of Ab3 containing sera or Ab1 preparation and HMFG (or HMFG-associated cells, such as MCF-7 or SKBR3). These tests are illustrated for intact 11D10 in Example 1.

As is evident to one of skill in the art, the Ab3 can be used in turn to characterize 11D10 polypeptides, using the assays described above.

Another way of characterizing a 11D10 polypeptide is by testing its ability to elicit an antibody that is cytoxic. For determination of complement mediated cytotoxicity (CMC), SKBR3 (target) cells (i.e., cells that express HMFG) are labeled with $^{51}$Cr. Labeling may be accomplished by incubating about $10^6$ cells with approximately 200 µCi $Na_2SO_4$ for 60 minutes at 37° C., followed by washing. The assay is conducted by adding and incubating serum suspected of containing antibody. Guinea pig serum pre-adsorbed with LS174-T cells (or other source of complement) is then added. After a suitable incubation period at 37° C., extent of $^{51}$Cr release is then measured and compared with that of unopsonized control cells. Release of $^{51}$Cr correlates with CMC activity. Herlyn et al. (1981) *Int. J. Cancer* 27:769.

Another way of characterizing a 11D10 polypeptide is by testing its ability to elicit an anti-HMFG antibody that participates in an ADCC response. Cheresh et al. (1986) *Cancer Research* 46:5112–5118. In this assay, cultured MCF-7 or SKBR3 cells (i.e., cells which express HMFG in their surface) are labeled with $^{51}$Cr and are used as target cells. Normal human peripheral blood mononuclear cells (PBMC) are used as effector cells. Preferably, the ADCC assay is conducted in the presence of heat-inactivated serum with an effector to target cell ratio of 100:1 for 4 hours, although other suitable conditions may be used. The amount of $^{51}$Cr released is then measured.

The 11D10 polypeptides of this invention can also be characterized by their ability to elicit a cellular response. As used herein, a "cellular response" is a response that involves T cells, and can be observed in vitro or in vivo.

One way of detecting a cellular immune response is by assaying for T cell proliferative activity. In this test, cellular immune response is measured by proliferation of peripheral blood mononuclear cells (PBMs) incubated with 11D10 polypeptide(s). Peripheral blood mononuclear cells are isolated from blood after a requisite number of administrations of 11D10 polypeptide(s) and are incubated with varying concentrations of 11D10 polypeptide(s). If mice are used, T cells are obtained from spleen. T cells may be enriched, for example, by centrifugation on a gradient such as Ficoll™. A non-specific mitogen such as PHA serves as a positive control; incubation with an unrelated anti-idiotype antibody serves as a negative control. Preferably, the stimulator cells are autologous with the responder cells, particularly in terms of histocompatibility Call II antigens. After incubation of the PBMs for an appropriate number of days to allow proliferation, [$^3$H]thymidine incorporation is measured. In many instances a suitable time is five days. If desired, determination of which subset of T cells are proliferating can be performed using flow cytometry. Optionally, splenic T cells can be pre-depleted of either CD4$^+$ or CD8$^+$ cells before the proliferation assay by incubation with monoclonal antibody RL 172 (anti-CD4$^+$) or mAb.168 (anti-CD8$^+$) and complement.

Another way of detecting a cellular immune response is to test for T cell cytotoxicity (CTL) activity. In this test, T lymphocytes (i.e., an enriched T cell population) are isolated (typically from spleen cells) for use as targets in a standard $^{51}$Cr release assay. Kantor et al. (1992) *J. Natl. Cancer Inst.* 84:1084–1091. An example of a $^{51}$Cr release assay is the following. Briefly, HMFG-positive tumor cells (typically 1–2×10$^6$ cells) are radiolabeled as target cells with about 200 µCi of Na$_2$ $^{51}$CrO$_4$ (Amersham Corp., Arlington Heights, Ill.) for 60 minutes at 37° C., followed by thorough washing to remove unincorporated isotopes. T cells and targets (1×10$^4$/well), both resuspended in culture medium, are then be combined at various effector-to-target ratios in 96-well, U-bottom plates (Costar Corp.). The plates are centrifuged at 100×g for 5 minutes to initiate cell contact and are incubated for 4 or 16 hours at 37° C. with 5% CO$_2$. After incubation, supernatants are collected using a Supernatant Collection System (Skatron, Inc., Sterling, Va.) and radioactivity will be quantitated in a gamma counter (Beckman Instruments). Spontaneous release of $^{51}$Cr is determined by incubation of targets in the absence of effectors, while maximum or total release of $^{51}$Cr will be determined by incubation of targets in 0.1% Triton X-100. Percentage of specific release of $^{51}$Cr is determined by the following equation:

$$\text{Percent specific release} = [(\text{experimental} - \text{spontaneous})/(\text{maximum} - \text{spontaneous})] \times 100.$$

Another way of characterizing 11D10 polypeptides is testing their ability to ameliorate, delay the progression of and/or reduce the extent of HMFG-associated tumors. Such tests may include inflammatory indicators, radioscintigraphy, or measurement of circulating HMFG levels (such assays are available commercially).

Uses of and Methods Using 11D10 Polypeptides

11D10 polypeptides have a number of uses. 11D10 polypeptides can be used to induce an immune response in an individual, preferably an anti-HMFG response. They can also be used to detect and monitor levels of Ab3, or to purify Ab3. 11D10 polypeptides are also useful for treatment of HMFG-associated disease, for example, colorectal cancer, certain lung cancers (adenocarcinomas), gastric cancer, pancreatic cancers, and certain breast cancers.

Thus, the present invention includes methods of inducing an immune response in an individual comprising administering a 11D10 polypeptide in an amount effective to induce an immune response. Preferably, the individual has HMFG-associated tumors. In this context, an "effective amount" is an amount sufficient to elicit a measurable immune response, whether humoral and/or cellular. An effective amount can be administered in one or more administrations.

The invention also encompasses methods of detecting an antibody that binds to 11D10 (i.e., Ab3 and/or Ab1) in a biological sample. These methods are applicable in the clinical setting, for example, for monitoring Ab1 or Ab3 levels in an individual, as well as an industrial setting, in which commercial production of Ab3 is desired. These methods entail contacting the Ab3 and/or Ab1 in the sample with a 11D10 polypeptide under conditions suitable to allow the formation of a stable complex between Ab3 and/or Ab1 and the 11D10 polypeptide, and detecting a stable complex formed, if any. A number of immunoassay methods are known in the art and have been described herein. For further illustration, a test sample potentially containing Ab3 and/or Ab1 can be mixed with a pre-determined non-limiting amount of the 11D10 polypeptide which typically detectably labeled (such as with a radioisotope or enzyme). In a liquid phase assay, unreacted reagents are removed by a separation technique, such as filtration or chromatography. In these immunoassay techniques, the amount of label associated with the complex positively correlates with the amount of Ab3 and/or Ab1 present in the sample. Similar assays can be designed in which Ab3 and/or Ab1 in the test sample competes with labeled antibody for binding to a limiting amount of the 11D10 polypeptide. Here, the amount of label negatively correlates with the amount of Ab3 and/or Ab1 in the sample. Suitable samples in which to measure Ab3 and/or Ab1 levels are biological samples, including serum or plasma, preferably serum. Other samples include tissue samples.

Further, the invention also includes methods of purifying Ab3 (or Ab1), comprising contacting a biological sample containing Ab3 (and/or Ab1) with a 11D10 polypeptide, and obtaining a complex formed thereby, if any. Typically, the 11D10 polypeptide(s) is coupled to an affinity matrix for affinity column purification. Such methods are routine in the art and need not be described in detail herein.

Also included in this invention are methods of treating HMFG-associated disease, such as HMFG-associated tumor, comprising administering an effective amount of a 11D10 polypeptide. A "HMFG associated tumor" is one that contains HMFG, especially expressed on the surface of tumor cells, examples of which have been described above. In this context, an effective amount for treatment is amount sufficient to palliate the disease state. An effective amount can be given in one or more than one administration. Treatment of individuals with an effective amount of 11D10 polypeptide may, for example, decrease the rate of progression of disease, in comparison with individuals not so treated.

In another embodiment, methods are provided for stimulating a T cell response in an individual having HMFG-associated disease. This T cell response can be manifested as proliferation of T cells and/or promoting cytotoxic T cell activity using 11D10 polypeptides, particularly 11D10 polypeptides that are homologous to HMFG. The 11D10 polypeptides can be administered directly (either as polypeptides or plasmids containing polynucleotides encoding 11D10 polypeptide(s)), or added to an ex vivo culture of suitable cells. 11D10 polypeptides are added, for example, to isolated peripheral blood mononuclear cells, in an amount effective to stimulate the desired T cell activity. The stimulated T cells are then reintroduced to the individual. The amount(s) of 11D10 polypeptide(s) added will depend upon several factors, such as the condition of the individual, previous and/or concurrent treatment procedures, and other substances used.

The polypeptides of this invention can be used alone or in conjunction with other agents which promote the desired activity/objective. 11D10 polypeptides can also be used in various combinations with each other. In this context, an "agent" can be any of a variety of substances. Further, "in conjunction with" means that the agent can be used concomitantly, before, or after the polypeptide(s). The agent can also be covalently linked to the polypeptide, such as a fusion protein; or in close physical proximity with the polypeptide. A desired activity is any activity which facilitates, enhances promotes, or modulates the desired objective in using the 11D10 polypeptides.

Agents which may be used include, but are not limited to, cytokines, lymphokines, adjuvants, and drugs. Agents also include substances which facilitate delivery of the polypeptides, such as liposomes, or substances which promote delivery of the polypeptides to a particular target, for example, a cellular receptor. For example, one or more 11D10 polypeptides can be produced as fusion protein(s) which also contain a cytokine, such as GM-CSF. Alternatively, one or more 11D10 polypeptides can be administered with a cytokine such as GM-CSF.

The invention also encompasses methods using 11D10 polypeptides to remove a label, for example radioactivity, from an individual who has received a labeled anti-HMFG antibody (Ab1), for example, for radioscintiligraphy or radiotherapy. This invention also includes methods of treatment in which a radiolabeled anti-HMFG antibody is administered in a therapeutic dose, and followed by a molar excess of 11D10 polypeptide.

Use of 11D10 for this purpose has been discussed above, and those principles likewise apply to 11D10 polypeptides. An amount of 11D10 polypeptide is chosen that is in sufficient molar excess over the labeled anti-HMFG to locate and bind any anti-HMFG that is not localized at the tumor site. The timing of administration and amount of 11D10 polypeptide will depend upon the nature of the radiolabeled antibody, the type of radioisotope used and the condition of the individual. Preferably, the molar ratio of 11D10 polypeptide to the anti-HMFG antibody is at least about 5:1, more preferably about 25:1 to 200:1. Preferably, 11D10 polypeptide is administered 5 to 24 hours after the individual has received the anti-HMFG antibody.

For 11D10 polypeptides that bind to an anti-HMFG antibody, particularly MC-10, detection of anti-HMFG on the surface of a tumor cell can be accomplished by contacting the tumor cell with the 11D10 polypeptide(s) for a sufficient time to allow binding to the anti-HMFG antibody, and detecting the presence of any 11D10 which is bound to the anti-HMFG antibody. Development of experimental parameters (such as amount of 11D10 polypeptide or the time of reaction) are empirical determinations well within the skill of the art.

Pharmaceutical Compositions and Vaccines Comprising 11D10, 11D10 Polynucleotides and/or 11D10 Polypeptides The present invention encompasses pharmaceutical compositions and vaccines containing 11D10, 11D10 polynucleotide(s) and/or 11D10 polypeptide(s). Such pharmaceutical compositions/vaccines are useful for eliciting an immune response, and/or for treatment of HMFG-associated disease, such as breast cancer. The pharmaceutical compositions/vaccines may palliate or ameliorate HMFG-associated disease either alone or in conjunction with other forms of therapy, such as chemotherapy or radiotherapy. These pharmaceutical compositions, comprised of an effective amount of 11D10, 11D10 polynucleotide(s) and/or 11D10 polypeptide(s) in a pharmaceutically acceptable excipient, are suitable for systemic administrations to humans and animals in unit dosage forms, sterile parenteral solutions or suspensions, sterile non-parenteral solutions or oral solutions or suspensions, oil in water or water in oil emulsions and the like. Formulations or parenteral and nonparenteral drug delivery are known in the art and are set forth in Remingtons' Pharmaceutical Sciences, 18th Ed. Mack Publishing (1990).

A pharmaceutically acceptable excipient is a relatively inert substance that facilitates administration of a pharmacologically effective substance. For example, an excipient can give form or consistency to a vaccine composition, or act as a diluent. Suitable excipients include but are not limited to stabilizing agents, wetting and emulsifying agents, salts for varying osmolarity, encapsulating agents, buffers, and skin penetration enhancers. Examples of pharmaceutically acceptable excipients are described in Remington's Pharmaceutical Sciences (1990), supra.

In one embodiment, a pharmaceutical composition comprising a 11D10 polypeptide(s) is used to stimulate, for example, ex vivo cultures of peripheral blood monocytes (PBMs) from an individual. The PBM's are then reintroduced into the individual. The pharmaceutical composition is used alone or in combination with other bioresponse modifiers such as lymphokines.

One type of pharmaceutical composition is a vaccine. Accordingly, the present invention also includes vaccines comprising an effective amount of 11D10, 11D10 polynucleotide(s), 11D10 polypeptide(s), or combinations thereof, and a pharmaceutically acceptable excipient. These vaccines can be used, inter alia, to elicit an immune response in a individual, particularly individuals with advanced HMFG-associated disease such as HMFG-associated tumors. Preferably, the immune response includes the production of anti-human milk fat globule antibody. These vaccines are especially useful for the treatment, modulation, and/or palliation of HMFG-associated disease.

Administration of vaccines containing 11D10 has been discussed above.

Vaccines containing 11D10 polynucleotides described above can be used for so-called "genetic immunization", or DNA vaccines, in which polynucleotides encoding an antigenic polypeptide are introduced into host cells in order to elicit a protective immune response. Tang et al. (1992) Nature 356: 152–154. Once in the cell nuclei, the plasmids may persist as circular non-replicating episomes leading to dose-dependent and long-lived expression. Spooner et al. (1995) Gene Therapy 2:173–180. Immunization using polynucleotides has been shown to generate cellular as well as humoral responses. Spooner et al. (1995); Wang et al. (1995) Human Gene Therapy 6:407–418. Genetic immunization has many of the advantages of live or attenuated microorganisms as vehicles for eliciting an immune response without the rick of infection.

Preferably, 11D10 polynucleotides are introduced as plasmid vectors containing appropriate control sequences for transcription and translation, such as promoters, enhancers, and signal sequences. One or more 11D10 polynucleotides can be used within a single cloning vector, and/or multiple vectors can be used. If multiple 11D10 polynucleotides are used, they should be inserted in-frame within the vector, or be under the control of separate promoters. The length and/or type of 11D10 polynucleotide used can vary and will depend upon several factors, such as the clinical objective of administering the vaccine, the condition of the individual, and the immunological profile of the individual. In addition, polynucleotides encoding other substances which will enhance, facilitate, and/or augment the immune response can also be inserted into the vector. Examples of such substances, such as GM-CSF, have been described above.

For example, in one embodiment, a polynucleotide encoding an scFv of 11D10 is inserted into one of the expression vectors (plasmids) described above. In another example, polynucleotides encoding 11D10 fragments depicted in FIG. 19 are inserted into the expression vector for administration as a vaccine. In another example, a polynucleotide encoding an immunogenic fragment of 11D10 is inserted into an expression vector.

Another type of vaccine employing 11D10 polynucleotides is so-called expression library immunization, in which an expression library of 11D10 polynucleotides (encoding various portions of 11D10) is used to immunize a host. Barry et al. (1995) Nature 377:632–635. The resultant multi-partite non-infectious vaccine can prove to be especially beneficial, as it presents multiple peptides as potential immunogens. Presentation of multiple immunogens has the added advantage that each particular host (i.e., individual) in which it is administered is able to select the immunologically effective polypeptides, which may vary from individual to individual. The expression library used for expression of 11D10 polypeptides can be comprehensive, that is, collectively encoding the entire 11D10 molecule, or can be partial. The expression library for immunization is made by general recombinant methods described above, using a suitable vector system. Typically, 11D10 polynucleotides are fused in frame to a signal sequence that mediates secretion.

The amount of 11D10 polynucleotide to be administered will depend upon several factors, such as the mode and route of administration (i.e., direct injection versus ex vivo culture and transfection), the 11D10 polypeptide encoded by the 11D10 polynucleotide, the condition of the individual (such as the immunological and/or disease condition), and the desired objective. Typically, if administered directly, the amount per administration is about 10 µg to 1 mg, preferably 25 µg to 500 µg, more preferably 30 µg to 250 µg, even more preferably 50 to 100 µg.

In another embodiment, 11D10 polynucleotides are used in live or attenuated viruses or viral vectors which can express an encoded 11D10 polypeptide(s) for vaccine formulations. Examples include, but are not limited to, adenovirus, adeno-associated retroviruses (AAV), and SV40. Preferably, the virus is vaccinia. Recombinant vaccinia virus can provide a powerful agent for effectively co-presenting the 11D10 polypeptide(s) encoded by the 11D10 polynucleotide(s) along with the immunogenic viral particle. Construction of vaccinia virus vectors has been described above. Generally, recombinant viral vectors are added in an amount sufficient to effect in vivo infection of host cells. The amount depends upon the type of virus used, the nature of the 11D10 polypeptide encoded, the condition of the individual, and the desired result. Recombinant vaccinia (which can encode 11D10 polypeptides or 11D10 variants containing 11D10 polypeptides, such as scFv) can be used directly for vaccination at about 10⁷ to 10⁸ plaque forming units per dose. Vaccinia can be administered parenterally, by subcutaneous or intramuscular injection, for example, as well as through mucosal membranes, such as nasally, orally or by inhalation. Alternatively, vaccinia can be administered via vaccinia-infected cells. In this technique, suitable cells, such as tumor cells, are infected with vaccinia in culture. The infected cells are then reintroduced to the individual. Methods for infecting cells with vaccinia and reintroducing these infected cells, have been described. See, e.g., Moss (1991).

Vaccines can also be prepared from one or more 11D10 polypeptides. 11D10 polypeptides can be prepared by any of the methods described above, especially by purification from a suitable expression vector. In one embodiment, the vaccines comprise one or more 11D10 polypeptide(s). 11D10 polypeptides can be formulated into a vaccine as neutral or salt forms. Pharmaceutically acceptable salts include the acid addition salts (formed with free amino groups of the 11D10 polypeptide) and which are formed with inorganic acids such as, for example, hydrochloric or phosphoric acids, or such organic acids such as acetic, oxalic, tartaric, maleic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

In another embodiment, vaccines are provided that contain a 11D10 polypeptide fused to a viral particle, such as the hepatitis b surface antigen.

The preparation of vaccines which contain 11D10 polynucleotides or polypeptides as an active ingredient involves standard practice in the art. Typically, such vaccines are prepared as injectables, either as liquid solutions or suspensions; solid forms suitable for solution in, or suspension in, liquid prior to injection can also be prepared. The vaccine may also be emulsified, or the 11D10 polypeptide(s) and/or polynucleotide(s) associated with liposomes.

The 11D10, 11D10 polypeptides and/or 11D10 polynucleotides in the vaccines may be used neat but are often mixed with pharmaceutically acceptable excipients. Suitable excipients are, for example, water, saline, physiologically buffered saline, dextrose, glycerol, ethanol and combinations thereof. If desired, the vaccine can also contain minor amounts of auxiliary substances such as wetting or emulsifying agents, pH buffering agents, stabilizers and/or adjuvants. Examples of adjuvants have been described above. For veterinary use and for production of antibodies in animals, mitogenic components of Freund's adjuvant can be used. The choice of an adjuvant will depend, in part, on the stability of the vaccine in the presence of the adjuvant, the route of administration, and the regulatory acceptability of the adjuvant, particularly when intended for human use. For instance, alum is approved by the United States Food and Drug Administration (FDA) for use as an adjuvant in humans. For enhancing the immune response using a vaccine containing a 11D10 polynucleotide, encapsulation in cationic lipids can be used. For delivery of 11D10 polypeptides, encapsulation in liposomes can also be appropriate. Liposomes suitable for packaging polynucleotides and/or polypeptides for delivery to cells are known in the art.

11D10 polypeptide(s) can optionally be treated chemically to enhance its immunogenicity, especially if a 11D10 polypeptide comprises 100 amino acids or less. Such treatment may include cross-linking, for example, with glutaraldehyde; linking to a protein carrier, such as keyhole limpet hemaocyanin (KLH) or tetanus toxoid.

If a sub-optimal immune response is deemed to be due to suppressor T cells induced by a vaccine of this invention, cyclophosphamide (100 mg/kg body weight) can also be administered interperitoneally.

The vaccines of the present invention are typically administered parenterally, by injection for example, either subcutaneously, intramuscularly, intraperitoneal or intradermally. Administration can also be intranasal, intrapulmonary (i.e., by aerosol), oral and intravenous. Additional formulations which are suitable for other modes of administration include suppositories and, in some cases, oral formulations. The route of administration will depend upon the condition of the individual being treated and the desired clinical effect.

Administrations can begin on a weekly or biweekly basis until a desired, measurable parameter is detected, such as elicitation of an immune response (humoral and/or cellular). Administration can then be continued on a less frequent basis, such as biweekly or monthly. For vaccines containing 11D10, the administrations are preferably given biweekly for the first four administrations, followed by monthly administrations.

The vaccines are administered in a manner compatible with the dosage formulation, and in such amount as will be prophylactically and/or therapeutically effective. The quantity to be administered depends on the individual to be treated, the capacity of the individual's immune system to synthesize antibodies, the route of administration, and the degree of protection desired. Precise amounts of active ingredient required to be administered may depend on the judgment of the practitioner and may be peculiar to the individual. General dosage ranges for 11D10, 11D10 polynucleotides and 11D10 polypeptides have been given above.

Typically, the vaccine is administered as a series of doses, beginning with a group of doses to prime the immune response, followed by less closely spaced "maintenance" doses. For example, the vaccine can be administered on a weekly basis to establish an immune response, followed by bi-weekly or monthly injections to maintain the response.

The 11D10 polypeptides and/or 11D10 polynucleotides in the vaccines can be given alone, in combination with other 11D10 polypeptides and/or polynucleotides, in combination with intact 11D10 and/or in combination with other substances, such as lymphokines and drugs, that enhance, facilitate, or modulate the desired effect. Examples of such substances have been described above. 11D10 polypeptides can be combined by preparing a mixture of the 11D10 polypeptides in solution or by synthesizing a fusion protein.

The vaccines of this invention can also be administered in conjunction with recombinant vaccinia containing a polynucleotide encoding HMFG or a fragment thereof and/or recombinant vaccinia containing a polynucleotide encoding a lymphokine such as GM-CSF. Further, it is understood that the vaccines of this invention can be used in conjunction with other modes of therapy, whether established or experimental. Such use is indicated, for example, when administration of the vaccine improves the clinical results as compared to administration of other mode(s) of therapy alone, such as chemotherapy or radiotherapy.

The immunogenicity of a 11D10 vaccine can be monitored by measuring levels of Ab3 and/or monitoring the disease state. Detection and measurement of Ab3 using RIA or ELISA and measurement of T cell activity (i.e., proliferation and/or cytotoxic activity) has been described above. As an example, Ab3 can be quantitated as follows. Microtiter plates are coated with MC-10 (Ab1) and reacted with a fixed amount of 125I-labeled 11D10 polypeptide. A standard inhibition curve is generated using purified MC-10 as the inhibitor. Sera at different dilutions is tested for ability to inhibit the Ab1-Ab2 reaction and the amount of Ab3 in the sera is estimated from the standard inhibition curve. Alternatively, T cell response can be measured using any of the assays described above. The disease state can be monitored using standard techniques in the art, such as measurement of a tumor-associated marker, X ray, CT scan, and other measurable clinical manifestations.

It is recognized that a number of alternative vaccine compositions, not limited to those described herein, may be efficacious in inducing an immune response. All such compositions are embodied within the present invention, providing they include a 11D10 polynucleotide or polypeptide as an active ingredient.

Kits Comprising 11D10, 11D10 Polynucleotides and/or 11D10 Polypeptides

The present invention also encompasses kits containing 11D10, 11D10 polynucleotide(s) and/or polypeptide(s), preferably diagnostic kits. Diagnostic procedures using 11D10, 11D10 polynucleotides and/or 11D10 polypeptides of this invention can be performed by diagnostic laboratories, experimental laboratories, practitioners, or private individuals. Kits embodied by this invention include those that allow someone to conduct an assay for anti-HMFG or anti-11D10 activity, such as any of those disclosed herein, thus detecting an/or quantitating those activities. The kits embodied by this invention also include kits that allow detection of 11D10 polynucleotides in, for example, ex vivo or in vivo transfected cells. These kits can be used for detection or quantitation of a polynucleotide that comprises a polynucleotide encoding a variable region of 11D10 or a portion thereof. 11D10 polynucleotides that can hybridize (that is, form a stable hybrid) with 11D10 variable regions, but not with polynucleotides of other variable regions (known at the time of filing this application), as have been described herein, are especially suitable.

For example, the presence of Ab3 in a biological sample can be tested for using a 11D10 polypeptide. The sample can optionally pre-treated for enrichment of Ab3.

The kits of this invention comprise 11D10, 11D10 polynucleotide(s) and/or polypeptide(s) in suitable packaging. The kit may optionally provide additional components that are useful in the procedure. These optional components include, but are not limited to, buffers, capture reagents, developing reagents, labels, reacting surfaces, means for detection, control samples, instructions, and interpretive information.

The following examples are provided to illustrate but not limit the present invention.

EXAMPLES

Example 1

Generation and Characterization of 11D10 Anti-Idiotype Antibody

The hybridoma cell line producing monoclonal anti-idiotype antibody 11D10 was created and identified according to the following description. Aspects of both the immunization procedure and the screening procedure were important to obtain an antibody with the desired specificity and functionality. 11D10 was one of a number of Ab2 that were initially produced, and was identified as the candidate with the most desirable features.

The immunizing antibody (Ab1) was the mouse anti-HMFG monoclonal antibody MC-10, referred to in this section as BrE-1. Since the responding animal was also a mouse, the Ab2 generated were expected to be directed against idiotypic features of BrE-1. However, only a fraction of those would be directed against the BrE-1 paratope, an even smaller proportion would be immunogenic and capable of eliciting an Ab3, and a still smaller proportion would elicit Ab3 that cross-reacted with the tumor-associated antigen.

To render BrE-1 sufficiently immunogenic in an autologous species, it was conjugated to the carrier KLH, and emulsified in Fruend's adjuvant. It was administered repetitively into the recipient animals on an unusual schedule with only 2 weeks between doses. Five mice were immunized according to this schedule. Substantial responses arose in about 3 mice only after the fourth immunization. Responding animals were boosted with a fifth dose of BrE-1 i.v., spleen cells were isolated, and hybridomas were prepared separately from each animal. Cloning was performed according to standard techniques.

The screening procedure comprised four important steps: (1) Positive selection for antibody binding to BrE-1; (2) Negative selection against antibody recognizing isotypic or allotypic determinants; (3) Positive selection for an ability to inhibit the binding of BrE-1 to HMFG; and (4) Positive selection for an ability to induce a humoral immune response against the original tumor-associated antigen (HMFG) in both mice and rabbits. The rest of this section provides an overview of the screening procedure, which is given in more detail in the sections that follow.

Initial screening was conducted by immunoassay to identify the clones that reacted with BrE-1, but not with other target monoclonal antibodies sharing the same allotypic or isotypic determinants. A critical assay was a sandwich RIA in which BrE-1 is attached to a solid phase, overlayed with culture supernatant, and developed with radioiodinated BrE-1. This assay requires the antibody in the hybridoma supernatant to be functionally bivalent, and be able to span between the capture BrE-1 and the developing BrE-1. Several clones that were idiotype specific and gave a strong signal in this assay were selected for further study.

Subsequent screening was conducted by competition assays, in which the Ab2 was required to block the binding of BrE-1 to HMFG. This established that Ab2 recognized the paratope of BrE-1. HMFG was provided in the form of MCF-7 cells, a human breast cell tumor line expressing HMFG at the cell surface. The nature of the assay requires the Ab2 to block the interaction between BrE-1 and the tumor antigen in its particular manner of presentation on tumor cells. At a minimum, candidate Ab2s which had passed the earlier screening tests were required to inhibit the binding of BrE-1 to the cells by at least 85%. There were about three Ab2 that substantially exceeded the minimum, with 11D10 providing about the highest level of inhibition.

The ultimate screening test was a determination of whether the candidate Ab2 were capable of eliciting an Ab3 of the desired specificity when injected into a recipient. Sufficient quantities of Ab2 were prepared from mouse ascites, and tested in mice and rabbits. Sera from the test animals were first assayed for the presence of Ab3 in a sandwich immunoassay using the same labeled Ab2 used for immunization. Sera testing positively were then assayed for ability of the Ab3 to react against the tumor-associated antigen, namely HMFG. A semipure preparation of HMFG was used to coat microtiter plates, overlayed with the test serum in serial dilutions, and the Ab3 that bound was detected using labeled anti-immunoglobulin. The titer of the Ab3 binding to HMFG defined the "quality" of Ab2, as a reflection of its capacity as an inducer of anti-HMFG.

Monoclonal antibody 11D10 emerged as the anti-idiotype with the highest quality, and is the basis for various compounds, compositions, and procedures embodied in this invention.

Materials and Methods

Cells: The fusion partner used to produce the hybridoma lines was the mouse non-secretory myeloma cell line P3-653, ancestrally related to P3X63Ag8.653, available from the ATCC as No. CRL-1580. Established human cell lines were cultured in RPMI 1640 supplemented with 5% fetal calf serum as described elsewhere (Seon et al. (1984) J. Immunol. 132:2089).

HMFG: Defatted HMFG was supplied by Roberto L. Ceriani, and was prepared according to his protocol (Ceriani et al. (1977) Proc. Natl. Acad. Sci. USA 74:582–586). Briefly, the washed cream fraction of human milk was extracted twice with two volumes of chloroform, and twice with 1 volume of either, and then lyophilized. Protein concentration was determined by the Lowry method.

BrE-1 antibody: Murine monoclonal antibody BrE-1 (MC-10) was generously provided by Dr. R. L. Ceriani, and is described in WO 89/07268. Ascites of BrE-1 hybridomas were prepared by injecting individual pristane-primed mice i.p. with $2–10 \times 10^6$ viable cells. The IgG fraction was isolated from ascites by 45% saturated ammonium sulfate precipitation and subsequent chromatography on Protein A Sepharose™ CL-4B (Ey et al. (1978) Immunochemistry 15:429). The purity of the isolated IgG was checked by immunodiffusion, immunoelectrophoresis, and high pressure liquid chromatography (HPLC) fractionation. Other unrelated Ab1 and Ab2 of different isotypes were used as controls.

Preparation of F(ab')$_2$ fragments of BrE-1: The F(ab')$_2$ fragments were prepared by standard pepsin digestion (Parham (1983) J. Immunol. 131:2895). Briefly, the IgG fraction from the BrE-1 ascites was dialyzed against 0.1 M citrate buffer, pH 3.5, and digested with pepsin (25 Tg/mg IgG) at 370 C for 8 hours. After cleavage, the pH was adjusted to 7.0 with 3.0 M tris buffer, pH 8.6, and the solution was dialyzed against phosphate-buffered saline (PBS) in the cold. The digest was separated by HPLC using a Sepharose™ 6 column. The purity of the isolated F(ab')$_2$ was determined by immunodiffusion and by reaction with anti-isotype reagents in a standard ELISA.

Coupling of antibody with KLH: BrE-1 was coupled to keyhole limpet hemocyanin (KLH) according to a method described by Maloney et al. (1985) Hybridoma 4:191). Antibody stock solution (1 mg/ml) was mixed with KLH (1 mg/ml) in PBS in the presence of freshly diluted glutaraldehyde solution (final concentration 0.05%). The mixture was rotated end-over-end for 1 hour at room temperature, and then dialyzed exhaustively against PBS at 40 C.

Immunization of syngeneic BALB/c mice: BALB/c females were immunized four times over a period of 2 months. The first injection was given i.p. using 100 Tg of BrE-1, emulsified in complete Freund's adjuvant. The next two injections were given with 100 Tg of BrE-1 coupled to KLH in incomplete Freund's adjuvant, either s.c. or i.p. Mice were bled from time to time, and sera were checked for anti-idiotype activity by ELISA in a binding assay by using F(ab')$_2$ fragments of BrE-1 and normal pooled BALB/c mouse serum IgG as control. Three days before the fusion, the mice were boosted i.v. with BrE-1 in PBS.

Production of Anti-Idiotype Hybridomas

The fusion partner used to produce the hybridoma lines was the mouse non-secretory myeloma cell line P3-653, ancestrally related to P3X63Ag8.653, available from the ATCC as No. CRL-1580. Established human cell lines were cultured in RPMI 1640 supplemented with 5% fetal calf serum as described elsewhere (Seon et al. (1984) J. Immunol. 132:2089).

Hybridomas were produced essentially following the method of Oi and Herzenberg ((1980) Selected Methods of Cellular Immunology, Mishell & Shiigi eds., Freeman Publs., at 351–372). Speen cells from immunized mice were mixed with P3-653 cells at a ratio of 1:1 to 10:1, in the presence of 50% polyethylene glycol (PEG, mw ~4500). Fused cells were then washed and cultured. Hybrids were selected using hypoxanthine-aminopterin-thymidine media.

Initial Selection of Anti-Idiotype Antibody (Ab2) Secreting Hybridoma Clones:

Initial screening of the hybridoma clones was performed by RIA. Purified BrE-1 was radioiodinated by the chloramine T method (Hunter (1970) *Proc. Soc. Exp. Biol. Med.* 133:989). BrE-1, or control antibody (monoclonal antibodies of various isotypes and unrelated specificities, and BALB/c normal IgG) was coated onto PVC plates at 500 ng/well. After incubating overnight at 40 C, the plates were blocked with 1% bovine serum albumin (BSA) in PBS. Coated plates were incubated with serial dilutions of hybridoma supernatant for 4 hours, and developed using ~50,000 cpm of $^{125}$I-BrE-1. The RIA assay is a stringent specificity test for the antibody, and also requires that the antibody be able to span between two BrE-1 molecules.

In addition, ELISA assays were conducted to determine the class and subclass of each clone. The ELISA was conducted by coating microtiter plate wells with BrE-1 antibody (or control) at 500 ng/well. After incubating overnight at 40 C, the plates were blocked with 1% BSA in PBS. 100 Tl of hybridoma culture supernates or 20×concentrate was incubated in the well for 4 hours at room temperature. After washing with PBS, the plates were further incubated for 4 hours at room temperature or overnight at 40 C with alkaline phosphatase-labeled anti-isotype reagents, and developed with the substrate. Antibody of certain IgG subclasses is easily purified by protein A chromatography, and may have useful effector functions.

The culture supernatants from 1300 primary fusion wells were initially screened. Forty-two Ab2 hybridomas were obtained that reacted with BrE-10 in the RIA, but not with isotype or allotype matched control immunoglobulins.

Figure 6:
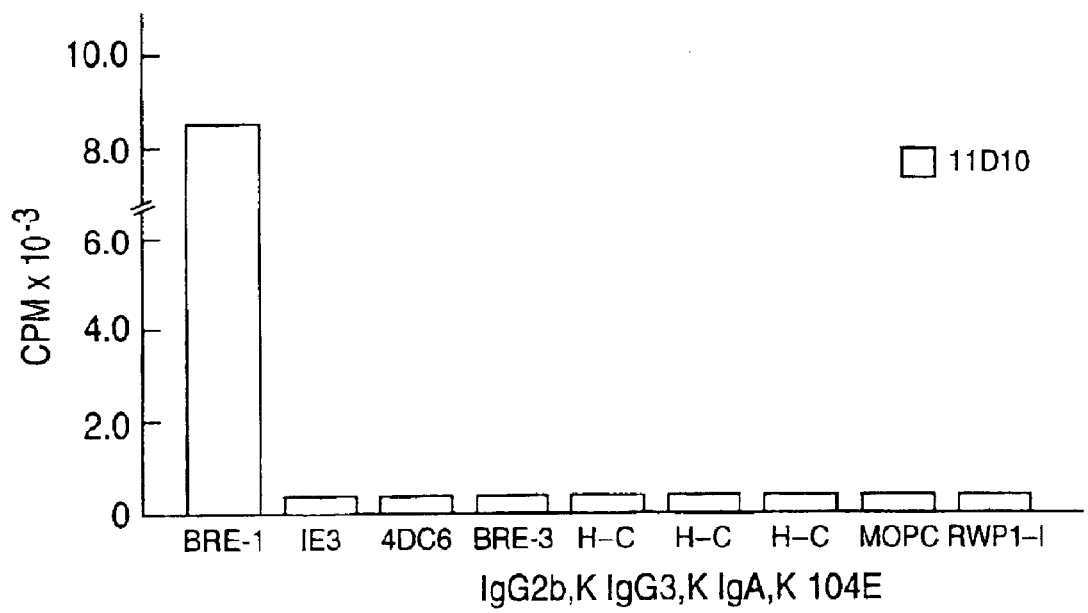

A number of monoclonal Ab2 secreting cell lines emerged from these screening assays with the desired properties. Among them was monoclonal antibody 11D10.
Confirmation that Monoclonal Ab2 are Specific for BrE-1 Idiotype Idiotype specificity of Ab2 was confirmed by direct binding to Ab1. Various purified Ab2 were labeled with $^{125}$I, and tested for binding to plates coated with a panel of monoclonal anti-TAA Ab1. Results for an experiment using $^{125}$I-11D10 are shown in FIG. 6. The results are presented in mean cpm (n=3, S.D.<10%). 11D10 bound almost exclusively to BrE-1; there was virtually no cross-reactivity with any of the other Ab1 tested.

Idiotype specificity of Ab2 was also confirmed by reversing the position of the Ab1 and Ab2. Plates were coated with 100 ng, 300 ng and 1000 ng of purified Ab2, and reacted with various labeled Ab1. Included were $^{125}$I-BrE-1, and $^{125}$I-BrE-3. BrE-3 is an IgG1 specific for another tumor associated HMFG epitope, and served as a control. Results of an experiment in which 11D10 was tested by this method are shown in Table 1, and confirm the specificity for BrE-1.

TABLE 1

Binding of mAb1 BrE-1 and BrE-3 to anti-idiotype (11D10)

| Ab2 | Concentration cpm | BrE-1 (IgG2b) cpm | BrE-3 (IgG1) cpm |
| --- | --- | --- | --- |
| 11D10 | 100 ng | 6,149 ± 301 | 263.0 ± 43.4 |
|  | 300 ng | 16,731 ± 483 | 260.0 ± 12.3 |
|  | 1000 ng | 44,177 ± 1,392 | 374.3 ± 23.8 |

Specificity for the BrE-1 idiotype was further established in competition experiments. Various label d Ab2 were mixed different members of a panel of unlabeled competitors comprising Ab2s, Ab1, and other mouse immunoglobulins. The Ab2s were then tested for binding to BrE-1 coated plates. For the best Ab2, an inhibition of greater than 90% was observed using 250 ng of unlabeled Ab2 or BrE-1 as competitor. Virtually no inhibition was obtained, up to a concentration of 10 Tg, using the other immunoglobulins as potential competitors. Representative results in which 11D10 was the Ab2 tested are shown in Table 2 (mean cpm, n=3, s.d.<10%).

TABLE 2

Inhibition of idiotype-Antiidiotype Binding

| Inhibitor | cpm Bound | % Inhibition |
| --- | --- | --- |
| None | 37,071 | 0 |
| 11D10 (Ab2), 0.250 µg | 1,853 | 95 |
| BrE-1 (Ab1), 0.250 µg | 2,594 | 93 |
| SN2, 10 µg | 37,085 | 0 |
| CLL-2, 10 µg | 37,482 | 0 |
| 4EA2, 10 µg | 38,904 | 0 |
| RWP 1.1, 10 µg | 37,082 | 0 |
| 3F3, 10 µg | 38,132 | 0 |
| MOPC, 10 µg | 37,161 | 0 |
| 1E3, 10 µg | 38,523 | 0 |
| 3A4, 10 µg | 38,064 | 0 |
| F6/32, 10 µg | 37,904 | 0 |

Screening for Anti-Idiotypes Directed Against the BrE-1 Paratope

To determine whether the Ab2 were directed against the paratope of BrE-1, the Ab2 were used to compete for the binding of radiolabeled BrE-1 to HMFG, as expressed on human breast carcinoma cell lines MCF-7 or SKBR3.

To conduct the assay, the target cells were grown as confluent monolayer in 96-well tissue culture plates. Various dilutions of the test Ab2 (either culture supernatant or purified antibody) were mixed with the labeled BrE-1, and then added to confluent cell cultures in microtiter plate wells. Percent inhibition of the assay was calculated according to the formula:

$$\% \text{ inhibition} = \left[1 - \left(\frac{R_T - R_C}{R_{MAX} - R_C}\right)\right] \times 100\%$$

where $R_T$ is the average cpm of the experimental well with inhibitors; $R_C$ is the average background cpm; and $R_{MAX}$ is the average maximum binding without any inhibitors.

FIG. 7 shows results of this type of experiment, conducted using 11D10 as the competing antibody. 250 ng of the Ab2 11D10 inhibited the binding of labeled BrE-1 to the HMFG expressing cells by over 90% (FIG. 7).

About 24 of the 42 monoclonal antibodies tested at this stage (including 11D10) inhibited the binding of labeled BrE-1 to the HMFG expressing cells or to the HMFG extract in a plate-binding assay at amounts as low as about 25 ng. Purified 3H1 (a mouse monoclonal antibody of irrelevant specificity) was used as a control competitor, and did not inhibit the binding of BrE-1 to the cells. Generally, an Ab2 producing at least 85% inhibition was considered to have passed this step in the screening process.
Confirmation of the Binding Specificity For the most promising Ab2, confirmation experiments were conducted to confirm the specificity of binding to BrE-1 using HMFG.

About 40,000 cpm of $^{125}$I-BrE-1 was coincubated with a semipurified preparation of HMFG. The antibody-Ag mixture was added to Ab2-coated plates (500 ng/well), and the ability of HMFG to inhibit the binding was determined. The amount of Ab2 was non-limiting with respect to the amount of BrE-1 that could bind, and was therefore a sensitive indicator for small amounts of competing HMFG.

Six of the 24 antibody-producing clones testing positively in the screening tests described so far were used to prepare mouse ascites as a source of Ab2. The Ab2 were purified by chromatography using a Protein A affinity resin by standard techniques.

The binding of BrE-1 to 11D10 was inhibited by HMFG. Screening for Anti-Idiotypes Capable of Eliciting a Tumor-Specific Immune Response Since a central purpose of these experiments was to find an anti-idiotype capable of eliciting an anti-HMFG immune response, the next screening step was to test its immunogenicity in animal models. The Ab2 would have to be not only immunogenic, but capable of raising Ab3 that cross-reacted back to the tumor antigen HMFG.

Accordingly, the Ab2s that gave the strongest result in the competition experiments with the HMFG-expressing cells were brought forward for testing in immunization experiments.

For each Ab2 to be tested, 5 BALB/c mice and two New Zealand while rabbits were immunized. For the mice, Ab2 was conjugated to KLH. 50 µg was injected per mouse and 200 µg was injected per rabbit on a biweekly schedule. Initial injections were prepared in complete Freund's adjuvant, and subsequent injections were prepared in incomplete Freund's adjuvant. Sera were collected regularly for analysis. Initially, Ab3 titers were measured in a standard sandwich radioimmunoassay using Ab2 both as capture and detecting antibody. The antibody response against Ab2 reached substantial levels after the 5th immunization.

Subsequently, an assay was conducted in which plates were coated with the HMFG preparation. Sera were incubated in the well, and antibody bound was detected with enzyme-linked anti-immunoglobulin. This assay requires the antibody to bind the original tumor-associated antigen, and establishes that at least a portion of the Ab3 induced by immunizing with the anti-idiotype is tumor antigen specific. The level of HMFG-specific Ab3 was titered by serial dilution, and defined the "quality" of the immunizing Ab2.

The 11D10 monoclonal antibody emerged as having the highest quality among the candidates tested.
Confirmation that the Ab3 Elicited by 11D10 had the Desired Specificity Since the therapeutic objective of 11D10 lies in its ability to elicit a response reactive against the tumor associated antigen, the specificity of the Ab3 obtained was confirmed in a number of subsequent experiments.

Ab3 containing sera (depleted for anti-isotypic and anti-allotypic activity) almost completely inhibited the binding of labeled BrE-1 to 11D10 or vice versa. This indicates that the Ab3 antibodies share idiotopes with Ab1. Similar results were obtained whether the Ab3 producing animals had been immunized with 11D10 conjugated to KLH, or 11D10 emulsified in Freund's adjuvant.

Spleen cells from mice immunized with 11D10 were used to generate monoclonal Ab3 producing cell lines. Competition experiments similar to those described in the previous paragraph showed that the monoclonal Ab3 bound to HMFG in an identical fashion as BrE-1.

Figure 8:
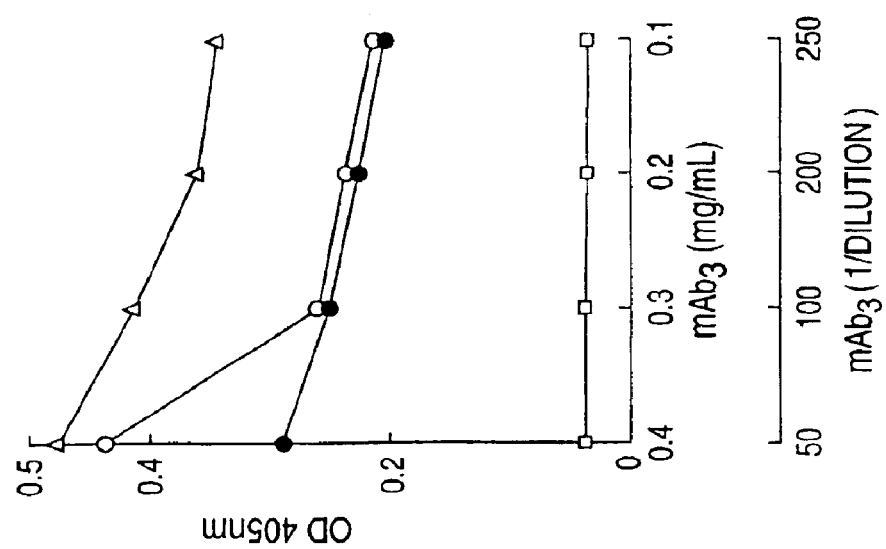
FIG. 8 is a graph depicting binding of absorbed polyclonal mice and rabbit Ab3 sera as well as mAb3 to breast carcinoma cell line SKBR3 by ELISA. Open circles denote 11D10-2F7 (mAb3); closed circles denote mouse Ab3 sera, open triangles denote rabbit Ab3 sera; open squares denote 1E3 control.

Binding experiments were conducted to determine whether the Ab3 induced by 11D10 was capable of binding to HMFG as it is expressed on tumor cell lines. FIG. 8 shows results of direct binding of various Ab3 preparations to the breast carcinoma cell line SKBR3. Polyclonal mouse Ab3, polyclonal rabbit Ab3, and monoclonal mouse Ab3 were prepared by adsorbing with mouse immunoglobulin, and tested for binding at several dilutions. Both polyclonal and monoclonal Ab3 sera from 11D10 immunized animals bound to HMFG positive cell lines MCF-7 and SKBr3, but not to antigen negative melanoma cell line M21/P6.

Figure 9:
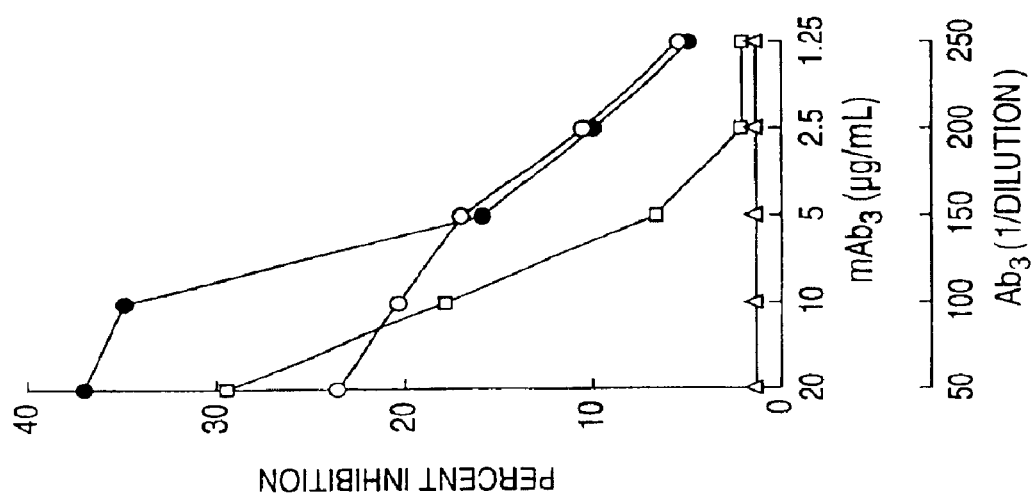
FIG. 9 is a graph depicting inhibition of MC-10 (BrE-1) binding to SKBR3 cells by mAb3 and polyclonal mouse and rabbit Ab3 sera. Closed circles denote rabbit (Ab3) sera (#123), open circles denote 11D10-2F7 (mAb3); open squares denote mouse Ab3 sera; open triangles denote pre-immune sera (control).

Various competition experiments were conducted to confirm that the Ab3 induced by 11D10 had the desired specificity. Confluent monolayer cultures of SKBR3 cells in microtiter wells were reacted with 50,000 cpm of $^{125}$I-BrE1 and various dilutions of Ab3 as competitor. A monoclonal antibody of unrelated specificity, 1E3, was used as negative control. The results are shown in FIG. 9. Twenty µg of a monoclonal Ab3 inhibited binding by 25%. Mouse or rabbit sera containing polyclonal Ab3 sera diluted 1/50 dilution produced 38% and 30% inhibition, respectively. This indicated that the Ab3 bind to the same HMFG epitope as Ab1. Incomplete inhibition under these conditions suggests that some Ab3 may have lower affinity and avidity for HMFG than Ab1.

Spleen cells from mice immunized with 11D10 were also used in a T-cell proliferation assay. The spleen cells were cultured for 5 days in the presence of semipurified HMFG, and then pulsed with [$^3$H]thymidine. Greater uptake in cells from 11D10 immunized animals than with controls is consistent with the presence of an Id-specific cellular immune response. 11D10-Alugel immunized rabbits showed some DTH skin reactions against semipurified preparation of HMFG, but not against pure CEA (a negative specificity control). Since HMFG comprises several epitopes and is not available in purified form, we cannot be certain about the specificity of the reaction.
Dot Blot Analysis of mAb1 and mAb3

Figure 10:
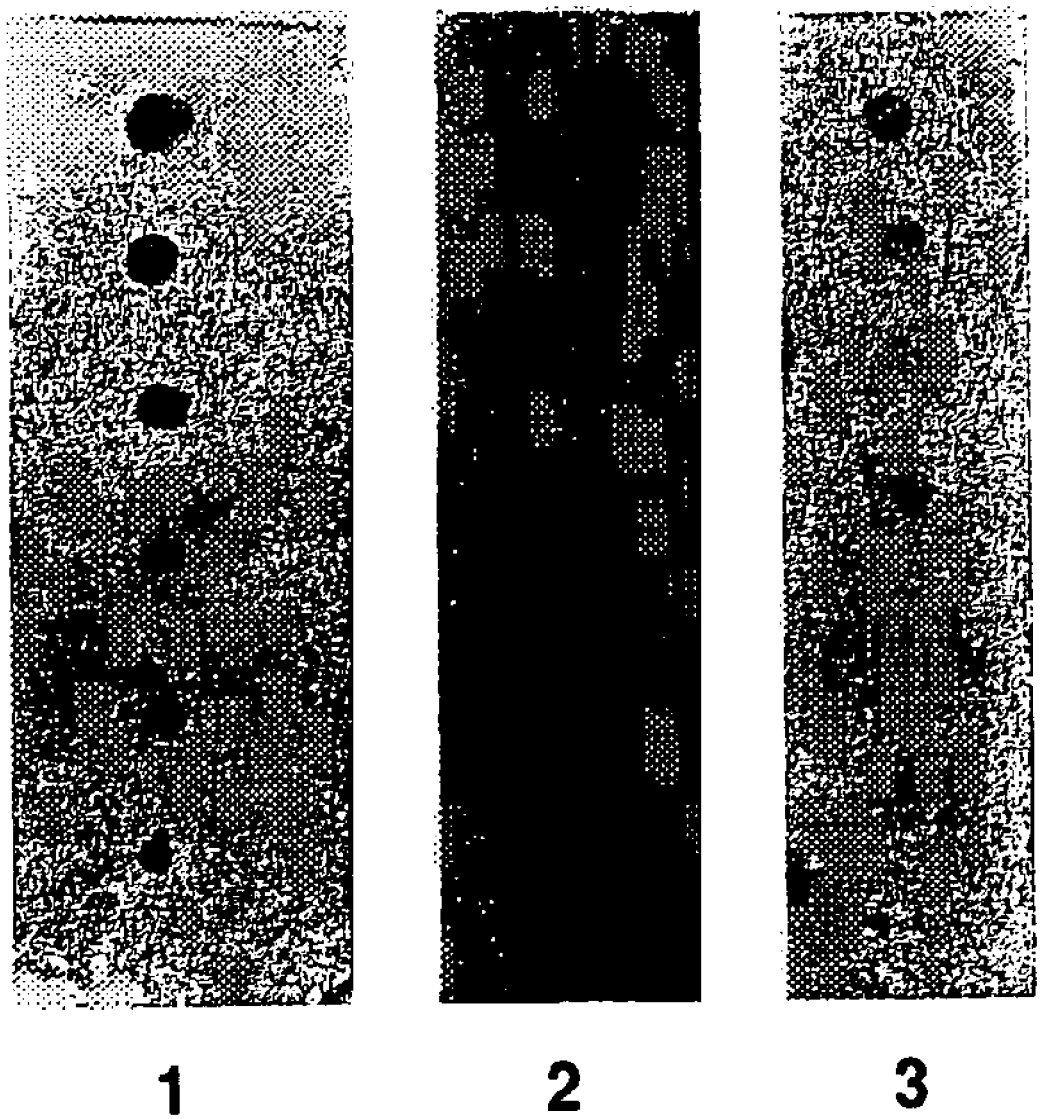
FIG. 10 is a half-tone reproduction of a transblot analysis of HMFG on nitrocellulose paper with mAb1 and mAb3. Lane 1, MC-10 (10 μg/ml); lane 2, 1E3 IgG1 (control; 50 μg/ml); lane 3, mAb3 IgG1 (50 μg/ml)

HMFG antigen at different dilutions were transblotted to nitrocellulose filters and reacted with BrE-1 (Ab1) and mAb3 (FIG. 10). Lanes 1–3 were transblotted with HMFG and incubated with BrE-1, 10 µg/ml, control 1E3 IgG1, 50 µg/ml and mAb3 IgG1, 50 µg/ml, respectively. The reaction was developed by using goat anti-mouse IgG alkaline phosphatase reagents and substrate. The staining was identical but more intense with Ab1 while the control antibody was negative.
Matching Experiment for Cross-Reacting Idiotype in Breast Cancer Patients We studied sera from 50 randomly selected breast cancer patients to determine if any of them had pre-existing matching idiotype which would be recognized by Ab2 11D10. Microtiter plates were coated with 250 ng/well of purified F(ab')$_2$ fragment of 11D10 (Ab2) and incubated with 1:100 dilution of patients' sera and developed with goat anti-human IgG enzyme labeled antibodies. The binding of the sera to Ab2 was detected using alkaline phosphatase conjugated anti-human IgG (γ chain specific) antibody and substrate.

Figure 11:
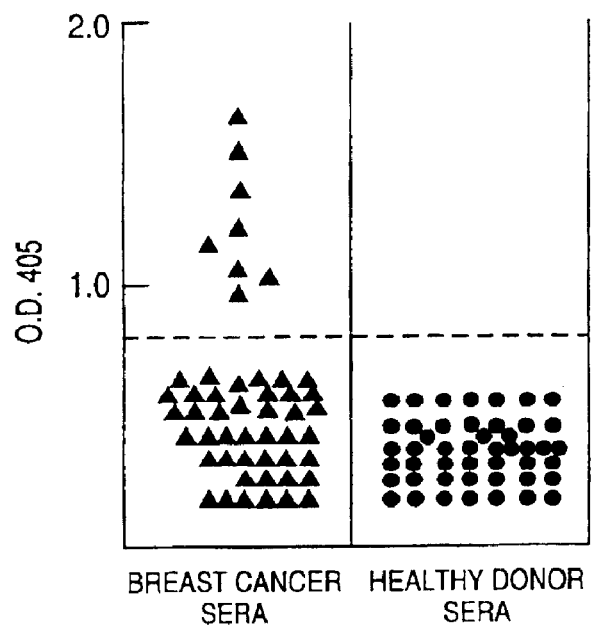
FIG. 11 is a graph depicting the level of expression of 11D10 anti-Id reactive antibodies in the sera of breast cancer patients.

As shown in FIG. 11, a small number (8/50) of these breast cancer patients' sera have elevated levels of antibodies reactive with 11D10. The selective criteria in anti-Id therapy is based on the assumption that the disease itself induces a state of priming B cells and T cells in the host. It is hypothesized that in patients who express a corresponding matching Id, Ab2 stimulation would then be able to effectively stimulate such already primed B and T cells. The finding of Id matching sera from breast cancer patients suggest that they may be specially suitable as potential candidates for active anti-Id immunotherapy with Ab2 11D10.
Clearance Study of $^{111}$In-BrE-1 in MX-1 Tumor Bearing BALB/c Nude Mice To determine whether 11D10 would be suitable as a second reagent to bind to excess radiolabeled antibody in radioimmunotherapy, we performed a clearance study. Each BALB/c nude mouse was injected with 20 µCi of 2.9 µg of $^{111}$In-BrE-1. After 24 hours 20 µg of anti-Id 11D10 was injected to one group of six mice to be sacrificed at 30 minutes and another group at 40 hours. The control groups of mice at 30 minutes and 40 hours were not injected with anti-Id 11D10. After sacrificing the mice, blood and organs were removed for measuring radioactivity levels. The results are shown in Table 3 and expressed as percent dose per gm of $^{111}$In-BrE-1±SEM. Values are expressed as mean % SEM. At both 30 minutes and 40 hours there was significant clearance of radioactivity in almost all organs (specially in blood, kidney, muscle and lung) except liver in experimental groups as compared to controls. The tumor retention was not affected at 30 minutes; however, after 40 hours there was some clearance in the treated group.

TABLE 3

Percent dose per gram of $^{111}$In BrE-1 in BALB/c Nude Mice with MX-1 Tumor

|  | BrE-1 Control 30 min | BrE-1 + anti-idiotype 30 min | BrE-1 Control 40 HR | BrE-1 + anti-idiotype 40 HR |
|---|---|---|---|---|
| Blood | 11.38 ± 1.57 | 6.92 ± 1.74 | 6.01 ± 1.13 | 1.34 ± 0.83 |
| Skin | 2.90 ± 0.36 | 3.11 ± 0.54 | 2.49 ± 0.14 | 2.28 ± 0.39 |
| Muscle | 1.23 ± 0.26 | 1.16 ± 0.16 | 1.00 ± 0.07 | 0.59 ± 0.14 |
| Lung | 7.08 ± 1.33 | 3.43 ± 0.80 | 5.48 ± 0.11 | 0.94 ± 0.35 |
| Kidney | 3.59 ± 0.62 | 2.10 ± 0.31 | 3.27 ± 0.29 | 0.97 ± 0.26 |
| Spleen | 2.66 ± 0.49 | 2.13 ± 0.31 | 2.65 ± 0.03 | 1.35 ± 0.47 |
| Liver | 3.73 ± 0.78 | 8.74 ± 3.33 | 3.63 ± 0.11 | 9.12 ± 1.24 |
| Stomach | 0.87 ± 0.21 | 1.23 ± 0.36 | 0.28 ± 0.10 | 0.57 ± 0.06 |
| Intestine | 1.01 ± 0.16 | 0.81 ± 0.02 | 0.80 ± 0.03 | 0.46 ± 0.07 |
| Bone | 1.02 ± 0.12 | 0.84 ± 0.07 | 0.75 ± 0.02 | 0.26 ± 0.04 |
| Marrow | 3.05 ± 0.50 | 1.51 ± 0.17 | 1.83 ± 0.66 | 1.16 ± 0.09 |
| Tumor | 3.28 ± 0.22 | 4.13 ± 0.66 | 4.35 ± 0.27 | 2.51 ± 0.36 |

Example 2

Cloning and Sequencing of 11D10 cDNA

Unless otherwise specified, all cloning techniques were essentially as described by Sambrook et al. (1989) and all reagents were used according to the manufacturer's directions.

The polynucleotide sequence was obtained for the 11D10 antibody by isolating messenger RNA from the 11D10 producing cell line. For each sequence determination, total RNA was isolated from 1×107 11D10 hybridoma cells. Messenger RNA was prepared by passage through two cycles of chromatography of oligothymidylate-cellulose columns. The yield of mRNA was about 100 µg. First strand cDNA was synthesized using SuperScript Preamplification kit (GIBCO/BRL).

To sequence the heavy chain variable region, PCRs were conducted on the cDNA using a reverse (3') primer corresponding to amino acids 126 to 119 of the murine γ1 constant region:

5'-CCCAAGCTTCCAGGGRCCARKGGATARACIGRTGG-3' (SEQ ID NO:36)

and various mixtures of forward primers, corresponding to the N-terminal leader sequences of murine variable region subgroups. The (5') forward primer that gave a positive reaction was:

5'-GGGAATTCATGRAATGSASCTGGGTYWTYCTCTT-3' (SEQ ID NO:37)

corresponding to amino acids −20 to −13 (I=inosine, R=A or G, Y=C or T, K=G or T, S=C or G, W=A or T).

The amplified fragment of cDNA was subcloned into pT7 plasmid and NovaBlue competent cells were transformed using a protocol provided by the supplier (Novagen). Recombinant colonies were picked up by color selection and plasmid DNA was prepared by miniprep procedure. The DNA sequence of the double stranded plasmid was determined using a Sequenase Version 2.0 kit (USB, Cleveland, Ohio). The sequence of the DNA insert in the plasmid was determined from both orientations using primers specific for the plasmid; namely T7 promoter primer (TAATACGACTCACTATAGGG—SEQ ID NO:38) and U-19 primer (GTTTTCCCAGTCACGACGT—SEQ ID NO:39). At least 8 clones were picked for sequence determination.

The sequence of the 11D10 light chain variable region was determined in a similar fashion. The forward and reverse primers giving a positive result in the FCR were:

5'-ACTAGTCGACATGAGGRCCCCTGCTCAG-WTTYTTGGIWTCTT-3' (SEQ ID NO:40)

5'-CCCAAGCTTACTGGATGGTGGGAAGATGGA-3' (SEQ ID NO:41)

corresponding to amino acids −20 to −10 of the leader sequence, and 122 to 116 of the mouse κ chain constant region, respectively.

In order to minimize the error rates in PCR amplification, pfu DNA polymerase (Stratagene, San Diego) was used for amplification in all subsequent experiments. Mutant frequency with this thermostable DNA polymerase is 1/10 compared to Taq DNA polymerase.

Confirmation that the isolated cDNA correspond to the 11D10 heavy and light chains was obtained by amino acid sequencing of the N-terminal of the isolated antibody. Fifty µg of purified 11D10 antibody is diluted with sample loading buffer (50 mM Tris-HCl, pH 6.8, 1% SDS, 1% glycerol, 0.1% β-mercaptoethanol) and heated to 100° C. for 3 minutes. The denatured protein was loaded onto a 7.5% polyacrylamide gel (BioRad Miniprotean II Dual Slab Cell) containing SDS and subjected to electrophoresis at 200 V for 1 hour. Proteins in the gels were transferred to polyvinylidine difluoride (PVDF) membranes by the procedure described by Towbin et al. ((1979) Proc. Natl. Acad. Sci. USA. 78: 4350–4354) at 150 mA overnight. The transfer buffer contains 25 mM Tris, 192 mM glycine, 20% (v/v) methanol. The membranes were stained by quick dipping in 0.1% Coomasie Brilliant blue in 50% methanol-50% acetic acid, followed by washing in a solution containing 40% methanol plus 10% acetic acid. After drying the membrane at room temperature, the stained heavy and light chain bands were excised with a clean razor blade. The proteins on the membrane slices were subjected to N-terminal microsequencing by automated Edman degradation using an Applied Biosystem Model 477A protein sequencer employing pulsed-liquid chemistry and on-line phenylethiohydantion amino acid identification. Each protein was subjected to 10–15 degradative cycles and the converted cleavage products from each cycle were analyzed by reverse-phase HPLC.

The nucleic acid sequence and the corresponding amino acid sequence for the heavy and light chain variable regions of monoclonal antibody 11D10 is shown in FIGS. 1 and 2, respectively.

The nucleic acid sequence was obtained as described earlier in this example by PCR amplification of messenger RNA from the antibody producing cell line. The amino acid sequence was obtained subsequently by translation of the polynucleotide sequence using the genetic code. The correct amino acids are self-evident because of the genetic code. The correct amino acid sequence is also inherent in the antibody producing cell line deposited with the ATCC under Accession No. HB-12020 in support of this disclosure.

The heavy and light chain polynucleotide and amino acid sequences were compared using the BLAST algorithm at the National Center for Biotechnology Information with sequences available from the PDB, SwissProt, PIR, SPUpdate, GenPept, and GPUpdate databases. The comparison was performed on Jan. 19, 1996.

Among the 10 database DNA sequences matched most closely to that of the 11D10 light chain variable region, none was identical. There were about 8–27 differences with the 11D10 DNA sequence, corresponding to about 6–17 amino acid differences. The sixth matched sequence (designation >gb/M59920/MUSIQKAA3) was a mouse kappa VJ germ-like sequence, and probably represents the prototype gene from which the 11D10 light chain was derived. The 11D10 DNA sequences differ from the germline sequence at 14 positions, corresponding to about 7 amino acid point differences.

DNAs and those encoded by the most closely matched database DNAs. The point differences likely have arisen by somatic mutation of germline sequences during development of the antibody-producing cell in the animal used to generate it.

FIG. 4 shows the ten most closely matched polynucleotide sequences to the 11D10 light chain variable region encoding sequence. FIG. 5 shows the ten most closely matched polynucleotide sequences to the 11D10 heavy chain variable region encoding sequence.

The light and heavy chain variable region amino acid sequences were compared with other known sequences using the BLAST algorithm at the National Center for Biotechnology Information with sequences available from the PDB, SwissProt, PIR, SPUpdate, GenPept, and GPUpdate databases. The comparison was performed on Jan. 19, 1996.

The 15 closest amino acid sequences found in the BLAST search have the identifiers shown in Table 6.

TABLE 6

Matched immunoglobulin amino acid sequences

Light Chain Variable Region

| | | |
|---|---|---|
| 1 | gp\|L41880\|MUSIKCC__1 | immunoglobulin kappa chain [Mus mu . . . |
| 2 | gp\|J00550\|MUSIGKAC2__1 | immunoglobulin kappa chain variabl . . . |
| 3 | sp\|P01639\|KV5G_MOUSE | IG KAPPA CHAIN PRECURSOR V-V REGIO . . . |
| 4 | gp\|V00808\|MMIGK7__1 | immunoglobulin kappa [Mus musculus] |
| 5 | pir\|PL0260\|PL0260 | Ig kappa chain V region (anti-DNA, . . . |
| 6 | gp\|M59920\|MUSIGKAA3__1 | Ig kappa chain [Mus musculus] |
| 7 | pir\|PL0259\|PL0259 | Ig kappa chain V region (anti-DNA, . . . |
| 8 | gp\|Z22118\|MDIGKVBS__1 | immunoglobulin variable region [Mu . . . |
| 9 | gp\|M36246\|MUSIGLAFA__1 | immunoglobulin kappa-chain VK-1 [M . . . |
| 10 | pdb\|2GFB\|A | Igg2a Fab Fragment (Cnj206) > pdb\|2 . . . |
| 11 | gp\|M64168\|MUSIGKAFT__1 | immunoglobulin kappa-chain VK-1 [M . . . |
| 12 | pir\|PL0262\|PL0262 | Ig kappa chain V region (anti-DNA, . . . |
| 13 | gp\|X02177\|MMIGGVJ1__1 | Immunoglobulin G kappa light chain . . . |
| 14 | gp\|U25098\|MMU25098__1 | immunoglobulin light chain [Mus mu . . . |
| 15 | pir\|B47271\|B47271 | nitrophenyl phosphonate-specific a . . . |

Heavy Chain Variable Region

| | | |
|---|---|---|
| 1 | gp\|X64805\|MMAIDHCH__1 | anti-Id mAB 114 haevy chain, V-reg . . . |
| 2 | gp\|M17953\|MUSIGHXW__1 | immunoglobulin heavy chain [Mus mu . . . |
| 3 | gp\|Z22117\|MDIGGVBC__1 | immunoglobulin variable region [Mu . . . |
| 4 | pir\|S38950\|S38950 | Ig gamma chain - mouse |
| 5 | gp\|Z22034\|MDIGGVAG__1 | immunoglobulin variable region [Mu . . . |
| 6 | gp\|U40581\|MMU40581__1 | sFv antibody [Mus musculus] |
| 7 | gp\|A13735\|A13735__1 | V region monoclonal antibody,cross . . . |
| 8 | pir\|S41394\|S41394 | Ig heavy chain V region - mouse |
| 9 | gp\|Z22088\|MDIGGVAR__1 | immunoglobulin variable region [Mu . . . |
| 10 | gp\|L22747\|MUSF__1 | immunoglobulin heavy chain [Mus mu . . . |
| 11 | gp\|M28251\|MUSIGHMX__1 | Mouse Ig rearranged gamma-chain (G . . . |
| 12 | gp\|M36225\|MUSIGHAEF__1 | Immunoglobulin heavy chain V-regio . . . |
| 13 | pir\|S40295\|S40295 | Ig gamma.2a chain (mAb735) - mouse |
| 14 | gp\|L22749\|MUSLI__1 | immunoglobulin heavy chain [Mus mu . . . |
| 15 | gp\|M31287\|MUSIGHAVA__1 | IgG gene product [Mus musculus] |

Among the 10 database DNA sequences matched most closely to that of the 11D10 heavy chain variable region, none was identical. 9 of the 10 sequences were 3–12 base pairs longer, due to splicing differences within the VDJ junction. In addition, there were about 15–43 point differences compared with the 11D10 DNA sequence outside the junction, corresponding to about 11–23 amino acid differences.

Thus, there were at least about 18 amino acid differences between the amino acid sequences encoded by the 11D10

FIGS. 26(A) and (B) is a comparative depiction of the 11D10 light and heavy chain amino acid sequence with the 15 closest sequences found in the BLAST search. Panel (A) shows the light chain comparison. Panel (B) shows the heavy chain comparison. Residues identical with the 11D10 sequences are indicated with a dot (.). Gaps introduced to improve alignment about the heavy chain VDJ junction are indicated with a double line (=).

Among the 50 database amino acid sequences matched most closely to that of the 11D10 light chain variable region, none was identical. 11D10 differed from the fifteen closest sequences by a minimum of 7 and an average of about 12 substitution differences. A cluster of differences occurred near the end of CDR1. Other differences occurred in CDR3 and the framework.

Among the 50 database amino acid sequences matched most closely to that of the 11D10 heavy chain variable region, none was identical. The following summarizes the main points deduced from the comparison.

The closest match was with a heavy chain variable region indicated by its GenBank designation as being another anti-idiotype (designation gp|X64805|MMAIDHCH_1). There were 11 substitutions between residues 1 and 98 (before the VDJ junction), 7 substitution differences after residue 98.

11D10 differed in length from 40 of the heavy chain sequences. The other sequences were longer by up to 5 residues or shorter by as many as 2 residues about the VDJ junction.

Except for the two most closely matched sequences, there were at least 18 and an average of about 22 substitution differences between residues 1 and 98.

A variety of D and J region genes appear to be used with the prototype V gene. Only one of the 50 sequences appeared to be using the same D region. There was a point difference within the D region, and a splicing difference of 3 residues.

For the most closely matched of the 50 sequences, there was a total of 18 insertions, deletions and substitution differences. The other 49 sequences had a total of at least 25 and an average of about 30 insertions, deletions and substitution differences.

Differences appeared throughout the variable region.

FIG. 26(C) shows amino acid consensus sequences for the light and heavy chain variable regions of the 15 most closely matched sequences (SEQ ID NO:47 and SEQ ID NO:48). These represent prototypes for the assembled light chain VJ gene and heavy chain VDJ gene. Residues in the 11D10 sequence that are identical with the consensus sequence are indicated by dots (.). CDRs are indicated by asterisks (*). Also shown are fragments from human milk fat globulin (HMFG) in N→C (upper case) or C→N (lower case) orientation.

The following points may be deduced:

11D10 has at least about 18 departures from the consensus sequence. 7 of these occur in the light chain and 11 occur in the heavy chain.

The point differences occur throughout the 11D10 light and heavy chain variable region sequences. Eight occur within CDRs and 10 occur outside CDRs.

The alignment of the 11D10 sequences with HMFG fragments does not depend on the point mutations.

Variable region fragment sequences, particularly those encompassing the heavy chain VDJ junction or any of the point differences shown in FIG. 26(c) are of interest in developing polypeptides of this invention having the immunological activity of 11D10. Encoding sequences about the VDJ junction or any of the point differences are of interest in developing polynucleotides of this invention.

Example 3

Induction of a Breast Cancer Specific Response by 11D10 in Monkeys

Cell Lines

The human breast carcinoma cell line MCF-7, which expresses HMFG antigen, was grown in RMP1 1640 medium supplemented with 10% FCS, 1% L-glutamine, penicillin, and streptomycin, and was used for the detection of antitumor responses. The human melanoma cell line M21/P6 (kindly provided by Dr. Ralph Reisteid, Scripps Research Institute, La Jolla, Calif.) and the T-cell line MOLT-4, both of which are HMFG negative, were grown in the same medium and were used as negative controls.

Antibodies

The Ab1 mAb MC-10 (IgG2b, κ), which recognizes a distinct and specific epitope on the MW400,000 HMFG molecule, was used to immunize syngeneic BALB/c mice for the production of anti-Id mAb 11D10 (IgG1-κ), as described in Example 1. The mAb2 3H1 (IgG1-κ) is a murine anti-Id mAb which is related to the human CEA (Bhattacharya-Chatterjee et al. (1990) *J. Immunol.* 14S:Z758–2765) and was used as a control.

Adjuvant

To augment the immunogenicity of the anti-Id vaccine an adjuvant is required. Aluminum hydroxide is approved by the United States Food and Drug Administration for use as an adjuvant in humans. We therefore immunized monkeys in this preclinical study with Ab2 11D10 precipitated with aluminum hydroxide as described below.

Antibody Preparation

11D10 was obtained as described in Example 1. The mAb2 3H1 (an IgG1-κ) is a murine anti-Id mAb which is related to the human CEA (Bhattacharya-Chatterjee et al. (1990) *J. Immunol.* 14S:Z758–2765) and was used as a control.

Aluminum Hydroxide Precipitation

An adjuvant was used to augment the immunogenicity of the anti-Id vaccine. Aluminum hydroxide is approved by the United States Food and Drug Administration for use as an adjuvant in humans. We therefore immunized monkeys in this preclinical study with Ab2 11D10. Briefly, to 5-mg aliquots of purified mAb anti-Id (Ab2), 1 ml of 2% Alu-Gel S (Serva Fine Biochem, Inc., Garden City, Long Island, N.Y.) was added. The volume was then adjusted to 10 ml with Dulbecco's-PBS and the mixture was incubated on a vortex for 1 hr at room temperature. The mixture was then centrifuged at 2000 rpm at 24° C. for 10 minutes. The amount of mAb bound in the gel layer was determined by measuring spectrophotometrically the amount of unbound antibody in the supernatant. The Alu-Gel-precipitated antibody was stored at 4° C. until use. These procedures were performed aseptically in a laminar flow hood, and the final product was sterile and clearly labeled as anti-Id 11D10 Alu-Gel and aliquoted into pyrogen-free, sterile glass vials.

Immunization of Monkeys

Cynomolgus monkeys were immunized with 11D10 or with the 3H1 control. Monkeys were housed at the White Sands Research Institutes (Alamogordo, N. Mex.). A pair of male and female monkeys, weight 3–4 kg, was immunized with either 2 mg of 11D10 or 3H1 intracutaneously at four different sites on days 0, 14, 28 and 42, respectively. Only two monkeys were used for each anti-Id (Ab2) at a single does for financial reasons. The 2-mg dose was selected based on previous preclinical and clinical studies with different anti-Id vaccines. Blood samples were collected before immunization and 10 days after each immunization.

Toxicity

The induction of Ab3 responses in monkeys did not cause any apparent side effects in animals. Only mild local swelling and irritation were observed at the injection site as a result of multiple immunizations. The monkeys were routinely checked by physical examinations and weight measurements. They did not show any signs of abnormalities.

Development of Humoral Immunity Induced by Immunization with Aluminum Hydroxide-Precipitated Ab2

Specific Ab3 Response to Ab2. Sera from immunized monkeys were tested for the presence of anti-anti-Id antibodies. Sera were preincubated with normal murine immunoglobulin to block monkey antibodies against isotypic and allotypic determinants and then checked for the presence of anti-anti-Id (Ab3) by reaction with the immunizing anti-Id (11D10) coated onto microtiter plates, by RIA. Unrelated Ab2 was used as the control. After washing, the antigen-antibody reaction was tagged with the use of $^{125}$I-labeled anti-Id reagent in a homogeneous sandwich RIA. Preimmune sera and sera from monkeys immunized with control Ab2 3H1 were also used in these assays. In addition, $^{125}$I-labeled monoclonal Ab2 3H1 was used as control.

Idiotope Analysis of Ab3. If a positive reaction is obtained in the method described above, Ab3 sera from those monkeys were checked for their ability to inhibit the binding of $^{125}$I-labeled 11D10 to BrE-1 (Ab1) bound to microtiter plates or vice versa (inhibition of the binding of radiolabeled BrE-1 to 11D10 on the plate). An unrelated Ab1-Ab2 system was used as a control (Bhattacharya-Chatterjee et al. (1990); Bhattacharya-Chatterjee et al. (1987) *J. Immunol.* 139:1354–13605). This demonstrated whether Ab3s in monkey sera share idiotopes with BrE-1 (Ab1). This inhibition assay of Ab1-Ab2 binding by Ab3 sera also demonstrates whether Ab3 is a true anti-anti-Id.

Binding of Ab3 to Tumor Antigen. To assess humoral immune responses directed against native, target antigens, monkey Ab3 sera were tested for reactivity with cell lines known to express HMFG in a RIA. In addition, the sera were checked for reactivity against a solubilized semipurified preparation of HMFG antigen coated onto microtiter plates. The antigen-antibody reaction was detected by using $^{125}$I-labeled anti-human immunoglobulin reagents or alkaline phosphatase labeled anti-human immunoglobulin in ELISA. Preimmune sera was used as a control. The unrelated CEA was also used as a control in this assay. The isotype of monkey Ab3 sera binding to HMFG antigen was determined by ELISA using anti-human isotype-specific reagents.

Binding of Ab3 to tumor cell lines was also checked by immune flow cytometry. Antigen-positive MCF-7 cells ($1 \times 10^6$ per well) were reacted with Ab1 (MC-10) and Ab3 at 100 µl at 4° C. for 60 minutes. After washing, the cells were incubated with either goat anti-mouse or goat anti-human F(ab')$_2$ IgG-FITC labeled antibody (Tago, Burlingame, Calif.) for 30 minutes at 40° C. They were then washed twice, fixed in 2% paraformaldehyde, and analyzed by immune flow cytometry (FACStar, Becton Dickinson, San Jose, Calif.). Antigen-negative MOLT-4 cells were used as a control in this assay.

Purification of Anti-anti-Id Antibody (Ab3) from Hyperimmunized Monkey Sera. Twenty ml of hyperimmune serum were passed over an immunoadsorbent column consisting of immunizing anti-Id immunoglobulin (11D10-IgG1) coupled to Sepharose 4B. Anti-anti-Id antibodies (Ab3) were eluted with 0.1 M glycine-hyrochloric acid buffer (pH 2.4) and neutralized to pH 7.0 with 3 M Tris. The eluted antibody was then passed over an immuno-adsorbent column consisting of an unrelated isotype-allotype-match d anti-Id mAb coupled to Sepharose 4B to remove anti-isotype and antiallotypic reactivities. Antibody that passed through was concentrated and used as purified Ab3. The isotype of Ab3 was determined by ELISA using human anti-isotype-specific reagents (Tago).

Epitope Analysis of Ab3. To demonstrate that Ab3s generated in monkeys and Ab1 (BrE-1) bind to the same antigenic determinant, inhibition of BrE-1 binding to the antigen-positive tumor cell line MCF-7 or HMFG antigen by purified Ab3 was checked by RIA as described (Bhattacharya-Chatterjee et al). (1990).

Slot Blot Analysis of Purified Ab3 with HMFG. Polyvinylidene difluoride membrane was activated in methanol for 5 minutes and transferred to 0.02 M PBS, pH 7.0. Different concentrations of proteins (5 µg, 2 µg, 1 µg) were adsorbed on the membrane using the Hybrislot instrument (BRL Life Technologies, Gaithersurg, Md.). The membrane was then blocked with 2% BSA in PBS for 2 hours with shaking, followed by incubation with 5 ml of a solution of 20 µg/ml Ab1 or Ab3 for 3 hours with shaking. The membranes were then washed 5 times with 1% BSA in PBS and incubated with alkaline phosphatase-labeled goat-anti-human immunoglobulin or goat-anti-mouse immunoglobulin (1:100 dilution) for 90 minutes, washed, and developed with substrate supplied in the Bio-Rad kit.

Assay for Id-Specific Proliferative Response.

Fresh peripheral blood mononuclear cells were isolated by standard Ficoll-Hypague density gradient centrifugation methods, and $5 \times 10^3$ cells/well were incubated with different concentrations of 11D10 and control 3H1 (10 ng to 2 µg) in RPMI 1640 medium with 5% heat-inactivated FCS, penicillin, and streptomycin. The nonspecific mitogen phytohemagglutinin-P was used as a positive control at 2 and 1 µg/well. After the cells were incubated for 5 days at 37° C. in an atmosphere containing 5% carbon dioxide, they were pulsed with [$^3$H]thymidine (1 µCi/well) for 20 hours. Data are expressed as mean counts (triplicate wells)/min of [$^3$H]thymidine incorporation. The SD of the data was <10% for each determination.

Results

Induction of Anti-anti-Id (Ab3) Responses in Monkeys. The sera from monkeys were obtained 10 days after the fourth immunization and analyzed for Ab3 responses by sandwich RIA and inhibition of Ab2 binding to Ab1 (Table 4). For these assays, the sera were pretreated with normal mouse immunoglobulin (500 µg/ml) to block anti-isotypic and antiallotypic reactivities. For the sandwich RIA, AB3 sera obtained after the fourth immunization was diluted with PBS containing normal mouse immunoglobulin (500 mg/ml). The sera were preincubated with normal mouse IgG prior to the assay. Ab3 at a 1:40 dilution was incubated with anti-Id mAb 11D10 or 3H1, coated on the microtiter plate, and then reacted with $^{125}$I-labeled 11D10 or 3H1 (~50,000 cpm) in a sandwich assay. The results are expressed as bound cpm in a sandwich assay. The results are presented as mean cpm (n=3). The SD of the data was <10%. We then tested binding of monkey Ab3 sera to semi-purified HMFG. Ab3 sera from monkeys (PRO 723 and PRO 872) immunized with 11D10 bound specifically to the immunizing Ab2 (11D10) with minimal reactivity with unrelated Ab2 (3H1). Monkey Ab3 were also inhibited the binding of radiolabeled Ab2 to Ab1 by 91 and 95%, respectively, even at a dilution of 1:40 (Table 4). There was no inhibition with preimmune sera or sera obtained from monkeys (PRO 541 and PRO 667) immunized with the unrelated Ab2 3H1. Purified 11D10 was used to coat the plate (250 ng/well), and the binding of radiolabeled BrE-1 (~50,000 cpm) to 11D10 was tested for inhibition in the presence of different dilutions of Ab3 sera. In a parallel control experiment, an unrelated Ab1-Ab2 system (mAb 5019-3H1) was used as the control. The kinetics of Ab3 response are shown in FIG. 12 using sera from monkey PRO 723, demonstrating inhibition of the binding of radiolabeled Ab1 to Ab2. Similar reactivity was seen with sera from monkey PRO 872. These results indicate that monkey Ab3 sera share idiotypes with the Ab1.

TABLE 4

Analysis of monkey anti-anti-ID sera generated with anti-id-mAb 11D10

| | | | Sample | | | | |
|---|---|---|---|---|---|---|---|
| | | | Ab3 sera | | | Ab3 sera (control) | |
| Assay | Plate coated with | 125 I-labeled anti-Id | PRO 723 | PRO 872 | Pre-immune sera (pool) | PRO 541 | PRO 667 |
| Sandwich R/A | 11D10 (Ab2) | 11D10 | 12,913 | 13,160 | 109 | 686 | 647 |
| | 3H1 (unrelated Ab2) | 11D10 | 301 | 532 | 167 | 887 | 1049 |
| | 11D10 (Ab2) | 3H1 | 1,074 | 978 | 349 | 382 | 410 |
| Inhibition | BrE-1 (Ab1) | | 91 | 95 | 2 | 6 | 8 |

Induction of Antitumor Cell Antibody Response. To determine whether 11D10 immunized monkey sera bound specifically to HMFG-positive breast carcinoma cells, the binding of monkey Ab3 sera to the breast cancer cell line MCF-7 was tested by ELISA. Ab3 sera at different dilutions were added to confluent monolayers of cells grown in 96-well microtiter plates and developed with goat anti-human IgG (H and L chain specific) enzyme-labeled antibodies. The absorbance (OD) was read after 1 hour. Monkey PRO 872 was immunized with Ab2 11D10. Monkey PRO 667 was immunized with control unrelated Ab2 (3H1). Preimmune monkey sera was also use as control. Binding of monkey Ab3 sera ( . . . ) to the melanoma cell line M21/P6 ELISA was tested following the same protocol. The results are presented as the mean absorbance at 405 nm (n=3). The SD of the data was <10% for each assay. As shown in FIG. 13, Ab3 sera, obtained after the fourth immunization at different dilutions, reacted with MCF-7 cells but not with the antigen-negative melanoma cell line M21/P6. We then tested binding of monkey Ab3 sera to semi-purified HMFG. The plate was coated with HMFG (2 mg/well) and reacted with Ab3 sera (1:100 dilution) from the monkey (PRO 723) immunized with Ab2 11D10 and from monkey (PRO 667) Immunized with unrelated Ab2 3H1 of the same isotype and allotype. Preimmune sera and PBS-BSA were also used as controls. The results are in FIG. 9 and are presented as the mean absorbance (OD) at 405 nm. In a parallel control experiment, the same sera were checked on a plate coated with purified CEA. There was no reactivity with 11D10 immunized monkey sera; the absorbance obtained was comparable to that obtained with FBS-BSA control. The results are presented as the mean absorbance at 405 nm (n=3). The SD of the data was <10%. The differences between experimental and control values were statistically significant. The Ab3 sera also bound specifically to semipurified HMFG coated onto microtiter plates by ELISA (FIG. 14). Control sera from preimmune monkeys or monkeys immunized with unrelated Ab2 (3H1) did not show appreciable binding to HMFG. In parallel experiments, the same Ab3s from monkey PRO 723 were compared on a plate coated with CEA and were negative.

To determine the reactivity with cell surface HMFG, MCF-7 cells were tested by immune flow cytometry. As shown in FIG. 10, Ab3 from Ab2-immunized monkeys showed distinct binding (FIG. 15-A) that was similar to the binding pattern obtained with Ab1 (not shown). Significant binding was not obtained with MOLT-4 cells which do not express HMFG (FIG. 15-B).

The Ab3 antibodies were then purified from sera as described above. The reactivity of purified Ab3 was checked by ELISA). The plate was coated with HMFG (2 mg/ml, 100 ng/well) and incubated overnight at room temperature. The plate was blocked with 1% BSA in PBS and reacted with purified Ab3 (20 mg/ml) from monkeys immunized with either 11D10 or control Ab2 (3H1). PBS-BSA was used as negative control. In the plate coated with CEA, mAb 8019 (anti-CEA) was used as a positive control. The results are in FIG. 16 and are presented as the mean absorbance (OD) as 405 nm (n=3). The SD of the data was <10%. Monkey Ab3 reacted specifically with HMFG coated onto microtiter plates, whereas no reactivity was obtained with control CEA-coated plates.

The specificity of purified Ab3 for HMFG was further confirmed by Slot blot analysis (FIG. 17). In FIG. 6, Lanes 1 and 2 were coated with semipurified HMFG, and Lanes 3 and 4 were coated with purified CEA. The membranes were incubated with Ab1 (lane 1), purified Ab3 (lanes 2 and 3), and anti-CEA in mAb8019 (lane 4). Reactivity with HMFG and not with CEA was demonstrated.

Competition of Murine Ab1 and Monkey Ab3 for MCF-7 Cell Binding. If Ab3 has a similar binding site as Ab1, it should compete with Ab1 for binding to HMFG on MCF-7 cells. Confluent monolayers of MCF-7 cells in microtiter plates were reacted with different concentrations of purified Ab3 and a fixed amount of $^{125}$I-labeled Ab1 (~50,000 cpm). Percent inhibition was calculated and plotted against the Inhibitor (mg Ab3). A fixed amount of radiolabeled Ab1 was coincubated with different amounts of purified Ab3 or control Ab3 preparations and MCF-7 cells (FIG. 18). One hundred ng of purified Ab3 inhibited binding by 60%, and 1 mg of purified Ab3 gave over 80% inhibition, whereas the control Ab3 used at a 5-mg concentration did not produce any inhibition. These results indicate that Ab2-immune monkey antibody binds to the same antigen as Ab1; therefore, the Ab3 preparation contains antibody molecules with Ab1' properties.

Cellular responses to Anti-Id. Cellular immune responses were measured by the proliferation of peripheral blood mononuclear cells incubated with aluminum hydroxide-precipitated anti-Id antibody (11D10) and aluminum hydroxide-precipitated anti-iD antibody (3H1). Peripheral blood lymphocytes (PBL) obtained from immunized monkeys were assayed for their responsiveness to stimulation with 11d10-Alugel or 3H1-Alugel in vitro. PBL were cultured for 5 days with 11D10 Alugel™ (2 µg to 100 ng) and 3H1-Alugel (2 µg to 100 ng) and proliferation was measured by incorporation of $^3$H-thymidine. Peripheral blood mononuclear cells obtained from monkey PRO 723 were stimulated in vitro with 11D10 (1 mg/ml); control unrelated Ab2 3H1 (1 mg/ml). Similarly, peripheral blood mononuclear cells obtained from monkey PRO 872 were stimulated in vitro with 11D10 (1 mg/ml); unrelated Ab2 3H1 (1mg/ml). Stimulation was measured by the degree of incorporation of a pulse of [$^3$H]thymidine. Culture medium without any antigen was also used as a control. The postimmunization peripheral blood mononuclear cells were collected 10 days after the third immunization. The results are shown in FIG. 19 and are expressed as mean cpm of triplicate wells. The SD of the data was <10% for each determination. The differences between experimental and control values were statistically significant. Positive proliferative responses were seen in both monkeys PRO 872 and PRO 723 that were nearly comparable to the responses to the mitogen phytohemagglutinin-P. Preimmune cells had no proliferative response to the anti-Id antibody, while postimmune cells had a significant response. There was also a minor but significant response to the isotype-matched 3H1 anti-Id antibody that was significantly less than that of the 11D10 response; this likely represents a response to the non-Id components of the immunoglobulin molecule. Proliferative responses were first noted after the third injection, and similar reactivity was obtained after the fourth immunization. Due to a limited supply of blood, we could not test T-cell proliferation in the presence of semipurified HMFG antigen and thus establish the antigen specificity of the cellular immune responses induced in the lymphocytes, as well as the phenotypes of these lymphocytes.

Example 4

Administration of 11D10 to Humans

Immunization with Alum-precipitated Anti-Id 11D10 at either 1, 2, 4 or 8 mg 11D10 per Injection Patients are randomized to receive one of the four doses of 11D10 with intracutaneous injections on days 0, 14, 28 and 42. Each dose group includes 3 to 8 patients. Aluminum hydroxide precipitation is performed following the method of Herlyn, et al. (1987) *Proc. Natl. Acad. Sci. USA* 84:805S. Briefly, the vaccine consists of anti-Id 11D10 after aluminum hydroxide precipitation containing 0.2% Alu-Gel S. To 5 mg aliquots of purified monoclonal anti-Id (Ab2), 1 ml of 2% Alu-Gel S (Serva Fine Biochem, Inc., Garden City, Long Island, N.Y.) is added. The volume is then adjusted to 10.0 ml with D-PBS and the mixture incubated on a vortex for 1 hour at room temperature. The mixture is then centrifuged at 2000 rpm at 24° C. for 10 minutes. The amount of antibody bound in the gel layer is determined by measuring spectrophotometrically the amount of unbound antibody in the supernatant. The Alu-Gel precipitated Ab is stored at 4° C. until use. The whole operation is done aseptically under a laminar flow hood. The final product is sterile and clearly labeled as anti-Id 11D10-Alu-Gel and portioned into pyrogen-free, sterile glass vials. The activity of the aluminum hydroxide precipitated idiotope is monitored by testing the binding to Ab1 F(ab')2 in ELISA. Finally, the biological activity of the lot is checked in the sera of small animals after immunization with the idiotope carriers as described (Bhattacharya-Chatterjee et al. (1987) *J. Immunol.* 139:1354; Bhattacharya-Chatterjee et al. (1988) J. Immunol. 141=1398). The final filled product is tested for endotoxin, sterility, and general safety in guinea pigs. The aluminum-hydroxide precipitated 11D10 is then heat treated at 45° for 30 minutes in a water bath prior to administration.

Humoral Immunity

Humoral immune responses of those patients who develop anti-anti-Id antibodies (Ab3) is characterized. Antibodies are evaluated for (a) binding to tumor cells or isolated semi-purified antigen to determine if the Ab3 indeed contain Ab1 antibodies; (b) cytotoxic activity against breast cancer cells with effector cells or complement as mediator of cytotoxic effects; (c) isotype characterization with anti-human isotype specific reagents; (d) idiotope analysis of Ab3 (i.e., sharing of idiotopes with Ab1); and (e) epitope analysis of Ab3 (i.e., binding to the same epitope as Ab1).

The development of humoral immunity induced by immunization with alum-precipitated Ab2 is assessed by testing sera obtained from patients at different time points as noted in the protocol. The sera is initially tested for total human anti-murine-antibody (HAMA) responses (anti-iso/ allo/and anti-anti-idiotype antibodies) by sandwich RIA. Briefly, microtiter plates are coated with 11D10 and incubated with different dilutions of patients' sera. After washings, the antigen-antibody reaction is tagged using $^{125}$I-labeled anti-Id 11D10 in a homogeneous sandwich RIA. Since 11D10 is injected as intact IgG1, patients are expected to mount HAMA responses.

(a) Specific Ab3 response to Ab2: Sera from immunized patients with positive HAMA responses are tested for the presence of anti-anti-idiotypic antibodies. Sera are pre-incubated with normal murine immunoglobulin to block human antibodies against isotypic and allotypic determinants and then checked for the presence of anti-anti-Id (Ab3) by reaction with the immunizing anti-Id (11D10) coated onto microtiter plates, by RIA. Unrelated Ab2 is used as control. After washings, the antigen-antibody reaction is tagged using $^{125}$I-labeled anti-Id reagent in a homogeneous sandwich RIA as above. Pre-treatment, non-immune sera and sera from normal donors are used as control in these assays.

(b) Idiotope analysis of Ab3: If a positive reaction is obtained in (a) above, Ab3 sera from those treated patients is checked for its ability to inhibit the binding of $^{125}$I-labeled 11D10 to MC-10 (Ab1) bound to microtiter plates or vice versa (inhibition of the binding of radiolabeled MC-10 to 11D10 on the plate). An unrelated Ab1-Ab2 system is used as a control. This test demonstrates whether Ab3 in patient's sera share idiotopes with MC-10 (Ab1). This inhibition assay of Ab1-Ab2 binding by Ab3 sera also demonstrates whether Ab3 is a true anti-anti-idiotype.

(c) Binding of Ab3 to tumor antigen: To assess humoral immune responses directed against native target antigens, patient's Ab3 sera is tested for reactivity with cell lines known to express HMFG in a RIA. In addition, the sera is checked for reactivity against a solubilized semi-purified preparation of HMFG antigen coated onto microtiter plates. The antigen-antibody reaction is detected by using $^{125}$I-labeled anti-human Ig reagents or alkaline phosphatase labeled anti-human-Ig in ELISA. Pre-immune sera and unrelated antigen are used as controls. The isotype of human Ab3 sera binding to HMFG antigen is determined by ELISA using anti-human isotype specific reagents. For these experiments, HMFG is obtained as a fusion protein from *E. coli* according to the method of Larocca et al. (1992) *Hybridoma* 11(2):191–201).

(d) Epitope analysis of Ab3: To demonstrate that Ab3 generated in treated patients and Ab1 (MC-10) bind to the same antigenic determinant, inhibition of MC-10 binding to Ag positive tumor cell line MCF-7 or HMFG antigen by Ab3 sera is checked by RIA.

(e) Cytotoxic activities of Ab3: If Ab3 in patient's sera bind specifically to tumor cells, the ability of Ab3 to lyse these cells in conjunction with effector cells and/or complement is tested by standard ADCC (Cheresh et al. (1985) Proc. Natl. Acad. Sci USA 83:515) or CMC assays (Herlyn et al. (1981) *Int. J. Cancer* 27:769). However, cytotoxic activity of the Ab3 may be dependent on its isotype, IgG1 being effective in ADCC and IgG1, IgG2, IgG3 and IgM in CMC.

Determination of the Effects of 11D10 Immunization on Patients' Cellular Immune Responses To test whether immunization of patients having advanced breast cancer with 11D10-Alugel leads to activation of T cells, some of which might display cytolytic activity against their own tumor cells, Patients' T cells, if activated in vivo by Ab2β, should respond to in vitro stimulation with Ab2β, antigen, or autologous tumor cells with proliferation and possibly CTL induction.

(a) The proliferative response of patients' peripheral blood mononuclear cells (PBMC) is tested in the presence of immunizing anti-Id 11D10, control Ab2 or semi-purified HMFG antigen. Alternatively, PBMCs are stimulated with autologous irradiated tumor cells (cryopreserved during surgery or maintained in short-term culture, where feasible). If the cells proliferate they are phenotyped by flow cytometry to determine the subtype of cells involved in proliferation. The proliferative response is measured by the incorporation of $^3$H-thymidine and compared to the pre-therapy PBMC Stimulation Index. For this assay, blood samples are collected after the third and fourth immunizations and one month after the last therapy.

(b) In Vitro Cytotoxic Activity. The cellular immune profile is assessed by testing the in vitro cytotoxic activity of T-cells for autologous cancer cells (where feasible) or allogeneic MC-10 Ag positive tumor cells in a $^{51}$Cr release assay. As suggested by Ertle et al., (22) the ability of anti-Id antibody to induce cytotoxic T cells which are not MHC restricted at the level of the effector phase may overcome the difficulty of using autologous tumor cells as targets and may facilitate the use of allogeneic tumor cells as well. Peripheral blood lymphocyte preparations from breast cancer patients and healthy donors are incubated with different doses of anti-Id (10 ng to 100 μg range) insolubilized to bio-beads or coated onto plastic plates. The optimal number of lymphocytes is cultured in a 135 mm petri dish with optimal concentrations of idiotope vaccines in 2 ml of Mishell-Dutton culture media. Cells are harvested 5–6 days later and used as effector cells in a 4 hr or 18 hr $^{51}$Cr release cytotoxicity assay against $^{51}$Cr labeled targets as described (84). Whenever possible, autologous tumor cells (cryopreserved during diagnosis or before therapy) are used as target cells. It might be feasible to have a supply of autologous cells by propagating and maintaining fresh tumor cells in nude mice or in cell culture, at least in some selected patients. Allogeneic MC-10 Ag positive tumor cell lines are also tested simultaneously as targets. If there is tumor cell killing, the following experiments to characterize the specificity:

(i) If lymphocytes become cytotoxic to breast tumor cells they are tested in the cytotoxic assay with a number of targets which do not express antigen (i.e. lymphoid cells, other carcinoma cells lines). Lack of cytotoxicity suggests that the target is probably breast cancer related Ag.

(ii) Lymphocytes are incubated with unrelated anti-idiotypic hybridoma of the same isotype as the Ab2β used and tested in the cytotoxic assay with $^{51}$Cr-labeled target tumor cells. Lack of cytotoxicity shows that the effect of anti-Id is specific.

In separate experiments, the patient's lymphocytes are incubated with autologous irradiated tumor cells (where possible). Cells will be harvested 5–6 days later and live cells are purified over lymphocyte separation media. Cytotoxicity is measured against $^{51}$Cr labeled autologous target tumor cells.

This in vitro cytotoxic assay utilizes PBMC isolated from blood obtained after pretherapy, after the fourth immunization and one month after the last immunization.

Determination of the Optimal Dose of 11D10

The optimal dose for further clinical testing is selected according to two criteria:
(a) The Ab2 dose that induces the maximum Ab3 response is determined. This can be determined by an inhibition assay.
(b) The Ab2 dose that induces the maximum Ab3 binding response to the tumor (Ab1' response).

Quantitation of the Ab3 and Ab1' Response

The expression of anti-anti-Id antibody (Ab3) in the patient's sera is quantitated by RIA inhibition studies as follows. Briefly, microtiter plates are coated with MC-10-IgG1 (Ab1) and reacted with a fixed amount of $^{125}$I-labeled Ab2. A standard inhibition curve is generated using purified MC-10 IgG1 as inhibitors. Next, patient's sera depleted of anti-iso-allotypic activity is checked for its ability to inhibit the Ab1-Ab2 reaction at different dilutions and the amount of Ab1-like antibody in the sera is estimated from the standard inhibition curve. The induction of Ab3 response as well as duration can be compared among different dose levels. If there is no statistical difference between Ab3 responses or duration at a number of doses, the titer of specific anti-tumor response (Ab1') in the sera by ELISA assay against semi-purified HMFG antigen coated plates is compared.

In vitro Studies. If circulating Ab1' or Ab3 positive patients' sera, that may indicate that they may be bound to patients' tumor cells, or to circulating tumor antigen (even though the Ag is secreted in blood in minute quantity) or they are of low affinity. Patients' PBMC are stimulated in vitro with antigen or Ab2 for the induction of tumor specific antibody. For this, peripheral blood mononuclear cells (PBMC) obtained from blood collected before therapy and then one month after the fourth immunization are cultured with various concentrations of 11D10, or unrelated Ab2, or HMFG antigen (10 μg to 110 ng) in a modified Mishell-Dutton culture (DeFreitas et al. (1985) *Curr. Top Microbiol. Immunol.* 119:75). Culture supernatants are harvested and checked first for the production of specific human immunoglobulins by ELISA assay and for binding to an insolubilized preparation of Ab2 by radioimmunoassay. In addition, the supernatants are tested for the content of idiotope bearing molecule by their ability to inhibit the reaction between the $^{125}$I-labeled MC-10 (Ab1) to Ab2β. The supernatants are also checked for their reactivity with MC-10 Ag-positive human breast carcinoma cells and Ag-negative lymphoid cells in a binding assay with $^{125}$I-labeled anti-human Ig reagents by RIA or ELISA assay (sensitivity>1 ng) for the evaluation of Ab1' antibody.

The specificity of the effect of Ab2β is monitored by incubating PBMC with unrelated Ab2 of the same isotype. Since only Ab3 positive patients will be included in this in vitro study, PBMC stimulated with Ab2β should secrete antibodies binding to Ab2β (11D10) and serve as a positive control.

Possible Induction of Ab4 Response

According to network hypothesis, patients immunized with Ab2 may eventually also induce an Ab4 response (anti-anti-anti-Id) which may mimic the specificity of Ab2. To study this possibility, Ab3 positive patients' sera (depleted of anti-iso and anti-allotype antibodies) is reacted with MC-10 (Ab1) by ELISA or RIA as described. Positive and negative controls will be included as described for the Ab3 assay. Sera for this assay will be obtained three months after the last therapy.

Example 5

Analysis of Immune Response Elicited by Administration of 11D10 to Patients with Advanced HMFG-Associated Disease We obtained an IND from the U.S. FDA for the clinical trial of breast cancer patients with anti-Id 11D10 precipitated with alum (BB-IND #5745). We enrolled five patients into this Phase Ib trial. All patients had advanced breast cancer which had been previously treated with standard therapy and their tumor cells were positive for breast cancer antigen, HMFG, as defined by the monoclonal antibody MC-10 (BrE1). Patients were randomized to either 1 mg, 2 mg, 4 mg or 8 mg doses of 11D10-Alugel (alum) per injection. They were immunized intracutaneously, biweekly for a minimum of four injections. Therapy continued on a monthly basis until the patient's disease progressed.

The first patient has received eight immunizations of 8 mg thus far, the second patient has received four immunizations of 4 mg; the third patient has received four immunizations of 2 mg. The fourth and fifth patients, receiving doses of 1 mg and 4 mg, respectively, have recently entered the study.

Toxicity

Toxicity was minimal with only local reactions at the injection site with mild erytherma and induration. The anti-Id treatment did not have any deleterious effect on hematopoietic cells, renal or hepatic function.

Humoral Responses to Anti-Idiotype

The development of humoral immunity induced by immunization with alum precipitated anti-Id 11D10 (prepared as described in Example 4) was assessed by testing sera from patients before therapy and after each treatment with the vaccine. Hyperimmune sera (after 4th immunization) from the first three patients showed significant levels of total human anti-mouse antibody responses including anti-iso/allo/anti-anti-idiotypic responses against immunizing Ab2 11D10. Representative data from the first patient is shown in FIG. 20. Next, the sera from these patients were checked for their ability to inhibit the binding of $^{125}$I-MC-10 (Ab1) to Ab2 11D10 on the plate by radio-immunoassay or vice versa (inhibition of radiolabeled Ab2 binding to Ab1 on the plate). These reactions were done in the presence of excess normal murine Ig to block human antibodies against isotypic and allotypic determinants. FIG. 21 demonstrates data on the first patient. About forty percent inhibition was obtained at a 1:40 dilution of serum, whereas, only 9% and 22% inhibition was obtained with the second and third patient's sera at the same dilution. After the seventh immunization, the first patient showed 83% inhibition at a 1:40 dilution of sera. Pre-immune sera from all three patients did not show any inhibition. These results indicate that patient #1 has mounted significant anti-anti-idiotypic antibodies (Ab3) and the other two patients had some Ab3 reactivity.

Next, we investigated whether anti-Id 11D10 could induce an anti-tumor antigen (HMFG) specific antibody response in immunized patients. For this, the sera obtained after fourth immunizations were tested against HMFG antigen (fusion protein obtained from Dr. Ceriani; Larocca et al. (1992)) coated onto microtiter plates by an ELISA assay. The results are shown in Table 5 and are expressed as mean of triplicate wells (S.D.<10%).

TABLE 5

Binding of Ab3 sera to HMFG antigen by ELISA

| Dilution | Patient #1 | | Patient #2 | | Patient #3 | |
|---|---|---|---|---|---|---|
| | Pre O.D 405 nm | Post O.D 405 nm | Pre O.D 405 nm | Post O.D 405 nm | Pre O.D 405 nm | Post O.D 405 nm |
| 1:10 | 1.05 | 2.82 | 1.47 | 1.67 | 0.96 | 2.05 |
| 1:40 | 0.28 | 0.72 | 1.0 | 0.92 | 0.48 | 1.33 |

Ab3 sera from Patient #1 and #3 showed specific binding to HMFG antigen as compared to pre-immune sera. Both pre- and post-immune sera from patient #2 showed non-specific binding to HMFG, which did not increase with immunization.

Cellular Immune Responses to Anti-Idiotype

Cellular immune responses were measured by the proliferation of peripheral blood mononuclear cells incubated with alum-precipitated anti-Id 11D10 and the iso, allotype matched control anti-Id 3H1. Positive proliferative responses were seen in only patient #1 (FIG. 22) but not in the other two patients. Pre-immune cells from patient #1 had no proliferative response while hyperimmune cells had a significant response to anti-Id 11D10. There was also a response to the control anti-Id 3H1; this response was significantly less than that of the 11D10 response, likely representing a response to the non-idiotypic components of the murine immunoglobulin molecule.

The results suggest that anti-Id 11D10 can induce both humoral and cellular immune responses in advanced breast cancer patients.

Example 6

Construction of a Recombinant Vaccinia Vector Encoding a 11D10 Polypeptide Fragment Plasmid Construction and Production of Recombinant Vaccinia Viruses The scheme for construction of a general vaccinia vector (rvv) is shown in FIG. 18. We retrieved the complete sequence of TK gene of the wild type WR strain of vaccinia virus (GenBank, accession number J02425,) from the National Center for Biotechnology Information (NCBI) by the BLAST program. Aitschul et al. (1990) *J. Mol. Biol.* 215:403–410. From the sequence data, forward and reverse PCR primers 5'-CAGATGGAAGGGCCCAAC (SEQ ID NO:42) and 5'-GATTGATGCATATCATTACC (SEQ ID NO:43) were synthesized, corresponding to nucleotides 22–39 and 727–708 respectively of the TK sequence Hruby et al. (1983) Pro. Natl. Acad. Sci. USA 80:3411–3415. An Apa I site (underlined) was introduced into the forward primer and a Nsi I site (underlined) in the reverse primer for insertion into the plasmid pGEM-7Zf(+) (Promega). DNA from the wild type WR strain of vaccinia was isolated and TK gene was amplified by PCR. A DNA fragment of expected size (about 700 bp) was obtained by PCR. This DNA was separated by electrophoresis in low melting point agarose and purified by digestion with GELase (Epicentre Tech.). The TK DNA fragment was ligated to the pGEM-72f (+) after digestion with Apa I plus Nsi I. The resulting plasmid (pGEM-TK) was amplified by standard transformation techniques. Insertion was verified by restriction mapping.

Promoter 7.5 K was amplified from wild type vaccinia virus by PCR using the forward primer 5'-GTT ATCGATGTCGAATAGCC (SEQ ID NO:44) and the reverse primer 5'-TTGCTGCAGATTGAGTACTGTTCT (SEQ ID NO:45), corresponding to nucleotides 69–88 and 335–312 of the 7.5 K promoter sequence. Cochran et al. (1985) *J. Virol.* 54:30–37. A Cla I site (forward) and a Pst I site (reverse) were included in the primers. The amplified DNA fragment was digested with Pst I. A polynucleotide adaptor was synthesized with the smaller oligonucleotide being phosphorylated at the 5'-end by polynucleotide kinase. The hemi-phosphorylated adaptor was ligated to Pst I digested PCR amplified 7.5 K promoter DNA fragment. The product was digested with Cla I/EcoRI digested pGEM-TK.

A cDNA insert encoding a 11D10 polypeptide is inserted between the Nco I and XmaI (SmaI) sites of pVV. This plasmid also contains the leader sequence of the $V_H$ at the 5' end of the scFv cDNA. If desired, a vaccinia control plasmid can be constructed containing cDNA for E. coli β-galactosidase.

Construction of rvv

Rvvs are constructed by homologous recombination of vaccinia plasmids and wild-type W'R strain of vaccinia virus according to the procedure of Mackett et al. (DNA Cloning, Vol. II, D. M. Glover, ed., IRL Press 1985) using CV-1 cells. Recombinant viral clones expressing β-galactosidase (controls) are selected by growth on TK' 143B cells in the presence of 5'-bromodeoxyuridine and 5-bromo-4-chloro-3-indoyl-β-D-galactosidase (X-Gal). Blue recombinant viruses are picked by pasteur pipettes and plaque purified. As a second step in clone selection, Southern blot of extracted DNA is performed, using 11D10 cDNA as the probe. Further selection of rvv is made by assay of culture supernatant of the virally infected CV-1 or any other eukaryotic cells by ELISA. If cell-associated 11D10 polypeptide is in the rvv (i.e., if the leader sequence is deleted), cell lysate is assayed. Western blotting with MC-10 (Ab1) as probe is also performed. Biological activity of the 11D10 polypeptide synthesized by the vaccinia virus is determined by cell binding inhibition assay, as described above. Rvv clones containing 11D10 polynucleotides are selected by staining with 0.1% neutral red and plaque purified as above. Viral clones are grown into a high-titer lysate using standard techniques. Mackett et al (1982) *Proc. Natl. Acad. Sci.* USA 79:7415–7419. Typically a clone producing the highest amount of 11D10 polypeptide is selected for further studies.

Assay of 11D10 Polypeptides (Foreign Proteins) Expressed By Recombinant Vaccinia Virus CV-1 cells are propagated in Dulbecco's modified Eagle's medium (DMEM) supplemented with 10% fetal calf serum and 100 units of penicillin and 100 μg of streptomycin per ml in 25-$cm^2$ flasks or 6-well Cluster flasks. Cells are inoculated with rvv at a MOI of 30. The virus is allowed to absorb for 2 hours at 37° C. in a tissue culture incubator, following which the inoculum is replaced with the culture medium and the incubation was continued. Supernatant is removed after incubation for indicated time and the 11D10 polypeptide secreted is assayed. As a control, supernatant from mock infected cells is used. Assay of 11D10 polypeptides can be performed by testing for binding to MC-10 (Ab1), for example as described in Examples 1 and 5. β-D-galactopyranoside by rvv-lacZ is assayed according to Miller (Experiments in Molecular Genetics, Cold Spring Harbor Pines 1972) with p-nitro-β-D-galactopyranoside as the substrate. Culture supernatant from virus infected cells is treated with β-propionate to inactivate the virus before assay Corcoran et al. (1988) *J. Parasit.* 74:763. Incorporation of $^3$H-thymidine by NFS60 cells was used as a measure of cell proliferation Jaffee et al. (1993) *Cancer Res.* 53:2221–2226. Radioactivity due to $^3$H-thymidine incorporation in the presence of supernatant from mock infected CV-1 cells is subtracted as background. As positive control and for standard of biological activity, intact 11D10 is used. Alternatively, standard solutions of GM-CSF can be used.

Testing Vaccinia 11D10 Vaccines

For administration of vaccinia, a virus titer of $10^4$ to $10^7$ pfu is injected in a mouse. Injections can be subcutaneous, intramuscular, intradermal or interperitoneal. Immunizations are performed weekly. Mice are bled 7 days after every immunization for determination of Ab3 (including Ab1'). Testing for development of T cell immunity is performed 10 days after the booster immunization. Mice can also be tested by tumor challenge, in which survival after injection with tumor cells is monitored.

For administration of vaccinia via virally infected tumor cells, autologous tumor cells are maintained in Eagles medium containing 10% (vol/vol) fetal calf serum, 2 mM glutamine and gentamicin. A monolayer of confluent cells in a 75-cm2 flask is inoculated with (3×108) plaque forming units (pfu) of rvv. After 2 hours at 37° C., the inoculum is replaced by DMEM and the incubation was continued for another 24 hours. After examination under microscope, cells are collected by scraping and washed two times with PBS and resuspended in PBS at a desired concentration. ($10^3$ to $10^5$/200 μl). Female C57BL/6 mice, 6–8 weeks old are purchased from Harlan Bioproducts for Science Inc., (IN). Animals are injected subcutaneously with the cellular vaccine in the rear left flank and two weeks later tumor cells are injected at the rear right flank for challenge. Survival of mice following tumor challenge and the presence of tumor is monitored daily. If the tumor is measurable, tumors are measured weekly by a caliper in two dimensions and the volumes are calculated using the formula ($width^2$×length)/2. Tumors which are palpable but too small for measuring the volume accurately are recorded as zero volume, but tumor incidence is recorded as positive. Tumor volumes are averaged only for those that actually develop tumors over the observation period of 120 days. Zero values are included for those mice that eventually develop tumors but were tumor-free at a given time point.

Statistical Evaluation

Statistical evaluation is done using SigmaStat software (Jandel, Inc. San Rafael, Calif., USA). A P value of <0.05 was considered to indicate statistical significance.

Example 7

Construction of Expression Vectors Encoding 11D10 Fusion Proteins cDNA encoding the VDJ variable region of the heavy chain of 11D10 was isolated from plasmid pUC911D10V and ligated into the vector shown in FIG. 25. In this vector, a DNA fragment encoding the mature peptide of murine GM-CSF or IL-2 was ligated 3' to the $CH_3$ exon. This was accomplished by generating a ClaI site between the last codon and the stop codon of the $C_H3$ exon and a NotI site 3' to the stop codon. cDNA encoding the light chain of 11D10 was incorporated into expression plasmid pSV184-Δ Hneo as shown in FIG. 25. The pSV184 ΔHneo plasmid was previously described by Shin et al. ((1989) *Meth. Enzymol.* 178:459–476).

After the first transfection, the plasmid containing the 11D10 light chain was transfected into the above cells by electroporation following a modified method of Shin et al. (1989) as follows. Cells were removed from growth medium by centrifugation and washed twice with Iscove's modified Dulbecco's medium (IMDM, GIBCO). Cells were resuspended in cold IMDM (without serum) at a concentration of 4.5×$10^6$/ml. From this suspension 0.9 ml (4×$10^6$ cells) were added to a 0.4 cm BioRad cuvette. About 20 μg of pSV211D10$V_H$-cytokine DNA was linearized with a restriction enzyme not present between the EcoRI sites of pSV211D10$V_H$-cytokine such as PvuII. After phenol/chloroform extraction and ethanol precipitation, DNA was suspended in <50 μl of IMDM and added to the cell suspension. After chilling the cell suspension-DNA mixture in ice for 10 minutes, an electric pulse was applied at 200 volts, 960 μF capacitance by a Bio-Rad Gene Pulser Transfection Apparatus. Following incubation in ice for 10 minutes, cells were suspended in 96 ml of IMDM containing 10% fetal calf serum and distributed in eight 96-well plates, 125 µl/well, with multi-channel pipettes, providing 5×10³ cells/well. After 2 days, 125 µl of IMDM containing 10% fetal calf serum and 25 µg/ml mycophenolic acid was added per well. Four days later, half of the medium was removed from each well and 125 µl of 1×IMDM-mycophenolic acid medium was added. After clones become visible (about 10–15 days), cultured supernatant was removed for assay with MC-10 for the detection of transfectomas.

Table 6 shows the various expression plasmids constructed. mIL-2 and mGM-CSF denote murine IL-2 and GM-CSF, respectively. $V_H$ and $V_L$ contained the signal peptides.

TABLE 6

Eukaryotic expression vectors for 11D10 heavy and light chains

| Name | Description |
|---|---|
| pSV-11D10$V_{H\text{-}mIL\text{-}2}$ | 11D10 $V_H$-human gamma CH1—H—CH2—CH3-mIL-2 |
| pSV2-11D10$V_H$-mGM-CSF | 11D10 $V_H$human gamma CH1—H—CH2—CH3-mGM-CSF |
| pSV184-11D10$V_L$ | 11D10 $V_L$-human kappa CH |

For the detection of high producing transfectomas, the cells are plated in 96-well plates after limiting dilution (1 cell/well). When the clones in microwells become visible, but still remain small, cultured supernatant will be assayed for the detection of functional antibody by sandwich radioimmunoassay. 96-well plates are coated with MC-10 and 50 µl culture supernatant from transfectomas are allowed to react with the coated antibody. The amount of functional antibody produced by each transfectoma is determined by radioimmunoassay with $^{125}$I-labeled MC-10. For further evaluation of the high antibody producing transfectants, various dilutions of the culture supernatants from selected clones are similarly assayed.

A plasmid containing the heavy chain GM-CSF fusion was transfected into Sp2/0 cells by protoplast fusion using the technique of Oi et al. (1986) *BioTechniques* 4:214–221. High producing clones were selected for initial biochemical characterization of the fusion proteins.

Two ELISAs were conducted as follows. In Assay 1, microtiter plates were coated with goat anti-human kappa light chain (Orgomon Teknika Corp., West Chester, Pa.) at standard concentrations, blocked with BSA and washed. Supernatants from cultures of cells expressing various test constructs were then incubated in the wells. After washing, the wells were overlayed with alklaine phosphatase conjugated heavy chain specific goat anti-human IgG1 (Sigma) and developed in the usual manner. A positive reaction indicated that the supernatant contained an immunoglobulin with both human heavy and light chain constant regions of the expected type. Assay 2 was conducted in a similar fashion, but developed using biotin conjugated rat anti-mouse GM-CSF (Pharmingen), followed by avidin peroxidase conjugate (Sigma). A positive reaction indicated that the supernatant contained an immunoglobulin with a human light chain and a GM-CSF component, which was expected in the heavy chain C terminus.

Table 7 shows the results of assays of supernatants of 9 clones for the presence of light chain coupled to heavy chain (Assay 1) and for GM-GSF activity (Assay 2). The results indicate that a number of fusion proteins have been obtained which contain determinants for light chain, heavy chain, and GM-CSF on the same molecule.

Fusion proteins were isolated by affinity chromatography using Sepharose-protein A columns and are characterized as follows, using the following antibodies and standards: monoclonal mouse anti-human IL-2 (Genzyme, code, DMA-1), standard natural human IL-2 (BRL cat. #13288-014); monoclonal anti-mouse IL-2 (UBI, cat. #05-115), standard mouse recombinant IL-2 (Sigma, cat. #1 4517); human GM-CSF assay kit with human GM-CSF standard (R&D system cat. DGM00), rat anti-murine GM-CSF (BRL, cat. #13306-014), standard mouse recombinant GM-CSF (UBI, cat. #01-167).

TABLE 7

ELISA for 11D10-Murine GM-CSF Fusion Protein Optical Density

| Clone | Assay 1 | Assay 2 |
|---|---|---|
| 4 | 0.184 | 0.216 |
| 22 | 0.314 | 0.397 |
| 23 | 0.237 | 0.205 |
| 41 | 0.159 | 0.195 |
| 50 | 0.132 | 0.167 |
| 51 | 0.181 | 0.314 |
| 52 | 0.178 | 0.155 |
| 55 | 0.224 | 0.298 |
| 58 | 0.142 | 0.179 |
| control | 0.041 | 0.099 |

Purified chimeric (i.e., fusion) proteins are analyzed by SDS polyacrylamide gel electrophoresis under reducing and non-reducing conditions. Molecular weight standards and purified 11D10 are included in this experiment. The protein bands are stained by Coomassie brilliant blue staining. The effect of the purified fusion protein on the binding of MC-10 (Ab1) to 11D10 (original Ab2) and to HMFG (the nominal antigen) is studied by inhibition RIA as previously done for the characterization of the Ab2 to establish the Ab1 binding specificity of the fusion protein. Inhibition of binding of labeled Ab1 to SKBR3 (breast cancer cell lines expressing HMFG) cells by the fusion protein provides additional support for the specificity of antigen-antibody binding. The biological activity of murine IL-2 is determined by cell proliferation assay using suspensions of CTLL-2 T cells. Samples and standards are serially diluted in complete RPMI-10 medium and 50 µl aliquots placed in wells of 96-well plates. CTLL-2 cells are grown to active log phase and washed with complete RPMI-10 to remove residual IL-2. Cells are suspended in complete RPMI-10 at 1×10⁵ cells/ml. The cells are divided into 3 groups, one set receiving monoclonal anti-mouse IL-2, one set receiving anti-human IgG γ-chain, and the other receiving the solution used for dilution of these antibodies. Cell suspensions (50 µl, 5×10³ cells) are added to each well. The cells are incubated at 37° C. in a $CO_2$ incubator for 24 hours. ³H-thymidine is added and the incubation is continued for another 24 hours, followed by harvesting and determination of radioactivity incorporated. Differential counts in wells with and without antibodies are considered as the net biological activity of the sample or standard. 11D10 is also included in these assays to determine if the antibody itself can induce cell proliferation of CTLL-2. The biological activity of human IL-2 is similarly evaluated with CTLL-2 cells, in the presence and absence of the specific antibody. For the biological assay of GM-CSF, similar cell proliferation assays are performed. For murine and human GM-CSF, NFS-60 cells (Holmes et al. (1985) *Proc. Natl. Acad. Sci (USA)* 82:6687–6691) and M-07e cells (Genetics Institute) respectively are used.

Data interpretation, expected results, potential problems and alternative strategy. SDS-PAGE under reducing conditions is expected to show protein bands around 25 kd for both 11D10 and the fusion proteins; higher molecular weight banding will indicate that the transfectoma has produced the cytokine-antibody fusion protein fused to the heavy chain. By electrophoresis under non-reducing conditions, it is possible to determine whether tetrameric immunoglobulin has been formed. In that case the fusion protein will produce a single band whose molecular weight should be higher by an amount which is twice equivalent to the cytokine molecule, i.e., the fusion protein is dimeric with respect o the cytokine. ELISA and biological assays for the cytokines will indicate whether the cytokine molecule is being expressed and is biologically active. Quantitative assay with standard recombinant cytokine will indicate whether the biological activity of the cytokine present as the fusion protein is comparable to or enhanced compared to free cytokine. Inhibition of the biological activity or the cytokine by its corresponding antibody compared to a control antibody indicates that the action of the cytokine is specific. Inhibition of the biological activity of the cytokine by anti-human IgG γ-chain will demonstrate that the cytokine moiety is present as a fusion molecule with the Ig.

Example 8

Expression and Characterization of a 11D10 scFv

A cDNA construct encoding $V_H$-(GGGS)$_3$-$V_L$ (SEQ ID NO:46) for 11D10 is prepared. A cDNA for this 11D10 fragment is incorporated into the pET-22b(+) plasmid vector (Novagen, Madison, Wis.) and expressed in E. coli. Sequence analysis is performed to confirm the plasmid construct, which contains the carboxy end of $V_H$ linked to the framework of $V_L$ and does not contain the leader region. pET-22b(+) contains a nickel ion binding domain consisting of 6 sequential histidine residues (His$_6$). The His$_6$ domain has a high affinity for nickel, which is used for the purification of the recombinant 11D10 scFv.

A cell binding competition assay is performed to investigate whether the 11D10 scFv retains the antigen mimicry shown by intact 11D10. HMFG-positive MCF-7 or SKBR3 (1×10$^5$ cells/well in 50 µl volume) and placed in a 96-well plate. The cells are incubated for 2 hours at room temperature with [$^{125}$I] MC-10 (Ab1), 100,000 cpm, in the absence and presence of increasing concentrations of 11D10 or the 11D10 scFv fragment. Percent inhibition is calculated according to the following formula:

$$\% \text{ inhibition} = \left[1 - \left(\frac{R_T - R_C}{R_{MAX} - R_C}\right)\right] \times 100\%$$

Where $R_T$ is the average radioactivity of an experimental well, $R_{Max}$ is the radioactivity in the absence of any protein, and $R_C$ is the background radioactivity.

Example 9

Testing Recombinant 11D10 Polynucleotide Vaccines in Mice

Recombinant candidate 11D10 polynucleotide vaccines are prepared as described herein. Two groups of 10–15 female C57BL/6 mice (6–8 weeks old) are immunized intramuscularly with doses of 50–100 µg purified plasmid which is coupled to KLH using glutaraldehyde as described by Bhattacharya-Chatterjee et al. (1988).

In addition, various routes of administration are compared, such as intramuscular, intradermal, subcutaneous and interperitoneal.

Mice are bled 7 days after every immunization for determination of Ab3 (including Ab1') production as described above. Three mice are sacrificed from each group for isolation of spleens for the T cell proliferation assay 10 days after a booster immunization.

To determine whether any observed effect is specific, as opposed to non-specific humoral or cellular immunity (by indirect mechanisms such as cytokine production induced by the injected polynucleotide), the following controls are used: (a) plasmid without 11D10 polynucleotide insert; (b) plasmid with 11D10 polynucleotide insert in the opposite (i.e., antisense) orientation; and (c) plasmid containing a polynucleotide encoding an unrelated Ab2.

Example 10

Further Analysis of Immune Response Elicited by Administration of 11D10 to Patients with Advanced HMFG-Associated Disease The Phase Ib U.S. FDA for the clinical trial of breast cancer patients with anti-Id 11D10 precipitated with alum (BB-IND#5745) as described in Example 5 was expanded to include 12 patients. All patients had advanced breast cancer which had been previously treated with standard therapy and their tumor cells were positive for breast cancer antigen, HMFG, as defined by the monoclonal antibody MC-10 (BrE1). Patients were randomized to either 1 mg, 2 mg, 4 mg or 8 mg doses of 11D10-Alugel (alum) per injection. They were immunized intracutaneously, biweekly for a minimum of four injections. Therapy continued on a monthly basis until the patient's disease progressed. Patients were monitored very closely for disease activity and have all been removed from the study due to disease progression or death. Details of the 12 patients of this study are provided in Table 8.

TABLE 8

Details of Breast Cancer Patients in Phase 1b Clinical Study

| Patient # | Age | Dose in mg | # of Rx | Humoral Response (Ab3) | Cellular Response (T-cell proliferation) |
|---|---|---|---|---|---|
| 1 | 68 | 8 | 10 | + | + |
| 2 | 48 | 4 | 4 | − | − |
| 3 | 41 | 2 | 4 | − | − |
| 4 | 41 | 1 | 3 | ND | ND |
| 5 | 83 | 4 | 6 | + | + |
| 6 | 51 | 1 | 4 | + | + |
| 7 | 54 | 2 | 4 | + | − |
| 8 | 54 | 8 | 4 | − | − |
| 9 | 72 | 2 | 4 | − | − |
| 10 | 47 | 1 | 2 | ND | − |
| 11 | 58 | 8 | 4 | − | − |
| 12 | 27 | 4 | 6 | + | + |

Toxicity

Toxicity was minimal with only local reactions at the injection site with mild erytherma and induration. The anti-Id treatment did not have any deleterious effect on hematopoietic cells, renal or hepatic function.

Humoral Responses to Anti-Idiotype

The development of humoral immunity induced by immunization with alum precipitated anti-Id 11D10 (prepared as described in Example 4) was assessed by testing sera from patients before therapy and after each treatment with the vaccine. Hyperimmune sera (after 4th immunization) from five out of ten patients showed significant levels of total human anti-mouse antibody responses including anti-iso/allo/anti-anti-idiotypic responses against immunizing Ab2 11D10. Next, the sera from these patients were checked for their ability to inhibit the binding of $^{125}$I-MC-10 (Ab1) to Ab2 11D10 on the plate by radioimmunoassay or vice versa (inhibition of radiolabeled Ab2 binding to Ab1 on the plate). These reactions were done in the presence of excess normal murine Ig to block human antibodies against isotypic and allotypic determinants.

FIGS. 27A and B show data from 10 patients, including patient #1. (Data from patient #1 are also discussed in Example 5.) Sera from patients #1, 5, 6, 7, and 12 showed significant inhibition even at a dilution of 1:100. Pre-immune sera from patients #1, 5, 6, 7, and 12 did not show any inhibition. In sum, these results indicate that patients #1, 5, 6, 7, and 12 had mounted significant anti-anti-idiotypic antibodies (Ab3) while the other patients (#2, 3, 8, 9, and 10) did not raise any significant Ab3 reactivity.

Next, we investigated whether anti-Id 11D10 could induce an anti-tumor antigen (HMFG) specific antibody response in immunized patients. For this, the sera obtained after fourth immunizations from patients #1, 6 and 12 were affinity purified on an anti-Id 11D10 column and purified Ab3 were tested against HMFG antigen (fusion protein obtained from Dr. Ceriani; Larocca et al. (1992)) coated onto microtiter plates by an ELISA assay.

The results are shown in FIG. 28. Purified Ab3 sera from patients #1, #6 and 12 showed specific binding to HMFG antigen as compared to purified Ab3 obtained from a colon cancer patient treated with control anti-Id 3H1. The isotype of the antibody (Ab1') in 11D10 immunized patients' sera was mostly IgG.

Cellular Immune Responses to Anti-Idiotype

Cellular immune responses were measured by the proliferation of peripheral blood mononuclear cells incubated with alum-precipitated anti-Id 11D10 and the iso, allotype matched control anti-Id 3H1. Positive proliferative responses were seen in patients #1, 5, 6, and 12 but not the other patients tested. FIGS. 29A and 29B show data from patient's #1 and #5, respectively. Pre-immune cells from patients had no proliferative response while hyperimmune cells had a significant response to anti-Id 11D10. There was also a response to the control anti-Id 3H1; this response was less than that of the 11D10 response, likely representing a response to the non-idiotypic components of the murine immunoglobulin molecule.

The results confirm the finding of Example 5 suggest that anti-Id 11D10 can induce both humoral and cellular immune responses in advanced breast cancer patients (who had also been heavily treated with different therapies).

Although the foregoing invention has been described in some detail by way of illustration and example for purposes of clarity and understanding, it will be apparent to those skilled in the art that certain changes and modifications will be practiced. Therefore, the description and examples should not be construed as limiting the scope of the invention, which is delineated by the appended claims.

SEQUENCE LISTING (1) GENERAL INFORMATION:

(iii) NUMBER OF SEQUENCES: 59

(2) INFORMATION FOR SEQ ID NO:1:

(i) SEQUENCE CHARACTERISTICS:
      (A) LENGTH: 435 base pairs
      (B) TYPE: nucleic acid
      (C) STRANDEDNESS: single
      (D) TOPOLOGY: linear (ii) MOLECULE TYPE: DNA (genomic)

(ix) FEATURE:
      (A) NAME/KEY: CDS
      (B) LOCATION: 1..435

(ix) FEATURE:
      (A) NAME/KEY: mat_peptide
      (B) LOCATION: 61

(xi) SEQUENCE DESCRIPTION: SEQ ID NO:1:

```
ATG GGG GCC CCT GCT CAG ATT CTT GGG TTC TTG TTG CTC TTG TTT CCA        48
Met Gly Ala Pro Ala Gln Ile Leu Gly Phe Leu Leu Leu Leu Phe Pro
-20             -15                 -10                 -5

GGT ACC AGA TGT GAC ATC CAG ATG ACC CAG TCT CCA TCC TCC TTA TCT        96
Gly Thr Arg Cys Asp Ile Gln Met Thr Gln Ser Pro Ser Ser Leu Ser
                 1               5                  10

GCC TCT CTG GGA CAA AGA GTC AGT CTC ACT TGT CGG GCA AGT CAG GAC       144
Ala Ser Leu Gly Gln Arg Val Ser Leu Thr Cys Arg Ala Ser Gln Asp
        15                  20                  25

ATT GGT ATT AAC TTA CAT TGG CTT CAG CAG GAA CCA GAT GGA ACT ATT       192
Ile Gly Ile Asn Leu His Trp Leu Gln Gln Glu Pro Asp Gly Thr Ile
```

```
            30                  35                  40
AAA CGC CTG ATC TAC GCC ACA TCC AGT TTA GGT TCT GGT GTC CCC AAA      240
Lys Arg Leu Ile Tyr Ala Thr Ser Ser Leu Gly Ser Gly Val Pro Lys
 45                  50                  55                  60

AGG TTC AGT GGC AGT AGG TCT GGG TCA GAT TAT TCT CTC ACC ATC AGC      288
Arg Phe Ser Gly Ser Arg Ser Gly Ser Asp Tyr Ser Leu Thr Ile Ser
                     65                  70                  75

AGC CTT GAG TCT GAA GAT TTT GTA GCC TAT TAC TGT CTA CAA TAT GCT      336
Ser Leu Glu Ser Glu Asp Phe Val Ala Tyr Tyr Cys Leu Gln Tyr Ala
                 80                  85                  90

AGT TCT CCG TAC ACG TTC GGA GGG GGG ACC AAG CTG GAA ATA AAA CGG      384
Ser Ser Pro Tyr Thr Phe Gly Gly Gly Thr Lys Leu Glu Ile Lys Arg
             95                  100                 105

GCT GAT GCT GCA CCA ACT GTA TCC ATC TTC CCA CCA TCC AGT AAG CTT      432
Ala Asp Ala Ala Pro Thr Val Ser Ile Phe Pro Pro Ser Ser Lys Leu
         110                 115                 120

GGG                                                                  435
Gly
125

(2) INFORMATION FOR SEQ ID NO:2:

(i) SEQUENCE CHARACTERISTICS:
        (A) LENGTH: 145 amino acids
        (B) TYPE: amino acid
        (D) TOPOLOGY: linear (ii) MOLECULE TYPE: protein (xi) SEQUENCE DESCRIPTION: SEQ ID NO:2:

Met Gly Ala Pro Ala Gln Ile Leu Gly Phe Leu Leu Leu Phe Pro
-20                 -15                 -10                 -5

Gly Thr Arg Cys Asp Ile Gln Met Thr Gln Ser Pro Ser Ser Leu Ser
                     1                   5                   10

Ala Ser Leu Gly Gln Arg Val Ser Leu Thr Cys Arg Ala Ser Gln Asp
             15                  20                  25

Ile Gly Ile Asn Leu His Trp Leu Gln Gln Glu Pro Asp Gly Thr Ile
         30                  35                  40

Lys Arg Leu Ile Tyr Ala Thr Ser Ser Leu Gly Ser Gly Val Pro Lys
 45                  50                  55                  60

Arg Phe Ser Gly Ser Arg Ser Gly Ser Asp Tyr Ser Leu Thr Ile Ser
                     65                  70                  75

Ser Leu Glu Ser Glu Asp Phe Val Ala Tyr Tyr Cys Leu Gln Tyr Ala
                 80                  85                  90

Ser Ser Pro Tyr Thr Phe Gly Gly Gly Thr Lys Leu Glu Ile Lys Arg
             95                  100                 105

Ala Asp Ala Ala Pro Thr Val Ser Ile Phe Pro Pro Ser Ser Lys Leu
         110                 115                 120

Gly

125

(2) INFORMATION FOR SEQ ID NO:3:

(i) SEQUENCE CHARACTERISTICS:
        (A) LENGTH: 461 base pairs
        (B) TYPE: nucleic acid
        (C) STRANDEDNESS: single
        (D) TOPOLOGY: linear
```

-continued (ii) MOLECULE TYPE: DNA (genomic)

(ix) FEATURE:
    (A) NAME/KEY: CDS
    (B) LOCATION: 1..459

(ix) FEATURE:
    (A) NAME/KEY: mat_peptide
    (B) LOCATION: 58

(xi) SEQUENCE DESCRIPTION: SEQ ID NO:3:

```
ATG GAA TGC AGC TGG GTC TTT CTC TTC CTC CTG TCA ATA ACT ACA GGT       48
Met Glu Cys Ser Trp Val Phe Leu Phe Leu Leu Ser Ile Thr Thr Gly
-19         -15                 -10                 -5

GTC CAC TCC CAG GCT TAT CTA CAG CAG TCT GGG GCT GAG CTG GTG AGG       96
Val His Ser Gln Ala Tyr Leu Gln Gln Ser Gly Ala Glu Leu Val Arg
            1               5                   10

TCT GGG GCC TCA GTG AAG ATG TCC TGC AAG GCT TCT GGC TAC ACA TTG      144
Ser Gly Ala Ser Val Lys Met Ser Cys Lys Ala Ser Gly Tyr Thr Leu
        15                  20                  25

ACC AGT TAC AAT ATG CAC TGG GTA AAG CAG ACA CCT GGA CAG GGC CTG      192
Thr Ser Tyr Asn Met His Trp Val Lys Gln Thr Pro Gly Gln Gly Leu
30                  35                  40                  45

GAA TGG ATT GGA AAT ATT TTT CCT GGA AAT GGT GAT ACT TAC TAC AAT      240
Glu Trp Ile Gly Asn Ile Phe Pro Gly Asn Gly Asp Thr Tyr Tyr Asn
                50                  55                  60

CAG AAG TTT AAG GGC AAG GCC TCA TTG ACT GCA GAC ACA TCC TCC AGC      288
Gln Lys Phe Lys Gly Lys Ala Ser Leu Thr Ala Asp Thr Ser Ser Ser
            65                  70                  75

ACA GCC TAC ATG CAG ATC AGC AGC CTG ACA TCT GAA GAC TCT GCG GTC      336
Thr Ala Tyr Met Gln Ile Ser Ser Leu Thr Ser Glu Asp Ser Ala Val
        80                  85                  90

TAT TTC TGT GCA AGA GGG AAC TGG GAG GGT GCT CTG GAC TAC TGG GGT      384
Tyr Phe Cys Ala Arg Gly Asn Trp Glu Gly Ala Leu Asp Tyr Trp Gly
    95                  100                 105

CAA GGA ACC TCA GTC ACC GTC TCC TCA GCC AAA ACG ACA CCC CCA CCC      432
Gln Gly Thr Ser Val Thr Val Ser Ser Ala Lys Thr Thr Pro Pro Pro
110                 115                 120                 125

GTC TAT CCA CTG GTC CCT GGA AGC TTG GG                               461
Val Tyr Pro Leu Val Pro Gly Ser Leu
                130
```

(2) INFORMATION FOR SEQ ID NO:4:

(i) SEQUENCE CHARACTERISTICS:
        (A) LENGTH: 153 amino acids
        (B) TYPE: amino acid
        (D) TOPOLOGY: linear (ii) MOLECULE TYPE: protein (xi) SEQUENCE DESCRIPTION: SEQ ID NO:4:

```
Met Glu Cys Ser Trp Val Phe Leu Phe Leu Leu Ser Ile Thr Thr Gly
-19         -15                 -10                 -5

Val His Ser Gln Ala Tyr Leu Gln Gln Ser Gly Ala Glu Leu Val Arg
            1               5                   10

Ser Gly Ala Ser Val Lys Met Ser Cys Lys Ala Ser Gly Tyr Thr Leu
        15                  20                  25

Thr Ser Tyr Asn Met His Trp Val Lys Gln Thr Pro Gly Gln Gly Leu
30                  35                  40                  45

Glu Trp Ile Gly Asn Ile Phe Pro Gly Asn Gly Asp Thr Tyr Tyr Asn
                50                  55                  60
```

```
Gln Lys Phe Lys Gly Lys Ala Ser Leu Thr Ala Asp Thr Ser Ser Ser
                65                  70                  75

Thr Ala Tyr Met Gln Ile Ser Ser Leu Thr Ser Glu Asp Ser Ala Val
            80                  85                  90

Tyr Phe Cys Ala Arg Gly Asn Trp Glu Gly Ala Leu Asp Tyr Trp Gly
        95                  100                 105

Gln Gly Thr Ser Val Thr Val Ser Ser Ala Lys Thr Thr Pro Pro Pro
110             115                 120                 125

Val Tyr Pro Leu Val Pro Gly Ser Leu
                130
```

(2) INFORMATION FOR SEQ ID NO:5:

(i) SEQUENCE CHARACTERISTICS:
        (A) LENGTH: 321 base pairs
        (B) TYPE: nucleic acid
        (C) STRANDEDNESS: single
        (D) TOPOLOGY: linear (xi) SEQUENCE DESCRIPTION: SEQ ID NO:5:

```
GACATCCAGA TGACCCAGTC TCCATCCTCC TTATCTGCCT CTCTGGGAGA AAGAGTCAGT    60

CTCACTTGTC GGGCAAGTCA GGACATTGGT AGTAGCTTAA ACTGGCTTCA GCAGGAACCA   120

GATGGAACTA TTAAACGCCT GATCTACGCC ACATCCAGTT TAGATTCTGG TGTGCCCAAA   180

AGGTTCAGTG GCAGTAGGTC TGGGTCAGAT TATTCTCTCA CCATCAGCAG CCTTGAGTCT   240

GAAGATTTTG TAGACTATTA CTGTCTACAA TATGCTAGTT CTCCGTACAC GTTCGGAGGG   300

GGGACCAAGC TGGAAATAAA A                                             321
```

(2) INFORMATION FOR SEQ ID NO:6:

(i) SEQUENCE CHARACTERISTICS:
        (A) LENGTH: 321 base pairs
        (B) TYPE: nucleic acid
        (C) STRANDEDNESS: single
        (D) TOPOLOGY: linear (xi) SEQUENCE DESCRIPTION: SEQ ID NO:6:

```
GANATCCAGA TGACCCAGTC TCCATCCTCC TTATCTGCCT CTCTGGGAGA AAGAGTCAGT    60

CTCACTTGTC GGGCAAGTCA GGACATTGGT AGTAGCTTAA ACTGGCTTCA GCAGGAACCA   120

GATGGAACTT TTAAACGCCT GATCTACGCC ACATCCAGTT TAGATTCTGG TGTCCCCAAA   180

AGGTTCAGTG GCAGTAGGTC TGGGTCAGAT TATTCTCTCA CCATCAGCAG CCTTGAGTCT   240

GAAGATTTTG TAGACTATTA CTGTCTACAA TATGCTAGTT GTCCGTACAC GTTCGGAGGG   300

GGGACCAAGC TGGAAATAAA A                                             321
```

(2) INFORMATION FOR SEQ ID NO:7:

(i) SEQUENCE CHARACTERISTICS:
        (A) LENGTH: 321 base pairs
        (B) TYPE: nucleic acid
        (C) STRANDEDNESS: single
        (D) TOPOLOGY: linear (xi) SEQUENCE DESCRIPTION: SEQ ID NO:7:

```
GACATCCAGA TGACCCAGTC TCCATCCTCC TTATCTGCCT CTCTGGGAGA AAGAGTCAGT    60

CTCACTTGTC GGGCAAGTCA GGACATTGGT AGTAGCTTAA ACTGGCTTCA GCAGGAACCA   120

GATGGAACTA TTAAACGCCT GATCTACGCC ACATCCAGTT TAGATTCTGG TGTCCCCAAA   180

AGGTTCAGTG GCAGTAGGTC TGGGTCAGAT TATTCTCTCA CCATCAGCAG CCTTGAGTCT   240
```

```
GAAGATTTTG TAGACTATTA CTGTCTACAA TATGCTAGTT CTCCGTGGAC GTTCGGTGGA    300

GGCACCAAGC TGGAAATCAA A                                              321
```

(2) INFORMATION FOR SEQ ID NO:8:

(i) SEQUENCE CHARACTERISTICS:
        (A) LENGTH: 321 base pairs
        (B) TYPE: nucleic acid
        (C) STRANDEDNESS: single
        (D) TOPOLOGY: linear (xi) SEQUENCE DESCRIPTION: SEQ ID NO:8:

```
GACATCCAGA TGACCCAGTC TCCATCCTCC TTATCTGCCT CTCTGGGAGA AAGAGTCAGT    60

CTCACTTGTC GGCCAAGTCA GGACATTGGT AGTAGCTTAA ACTGGCTTCA GCAGGAACCA    120

GATGGAACTA TTAAACGCCT GATCTACGCC ACATCCAGTT TAGATTCTGG TGTCCCCAAA    180

AGGTTCAGTG GCAGTAGGTC TGGGTCAGAT TATTCTCTCA CCATCAGCAG CCTTGAGTCT    240

GAAGATTTTG TAGACTATTA CTGTCTACAA TATGCTAGTT CTCCGTGGAC GTTCGGTGGA    300

GGCACCAAGC TGGAAATCAA A                                              321
```

(2) INFORMATION FOR SEQ ID NO:9:

(i) SEQUENCE CHARACTERISTICS:
        (A) LENGTH: 321 base pairs
        (B) TYPE: nucleic acid
        (C) STRANDEDNESS: single
        (D) TOPOLOGY: linear (xi) SEQUENCE DESCRIPTION: SEQ ID NO:9:

```
GACATCCAGA TGACCCAGTC TCCATCCTCC TTATCTGCCT CTCTGGGAGA AAGAGTCAGT    60

CTCACTTGTC GGCCAAGTCA GGACATTGGT AGTAGCTTAA ACTGGCTTCA GCAGGAACCA    120

GATGGAACTA TTAAACGCCT GATCTACGCC ACATCCAGTT TAGATTCTGG TGTCCCCAAA    180

AGGTTCAGTG GCAGTAGGTC TGGGTCAGAT TATTCTCTCA CCATCAGCAG CCTTGAGTCT    240

GAAGATTTTG TAGACTATTA CTGTCTACAA TATGCTAGTT CTCCGTGGAC GTTCGGTGGA    300

GGCACCAAGC TGGAAATCAA A                                              321
```

(2) INFORMATION FOR SEQ ID NO:10:

(i) SEQUENCE CHARACTERISTICS:
        (A) LENGTH: 318 base pairs
        (B) TYPE: nucleic acid
        (C) STRANDEDNESS: single
        (D) TOPOLOGY: linear (xi) SEQUENCE DESCRIPTION: SEQ ID NO:10:

```
ATCCAGATGA CCCAGTCTCC ATCCTCCTTA TCTGCCTCTC TGGGAGAAAG AGTCAGTCTC    60

ACTTGTCGGG CAAGTCAGGA CATTGGTAGT AGCTTAAACT GGCTTCAGCA GGAACCAGAC    120

GGAACTATTA AACGCCTGAT CTACGCCACA TCCAGTTTAG ATTCTGGTGT CCCCAAAAGG    180

TTCAGTGGCA GTAGGTCTGG GTCAGATTAT TCTCTCACCA TCAGCAGCCT TGAGTCTGAA    240

GATTTTGTAG ACTATTACTG TCTACAATAT GCTAGTTCTC CGTGGACGTT CGGTGGAGGC    300

ACCAAGCTGG AAATCAAA                                                  318
```

(2) INFORMATION FOR SEQ ID NO:11:

(i) SEQUENCE CHARACTERISTICS:
        (A) LENGTH: 303 base pairs (B) TYPE: nucleic acid
        (C) STRANDEDNESS: single
        (D) TOPOLOGY: linear (xi) SEQUENCE DESCRIPTION: SEQ ID NO:11:

TCTCCATCCT CCTTATCTGC CTCTCTGGGA GAAAGAGTCA GTCTCACTTG TCGGGCAAGT    60

CAGGACATTG GTAGTAGCTT AAACTGGCTT CAGCAGGAAC CAGATGGAAC TATTAAACGC   120

CTGATCTACG CCACATCCAG TTTAGATTCT GGTGTCCCCA AAAGGTTCAG TGGCAGTAGG   180

TCTGGGTCAG ATTATTCTCT CACCATCAGC AGCCTTGAGT CTGAAGATTT TGTAGACTAT   240

TACTGTCTAC AATATGCTAG TTCTCCGTAC ACGTTCGGAG GGGGGACCAA GCTGNAAATA   300

AAA                                                                303

(2) INFORMATION FOR SEQ ID NO:12:

(i) SEQUENCE CHARACTERISTICS:
        (A) LENGTH: 321 base pairs
        (B) TYPE: nucleic acid
        (C) STRANDEDNESS: single
        (D) TOPOLOGY: linear (xi) SEQUENCE DESCRIPTION: SEQ ID NO:12:

GACATCCAGA TGACCCAGTC TCCATCCTCC TTATCTGCCT CTCTGGGAGA AAGAGTCAGT    60

CTCACTTGTC GGGCAAGTCA GGAAATTAGT GGTTACTTAA GCTGGCTTCA GCAGAAACCA   120

GATGGAACTA TTAAACGCCT GATCTACAGC ACATCCACTT TAAATTCTGG TGTCCCAAAA   180

AGGTTCAGTG GCAGTAGGTC TGGGTCAGAT TATTCTCTCA CCATCAGCAG CCTTGAGTCT   240

GAAGATTTTG CAGACTATTA CTGTCTACAA TATGCTAGTT CTCCGTACAC GTTCGGAGGG   300

GGGACCAAAC TGGAAATAAA A                                            321

(2) INFORMATION FOR SEQ ID NO:13:

(i) SEQUENCE CHARACTERISTICS:
        (A) LENGTH: 303 base pairs
        (B) TYPE: nucleic acid
        (C) STRANDEDNESS: single
        (D) TOPOLOGY: linear (xi) SEQUENCE DESCRIPTION: SEQ ID NO:13:

TCTCCATCCT CCTTATCTGC CTCTCTGGGA GAAAGAGTCA GTCTCACTTG TCGGGCAAGT    60

CAGGACATTG GTAATAGCTT AAACTGGCTT CAGCAGGAAC CAGATGGAAC TATTAAACGC   120

CTGATCTACG CCACATCCAG TTTAGATTCT GGTGTCCCCA AAAGGTTCAG TGGCAGTAGG   180

TCTGGGTCAG ATTATTCTCT CACCATCAGC AGCCTTGAAT CTGAAGATTT TGTAGTCTAT   240

TACTGTCTAC AATATGCTAG TTATACGTAC ACGTTCGGAG GGGGGACCAA GTTGGAACTA   300

AAA                                                                303

(2) INFORMATION FOR SEQ ID NO:14:

(i) SEQUENCE CHARACTERISTICS:
        (A) LENGTH: 321 base pairs
        (B) TYPE: nucleic acid
        (C) STRANDEDNESS: single
        (D) TOPOLOGY: linear (xi) SEQUENCE DESCRIPTION: SEQ ID NO:14:

GACATCCAGA TGACCCAGTC TCCATCCTCC TTATCTGCCT CTCTGGGAGA AAGAGTCAGT    60

CTCACTTGTC GGGCAAGTCA GGAAATTAGT GGTTACTTAA GCTGGCTTCA GCAGAAACCA   120

```
GATGGAACTA TTAAACGCCT GATCTACGCC GCATCCACTT TAGATTCTGG TGTCCCAAAA      180

AGGTTCAGTG GCAGTAGGTC TGGGTCAGAT TATTCTCTCA CCATCAGCAG CCTTGAGTCT      240

GAAGATTTTG CAGACTATTA CTGTCTACAA TATCTTAGTT ATCCGCTCAC GTTCGGTGCT      300

GGGACCAAGC TGGAGCTGAA A                                                321

(2) INFORMATION FOR SEQ ID NO:15:

(i) SEQUENCE CHARACTERISTICS:
        (A) LENGTH: 294 base pairs
        (B) TYPE: nucleic acid
        (C) STRANDEDNESS: single
        (D) TOPOLOGY: linear (xi) SEQUENCE DESCRIPTION: SEQ ID NO:15:

CAGGCTTATN TACAGCAGTC TGGGGCTGAG CTGGTGAGGC CTGGGGCCTC AGTGAAGATG       60

TCCTGCAAGG CTTCTGGCTA CACATTTACC AGTTACAATA TGCACTGGGT AAAGCAGACA      120

CCTAGACAGG GCCTGGAATG GATTGGAGCT ATTTATCCAG GAAATGGTGA TACTTCCTAC      180

AATCAGAAGT TCAAGGGCAA GGCCACACTG ACTGTAGACA AATCCTCCAG CACAGCCTAC      240

ATGCAGCTCA GCAGCCTGAC ATCTGAAGAC TCTGCGGTCT ATTTCTGTGC AAGA            294

(2) INFORMATION FOR SEQ ID NO:16:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (xi) SEQUENCE DESCRIPTION: SEQ ID NO:16:

TGCTATGGAC TACTGGGGTC AAGGAACCTC AGTCACCGTC TCCTCA                      46

(2) INFORMATION FOR SEQ ID NO:17:

(i) SEQUENCE CHARACTERISTICS:
        (A) LENGTH: 360 base pairs
        (B) TYPE: nucleic acid
        (C) STRANDEDNESS: single
        (D) TOPOLOGY: linear (xi) SEQUENCE DESCRIPTION: SEQ ID NO:17:

CAGGCTTATG TACAGCAGTC TGGGGCTGAG CTGGTGAGGC CTGGGGCCTC AGTGAAGATG       60

TCCTGCAAGG CTTCTGGCTA CAGATTTACC AGTTACAATA TGCACTGGGT AAAGCAGACA      120

CGTAGACAGG GCCTGGAATG GATTGGAGCA ATTTATCCAG GAAATGGTGA TACTTCCTAT      180

AATCAGAAGT TCAAGGGCAA GGCCACACTG ATTGTAGACA AATCCTCCAG CACAGCCTAC      240

ATGCAGCTCA GCAGCCTGAC ATCTGAAGAC TCTGCGGTCT ATTTCTGTGC AAGAGAGAGG      300

GGTAACTACG TAGGACATAT GGACTACTGG GGTCAAGGAA CCTCAGTCAC CGTCTCCTCA      360

(2) INFORMATION FOR SEQ ID NO:18:

(i) SEQUENCE CHARACTERISTICS:
        (A) LENGTH: 354 base pairs
        (B) TYPE: nucleic acid
        (C) STRANDEDNESS: single
        (D) TOPOLOGY: linear (xi) SEQUENCE DESCRIPTION: SEQ ID NO:18:

CAGGCTTATC TACAGCAGTC TGGGGCTGAG CTGGTAAGGC CTGGGTCCTC AGTGAAGATG       60

TCCTGCAAGG CTTCTGGCTA CACATTTACC AGTTACAATA TGCACTGGGT AAAGCAGACA      120
```

```
CCTAGACAGG GCCTGGAATG GATTGGAGCT ATTTATCCAG GAAATGGTGA TACTTCCTAC      180

AATCAGAAGT TCAAGGGCAA GGCCACACTG ACTGTAGACA AATCCTCCAG CACAGCCTAC      240

ATGCAGCTCA GCAGCCTGAC ATCTGAAGAC TCTGCGGTCT ATTTCTGTGC AAGAGGGGAT      300

TACTCCGGTA GTATAGACTA CTGGGGCCAA GGCACCACTC TCACAGTCTC CTCA            354
```

(2) INFORMATION FOR SEQ ID NO:19:

(i) SEQUENCE CHARACTERISTICS:
        (A) LENGTH: 297 base pairs
        (B) TYPE: nucleic acid
        (C) STRANDEDNESS: single
        (D) TOPOLOGY: linear (xi) SEQUENCE DESCRIPTION: SEQ ID NO:19:

```
CAGGCTTATC TACAGCAGTC TGGGGCTGAG CTGGTGAGGC CTGGGGCCTC AGTGAAGATG       60

TCCTGCAAGG CTTCTGGCTA CACATTTACC AGTTACAATA TGCACTGGGT AAAGCAGACA      120

CCTAGACAGG GCCTGGAATG GATTGGAGCT ATTTATCCAG GAAATGGTGA TACTTCCTAC      180

AATCAGAAGT TCAAGGGCAA GGCCACACTG ACTGTAGACA AATCCTCCAG CACAGCCTAC      240

ATGCAGCTCA GCAGCCTGAC ATCTGAAGAC TCTGCGGTCT ATTTCTGTGC AAGAGTG         297
```

(2) INFORMATION FOR SEQ ID NO:20:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (xi) SEQUENCE DESCRIPTION: SEQ ID NO:20:

```
CTGGGGCACA GGGACCACGG TCACCGTCTC C                                      31
```

(2) INFORMATION FOR SEQ ID NO:21:

(i) SEQUENCE CHARACTERISTICS:
        (A) LENGTH: 297 base pairs
        (B) TYPE: nucleic acid
        (C) STRANDEDNESS: single
        (D) TOPOLOGY: linear (xi) SEQUENCE DESCRIPTION: SEQ ID NO:21:

```
CAGGCTTATC TACAGCAGTC TGGGGCTGAG CTGGTGAGGC CTGGGGCCTC AGTGAAGATG       60

TCCTGCAAGG CTTCTGGCTA CACATTTACC AGTTACAATA TGCACTGGGT AAAGCAGACA      120

CCTAGACAGG GCCTGGAATG GATTGGAGCT ATTTATCCAG GAAATGGTGA TACTTCCTAC      180

AATCAGAAGT TCAAGGGCAA GGCCACACTG ACTGTAGACA AATCCTCCAG CACAGCCTAC      240

ATGCAGCTCA GCAGCCTGAC ATCTGAAGAC TCTGCGGTCT ATTTCTGTGC AAGAGTG         297
```

(2) INFORMATION FOR SEQ ID NO:22:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:22:

```
CTGGGGCACA GGGACCACGG TCACCGTCTC                                        30
```

(2) INFORMATION FOR SEQ ID NO:23:

(i) SEQUENCE CHARACTERISTICS:
    (A) LENGTH: 300 base pairs
    (B) TYPE: nucleic acid
    (C) STRANDEDNESS: single
    (D) TOPOLOGY: linear (xi) SEQUENCE DESCRIPTION: SEQ ID NO:23:

AGGTCCAGCT GCAGCAGTCT GGACCTGAGC TGGTAAAGCC TGGGGCTTCA GTGAAGATAT    60

CCTGCAAGGC TTCTGGATAC ACATTCACTG ACTACTACAT GCACTGGGTG AAGCAGAAGC   120

CTGGGCAGGG CCTTGAGTGG ATTGGAGAGA TTTATCCTGG AAGTGGTAAT ACTTACTACA   180

ATGAGAAGTT CAAGGGYAAG GCCTCACTGA CTGCAGACAA ATCCTCCAGC ACAGCCTACA   240

TGCAGCTCAG CAGCCTGACA TCTGAGGACT CTGCAGTCTA TTTCTGTGCA AGACGTTACT   300

(2) INFORMATION FOR SEQ ID NO:24:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (xi) SEQUENCE DESCRIPTION: SEQ ID NO:24:

TGCTATGGAC TACTGGGGTC AAGGAACCTC AGTCACCGTC TCCTCA                   46

(2) INFORMATION FOR SEQ ID NO:25:

(i) SEQUENCE CHARACTERISTICS:
        (A) LENGTH: 295 base pairs
        (B) TYPE: nucleic acid
        (C) STRANDEDNESS: single
        (D) TOPOLOGY: linear (xi) SEQUENCE DESCRIPTION: SEQ ID NO:25:

CAGGTTCAGC TCCAGCAGTC TGGGGCTGAG CTGGCAAGAC CTGGGGCTTC AGTGAAGTTG    60

TCCTGCAAGG CTTCTGGCTA CACCTTTACT AGCTACTGGA TGCAGTGGGT AAAACAGAGG   120

CCTGGACAGG GTCTGGAATG GATTGGGGCT ATTTATCCTG GAGATGGTGA TACTAGGTAC   180

ACTCAGAAGT TCAAGGGCAA GGCCACATTG ACTGCAGATA AATCCTCCAG CACAGCCTAC   240

ATGCAACTCA GCAGCTTGGC ATCTGAGGAC TCTGCGGTCT ATTACTGTGC AAGAG        295

(2) INFORMATION FOR SEQ ID NO:26:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (xi) SEQUENCE DESCRIPTION: SEQ ID NO:26:

TGCTATGGAC TACTGGGGTC AAGGAACCTC AGTCACCGTC TCCTCA                   46

(2) INFORMATION FOR SEQ ID NO:27:

(i) SEQUENCE CHARACTERISTICS:
        (A) LENGTH: 294 base pairs
        (B) TYPE: nucleic acid
        (C) STRANDEDNESS: single
        (D) TOPOLOGY: linear (xi) SEQUENCE DESCRIPTION: SEQ ID NO:27:

CAGGTTCAGC TCCAGCAGTC TGGGGCTGAG CTGGCAAGAC CTGGGGCTTC AGTGAAGTTG    60

```
TCCTGCAAGG CTTCTGGCTA CACCTTTACT AGCTACTGGA TGCAGTGGGT AAAACAGAGG      120

CCTGGACAGG GTCTGGAATG GATTGGGGCT ATTTATCCTG GAGATGGTGA TACTAGGTAC      180

ACTCAGAAGT TCAAGGGCAA GGCCACATTG ACTGCAGATA AATCCTCCAG CACAGCCTAC      240

ATGCAACTCA GCAGCTTGGC ATCTGAGGAC TCTGCGGTCT ATTACTGTGC AAGA            294
```

(2) INFORMATION FOR SEQ ID NO:28:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (xi) SEQUENCE DESCRIPTION: SEQ ID NO:28:

```
TGCTATGGAC TACTGGGGTC AAGGAACCTC AGTCACCGTC TCCTCA                      46
```

(2) INFORMATION FOR SEQ ID NO:29:

(i) SEQUENCE CHARACTERISTICS:
        (A) LENGTH: 294 base pairs
        (B) TYPE: nucleic acid
        (C) STRANDEDNESS: single
        (D) TOPOLOGY: linear (xi) SEQUENCE DESCRIPTION: SEQ ID NO:29:

```
CAGGTTCAGC TCCAGCAGTC TGGGGCTGAG CTGGCAAGAC CTGGGGCTTC AGTGAAGTTG       60

TCCTGCAAGG CTTCTGGCTA CACCTTTACT AGCTACTGGA TGCAGTGGGT AAAACAGAGG      120

CCTGGACAGG GTCTGGAATG GATTGGGGCT ATTTATCCTG GAGATGGTGA TACTAGGTAC      180

ACTCAGAAGT TCAAGGGCAA GGCCACATTG ACTGCAGATA AATCCTCCAG CACAGCCTAC      240

ATGCAACTCA GCAGCTTGGC ATCTGAGGAC TCTGCGGTCT ATTACTGTGC AAGA            294
```

(2) INFORMATION FOR SEQ ID NO:30:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (xi) SEQUENCE DESCRIPTION: SEQ ID NO:30:

```
TGCTATGGAC TACTGGGGTC AAGGAACCTC AGTCACCGTC TCCTCA                      46
```

(2) INFORMATION FOR SEQ ID NO:31:

(i) SEQUENCE CHARACTERISTICS:
        (A) LENGTH: 296 base pairs
        (B) TYPE: nucleic acid
        (C) STRANDEDNESS: single
        (D) TOPOLOGY: linear (xi) SEQUENCE DESCRIPTION: SEQ ID NO:31:

```
CAGGTCCAAC TGCAGCAGCC TGGTGCTGAG CTTGTGAAGC CTGGGGCCTC AGTGAAGCTG       60

TCCTGCAAGG CTTCTGGCTA CACTTTCACC AGCTACTGGA TAAACTGGGT GAAGCAGAGG      120

CCTGGACAAG GCCTTGAGTG GATTGGAAAT ATTTATCCTG GTAGTAGTAG TACTAACTAC      180

AATGAGAAGT TCAAGAGCAA GGCCACACTG ACTGTAGACA CATCCTCCAG CACAGCCTAC      240

ATGCAGCTCA GCAGCCTGAC ATCTGACGAC TCTGCGGTCT ATTATTGTGC AAGACG          296
```

(2) INFORMATION FOR SEQ ID NO:32:

```
    (i) SEQUENCE CHARACTERISTICS:
        (A) LENGTH: 46 base pairs
        (B) TYPE: nucleic acid
        (C) STRANDEDNESS: single
        (D) TOPOLOGY: linear (xi) SEQUENCE DESCRIPTION: SEQ ID NO:32:

TGCTATGGAC TACTGGGGTC AAGGAACCTC AGTCACCGTC TCCTCA                     46

(2) INFORMATION FOR SEQ ID NO:33:

(i) SEQUENCE CHARACTERISTICS:
        (A) LENGTH: 20 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 9
        (D) OTHER INFORMATION: /note= "May also be the amino acid
            arginine(R)"

(ix) FEATURE:
        (A) NAME/KEY: Modified-site
        (B) LOCATION: 15
        (D) OTHER INFORMATION: /note= "May also be the amino acid
            glutamine(E)"

(ix) FEATURE:
        (A) NAME/KEY: Modified-site
        (B) LOCATION: 16
        (D) OTHER INFORMATION: /note= "May also be the amino acid
            serine(S)"

(ix) FEATURE:
        (A) NAME/KEY: Modified-site
        (B) LOCATION: 19
        (D) OTHER INFORMATION: /note= "May also be the amino acid
            proline(P)"

(xi) SEQUENCE DESCRIPTION: SEQ ID NO:33:

Gly Ser Thr Ala Pro Pro Ala His Gly Val Thr Ser Ala Pro Asp Thr
1               5                   10                  15

Arg Pro Ala Pro
            20

(2) INFORMATION FOR SEQ ID NO:34:

(i) SEQUENCE CHARACTERISTICS:
        (A) LENGTH: 23 amino acids
        (B) TYPE: amino acid
        (C) STRANDEDNESS: single
        (D) TOPOLOGY: linear (ix) FEATURE:
        (A) NAME/KEY: Modified-site
        (B) LOCATION: 12
        (D) OTHER INFORMATION: /note= "May also be the amino acid
            arginine(R)"

(ix) FEATURE:
        (A) NAME/KEY: Modified-site
        (B) LOCATION: 18
        (D) OTHER INFORMATION: /note= "May also be the amino acid
            glutamine(E)"

(ix) FEATURE:
        (A) NAME/KEY: Modified-site
        (B) LOCATION: 19
        (D) OTHER INFORMATION: /note= "May also be the amino acid
            serine(S)"

(ix) FEATURE:
```

```
        (A) NAME/KEY: Modified-site
        (B) LOCATION: 22
        (D) OTHER INFORMATION: /note= "May also be the amino acid
            proline(P)"

(ix) FEATURE:
        (A) NAME/KEY: Modified-site
        (B) LOCATION: 2
        (D) OTHER INFORMATION: /note= "May also be the amino acid
            proline(P)"

(xi) SEQUENCE DESCRIPTION: SEQ ID NO:34:

Pro Ala Pro Gly Ser Thr Ala Pro Pro Ala His Gly Val Thr Ser Ala
1               5                   10                  15

Pro Asp Thr Arg Pro Ala Pro
            20

(2) INFORMATION FOR SEQ ID NO:35:

(i) SEQUENCE CHARACTERISTICS:
        (A) LENGTH: 15 amino acids
        (B) TYPE: amino acid
        (C) STRANDEDNESS: single
        (D) TOPOLOGY: linear (xi) SEQUENCE DESCRIPTION: SEQ ID NO:35:

Gly Gly Gly Gly Ser Gly Gly Gly Ser Gly Gly Gly Gly Ser
1               5                   10                  15

(2) INFORMATION FOR SEQ ID NO:36:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ix) FEATURE:
        (A) NAME/KEY: misc_difference
        (B) LOCATION: replace(30, "")
        (D) OTHER INFORMATION: /note= "N represents the nucleotide
            Inosine"

(xi) SEQUENCE DESCRIPTION: SEQ ID NO:36:

CCCAAGCTTC CAGGGRCCAR KGGATARACN GRTGG                              35

(2) INFORMATION FOR SEQ ID NO:37:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO:37:

GGGAATTCAT GRAATGSASC TGGGTYWTYC TCTT                               34

(2) INFORMATION FOR SEQ ID NO:38:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:38:

TAATACGACT CACTATAGGG                                               20
```

```
(2) INFORMATION FOR SEQ ID NO:39:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:39:

GTTTTCCCAG TCACGACGT                                                 19

(2) INFORMATION FOR SEQ ID NO:40:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (xi) SEQUENCE DESCRIPTION: SEQ ID NO:40:

ACTAGTCGAC ATGAGGRCCC CTGCTCAGWT TYTTGGNWTC TT                        42

(2) INFORMATION FOR SEQ ID NO:41:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:41:

CCCAAGCTTA CTGGATGGTG GGAAGATGGA                                     30

(2) INFORMATION FOR SEQ ID NO:42:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO:42:

CAGATGGAAG GGCCCAAC                                                  18

(2) INFORMATION FOR SEQ ID NO:43:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:43:

GATTGATGCA TATCATTACC                                                20

(2) INFORMATION FOR SEQ ID NO:44:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:44:

GTTATCGATG TCGAATAGCC                                                20

(2) INFORMATION FOR SEQ ID NO:45:
```

```
        (i) SEQUENCE CHARACTERISTICS:
            (A) LENGTH: 24 base pairs
            (B) TYPE: nucleic acid
            (C) STRANDEDNESS: single
            (D) TOPOLOGY: linear (xi) SEQUENCE DESCRIPTION: SEQ ID NO:45:

TTGCTGCAGA TTGAGTACTG TTCT                                               24

(2) INFORMATION FOR SEQ ID NO:46:

(i) SEQUENCE CHARACTERISTICS:
            (A) LENGTH: 12 amino acids
            (B) TYPE: amino acid
            (C) STRANDEDNESS: single
            (D) TOPOLOGY: linear (xi) SEQUENCE DESCRIPTION: SEQ ID NO:46:

Gly Gly Gly Ser Gly Gly Gly Ser Gly Gly Gly Ser
1               5                   10

(2) INFORMATION FOR SEQ ID NO:47:

(i) SEQUENCE CHARACTERISTICS:
            (A) LENGTH: 107 amino acids
            (B) TYPE: amino acid
            (C) STRANDEDNESS: single
            (D) TOPOLOGY: linear (xi) SEQUENCE DESCRIPTION: SEQ ID NO:47:

Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Asp Ile Gly Ser Ser
                20                  25                  30

Leu Asn Trp Leu Gln Gln Glu Pro Asp Gly Thr Ile Lys Arg Leu Ile
            35                  40                  45

Tyr Ala Thr Ser Ser Leu Asp Ser Gly Val Pro Lys Arg Phe Ser Gly
        50                  55                  60

Ser Arg Ser Gly Ser Asp Tyr Ser Leu Thr Ile Ser Ser Leu Glu Ser
65                  70                  75                  80

Gly Asp Phe Val Asp Tyr Tyr Cys Leu Gln Tyr Ala Ser Ser Pro Tyr
                85                  90                  95

Thr Phe Gly Gly Gly Thr Lys Leu Glu Ile Lys
            100                 105

(2) INFORMATION FOR SEQ ID NO:48:

(i) SEQUENCE CHARACTERISTICS:
            (A) LENGTH: 118 amino acids
            (B) TYPE: amino acid
            (C) STRANDEDNESS: single
            (D) TOPOLOGY: linear (xi) SEQUENCE DESCRIPTION: SEQ ID NO:48:

Gln Val Gln Leu Gln Gln Ser Gly Ala Glu Leu Val Arg Pro Gly Ala
1               5                   10                  15

Ser Val Lys Met Ser Cys Lys Ala Ser Gly Tyr Thr Phe Thr Ser Tyr
                20                  25                  30

Trp Met His Trp Val Lys Gln Arg Pro Gly Gln Gly Leu Glu Trp Ile
            35                  40                  45

Gly Ala Ile Tyr Pro Gly Asn Gly Asp Thr Asn Tyr Asn Gln Lys Phe
        50                  55                  60
```

Lys Gly Lys Ala Thr Leu Thr Ala Asp Thr Ser Ser Thr Ala Tyr
65                  70                  75                  80

Met Gln Leu Ser Ser Leu Thr Ser Glu Asp Ser Ala Val Tyr Phe Cys
                85                  90                  95

Ala Arg Gly Xaa Xaa Xaa Gly Ala Met Asp Tyr Trp Gly Gln Gly Thr
            100                 105                 110

Ser Val Thr Val Ser Ser
        115

(2) INFORMATION FOR SEQ ID NO:49:

(i) SEQUENCE CHARACTERISTICS:
        (A) LENGTH: 4 amino acids
        (B) TYPE: amino acid
        (C) STRANDEDNESS: single
        (D) TOPOLOGY: linear (ix) FEATURE:
        (A) NAME/KEY: Region
        (B) LOCATION: 1..4
        (D) OTHER INFORMATION: /note= "position 54-57 of 11D10
            comparison sequence #8(Fig. 26B)"

(xi) SEQUENCE DESCRIPTION: SEQ ID NO:49:

Ser Asp Ser Tyr
1

(2) INFORMATION FOR SEQ ID NO:50:

(i) SEQUENCE CHARACTERISTICS:
        (A) LENGTH: 9 amino acids
        (B) TYPE: amino acid
        (C) STRANDEDNESS: single
        (D) TOPOLOGY: linear (ix) FEATURE:
        (A) NAME/KEY: Region
        (B) LOCATION: 1..9
        (D) OTHER INFORMATION: /note= "positions 118-126 of 11d10
            comparison sequence #2 and positions 100-108 of 11d10
            comparison sequence #6 (Fig. 26B)"

(xi) SEQUENCE DESCRIPTION: SEQ ID NO:50:

Xaa Xaa Xaa Xaa Xaa Xaa Xaa Xaa Xaa
1               5

(2) INFORMATION FOR SEQ ID NO:51:

(i) SEQUENCE CHARACTERISTICS:
        (A) LENGTH: 7 amino acids
        (B) TYPE: amino acid
        (C) STRANDEDNESS: single
        (D) TOPOLOGY: linear (ix) FEATURE:
        (A) NAME/KEY: Region
        (B) LOCATION: 1..7
        (D) OTHER INFORMATION: /note= "positions 99-105 of 11D10
            comparison sequence #3 and #8 (Fig. 26B)"

(xi) SEQUENCE DESCRIPTION: SEQ ID NO:51:

Xaa Xaa Xaa Xaa Xaa Xaa Xaa
1               5

(2) INFORMATION FOR SEQ ID NO:52:

(i) SEQUENCE CHARACTERISTICS:
        (A) LENGTH: 4 amino acids (B) TYPE: amino acid
        (C) STRANDEDNESS: single
        (D) TOPOLOGY: linear (ix) FEATURE:
        (A) NAME/KEY: Region
        (B) LOCATION: 1..4
        (D) OTHER INFORMATION: /note= "positions 100-103 of 11D10
            comparison sequence #12(Fig. 26B)"

(xi) SEQUENCE DESCRIPTION: SEQ ID NO:52:

Val Tyr Tyr Tyr
1

(2) INFORMATION FOR SEQ ID NO:53:

(i) SEQUENCE CHARACTERISTICS:
        (A) LENGTH: 4 amino acids
        (B) TYPE: amino acid
        (C) STRANDEDNESS: single
        (D) TOPOLOGY: linear (ix) FEATURE:
        (A) NAME/KEY: Region
        (B) LOCATION: 1..4
        (D) OTHER INFORMATION: /note= "positions 100-103 of 11D10
            comparison sequence #14(Fig. 26B)"

(xi) SEQUENCE DESCRIPTION: SEQ ID NO:53:

Phe Tyr Phe Tyr
1

(2) INFORMATION FOR SEQ ID NO:54:

(i) SEQUENCE CHARACTERISTICS:
        (A) LENGTH: 4 amino acids
        (B) TYPE: amino acid
        (C) STRANDEDNESS: single
        (D) TOPOLOGY: linear (ix) FEATURE:
        (A) NAME/KEY: Region
        (B) LOCATION: 1..4
        (D) OTHER INFORMATION: /note= "positions 100-103 of 11D10
            comparison sequence #15(Fig. 26B)"

(xi) SEQUENCE DESCRIPTION: SEQ ID NO:54:

Gly Leu Phe Thr
1

(2) INFORMATION FOR SEQ ID NO:55:

(i) SEQUENCE CHARACTERISTICS:
        (A) LENGTH: 20 amino acids
        (B) TYPE: amino acid
        (C) STRANDEDNESS: single
        (D) TOPOLOGY: linear (xi) SEQUENCE DESCRIPTION: SEQ ID NO:55:

Gly Ser Thr Ala Pro Pro Ala His Arg Val Thr Ser Ala Pro Glu Ser
1               5                   10                  15
Arg Pro Pro Pro
            20

(2) INFORMATION FOR SEQ ID NO:56:

(i) SEQUENCE CHARACTERISTICS:
        (A) LENGTH: 20 amino acids
        (B) TYPE: amino acid
        (C) STRANDEDNESS: single (D) TOPOLOGY: linear (xi) SEQUENCE DESCRIPTION: SEQ ID NO:56:

Pro Pro Pro Arg Ser Glu Pro Ala Ser Thr Val Arg His Ala Pro Pro
1               5                  10                  15

Ala Thr Ser Gly
            20

(2) INFORMATION FOR SEQ ID NO:57:

(i) SEQUENCE CHARACTERISTICS:
        (A) LENGTH: 8 amino acids
        (B) TYPE: amino acid
        (C) STRANDEDNESS: single
        (D) TOPOLOGY: linear (xi) SEQUENCE DESCRIPTION: SEQ ID NO:57:

Ala Pro Asp Thr Arg Pro Pro Pro
1               5

(2) INFORMATION FOR SEQ ID NO:58:

(i) SEQUENCE CHARACTERISTICS:
        (A) LENGTH: 145 amino acids
        (B) TYPE: amino acid
        (C) STRANDEDNESS: single
        (D) TOPOLOGY: linear (xi) SEQUENCE DESCRIPTION: SEQ ID NO:58:

Met Gly Thr Pro Ala Gln Ile Leu Gly Phe Leu Leu Leu Leu Phe Pro
1               5                  10                  15

Gly Thr Arg Cys Asp Ile Gln Met Thr Gln Ser Pro Ser Ser Leu Ser
            20                  25                  30

Ala Ser Leu Gly Gln Arg Val Ser Leu Thr Cys Arg Ala Ser Gln Asp
            35                  40                  45

Ile Gly Ile Asn Leu His Trp Leu Gln Gln Glu Pro Asp Gly Thr Ile
        50                  55                  60

Lys Arg Leu Ile Tyr Ala Thr Ser Ser Leu Gly Ser Gly Val Pro Lys
65                  70                  75                  80

Arg Phe Ser Gly Ser Arg Ser Gly Ser Asp Tyr Ser Leu Thr Ile Ser
            85                  90                  95

Ser Leu Glu Ser Gly Asp Phe Val Ala Tyr Tyr Cys Leu Gln Tyr Ala
            100                 105                 110

Ser Ser Pro Tyr Thr Phe Gly Gly Gly Thr Lys Leu Glu Ile Lys Arg
            115                 120                 125

Ala Asp Ala Ala Pro Thr Val Ser Ile Phe Pro Pro Ser Ser Lys Leu
            130                 135                 140

Gly

145

(2) INFORMATION FOR SEQ ID NO:59:

(i) SEQUENCE CHARACTERISTICS:
        (A) LENGTH: 4 amino acids
        (B) TYPE: amino acid
        (C) STRANDEDNESS: single
        (D) TOPOLOGY: linear (ix) FEATURE:
        (A) NAME/KEY: Region
        (B) LOCATION: 1..4
        (D) OTHER INFORMATION: /note= "position 2-5 of 11D10

-continued

```
            comparison sequence #15 (Fig. 26A)"

(xi) SEQUENCE DESCRIPTION: SEQ ID NO:59:

Glu Leu Val Leu
1
```

What is claimed is:

1. An isolated polynucleotide comprising a sequence encoding a polypeptide that upon administration to a mammal is capable of eliciting an anti-HMFG immunological response in said mammal, wherein the polypeptide comprises an immunoglobulin variable region containing the three light chain complementarity determining regions (CDRs) of antibody 11D10 and an immunoglobulin variable region containing the three heavy chain CDRs of antibody 11D10, wherein antibody 11D10 is produced by the hybridoma deposited under ATCC Accession No. HB-12020.

2. A cloning vector comprising the polynucleotide according to claim 1.

3. An isolated host cell comprising the polynucleotide of claim 1.

4. A polynucleotide according to claim 1, wherein the anti-HMFG immunological response comprises production of anti-HMFG antibody by the mammal.

5. A polynucleotide according to claim 1, wherein the anti-HMFG immunological response comprises production of anti-HMFG reactive T cells by the mammal.

6. A polynucleotide according to claim 1, wherein the light chain CDRs and the heavy chain CDRs are contained in SEQ ID NO:2 and SEQ ID NO:4, respectively.

7. An expression vector comprising the polynucleotide according to claim 1.

8. The expression vector of claim 7, wherein the expression vector is vaccinia.

9. A composition comprising the polynucleotide of claim 1 and a pharmaceutically acceptable excipient.

10. A composition according to claim 9, wherein the polynucleotide is a recombinant polynucleotide.

11. A kit for eliciting an anti-HMFG immunological response in a mammal comprising the polynucleotide of claim 1 in packaging.

12. A kit according to claim 11, wherein the polynucleotide is a recombinant polynucleotide.

13. A polynucleotide according to claim 1, wherein the encoding sequences for the variable region containing the three light chain CDRs and the encoding sequence for the variable region containing the three heavy chain CDRs are contained in the variable region encoding sequence in SEQ ID NO:1 and SEQ ID NO:3, respectively.

14. The polynucleotide of claim 1, wherein the polypeptide has the light and heavy chain variable region sequences contained in SEQ ID NO:2 and SEQ ID NO:4, respectively.

15. A polynucleotide according to claim 1, wherein the variable regions are joined by a linker polypeptide of about 5 to 20 amino acids.

16. An isolated polynucleotide encoding an immunoglobulin variable region containing the three light chain CDRs in SEQ ID NO:2.

17. A polynucleotide according to claim 16, wherein the variable region is contained in SEQ ID NO:2.

18. A method of preparing a light chain variable region of antibody 11D10, wherein antibody 11D10 is produced by the hybridoma deposited under ATCC Accession No. HB-12020, comprising expressing the polynucleotide of claim 16 in an isolated host cell.

19. An isolated polynucleotide encoding an immunoglobulin variable region containing the three heavy chain CDRs in SEQ ID NO:4.

20. A method of preparing a heavy chain variable region of antibody 11D10, wherein antibody 11D10 is produced by the hybridoma deposited under ATCC Accession No. HB-12020, comprising expressing the polynucleotide of claim 19 in an isolated host cell.

21. A polynucleotide according to claim 19, wherein the variable region is contained in SEQ ID NO:4.

22. A polynucleotide according to any of claims 13, 14, 4, 5, 15, or 6, 16, 19, 17, 21, wherein the polynucleotide is a recombinant polynucleotide.

23. An isolated host cell comprising the polynucleotide of any of claims 14, 6, 16, 19, 17, or 21, wherein the polynucleotide is a recombinant polynucleotide.

24. A composition comprising the polynucleotide of any of claims 15, 16, 19, 17, or 21 and a pharmaceutically acceptable excipient.

25. A composition according to claim 24, wherein the polynucleotide is a recombinant polynucleotide.

26. An isolated polynucleotide comprising a sequence encoding a polypeptide, wherein the polypeptide comprises an immunoglobulin variable region containing the three light chain complementarity determining regions (CDRs) of antibody 11D10 or an immunoglobulin variable region containing the three heavy chain CDRs of antibody 11D10, wherein antibody 11D10 is produced by the hybridoma deposited under ATCC Accession No. HB-12020.

27. A polynucleotide according to claim 26, wherein the polypeptide comprises an immunoglobulin variable region containing the three light chain CDRs of antibody 11D10.

28. A polynucleotide according to claim 26, wherein the polypeptide comprises an immunoglobulin variable region containing the three heavy chain CDRs of antibody 11D10.

29. A polynucleotide according to claim 26, wherein the immunoglobulin light chain variable region is contained in SEQ ID NO:2.

30. A polynucleotide according to claim 26, wherein the immunoglobulin heavy chain variable region is contained in SEQ ID NO:4.

31. A polynucleotide according to claim 26, wherein the encoding sequence is contained in the variable region encoding sequence in SEQ ID NO:1.

32. A polynucleotide according to claim 26, wherein the encoding sequence is contained in SEQ ID NO:3.

33. A composition comprising the polynucleotide of claim 26 and a pharmaceutically acceptable excipient.

34. An isolated polynucleotide comprising a sequence encoding a polypeptide, wherein the polypeptide comprises an immunoblobulin variable region containing the three light chain CDRs of antibody 11D10 and the an immunoglobulin variable region containing the three heavy chain CDRs of antibody 11D10, wherein antibody 11D10 is produced by the hybridoma deposited under ATCC Accession No. HB-12020, wherein the polypeptide has the light and heavy chain variable region sequences contained in SEQ ID NO:2 and SEQ ID NO:4, respectively.

* * * * *